(12) United States Patent
Smith et al.

(10) Patent No.: US 9,278,990 B2
(45) Date of Patent: *Mar. 8, 2016

(54) SUBSTITUTED NUCLEOTIDE ANALOGS

(71) Applicant: Alios BioPharma, Inc., South San Francisco, CA (US)

(72) Inventors: David Bernard Smith, San Mateo, CA (US); Jerome Deval, Pacifica, CA (US); Natalia Dyatkina, Mountain View, CA (US); Leonid Beigelman, San Mateo, CA (US); Guangyi Wang, Carlsbad, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/519,460

(22) Filed: Oct. 21, 2014

(65) Prior Publication Data

US 2015/0038451 A1 Feb. 5, 2015

Related U.S. Application Data

(63) Continuation of application No. 13/236,435, filed on Sep. 19, 2011, now Pat. No. 8,871,737.

(60) Provisional application No. 61/385,363, filed on Sep. 22, 2010, provisional application No. 61/426,461, filed on Dec. 22, 2010.

(51) Int. Cl.
| | |
|---|---|
| *C12N 5/00* | (2006.01) |
| *C12N 5/02* | (2006.01) |
| *A01N 43/04* | (2006.01) |
| *A61K 31/70* | (2006.01) |
| *C07H 19/10* | (2006.01) |
| *C07H 19/048* | (2006.01) |
| *C07H 19/06* | (2006.01) |
| *C07H 19/16* | (2006.01) |
| *C07H 19/20* | (2006.01) |
| *A61K 45/06* | (2006.01) |
| *A61K 31/7072* | (2006.01) |
| *A61K 31/7076* | (2006.01) |
| *A61K 31/708* | (2006.01) |

(52) U.S. Cl.
CPC .............. *C07H 19/10* (2013.01); *A61K 31/708* (2013.01); *A61K 31/7072* (2013.01); *A61K 31/7076* (2013.01); *A61K 45/06* (2013.01); *C07H 19/06* (2013.01); *C07H 19/16* (2013.01); *C07H 19/20* (2013.01)

(58) Field of Classification Search
CPC ........ C07H 19/06; C07H 19/10; C07H 19/16; C07H 19/20; A61K 45/06; A61K 31/708; A61K 31/7076; A61K 31/7072; A61K 2300/00

See application file for complete search history.

(56) References Cited

U.S. PATENT DOCUMENTS

| | | |
|---|---|---|
| 2,844,579 A | 7/1958 | Turner et al. |
| 3,180,859 A | 4/1965 | Hoeksema |
| 3,431,252 A | 3/1969 | Walton |
| 3,816,399 A | 6/1974 | Shaw et al. |
| 3,872,084 A | 3/1975 | Jones et al. |
| 3,872,098 A | 3/1975 | Jones et al. |
| 4,093,714 A | 6/1978 | Tolman et al. |
| 4,808,614 A | 2/1989 | Hertel |
| 5,378,825 A | 1/1995 | Cook et al. |
| 5,432,272 A | 7/1995 | Benner |
| 5,552,311 A | 9/1996 | Sorscher et al. |
| 5,578,718 A | 11/1996 | Cook et al. |
| 5,580,967 A | 12/1996 | Joyce |
| 5,602,240 A | 2/1997 | De Mesmaeker et al. |
| 5,610,289 A | 3/1997 | Cook et al. |
| 5,616,488 A | 4/1997 | Sullivan et al. |
| 5,620,676 A | 4/1997 | Jacobson et al. |
| 5,625,056 A | 4/1997 | Genieser et al. |
| 5,631,359 A | 5/1997 | Chowrira et al. |
| 5,631,360 A | 5/1997 | Usman et al. |
| 5,639,647 A | 6/1997 | Usman et al. |
| 5,646,128 A | 7/1997 | Firestein et al. |
| 5,658,780 A | 8/1997 | Stinchcomb et al. |
| 5,677,437 A | 10/1997 | Teng et al. |
| 5,681,940 A | 10/1997 | Wang et al. |
| 5,686,599 A | 11/1997 | Tracz |

(Continued)

FOREIGN PATENT DOCUMENTS

| | | |
|---|---|---|
| CA | 2252144 A1 | 4/2000 |
| CN | 1290707 A | 12/2001 |

(Continued)

OTHER PUBLICATIONS

Search and Examination Report dated Nov. 28, 2014 for ARIPO Application No. AP/P/2013/006824, filed Sep. 19, 2011.
Examination Report No. 1 dated Nov. 28, 2014 for Australian Application No. 2011305655, filed Sep. 19, 2011.
Office Action dated Mar. 13, 2015 for Chinese Application No. 201180055315.0, filed Sep. 19, 2011.
CAS Reg. No. 436084-92-3, Chemical Abstracts Service, STN Registry entry dated Jul. 2, 2002.

(Continued)

*Primary Examiner* — Lawrence E Crane
(74) *Attorney, Agent, or Firm* — Knobbe Martens Olson & Bear LLP

(57) ABSTRACT

Disclosed herein are phosphorothioate nucleotide analogs, such as thiophosphoramidate prodrugs and thiohosphates (including α-thiomonophosphates, α-thiodiphosphates, and α-thiotriphosphates), methods of synthesizing phosphorothioate nucleotide analogs, such as thiophosphoramidate prodrugs and thiohosphates, and methods of treating viral infections such as HCV, with the phosphorothioate nucleotide analogs, such as thiophosphoramidate prodrugs and thiohosphates.

31 Claims, 36 Drawing Sheets

(56) References Cited

U.S. PATENT DOCUMENTS

| | | | |
|---|---|---|---|
| 5,693,532 A | 12/1997 | McSwiggen et al. |
| 5,714,383 A | 2/1998 | Thompson |
| 5,721,350 A | 2/1998 | Chattopadhyaya |
| 5,728,684 A | 3/1998 | Cheng et al. |
| 5,744,595 A | 4/1998 | Srivastava et al. |
| 5,767,097 A | 6/1998 | Tam |
| 5,783,425 A | 7/1998 | Dudycz et al. |
| 5,804,683 A | 9/1998 | Usman et al. |
| 5,807,718 A | 9/1998 | Joyce et al. |
| 5,811,300 A | 9/1998 | Sullivan et al. |
| 5,831,071 A | 11/1998 | Usman et al. |
| 5,837,542 A | 11/1998 | Grimm et al. |
| 5,837,855 A | 11/1998 | Chowrira et al. |
| 5,871,918 A | 2/1999 | Thorp et al. |
| 5,892,024 A | 4/1999 | Chaturvedula et al. |
| 5,902,880 A | 5/1999 | Thompson |
| 5,952,478 A | 9/1999 | Baxter et al. |
| 5,965,721 A | 10/1999 | Cook et al. |
| 5,968,745 A | 10/1999 | Thorp et al. |
| 5,977,343 A | 11/1999 | Tracz |
| 5,985,621 A | 11/1999 | Usman et al. |
| 6,004,939 A | 12/1999 | Chen et al. |
| 6,017,896 A | 1/2000 | Sorscher et al. |
| 6,022,962 A | 2/2000 | Chowrira et al. |
| 6,030,957 A | 2/2000 | Uckun et al. |
| 6,063,566 A | 5/2000 | Joyce |
| 6,063,628 A | 5/2000 | Loeb et al. |
| 6,087,482 A | 7/2000 | Teng et al. |
| 6,130,326 A | 10/2000 | Ramasamy et al. |
| 6,132,971 A | 10/2000 | Thorp et al. |
| 6,156,501 A | 12/2000 | McGall et al. |
| 6,191,266 B1 | 2/2001 | Wang |
| 6,232,463 B1 | 5/2001 | Cook et al. |
| 6,326,174 B1 | 12/2001 | Joyce et al. |
| 6,353,098 B1 | 3/2002 | Usman et al. |
| 6,361,951 B1 | 3/2002 | Thorp et al. |
| 6,365,374 B1 | 4/2002 | Usman et al. |
| 6,437,117 B1 | 8/2002 | Usman et al. |
| 6,440,705 B1 | 8/2002 | Stanton, Jr. et al. |
| 6,455,513 B1 | 9/2002 | McGuigan et al. |
| 6,458,945 B1 | 10/2002 | Stanton, Jr. et al. |
| 6,469,158 B1 | 10/2002 | Usman et al. |
| 6,482,932 B1 | 11/2002 | Beigelman et al. |
| 6,491,905 B1 | 12/2002 | Sorscher et al. |
| 6,495,677 B1 | 12/2002 | Ramasamy et al. |
| 6,503,890 B1 | 1/2003 | Uckun |
| 6,528,640 B1 | 3/2003 | Beigelman et al. |
| 6,552,183 B1 | 4/2003 | Ramasamy et al. |
| 6,566,059 B1 | 5/2003 | Stanton, Jr. et al. |
| 6,569,630 B1 | 5/2003 | Vivekananda et al. |
| 6,573,248 B2 | 6/2003 | Ramasamy et al. |
| 6,582,923 B2 | 6/2003 | Stanton, Jr. et al. |
| 6,589,941 B1 | 7/2003 | Fahrig et al. |
| 6,596,700 B2 | 7/2003 | Sommadossi et al. |
| 6,617,438 B1 | 9/2003 | Beigelman et al. |
| 6,642,206 B2 | 11/2003 | Ramasamy et al. |
| 6,649,750 B1 | 11/2003 | Capaldi et al. |
| 6,649,751 B2 | 11/2003 | Usman et al. |
| 6,670,461 B1 | 12/2003 | Wengel et al. |
| 6,677,314 B2 | 1/2004 | Klecker et al. |
| 6,677,315 B2 | 1/2004 | Klecker et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,161 B2 | 8/2004 | Ismaili et al. |
| 6,787,526 B1 | 9/2004 | Bryant et al. |
| 6,794,499 B2 | 9/2004 | Wengel et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,875,752 B2 | 4/2005 | Aszodi et al. |
| 6,887,707 B2 | 5/2005 | Loeb et al. |
| 6,914,054 B2 | 7/2005 | Sommadossi et al. |
| 6,958,318 B2 | 10/2005 | Sorscher et al. |
| 6,974,865 B2 | 12/2005 | Cook et al. |
| 6,995,148 B2 | 2/2006 | Jones et al. |
| 7,018,989 B2 | 3/2006 | McGuigan et al. |
| 7,034,133 B2 | 4/2006 | Wengel et al. |
| 7,037,718 B2 | 5/2006 | Ealick et al. |
| 7,041,817 B2 | 5/2006 | Usman et al. |
| 7,049,068 B2 | 5/2006 | Thorp et al. |
| 7,064,114 B2 | 6/2006 | Yiv et al. |
| 7,081,449 B2 | 7/2006 | Pietrzkowski et al. |
| 7,091,315 B1 | 8/2006 | Ruben et al. |
| 7,094,768 B2 | 8/2006 | Roberts et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,112,406 B2 | 9/2006 | Behlke et al. |
| 7,125,855 B2 | 10/2006 | Bhat et al. |
| 7,138,501 B2 | 11/2006 | Rubn et al. |
| 7,141,574 B2 | 11/2006 | Beaulieu et al. |
| 7,141,665 B1 | 11/2006 | Joyce et al. |
| 7,148,206 B2 | 12/2006 | Sommadossi et al. |
| 7,151,089 B2 | 12/2006 | Roberts et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,235,649 B2 | 6/2007 | Gewirth et al. |
| 7,268,119 B2 | 9/2007 | Cook et al. |
| 7,285,658 B2 | 10/2007 | Cook et al. |
| 7,335,648 B2 | 2/2008 | Plourde, Jr. et al. |
| 7,339,054 B2 | 3/2008 | Xu et al. |
| 7,351,841 B2 | 4/2008 | Owada et al. |
| 7,365,057 B2 | 4/2008 | LaColla et al. |
| 7,368,438 B2 | 5/2008 | Plourde, Jr. et al. |
| 7,378,402 B2 | 5/2008 | Martin |
| 7,384,924 B2 | 6/2008 | LaColla et al. |
| 7,407,965 B2 | 8/2008 | Chen et al. |
| 7,427,636 B2 | 9/2008 | Cannizzaro et al. |
| 7,429,565 B2 | 9/2008 | Boojamra et al. |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,625,875 B2 | 12/2009 | Gosselin et al. |
| 7,629,328 B2 | 12/2009 | Roberts et al. |
| 7,635,689 B2 | 12/2009 | LaColla et al. |
| 7,645,747 B2 | 1/2010 | Boojamra et al. |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,953,557 B2 | 5/2011 | Johnson et al. |
| 8,871,737 B2 * | 10/2014 | Smith et al. ............ 514/47 |
| 8,916,538 B2 | 12/2014 | Kuldipkumar et al. |
| 2001/0011075 A1 | 8/2001 | Townsend et al. |
| 2002/0132237 A1 | 9/2002 | Algate et al. |
| 2002/0150922 A1 | 10/2002 | Stolk et al. |
| 2003/0004122 A1 | 1/2003 | Beigelman et al. |
| 2003/0008841 A1 | 1/2003 | Devos et al. |
| 2003/0073144 A1 | 4/2003 | Benson et al. |
| 2003/0144489 A1 | 7/2003 | Burgin et al. |
| 2003/0166064 A1 | 9/2003 | King et al. |
| 2003/0170891 A1 | 9/2003 | McSwiggen |
| 2003/0207271 A1 | 11/2003 | Holwitt |
| 2004/0009491 A1 | 1/2004 | Birse |
| 2004/0023265 A1 | 2/2004 | Vivekananda et al. |
| 2004/0023266 A1 | 2/2004 | Vivekananda et al. |
| 2004/0059104 A1 | 3/2004 | Cook et al. |
| 2004/0063658 A1 | 4/2004 | Roberts et al. |
| 2004/0077585 A1 | 4/2004 | Peterson et al. |
| 2004/0127436 A1 | 7/2004 | Daifuku et al. |
| 2004/0171028 A1 | 9/2004 | Baker et al. |
| 2004/0171032 A1 | 9/2004 | Baker et al. |

(56) References Cited

U.S. PATENT DOCUMENTS

| | | |
|---|---|---|
| 2004/0229839 A1 | 11/2004 | Babu et al. |
| 2004/0259934 A1 | 12/2004 | Olsen et al. |
| 2005/0031588 A1 | 2/2005 | Sommadossi et al. |
| 2005/0032067 A1 | 2/2005 | Prakash et al. |
| 2005/0042632 A1 | 2/2005 | Radka |
| 2005/0042647 A1 | 2/2005 | Baker et al. |
| 2005/0186568 A1 | 8/2005 | Bandman et al. |
| 2005/0203044 A1 | 9/2005 | Zinnen |
| 2005/0214901 A1 | 9/2005 | Ealick et al. |
| 2005/0233358 A1 | 10/2005 | Thorp et al. |
| 2005/0239733 A1 | 10/2005 | Jurk et al. |
| 2005/0245463 A1 | 11/2005 | Pham et al. |
| 2005/0256073 A1 | 11/2005 | Lipford |
| 2005/0261237 A1 | 11/2005 | Boojamra et al. |
| 2006/0003952 A1 | 1/2006 | Ravikumar et al. |
| 2006/0014689 A1 | 1/2006 | Vesely |
| 2006/0058254 A1 | 3/2006 | Dina et al. |
| 2006/0074035 A1 | 4/2006 | Hong et al. |
| 2006/0094678 A1 | 5/2006 | Vornlocher et al. |
| 2006/0100166 A1 | 5/2006 | De Koning et al. |
| 2006/0105976 A1 | 5/2006 | Soutschek et al. |
| 2006/0121086 A1 | 6/2006 | Boyer et al. |
| 2006/0122146 A1 | 6/2006 | Chun et al. |
| 2006/0142238 A1 | 6/2006 | McGuigan |
| 2006/0193869 A1 | 8/2006 | Barrat et al. |
| 2006/0217330 A1 | 9/2006 | Hartmann et al. |
| 2006/0229265 A1 | 10/2006 | Milburn et al. |
| 2006/0240462 A1 | 10/2006 | Todd et al. |
| 2006/0264404 A1 | 11/2006 | Boojamra et al. |
| 2006/0269517 A1 | 11/2006 | Blatt et al. |
| 2006/0287260 A1 | 12/2006 | Manoharan et al. |
| 2007/0027116 A1 | 2/2007 | Cho et al. |
| 2007/0032448 A1 | 2/2007 | Hong et al. |
| 2007/0037773 A1 | 2/2007 | Sommadossi et al. |
| 2007/0042350 A1 | 2/2007 | Li et al. |
| 2007/0042988 A1 | 2/2007 | Klumpp et al. |
| 2007/0066552 A1 | 3/2007 | Clarke et al. |
| 2007/0093446 A1 | 4/2007 | Douglass, III et al. |
| 2007/0105122 A1 | 5/2007 | Ota et al. |
| 2007/0105806 A1 | 5/2007 | Sah et al. |
| 2007/0123544 A1 | 5/2007 | Plourde, Jr. et al. |
| 2007/0135372 A1 | 6/2007 | MacLachlan et al. |
| 2007/0196824 A1 | 8/2007 | Stuyver et al. |
| 2007/0197463 A1 | 8/2007 | Chun et al. |
| 2007/0207973 A1 | 9/2007 | Daifuku et al. |
| 2007/0213292 A1 | 9/2007 | Stoffel et al. |
| 2007/0219365 A1 | 9/2007 | Joyce et al. |
| 2007/0231810 A1 | 10/2007 | Todd et al. |
| 2007/0238099 A1 | 10/2007 | Cohen et al. |
| 2007/0238678 A1 | 10/2007 | Barrat et al. |
| 2007/0258921 A1 | 11/2007 | Dalko |
| 2007/0259832 A1 | 11/2007 | Cook et al. |
| 2007/0265224 A1 | 11/2007 | Cook et al. |
| 2007/0275912 A1 | 11/2007 | Bhat et al. |
| 2007/0281899 A1 | 12/2007 | Bumcrot et al. |
| 2007/0299068 A1 | 12/2007 | Karp et al. |
| 2008/0009462 A1 | 1/2008 | Hostetler et al. |
| 2008/0015161 A1 | 1/2008 | Vornlocher et al. |
| 2008/0026362 A1 | 1/2008 | Ho et al. |
| 2008/0027068 A1 | 1/2008 | Owada et al. |
| 2008/0064753 A1 | 3/2008 | Palladino et al. |
| 2008/0070935 A1 | 3/2008 | Huang et al. |
| 2008/0152621 A1 | 6/2008 | Johansson et al. |
| 2008/0161246 A1 | 7/2008 | Klein et al. |
| 2008/0161324 A1 | 7/2008 | Johansen et al. |
| 2008/0199870 A1 | 8/2008 | Guenther et al. |
| 2008/0200423 A1 | 8/2008 | Cook et al. |
| 2008/0207542 A1 | 8/2008 | McSwiggen et al. |
| 2008/0207554 A1 | 8/2008 | Beigelman et al. |
| 2008/0261913 A1 | 10/2008 | Sommadossi et al. |
| 2008/0286230 A1 | 11/2008 | Sommadossi et al. |
| 2008/0293665 A1 | 11/2008 | Undheim et al. |
| 2009/0131372 A1 | 5/2009 | Chen et al. |
| 2009/0169504 A1 | 7/2009 | Sommadossi et al. |
| 2009/0176732 A1 | 7/2009 | Beigelman et al. |
| 2009/0181921 A1 | 7/2009 | Blatt et al. |
| 2009/0220950 A1 | 9/2009 | Stuyver et al. |
| 2009/0221684 A1 | 9/2009 | Grinstaff et al. |
| 2009/0227543 A1 | 9/2009 | Cannizzaro et al. |
| 2009/0233872 A1 | 9/2009 | Ariga et al. |
| 2009/0238790 A2 | 9/2009 | Sommadossi et al. |
| 2009/0247488 A1 | 10/2009 | Cannizzaro et al. |
| 2009/0275535 A1 | 11/2009 | Boojamra et al. |
| 2009/0280084 A1 | 11/2009 | Schinazi et al. |
| 2009/0280086 A1 | 11/2009 | Sommadossi et al. |
| 2009/0318380 A1 | 12/2009 | Sofia et al. |
| 2010/0016251 A1 | 1/2010 | Sofia et al. |
| 2010/0022467 A1 | 1/2010 | Boojamra et al. |
| 2010/0035835 A1 | 2/2010 | Narjes et al. |
| 2010/0081628 A1 | 4/2010 | Du et al. |
| 2010/0093656 A1 | 4/2010 | Adelfinskaya et al. |
| 2010/0137237 A1 | 6/2010 | Undheim et al. |
| 2010/0137576 A1 | 6/2010 | Stec et al. |
| 2010/0152128 A1 | 6/2010 | Attenni et al. |
| 2010/0249068 A1 | 9/2010 | Beigelman et al. |
| 2010/0297079 A1 | 11/2010 | Almond et al. |
| 2010/0305060 A1 | 12/2010 | Hecker et al. |
| 2010/0311684 A1 | 12/2010 | Cook et al. |
| 2010/0331397 A1 | 12/2010 | Beigelman et al. |
| 2011/0015383 A1 | 1/2011 | Stec et al. |
| 2012/0070411 A1 | 3/2012 | Beigelman et al. |
| 2012/0070415 A1 | 3/2012 | Beigelman et al. |
| 2012/0108533 A1 | 5/2012 | Herdewijn et al. |
| 2012/0165286 A1 | 6/2012 | Beigelman et al. |
| 2013/0017171 A1 | 1/2013 | Sommadossi et al. |
| 2013/0149283 A1 | 6/2013 | Sommadossi et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2013/0315862 A1 | 11/2013 | Sommadossi et al. |
| 2013/0315863 A1 | 11/2013 | Sommadossi et al. |
| 2014/0303113 A1 | 10/2014 | Krop et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |

FOREIGN PATENT DOCUMENTS

| | | |
|---|---|---|
| CN | 1337401 A | 2/2002 |
| CN | 1343673 A | 4/2002 |
| CN | 101108870 A | 1/2008 |
| DE | 3824110 A1 | 1/1990 |
| DE | 279247 A1 | 5/1990 |
| DE | 4341161 A1 | 6/1995 |
| EP | 0547008 A1 | 6/1993 |
| EP | 0629633 A2 | 12/1994 |
| EP | 0799834 A1 | 10/1997 |
| EP | 0742287 B1 | 1/2006 |
| EP | 2166016 | 3/2008 |
| GB | 1209654 A | 10/1970 |
| GB | 1319303 A | 6/1973 |
| GB | 2136425 | 9/1984 |
| JP | 04-046124 | 2/1992 |
| JP | 06-228186 A | 8/1994 |
| JP | 2006-248949 A | 9/2006 |
| JP | 2006-248975 A | 9/2006 |
| JP | 2007-509939 | 4/2007 |
| JP | 2008-504265 | 2/2008 |
| JP | 2009-504704 | 2/2009 |
| JP | 2009-526850 | 7/2009 |
| JP | 2010-510301 | 4/2010 |
| NZ | 216172 | 8/1989 |
| NZ | 224189 | 9/1991 |
| NZ | 226844 | 10/1991 |
| NZ | 231444 | 9/1992 |
| NZ | 505531 | 7/2001 |
| PL | 144471 B1 | 5/1988 |
| WO | WO 84/04748 A1 | 12/1984 |
| WO | WO 88/03147 A1 | 5/1988 |
| WO | WO 91/17159 | 11/1991 |
| WO | WO 92/12718 A1 | 8/1992 |
| WO | WO 92/20822 A1 | 11/1992 |

(56) References Cited

FOREIGN PATENT DOCUMENTS

| | | |
|---|---|---|
| WO | WO 94/17803 A1 | 8/1994 |
| WO | WO 94/22890 A1 | 10/1994 |
| WO | WO 95/18139 A1 | 7/1995 |
| WO | WO 96/07666 A1 | 3/1996 |
| WO | WO 96/23506 A1 | 8/1996 |
| WO | WO 96/29336 A1 | 9/1996 |
| WO | WO 96/30383 A1 | 10/1996 |
| WO | WO 97/26270 A2 | 7/1997 |
| WO | WO 98/00434 A1 | 1/1998 |
| WO | WO 99/10365 A2 | 3/1999 |
| WO | WO 99/46362 A1 | 9/1999 |
| WO | WO 99/55857 A2 | 11/1999 |
| WO | WO 00/00501 A1 | 1/2000 |
| WO | WO 00/14263 A2 | 3/2000 |
| WO | WO 00/56366 A1 | 9/2000 |
| WO | WO 01/27114 A1 | 4/2001 |
| WO | WO 01/49701 A1 | 7/2001 |
| WO | WO 01/68663 A1 | 9/2001 |
| WO | WO 01/72779 A1 | 10/2001 |
| WO | WO 01/90121 A2 | 11/2001 |
| WO | WO 02/03997 A1 | 1/2002 |
| WO | WO 02/18369 | 3/2002 |
| WO | WO 02/22660 A2 | 3/2002 |
| WO | WO 02/26930 A2 | 4/2002 |
| WO | WO 02/29103 A2 | 4/2002 |
| WO | WO 02/069903 A2 | 9/2002 |
| WO | WO 02/088385 A1 | 11/2002 |
| WO | WO 02/090526 A2 | 11/2002 |
| WO | WO 02/092006 A2 | 11/2002 |
| WO | WO 02/096927 A2 | 12/2002 |
| WO | WO 02/097031 A2 | 12/2002 |
| WO | WO 02/100415 A2 | 12/2002 |
| WO | WO 03/016475 A2 | 2/2003 |
| WO | WO 03/016497 A2 | 2/2003 |
| WO | WO 03/016572 A1 | 2/2003 |
| WO | WO 03/019189 A1 | 3/2003 |
| WO | WO 03/029271 A2 | 4/2003 |
| WO | WO 03/031419 A1 | 4/2003 |
| WO | WO 03/035012 A2 | 5/2003 |
| WO | WO 03/038052 A2 | 5/2003 |
| WO | WO 03/039348 A2 | 5/2003 |
| WO | WO 03/039523 A2 | 5/2003 |
| WO | WO 03/042357 A2 | 5/2003 |
| WO | WO 03/051896 A1 | 6/2003 |
| WO | WO 03/054152 A2 | 7/2003 |
| WO | WO 03/054219 A2 | 7/2003 |
| WO | WO 03/062257 A1 | 7/2003 |
| WO | WO 03/062376 A2 | 7/2003 |
| WO | WO 03/062379 A2 | 7/2003 |
| WO | WO 03/062385 A2 | 7/2003 |
| WO | WO 03/062391 A2 | 7/2003 |
| WO | WO 03/063688 A2 | 8/2003 |
| WO | WO 03/072602 A2 | 9/2003 |
| WO | WO 03/072729 A2 | 9/2003 |
| WO | WO 03/072757 A2 | 9/2003 |
| WO | WO 03/076586 A2 | 9/2003 |
| WO | WO 03/077875 A2 | 9/2003 |
| WO | WO 03/083082 A2 | 10/2003 |
| WO | WO 03/083084 A2 | 10/2003 |
| WO | WO 03/083085 A2 | 10/2003 |
| WO | WO 03/087300 A2 | 10/2003 |
| WO | WO 03/090674 A2 | 11/2003 |
| WO | WO 03/093439 A2 | 11/2003 |
| WO | WO 03/094848 A2 | 11/2003 |
| WO | WO 2004/001008 A2 | 12/2003 |
| WO | WO 2004/003000 A2 | 1/2004 |
| WO | WO 2004/003162 A2 | 1/2004 |
| WO | WO 2004/009797 A2 | 1/2004 |
| WO | WO 2004/026890 A1 | 4/2004 |
| WO | WO 2004/028454 A2 | 4/2004 |
| WO | WO 2004/041924 A2 | 5/2004 |
| WO | WO 2004/050899 A2 | 6/2004 |
| WO | WO 2004/080466 A1 | 9/2004 |
| WO | WO 2004/106356 A1 | 12/2004 |
| WO | WO 2005/003766 A2 | 1/2005 |
| WO | WO 2005/010150 A2 | 2/2005 |
| WO | WO 2005/020885 A2 | 3/2005 |
| WO | WO 2005/039552 A2 | 5/2005 |
| WO | WO 2005/040174 A1 | 5/2005 |
| WO | WO2005/042556 | 5/2005 |
| WO | WO 2005/047255 A1 | 5/2005 |
| WO | WO 2005/077966 A1 | 8/2005 |
| WO | WO 2005/123755 A2 | 12/2005 |
| WO | WO2006/012078 | 2/2006 |
| WO | WO 2006/034373 A2 | 3/2006 |
| WO | WO 2006/038865 A1 | 4/2006 |
| WO | WO 2006/062240 A1 | 6/2006 |
| WO | WO 2006/066080 A1 | 6/2006 |
| WO | WO 2006/094347 A1 | 9/2006 |
| WO | WO 2006/105440 A2 | 10/2006 |
| WO | WO 2006/106169 A1 | 10/2006 |
| WO | WO 2006/116512 A1 | 11/2006 |
| WO | WO2006/116557 | 11/2006 |
| WO | WO 2006/119507 A2 | 11/2006 |
| WO | WO 2006/121820 A1 | 11/2006 |
| WO | WO 2007/006544 A2 | 1/2007 |
| WO | WO 2007/020018 A1 | 2/2007 |
| WO | WO2007/020193 | 2/2007 |
| WO | WO 2007/027248 A2 | 3/2007 |
| WO | WO 2007/028051 A2 | 3/2007 |
| WO | WO 2007/056191 A2 | 5/2007 |
| WO | WO 2007/089731 A2 | 8/2007 |
| WO | WO2007/095269 | 8/2007 |
| WO | WO 2007/149554 A2 | 12/2007 |
| WO | WO 2008/033432 A2 | 3/2008 |
| WO | WO 2008/033466 A2 | 3/2008 |
| WO | WO 2008/039267 A2 | 4/2008 |
| WO | WO 2008/052770 A2 | 5/2008 |
| WO | WO2008/062206 | 5/2008 |
| WO | WO 2008/073661 A2 | 6/2008 |
| WO | WO 2008/083949 A2 | 7/2008 |
| WO | WO 2008/101157 A1 | 8/2008 |
| WO | WO 2008/103276 A2 | 8/2008 |
| WO | WO 2008/104408 A2 | 9/2008 |
| WO | WO 2008/106803 A2 | 9/2008 |
| WO | WO 2008/121634 A2 | 10/2008 |
| WO | WO 2009/005382 A2 | 1/2009 |
| WO | WO 2009/073506 A3 | 6/2009 |
| WO | WO 2009/127230 A1 | 10/2009 |
| WO | WO 2009/146123 A2 | 12/2009 |
| WO | WO 2010/019954 A2 | 2/2010 |
| WO | WO 2010/020786 A1 | 2/2010 |
| WO | WO 2010/030858 A1 | 3/2010 |
| WO | WO 2010/048552 A3 | 4/2010 |
| WO | WO2010/075549 | 7/2010 |
| WO | WO2010/081082 | 7/2010 |
| WO | WO 2010/091386 A2 | 8/2010 |
| WO | WO 2010/108140 A1 | 9/2010 |
| WO | WO 2011/005860 A2 | 1/2011 |
| WO | WO 2011/094489 A1 | 8/2011 |
| WO | WO 2011/156757 A1 | 12/2011 |
| WO | WO 2012/040126 A1 | 3/2012 |
| WO | WO 2012/040127 A1 | 3/2012 |
| WO | WO 2012/088155 A1 | 6/2012 |
| WO | WO 2012/142085 | 10/2012 |
| WO | WO 2013/142124 | 9/2013 |
| WO | WO 2013/142159 | 9/2013 |
| WO | WO 2013/142525 | 9/2013 |
| WO | WO 2014/134251 | 9/2014 |

OTHER PUBLICATIONS

CAS Reg. No. 436084-93-4, Chemical Abstracts Service, STN Registry entry dated Jul. 2, 2002.
CAS Reg. No. 436084-94-5, Chemical Abstracts Service, STN Registry entry dated Jul. 2, 2002.
CAS Reg. No. 436084-95-6, Chemical Abstracts Service, STN Registry entry dated Jul. 2, 2002.
Resolution No. 2763 dated Feb. 16, 2015, for Colombian Patent Application No. 13-089.868, filed Sep. 19, 2011.
Office Action dated Feb. 2, 2015, for Eurasian Patent Application No. 201390230, filed Sep. 19, 2011.
Examination dated Nov. 7 2014 for Mexican Application No. MX/a/2013/003153, filed Sep. 19, 2011.

(56) References Cited

OTHER PUBLICATIONS

Opposition dated Sep. 5, 2014 for Peruvian Application No. 619-2013, filed Sep. 19, 2011.
Office Action and Search report dated May 5, 2015, for ROC (Taiwan) Patent Application No. 100134051, filed Sep. 21, 2011.
Aivazashvili et al., Utilization of 5'-C-methylnucleoside triphosphates in RNA synthesis reaction catalyzed by *Escherichia coli* RNA-polymerase, Molekulyarnaya Biologiya (Moscow), 1987, vol. 21, Issue 4, pp. 1080-1091.
Aspelund et al., 5-Isopropyl- and 5-propyl-l-methyl-3-phenyldialuric acids, Acta Acad. Aboensis, Math. & Phys., 1958, vol. 21, Issue 11, pp. 3-11.
Bajwa et al., Thymidine nucleoside 3',5'-cyclic phosphoramidites and phosphites—configuration at phosphorus in trivalent and pentavalent cyclic nucleotides by phosphorus-31 and carbon-13 NMR, Tetrahedron Letters, 1978, vol. 5, pp. 421-424.
Baker et al., Synthesis of potential anticancer agents. VI. Use of the O-benzoyl blocking group from synthesis of 6-chloropurine nucleosides, Journal of Organic Chemistry, 1957, vol. 22, pp. 954-959.
Baker et al., Synthesis of potential anticancer agents. VII. Nucleosides derived from L-rhamnofuranose, Journal of Organic Chemistry, 1957, vol. 22, pp. 959-966.
Baker et al., Synthesis of potential anticancer agents. VIII. Nucleosides derived from L-rhamnofuranose, Journal of Organic Chemistry, 1957, vol. 22, pp. 966-971.
Baraniak et al., Ribonucleoside cyclic 3',5'-phosphoramidates: Synthesis, stereochemistry, and conversion into ribonucleoside cyclic 3',5'-phosphorothioates and -[180] phosphates, Journal of the Chemical Society, Perkin Transactions 1: Organic and Bio-Organic Chemistry, 1987, vol. 8, pp. 1645-1656.
Baraniak et al., Synthesis of adenosine cyclic 3',5'-phosphorofuoridate (cAMP-F), Tetrahedron Letters, 1995, vol. 36, Issue 44, Elsevier, pp. 8119-8122.
Baraniak, Deoxyribonucleoside cyclic 3',5'-phosphorofluoridates phosphorus, Sulfur Silicon Relat. Elem., 1996, vol. 111, p. 80.
Beaulieu et al., Inhibitors of the HCV NS5B polymerase: New hope for the treatment of hepatitis C infections, Curr. Opin. Invest. Drugs, 2004, vol. 5, Issue 8, pp. 838-850.
Beigelman et al., Synthesis of 5' -C-methyl-D-allo- & L-talo-ribonucleoside 3' -O-phosphoramidites & their incorporation into hammerhead ribozymes, Nucleosides & Nucleotides, 1995, vol. 14, Issue 5, pp. 901-906.
Bergstrom, Nucleoside phosphorylation and related modifications, Current Protocols in Nucleic Acid Chemistry, Chapter 13, John Wiley & Sons, 2008, Suppl. 33, pp. 13.0.1-13.0.2.
Bennett et al., Designer gene therapy using an *Escherichia coli* purine nucleoside phosphorylase/prodrug system, Chemistry & Biology, 2003, vol. 10, Issue 12, pp. 1173-1181.
Billich et al., Synthesis, conformation and enzymatic properties of 1-(β-D-allofuranosyl) uracil and some derivatives, Nucleic Acids Research, 1983, vol. 11, Issue 21, pp. 7611-7624.
Bindal et al., The relationship of vasodilator activity of adenosine analogs with molecular connectivity and van der Waals volume, Arzneimittel-Forschung, 1980, vol. 30, Issue 6, pp. 924-928.
Botelho et al., Inhibition of cAMP-dependent protein kinase by adenosine cyclic 3',5'-phosphorodithioate, a second cAMP antagonist, Journal of Biological Chemistry, 1988, vol. 263, Issue 11, pp. 5301-5305.
Bottka et al., Evidence for the stereoelectronic control of the acid hydrolysis of adenosine cyclic 3', 5'-phosphoramidate diastereoisomers, Nucleosides & Nucleotides, 1989, vol. 8, Issue 7, pp. 1217-1229.
Bruns, Adenosine receptor activation in human fibroblasts: nucleoside agonists and antagonists, Canadian Journal of Physiology and Pharmacology, 1980, vol. 58, Issue 6, pp. 673-691.
Bundgaard, "Design of prodrugs", Elsevier Science Publishers B.V. (1985), Table of Contents only.
Cahard et al., Aryloxy phosphoramidate triesters as pro-tides, Mini-Reviews in Medicinal Chemistry, 2004, vol. 4, pp. 371-381.
Cappuccino et al., Growth inhibition of clostridium feseri by carcinostatic purine and pyrimidine analogs. I. Effect of medium on growth inhibition, Cancer Research, 1964, vol. 24, pp. 1243-1248.
Carroll et al., Inhibition of hepatitis C virus RNA replication by 2'-modified nucleoside analogs, Journal of Biological Chemistry, 2003, vol. 278, Issue 14, pp. 11979-11984.
Carroll, S. S. et al., Nucleoside Analog Inhibitors of Hepatitis C Virus Replication, Infectious Disorders—Drug Targets, 2006, vol. 6, pp. 17-29.
Carey, Francis, Organic Chemistry, 2nd ed., McGraw Hill, Inc., New York (1992), pp. 328-331.
CAS Reg. No. 18883-94-8, STNEasy, Entry Date Nov. 16, 1984, (https://stneasy.cas.org), retrieved on Oct. 23, 2013.
CAS Reg. No. 71738-02-8, STNEasy, Entry Date Nov. 16, 1984, (https://stneasy.cas.org), retrieved on Oct. 23, 2013.
CAS Reg. No. 80875-87-2, STNEasy, Entry Date Nov. 16, 1984, (https://stneasy.cas.org), retrieved on Oct. 23, 2013.
CAS RN 486446-48-4, STNEasy, Entry Date Feb. 6, 2003, (https://stneasy.cas.org), retrieved on Nov. 17, 2011.
Cass et al., Mediated transport of nucleosides by human erythrocytes. Specificity toward purine nucleosides as permeants, Biochemica et Biophysica Acta, Biomembranes, 1973, vol. 291, Issue 3, pp. 734-746.
Chidgeavadze et al., Synthesis and substrate properties of C-methyl-2'-deoxynucleoside 5'-triphosphates in DNA synthesis reactions catalyzed by DNA polymerases, Bioorganicheskaya Khimiya, 1991, vol. 17, Issue 5, pp. 678-684.
Chidgeavadze et al., 5'-C- and 3'-C-Methyl-2'-deoxynucleoside 5'-triphosphates and their substrate properties in DNA-polymerase-catalyzed DNA synthesis reactions, Soviet Journal of Bioorganic Chemistry (a translation of Bioorganicheskaya Khimiya), 1992, vol. 17, Issue 5, pp. 389-395.
Cullis, The stereospecific conversion of p-chiral dialkyl phosphorothioates into $^{18}$O-phosphates, Tetrahedron Letters, 1983, vol. 24, Issue 50, pp. 5677-5680.
Cusack et al., Simple syntheses of glycofuranosylamines derived from D-xylose, D-mannose, and L-rhamnose, intermediates in the preparation of some N-glycofuranosyl uracils, Chemical Communications, 1971, vol. 4, pp. 190-191.
David et al., Synthesis of the two epimeric 5'-methylcytidines, their 5'-phosphates and [5-$^{3}$H]-5'-pyrophosphates, and the two 5'-methyldeoxycytidines. A novel cytosine anhydronucleoside with two oxygen bridges between the base and the sugar, Journal of the Chemical Society, Perkin Transactions 1: Organic and Bio-Organic Chemistry, 1982, vol. 2, pp. 385-393.
De Vroom et al., Synthesis of ribonucleoside 3',5'-cyclic phosphorothioates using a modified hydroxybenzotriazole phosphotriester approach, Recueil des Travaux Chimiques des Pays-Bas, 1987, vol. 106, Issue 11, pp. 577-580.
Del Vecchio et al., Small molecule and biologic inhibitors of hepatitis C virus: A symbiotic approach, Mini-Reviews in Medicinal Chemistry, Nov. 2006, vol. 6, Issue 11, pp 1263-1268.
Deval et al., Pyrophosphorolytic excision of nonobligate chain terminators by hepatitis C virus NS5B polymerase, Antimicrobial Agents and Chemotherapy, Aug. 2007, vol. 51, Issue 8, pp. 2920-2928.
De Zwart et al., A functional screening of adenosine analogs at the adenosine A2B receptor: A search for potent agonists, Nucleosides & Nucleotides, 1998, vol. 17, Issue 6, pp. 969-995.
Dutartre et al., General catalytic deficiency of hepatitis C virus RNA polymerase with an S282T mutation and mutually exclusive resistance towards 2'-modified nucleotide analogues, Antimicro. Agts. Chemother., 2006, vol. 50, Issue 12, pp. 4161-4169.
Dzhavadova et al., The molecular and crystal structures of 1-(6-deoxy-β-D-allofuranosyl) cytosine and 1-(6-deoxy-α-L-talofuranosyl) cytosine, Kristallografiya, 1988, vol. 33, Issue 6, pp. 1408-1414.
Dzhavadova et al., The molecular and crystal structure of 1- (2, 6-dideoxy-α-L-lyxo-hexofuranosyl) thymine, Bioorganicheskaya Khimiya, 1989, vol. 15, Issue 7, pp. 976-982.
Eliahu, S. et al, A Novel Insulin Secretagogue Based on a Dinucleoside Polyphosphate Scaffold, Journal of Medicinal Chemistry, 2010, vol. 53, No. 6, pp. 2472-2481.

(56) References Cited

OTHER PUBLICATIONS

Eppacher et al., Synthesis and incorporation of C(5')-ethynylated uracil-derived phosphoramidites into RNA, Helvetica Chimica Acta, 2004, vol. 87, pp. 3004-3020.
Estrada et al., In silico studies toward the discovery of new anti-HIV nucleoside compounds with the use of TOPS-MODE and 2D/3D connectivity indices. 1. Pyrimidyl derivatives, Journal of Chemical Information and Computer Sciences, 2002, vol. 42, Issue 5, pp. 1194-1203.
Feldwisch et al., Purification & characterization of a cAMP-binding protein of Volvox carteri f. nagariensis iyengar, European Journal of Biochemistry, 1995, vol. 228, Issue 2, pp. 480-489.
Ferrini et al., Free amino acids in the egg of Ciona intestinalis during some development stages, Ricerca Scientifica, Parte 2: Rendiconti, Sezione B: Biologica, 1964, vol. 5, Issue 3, pp. 213-220.
Fingl et al., The Pharmacological Basis of Therapeutics, 5th ed., MacMillan Publishing Co., Inc. (1975) Chapter 1, General Principles, pp. 1-46.
Fischer, B. et al., 2-Thioether 5'-o-(1-Thiotriphosphate)adenosine Derivatives as New Insulin Secretagogues Acting through P2Y-Receptors, Journal of Medicinal Chemistry, 1999, vol. 42, No. 18, pp. 3636-3646.
Follman et al., Novel nucleosides derived from 5'-C-methyl adenosine, Eur. Biophys. Congr., Proc., $1^{st}$, 1971, vol. 1, pp. 285-287.
Follman et al., Adenine nucleosides in solution. Stabilization of the anti-conformation by C-5' substituents, European Journal of Biochemistry, 1974, vol. 47, Issue 1, pp. 187-197.
Follman et al., Adenine nucleosides in solution: Circular dichroism studies and base conformation, European Journal of Biochemistry, 1975, vol. 58, Issue 1, pp. 31-41.
Gangjee et al., Vasodilator activity of adenosine analogs, Journal of Pharmaceutical Sciences, 1978, vol. 67, Issue 1, pp. 121-123.
Gerdner et al. "Comparative Kinetics of Nucleotide Analog Incorporation by Vent DNA Polymerase" *J. Bio. Chem.* (2004) 279(12):11834-11842.
Gemcitabine, The Merck Index ($15^{th}$ Ed. 2013) p. 809.
Gimisis et al., Tuning the reactivity of O-tert-butyldimethylsilylimidazolyl aminals towards organolithium reagents, Synlett, 2003, vol. 10, pp. 1451-1454.
Girardet et al., Synthesis and cytotoxicity of 4-amino-5-oxopyrido [2, 3-d] pyrimidine nucleosides, Journal of Medicinal Chemistry, 2000, vol. 43, Issue 20, pp. 3704-3713.
Gonzalez et al., A radial distribution function approach to predict A2B agonist effect of adenosine analogues, Bioorganic & Medicinal Chemistry, 2005, vol. 13, Issue 3, pp. 601-608.
Gopalakrishnan et al., A virtual screening approach for thymidine monophosphate kinase inhibitors as antitubercular agents based on docking and pharmacophore models, Journal of Chemical Information and Modeling, 2005, vol. 45, pp. 1101-1108.
Grant et al., Binding specificities of adenosine aminohydrolase from calf intestinal mucosa with dialdehydes derived from hexofuranosyladenine nucleosides, Journal of Medicinal Chemistry, 1980, vol. 23, Issue 1, pp. 39-42.
Grant et al., Hexofuranosyladenine nucleosides as substrates and inhibitors of calf intestinal adenosine deaminase, Journal of Medicinal Chemistry, 1979, vol. 22, Issue 8, pp. 1016-1018.
Greene et al., Protective Groups in Organic Synthesis, 3. Ed., John Wiley & Sons, (1999) Cover & Contents pages.
Gunic et al., Synthesis & cytotoxicity of 4'-C- and 5'-C-substituted toyocamycins, Bioorganic & Medicinal Chemistry, 2001, vol. 9, Issue 1, pp. 163-170.
Gurskaya et al., X-ray crystallographic studies of nucleoside analogs. I. The crystal structure of 1-(6-deoxy-β-D-allofuranosyl) cytosine, $C_{10}H_{15}N_3O_5$, Crystal Structure Communications, 1982, vol. 11, Issue 4, pp. 1245-1252.
Gwack et al. DNA Helicase activity of the hepatitis C virus nonstructural protein 3. European Houranl of Biochemistry, 1997, 250(1):47-54.
Hai et al., Species- or isozyme-specific enzyme inhibitors. 9. Selective effects in inhibitions of rat pyruvate kinase isozymes by adenosine 5'-diphosphate derivatives, Journal of Medicinal Chemistry, 1982, vol. 25, Issue 10, pp. 1184-1188.
Hai et al., Species- or isozyme-specific enzyme inhibitors. 7. Selective effects in inhibitions of rat adenylate kinase isozymes by adenosine 5'-phosphate derivatives, Journal of Medicinal Chemistry, 1982, vol. 25, Issue 7, pp. 806-812.
Hampton et al., Substrate properties of cycloadenosines with adenosine aminohydrolase as evidence for the conformation of enzyme-bound adenosine, Biochemistry, 1972, vol. 11, Issue 25, pp. 4736-4739.
Hampton et al., Interactions of epimeric 5'-C-methyl and 5'-C-carbamyl derivatives of adenosine monophosphate with adenosine monophosphate utilizing enzymes, Biochemistry, 1973, vol. 12, Issue 17, pp. 3328-3332.
Hayakawa et al., A strategy for the stereoselective preparation of thymidine phosphorothioates with the (R) or the (S) configuration at the stereogenic oligodeoxyribonucleotides with stereochemically pure phosphate/phosphorothioate chimeric backbones, European Journal of Organic Chemistry, 2006, vol. 17, pp. 3834-3844.
Hayatshahi et al., QSARs and activity predicting models for competitive inhibitors of adenosine deaminase, FEBS Letters, 2007, vol. 581, Issue 3, pp. 506-514.
Hebert et al., Structural features of the noncatalytic cGMP binding sites of frog photoreceptor phosphodiesterase using cGMP analogs, Journal of Biological Chemistry, 1998, vol. 273, Issue 10, pp. 5557-5565.
Heinemann et al., Comparison of the cellular pharmacokinetics and toxicity of 2'.2'-difluorodeoxycytidine and 1-beta-D-arabinofuranosylcytosine, Cancer Research, 1988, vol. 48, pp. 4024-4031.
Henderson et al., Inhibitors of adenine phosphoribosyltransferase, Cancer Chemotherapy Reports Supplement, 1968, vol. 1, Issue 2, pp. 363-373.
Henderson et al., Mechanisms of inhibition of adenine phosphoribosyltransferase by adenine nucleosides and nucleotides, Canadian Journal of Biochemistry, 1970, vol. 48, Issue 5, pp. 573-579.
Hiebl et al., Side-chain derivatives of biologically active nucleosides. Part 1. Side-chain analogs of 3'-azido-3'-deoxythymidine (AZT), Journal of Medicinal Chemistry, 1992, vol. 35, Issue 16, pp. 3016-3023.
Hiebl et al., Side-chain derivatives of biologically active nucleosides. Part 2: Synthesis and anti-HIV activity of 5'-C-methyl derivatives of 3'-fluoro-3'-deoxythymidine, Antiviral Chemistry and Chemotherapy, 1996, vol. 7, Issue 3, pp. 173-177.
Higuchi et al., "Pro-drugs as novel drug delivery systems", A.C.S. Symposium Series, American Chemical Society, 1975, vol. 14, pp. 155-183.
Hillaire-Buys, D. et al., Pharmacological Evaluation and Chemical Stability of 2-benzylthioether-5'-O-(1-thiotriphosphate)-Adenosine, A New Insulin Secretagogue Acting Through P2Y Receptors, Drug Development Research, 2001, vol. 53, No. 1, pp. 33-43.
Hong, J. A. et al., Identification of Critical Ligand Binding Determinants in *Mycrobacterium tuberculosis* Adenosine-5'-phosphosulfate Reductase, Journal of Medicinal Chemistry, 2009, vol. 52, No. 17, pp. 5485-5495.
Howgate et al., Conversion of 2',3'-O-isopropylideneadenosine into 9-(6-deoxy-β-D-allofuranosyl)- and 9-(6-deoxy-α-L-talofuranosyl) adenines, Carbohydrate Research, 1972, vol. 2, pp. 309-315.
Hrdlicka et al., Synthesis and biological evaluation of branched and conformationally restricted analogs of the anticancer compounds 3'-C-ethynyluridine (EUrd) and 3'-C-ethynylcytidine (ECyd), Bioorganic & Medicinal Chemistry, 2005, vol. 13, vol. 7, pp. 2597-2621.
Hrebabecky et al., Synthesis of 1-(3-azido-2,3-dideoxy-B-D-allofuranosyl)thymine, 1-(2,3-dideoxy-B-D-allofuranosyl)thymine, and 1-(2,3-dideoxy-B-D-erythro-hex-2-enofuranosyl)thymine, Carbohydrate Research, 1991, vol. 216, pp. 179-186.
Huang et al., Recent development of therapeutics for chronic HCV infection, Antiviral Research, 2006, vol. 71, Issue 2&3, pp. 351-362.
Hung et al., A New Nonhydrolyzable Reactive cGMP Analogue, (Rp) -Guanosine-3',5'-cyclic-S-(4-bromo-2,3-dioxobutyl)

(56) References Cited

OTHER PUBLICATIONS monophosphorothioate Which Targets the cGMP Binding Site of Human Platelet PDE3A, Bioorganic Chemistry, 2008, vol. 36, Issue 3, Elsevier Inc., pp. 141-147.

Hung et al., A new nonhydrolyzable reactive cAMP analog, (Sp)-adenosine-3',5' -cyclic-S-(4-bromo-2,3-dioxobutyl) monophosphorothioate irreversibly inactivates human platelet cGMP-inhibited cAMP phosphodiesterase, Bioorganic Chemistry, 2002, vol. 30, vol. 1, pp. 16-31.

Hung et al., New insights from the structure-function analysis of the catalytic region of human platelet phosphodiesterase 3A: A role for the unique 44-amino acid insert, Journal of Biological Chemistry, 2006, vol. 281, Issue 39, pp. 29236-29244.

Hung et al., A nonhydrolyzable reactive cAMP analogue, (Sp) -8-[4-bromo-2,3-dioxobutyl) thio]adenosine 3', 5'-cyclic S-(methyl) monophosphorothioate, irreversibly inactivates human platelet cGMP-inhibited cAMP phosphodiesterase at micromolar concentrations, Biochemistry, 2002, vol. 41, Issue 9, pp. 2962-2969.

Iimori et al., A study on conformationally restricted sangivamycins and their inhibitory abilities of protein kinases, Nucleic Acids Symposium Series, 1992, vol. 27, pp. 169-170.

Iimori et al., 2'-C-, 3'-C-, and 5'-C-Methylsangivamycins: Conformational lock with the methyl group, Tetrahedron Letters, 1991, vol. 32, Issue 49, pp. 7273-7276.

IUPAC-IUB Commission on Biochemical Nomenclature, Biochemistry, 1972, vol. 11, pp. 942-944.

Jacobson et al., Structure-activity relationships of 9-alkyladenine and ribose-modified adenosine derivatives at rat A3 adenosine receptors, Journal of Medicinal Chemistry, 1995, vol. 38, Issue 10, pp. 1720-1735.

Kappler et al., Isozyme-specific enzyme inhibitors. 10. Adenosine 5'-triphosphate derivatives as substrates or inhibitors of methionine adenosyltransferases of rat normal and hepatoma tissues, Journal of Medicinal Chemistry, 1986, vol. 29, Issue 3, pp. 318-322.

Kappler et al., Species- or isozyme-selective enzyme inhibitors. 8. Synthesis of disubstituted two-substrate condensation products as inhibitors of rat adenylate kinases, Journal of Medicinal Chemistry, 1982, vol. 25, Issue 10, pp. 1179-1184.

Karpeiskii et al., Conformational analogs of nucleotides. V. Synthesis of 5'-C-methylnucleosides from 6-deoxy-D-allose, Bioorganicheskaya Khimiya, 1979, vol. 5, No. 6, pp. 895-905.

Karpeiskii et al., Conformational analogs of nucleotides. V. Synthesis of 5'-C-methylnucleosides from 6-deoxy-D-allose, Soviet Journal of Bioorganic Chemistry (a translation of Bioorganicheskaya Khimiya), 1979, vol. 5, No. 1, pp. 672-680.

Karpeiskii et al., Study of substrate specificity of nuclease S1 from Aspergillus oryzae in the hydrolysis of low molecular weight substrates, Bioorganicheskaya Khimiya, 1982, vol. 8, Issue 3, pp. 386-395.

Karpeiskii et al., A study of substrate specificity of nuclease S1 from Aspergillus oryzae in the hydrolysis of low-molecular-weight substrates, Soviet Journal of Bioorganic Chemistry (a translation of Bioorganicheskaya Khimiya), 1983, vol. 8, Issue 3, pp. 196-204.

Karpeiskii et al., Synthesis of 5'-C-methyluridines (D-allo and L-talo), 5'-mono-, di- and triphosphates, and dinucleoside phosphates on their basis, Nucleic Acids Symposium Series, 1981, Issue 9, pp. 157-160.

Karpeiskii et al., Synthesis of 5'-mono-, di- and triphosphates of 5'-C-methyluridines, Bworganicheskaya Khimiya, 1982, vol. 8, Issue 7, pp. 933-939.

Karpeiskii et al., Synthesis of 5'-mono-, 5'-di- and 5'-triphosphates of 5'-C-methyluridines, Soviet Journal of Bioorganic Chemistry (a translation of Bioorganicheskaya Khimiya), 1983, vol. 8, Issue 7, pp. 498-504.

Kett et al., Heterocyclic derivatives of sugars: An NMR study of the formation of 1-glycosyl-3, 5-dimethyl-1H-pyrazoles from hydrazones, Carbohydrate Research, 1997, vol. 299, Issue 3, pp. 129-141.

Kim et al., The effect of thalidomide and its derivatives on thyroxine-induced metamorphosis of tadpole, Canadian Journal of Biochemistry and Physiology, 1965, vol. 43, Issue 6, pp. 769-779.

Klumpp et al., The novel nucleoside analog R1479 (4'-azidocytidine) is a potent inhibitor of NS5B-dependent RNA synthesis and hepatitis C virus replication in cell culture, Journal of Biological Chemistry, 2006, vol. 281, Issue 7, pp. 3793-3799.

Krakowiak et al., Stereochemistry of rHintl hydrolase assisted cleavage of P-N bond in nucleoside 5'-O-phosphoramidothioates, Chemical Communications, 2007, vol. 21, pp. 2163-2165.

Kiuru et al., Synthesis and enzymatic deprotection of biodegradably protected dinucleoside-2',5'-monophosphates: 3-(acetyloxy)-2,2-bis(ethoxycarbonyl)propyl phosphoesters of 3'-O-(acyloxymethyl)adenylyl-2',5'-adenosines, Chemistry and Biodiversity, 2011, vol. 8, Issue 2, pp. 266-286.

Lamivudine, The Merck Index ($15^{th}$ Ed. 2013) p. 994.

Lau et al., Synthesis and evaluation of antiviral activity of L-acosamine and L-ristosamine nucleosides of furanose configuration, Acta Chemica Scandinavica, 1991, vol. 45, Issue 6, pp. 616-620.

Lee, C., Discovery of Hepatitis C Virus NS5A Inhibitors as a New Class of Anti-HCV Therapy, Arch. Pharm. Res., 34(9) 2001, pp. 1403-1407.

Leisvouri et al., Chemical and enzymatic stability of amino acid derived phosphoramidates of antiviral nucleoside 5'-monophosphates bearing a biodegradable protecting group, Organic and Biomolecular Chemistry, 2010, vol. 8, Issue 9, pp. 2131-2141.

Lepage et al., Metabolism of purine nucleoside analogs, Cancer Research, 1965, vol. 25, pp. 46-52.

Lerner, 9-α-L-Rhamnofuranosyladenine. An improved synthesis of a 6-deoxyhexofuranosyl nucleoside, Nucleic Acid Chem., 1991, vol. 4, pp. 274-280.

Lerner, 9- (6-Deoxyhexofuranosyl) adenine nucleosides. Further studies on the acetolysis of hexofuranosides, Journal of Organic Chemistry, 1978, vol. 43, Issue 5, pp. 962-965.

Lerner, Adenine nucleosides derived from 6-deoxyhexofuranoses, Journal of Organic Chemistry, 1976, vol. 41, Issue 2, pp. 306-310.

Lerner, Interconversions of hexofuranosyl nucleosides. IV. Synthesis of nucleosides derived from 6-deoxy-L-glucose, Journal of Organic Chemistry, 1972, Issue 37, vol. 26, pp. 4386-4391.

Lerner, Interconversions of hexofuranosyl nucleosides. V. Synthesis and reexamination of the structure of 9- (6-deoxy-α-L- mannofuranosyl) adenine, Journal of Organic Chemistry, 1973, vol. 21, pp. 3704-3709.

Lerner et al., Preparation and antileukemic screening of some new 6' -deoxyhexopyranosyladenine nucleosides, J. Med. Chem., 1987, vol. 30, Issue 8, pp. 1521-1525.

Lerner, Preparation of nucleosides via isopropylidene sugar derivatives. V. Coupling reactions using the titanium tetrachloride method, Carbohydrate Research, 1970, vol. 14, Issue 3, pp. 297-303.

Lerner, Synthesis of 9-α-D-rhamofuranosyladenine, Carbohydrate Research, 1974, vol. 38, pp. 328-332.

Lesiak et al., A new approach to syntheses of organic phosphoroselenoates and phosphorodiselenoates. Proof of absolute configuration assignment in diastereomers of cTMPS [thymidine cyclic 3',5'-phosphorothioates], Polish Journal of Chemistry, 1979, vol. 53, Issue 10, pp. 2041-2050.

Lesnikowski et al., A simple procedure for synthesis of diastereoisomers of thymidine cyclic 3',5'-phosphate derivatives, Nucleic Acids Symposium Series, 1987, vol. 18, pp. 273-276.

Lesnikowski et al., Some aspects of the electron impact induced fragmentation of diastereoisomeric thymidine cyclic 3',5'-phosphoranilidothioates, Organic Mass Spectrometry, 1980, vol. 15, Issue 9, pp. 454-455.

Lin, C. et al. Synthesis of Dinucleotide Thiophosphoramidates as Anti-HIV New Prodrugs, Synthesis, 2003, No. 13, pp. 1989-1994.

Lin et al., Novel 3', 5'-cyclic nucleotide analog: Adenosine 3',5'-cyclic boranomonophosphate, Organic Letters, 2001, vol. 3, pp. 795-797.

Long et al., Structure-activity relationship for adenosine kinase from mycobacterium tuberculosis. II. Modifications to the ribofuranosyl moiety, Biochemical Pharmacology, 2008, vol. 75, Issue 8, pp. 1588-1600.

(56) References Cited

OTHER PUBLICATIONS

Malmsjo et al., "Characterization of Contractile P2 Receptors in Human Coronary Arteries by Use of the Stable Pyrimidine Uridine 5'-O-Thiodisphosphate and Uridine 5'-O-3-Thiotriphosphate" *J. Pharmcology and Experimental Therapeutics* (2000), 293(3):755-760.
Markiewicz et al., The reaction of 1,3-dichloro-1,1,3,3-tetraisopropyldisiloxane with cytosine arabinoside and 1-(6-deoxy-α-L-talofuranosyl) uracil, Collection of Czechoslovak Chemical Communications, 1980, vol. 45, Issue 6, pp. 1860-1865.
Marx et al., Synthesis of 4'-C-acylated thymidines, Helvetica Chimica Acta, 1996, vol. 79, Issue 7, pp. 1980-1994.
McGuigan et al., Phosphate prodrugs derived from N-acetyglucosamine have enhanced chondroprotective activity in explant cultures and represent a new lead in antiosteoarthritis drug discovery, Journal of Medicinal Chemistry, 2008, vol. 51, Issue 18, pp. 5807-5812.
McKenzie et al., Characteristics of the relaxant response of adenosine and its analogs in intestinal smooth muscle, European Journal of Pharmacology, 1977, vol. 41, Issue 2, pp. 183-192.
McKenzie et al., Effects of adenosine and related compounds on adenylate cyclase and cyclic AMP levels in smooth muscle, European Journal of Pharmacology, 1977, vol. 41, Issue 2, pp. 193-203.
McKenzie et al., Hepatic failure and lactic acidosis due to fialuridine (FIAU), an investigational nucleoside analogue for chronic hepatitis B, New England Journal of Medicine, 1995, vol. 333, pp. 1099-1105.
McMurry, Organic Chemistry, 5th ed., Brooks/Cole, Pacific Grove, CA (2000), Chapter 11.5, pp. 398 and 408.
McOmie, Protective Groups in Organic Chemistry, Plenum Press (1973), Cover & Contents pages only.
Miao et al., One pot synthesis of nucleoside 5'-thiophosphoramidate, Synthetic Communications, 2002, vol. 32, Issue 7, pp. 1069-1076.
Miao et al., A stepwise one pot synthesis of alkyl thiophosphoramidate derivitaves of nucleosides, Synthetic Communications, 2002, vol. 32, Issue 8, pp. 1159-1167.
Miao et al., One pot synthesis of aryl thiophosphoramidate derivatives of AZT, Synthetic Communications, 2002, vol. 32, Issue 21, pp. 3301-3309.
Mikhailov, Conformational analogs of nucleotides. Synthesis of 5'-C-methyl nucleosides, Sint. Issled. Biol. Soedin., Tezisy Dokl. Konf. Molodykh Uch., 1978, vol. 6, pp. 38-39.
Mikhailov et al., Conformational peculiarities of 5'-C-methylnucleosides, Bioorganicheskaya Khimiya, 1989, vol. 15, Issue 7, pp. 969-975.
Mikhailov et al., Conformational features of 5'-C-methylnucleosides, Soviet Journal of Bioorganic Chemistry (a translation of Bioorganicheskaya Khimiya), 1990, vol. 15, Issue 7, pp. 532-538.
Misiura et al., Synthesis, chemical and enzymatic reactivity, and toxicity of dithymidylyl-3',5'-phosphorofluoridate and -phosphorothiofluoridate, Bioorganic & Medicinal Chemistry, 2001, vol. 9, Issue 6, pp. 1525-1532.
Murai et al., A synthesis and an x-ray analysis of 2'-C-, 3'-C- and 5'-C-methylsangivamycins, Heterocycles, 1992, vol. 33, Issue 1, pp. 391-404.
Myers et al., Synthetic studies of the tunicamycin antibiotics. Preparation of (+)-tunicaminyluracil, (+)-tunicamycin-V, and 5'-epi-tunicamycin-V, Journal of the American Chemical Society, 1994, vol. 116, Issue 11, pp. 4697-4718.
Nelson et al., Synthesis and antitumor activity of 7- and 9-(6'-deoxy-α-L-talofuranosyl)-hypoxathine and 9-(6'-deoxy-α-L-talofuranosyl)-6-thiopurine, Journal of Medicinal Chemistry, 1983, vol. 26, Issue 10, pp. 1527-1530.
Nelson et al., Synthesis of hypoxanthine, guanine, and 6-thiopurine nucleosides of 6-deoxy-D-allofuranose, Journal of Medicinal Chemistry, 1983, vol. 26, Issue 7, pp. 1071-1074.
Nelson et al., Synthesis of methyl 3,5-di-O-benzoyl-2,6-dideoxy-β-L-lyxo-hexofuranoside, a nucleoside precursor, Carbohydrate Research, 1983, vol. 124, Issue 1, pp. 161-165.
Nutt et al., Branched-chain sugar nucleosides. II. 5',5'-Di-C-methyladenosine, Journal of Medicinal Chemistry, 1968, vol. 11, Issue 1, pp. 151-153.
Oivanen et al., Hydrolysis of isomeric cytidyl-(3',5')-5'-C-methyluridines by acids, bases and metal ions: Steric effects in the hydrolysis of the phosphodiester bonds of RNA, Acta Chemica Scandinavica, 1995, vol. 49, Issue 4, pp. 307-310.
Ora et al., Hydrolytic stability of nucleoside phosphotriesters derived from bis(hydroxymethyl)-1,3-dicarbonyl compounds and their congeners: Towards a novel pro-drug strategy for antisense oligonucleotides, J. Chem. Soc. Perkin Trans. 2, 2001, vol. 6, pp. 881-885.
Ora et al., Biodegradable protections for nucleoside 5'-monophosphates: Comparative study on the removal of O-acetyl and O-acetyloxymethyl protected 3-hydroxy-2,2-bis(ethoxycarbonyl)propyl groups, Journal of Organic Chemistry, 2009, vol. 74, Issue 14, pp. 4992-5001.
Padyukova et al., Synthesis of thymidine 5'-derivatives, Bioorganicheskaya Khimiya, 1990, vol. 16, Issue 5, pp. 668-673.
Padyukova et al., Synthesis of 5'-derivatives of thymidine, Soviet Journal of Bioorganic Chemistry (a translation of Bioorganicheskaya Khimiya), 1991, vol. 16, Issue 5, pp. 370-375.
Padyukova et al., Synthesis of dinucleoside phosphates containing 5'-O-bonded 1-(6-deoxy-β-D-allofuranosyl) uracil and 1-(6-deoxy-α-L-talofuranosyl) uracil, Collection of Czechoslovak Chemical Communications, 1980, vol. 45, Issue 9, pp. 2550-2557.
Panova et al., Substrate specificity of *Escherichia coli* thymidine phosphorylase, Biochemistry, 2007, vol. 72, Issue 1, pp. 21-28.
Parker et al., Design and evaluation of 5'-modified nucleoside analogs as prodrugs for an *E. coli* purine nucleoside phosphorylase mutant, Nucleosides Nucleotides and Nucleic Acids, 2005, vol. 24, Issues 5/6/7, pp. 387-392.
Pockros, P. J., Drugs in Development for Chronic Hepatitis C: A Promising Future, Expert Opin. Biol. Ther., 2001, vol. 11. No. 12, pp. 1611-1622.
Poijärvi et al., Towards nucleotide prodrugs derived from 2,2-bis(hydroxymethyl)malonate and its congeners: Hydrolytic cleavage of 2-cyano-2-(hydroxymethyl)-3-methoxy-3-oxopropyl and 3-(alkylamino)-2-cyano-2-(hydroxymethyl)-3-oxopropyl protections from the internucleosidic phosphodiester and phosphorothioate linkages, Helv. Chim. Acta., 2002, vol. 85, pp. 1869-1876.
Poijärvi et al., Towards oligonucleotide pro-drugs: 2,2-Bis(ethoxycarbonyl) and 2-(alkylaminocarbonyl)-2-cyano substituted 3-(pivaloyloxy)propyl groups as biodegradable protecting groups for internucleosidic phosphoromonothioate linkages, Lett. Org. Chem., 2004, vol. 1, pp. 183-188.
Poijärvi et al., 2,2-Bis(ethoxycarbonyl)- and 2-(alkylaminocarbonyl)-2-cyano-substituted 3-(pivaloyloxy)propyl groups as biodegradable phosphate protections of oligonucleotides, Bioconjugate Chem., 2005, vol. 16, pp. 1564-1571.
Prakash et al., Synthesis and evaluation of S-acyl-2-thioethyl esters of modified nucleoside 5'monophosphates as inhibitors of hepatitis C virus RNA replication, Journal of Medicinal Chemistry, 2005, vol. 48, Issue 4, pp. 1199-1210.
Pravdina et al, Inhibition by nucleoside 5'-triphosphate analogs of RNA synthesis catalyzed by RNA polymerase of influenza A virus, Molekulyarnaya Genetika, Mikrobiologiya I Virusologiya, 1990, vol. 11, pp. 22-25.
Ranganathan et al., Model analogs of nucleoside 3', 5'-cyclic phosphates. I. 5'-Mono- and dimethyl analogs of adenosine 3',5'-cyclic phosphate, Journal of Organic Chemistry, 1974, vol. 39, Issue 3, pp. 290-298.
Reimer et al, Inhibition of hepatitis B virus DNA polymerase by thymidine triphosphate analogs in vitro, Antiviral Chemistry and Chemotherapy, 1991, vol. 2, Issue 4, pp. 249-253.
Reist et al., Potential anticancer agents. LXXVII. Synthesis of nucleosides of purine-6-thiol (6-mercaptopurine) containing "fraudulent" sugars, Journal of Organic Chemistry, 1962, vol. 27, pp. 3279-3283.
Reist et al., Potential anticancer agents. VIII. Synthesis of nucleosides derived from L-talofuranose, Journal of the American Chemical Society, 1958, vol. 80, pp. 5775-5779.

(56) References Cited

OTHER PUBLICATIONS

Reist et al., Potential anticancer agents. IV. Synthesis of nucleosides derived from 6-deoxy-D-allofuranose, Journal of the American Chemical Society, 1958, vol. 80, pp. 3962-3966.
Reist et al., Potential anticancer agents. XI. Synthesis of nucleosides derived from 6-deoxy-L-idofuranose, Journal of Organic Chemistry, 1958, vol. 23, pp. 1757-1760.
Reist et al., Potential anticancer agents. X. Synthesis of nucleosides derived from 6-deoxy-D-glucofuranose, Journal of Organic Chemistry, 1958, vol. 23, pp. 1753-1757.
Roche, Bioreversible carriers in drug design: Theory and application, Pergamon Press: New York, 1987, pp. 14-21.
Saha et al., 5'-Methyl-DNA—A new oligonucleotide analog. Synthesis and biochemical properties, Journal of Organic Chemistry, 1995, vol. 60, Issue 4, pp. 788-789.
Sakai et al., Isolation from nocardioides sp. strain CT16, purification, and characterization of a deoxycytidine deaminase extremely thermostable in the presence of D,L-dithiothreitol, Biosci. Biotechnol. Biochem., 2002, vol. 66, Issue 8, pp. 1646-1651.
Scott et al., Mapping ligand interactions with the hyperpolarization activated cyclic nucleotide modulated (HCN) ion channel binding domain using a soluble construct, Biochemistry, 2007, vol. 46, Issue 33, pp. 9417-9431.
Secrist et al., Gene therapy of cancer: Activation of nucleoside prodrugs with *E. coli* purine nucleoside phosphorylase, Nucleosides & Nucleotides, 1999, vol. 18, Issue 4&5, pp. 745-757.
Severe Toxicity of Fialuridine (letters to the editor), New England Journal of Medicine, 1996, vol. 334, pp. 1135-1138.
Shaw et al., Mass spectrometry of nucleic acid components. Analogs of adenosine, Journal of the American Chemical Society, 1970, vol. 92, Issue 8, pp. 2510-2522.
Sheid et al., Enzymatic formation of potential anticancer and antiviral inosine analogs, Experientia, 1996, vol. 52, Issue 9, pp. 878-881.
Shigeura et al., Structural basis for phosphorylation of adenosine congeners, Nature, 1967, vol. 215, Issue 5099, pp. 419-420.
Shuto et al., Stereo- and regioselective intoduction of 1- or 2-hydroxyethyl group via intramolecular radical cyclization reaction with a novel silicon-containing tether. An efficient synthesis of 4'α-branched 2'-deoxyadenosines, Journal of Organic Chemistry, 1998, vol. 63, Issue 3, pp. 746-754.
Smith et al., The design, synthesis and antiviral activity of monofluoro and difluoro analogues of 4'-azidocytidine and against hepatitis C virus replication: The discovery of 4'-azido-2'-deoxy-2'-fluorocytidine and 4'-azido-2'-dideoxy-2',2'-difluorocytidine, Journal of Medicinal Chemistry, 2009, vol. 52, pp. 2971-2978.
Sopchik et al., Facile preparation of the individual diastereoisomers of thymidine 3',5'-cyclic phosphorothioate (cTMPS), Tetrahedron Letters, 1981, vol. 22, Issue 4, pp. 307-310.
Spormann et al., Synthesis and photoreaction of 4' -pivaloyl guanosides, Synthesis, 2001, vol. 14, pp. 2156-2164.
Srivastava et al., Enantiomeric forms of 9-(5,6-dideoxy-α-D-arabino-hex-5-enofuranosyl) adenine and preparation of 9-(6-deoxy-β-D-galaxtofuranosyl) adenine. Further results with the acetolysis of hexofuranosides, Tetrahedron, 1978, vol. 34, Issue 17, pp. 2627-2631.
Stanton, G. J., et al., Interferon Review, Invest. Radiol., 1987, vol. 22, No. 3, pp. 259-273.
Streitwieser et al., Introduction to Organic Chemistry, 2nd ed., Macmillan Publishing Co. Inc., New York, NY, 1981, pp. 169-171.
Sun et al., Effects of cGMP, cAMP and two other cAMP derivatives on the transcription system of isolated rat liver nuclei, Shengwu Huaxue Zazhi, 1987, vol. 3, Issue 5, pp. 455-461.
Tian et al., Synthesis of 8-chloroadenosine 3',5'-cyclophosphotriesters and phosphoramidates, Progress in Natural Science, 1994, vol. 4, Issue 6, pp. 726-731.
Tomassini et al., Inhibitory effect of 2'-substituted nucleosides on hepatitis C virus replication correlates with metabolic properties in replicon cells, Antimicrobial Agents and Chemotherapy, 2005, vol. 49, Issue 5, pp. 2050-2058.
Tomei et al., HCV antiviral resistance: The impact of in vitro studies on the development of antiviral agents targeting the viral NS5B polymerase, Antiviral Chemistry and Chemotherapy, 2005, vol. 16, Issue 4, pp. 225-245.
Trafelet et al., Synthesis of (5'S)-5'-C-alkyl-2'-deoxynucleosides, Helvetica Chimica Acta, 2001, vol. 84, Issue 1, pp. 87-105.
Tunitskaya et al., Substrate properties of C'-methyl UTP derivatives in T7 RNA polymerase reactions. Evidence for N-type NTP conformation, FEBS Letters, 1997, vol. 400, Issue 3, pp. 263-266.
Ueno et al., Nucleosides and nucleotides. 174. Synthesis of oligodexynucleotides containing 4'-C-[2-[[N-(2-aminoethyl)carbamoyl]oxy]ethyl]thymidine and their thermal stability and nuclease-resistance properties, Journal of Organic Chemistry, 1998, vol. 63, Issue 5, pp. 1660-1667.
Venkatachalam et al., A comparative study of the hydrolysis pathways of substituted aryl phosphoramidate versus aryl thiophosphoramidate derivatives of stavudine, European Journal of Medicinal Chemistry, 2004, vol. 39, pp. 665-683.
Vilar et al., Probabilistic neural network model for the in silico evaluation of anti-HIV activity and mechanism of action, Journal of Medicinal Chemistry, 2006, vol. 49, Issue 3, pp. 1118-1124.
Walczak et al., Synthesis of 1-(3-(1,2,4-triazol-1-yl)-2,3,6-trideoxy-L-arabino-hexofuranosyl) uracils via an α, β-unsaturated aldehydohexose, Monatshefte für Chemie, 1992, vol. 123, Issue 4, pp. 349-354.
Wang et al., Study on the structure-activity relationship of new anti-HIV nucleoside derivatives based on the Support Vector Machine method, QSAR & Combinatorial Science, 2007, vol. 26, Issue 2, pp. 161-172.
Wang et al., Synthesis and cytokine modulation properties of pyrrolo[2,3-d]-4-pyrimidone nucleosides, Journal of Medicinal Chemistry, 2000, vol. 43, Issue 13, pp. 2566-2574.
Wu et al., The cyclophosphorylation of adenosine, Huaxue Xuebao, 1986, vol. 44, Issue 6, pp. 635-638.
Yakovlev et al., Stereoelectronic effects in the enzymatic cleavage of dinucleoside phosphates by Rnases, Bioorganicheskaya Khimiya, 1985, vol. 11, Issue 2, pp. 205-210.
Yakovlev et al., Stereoelectronic effects in the reactions involved in the enzymatic cleavage of dinucleoside phosphates by Rnases, Soviet Journal of Bioorganic Chemistry (a translation of Bioorganicheskaya Khimiya), 1985, vol. 11, Issue 2, pp. 107-112.
Yakovlev et al., Stereoelectronic effects in Rnase-catalyzed reactions of dinucleoside phosphate cleavage, FEBS Letters, 1985, vol. 179, Issue 2, pp. 217-220.
Zhong W. et al. "Dinucleotide analogues as novel inhibitors of RNA-dependent RNA polymerase of hepatitis C virus." (Aug. 1, 2003) Antimicrobial Agents and Chemotherapy, American Society of Microbiology, US, 47(8):2674-2681.
Zinchenko et al., 2'-, 3'- and 5'-C-Methyl derivatives of uridine in the reaction of microbiological transglycosylation, Doklady Akademii Nauk SSSR, 1987, vol. 297, Issue 3, pp. 731-734.
Zinchenko et al., Substrate specificity of uridine and purine nucleoside phosphorylases of *Escherichia coli* whole cells, Biopolimery I Kletka, 1988, vol. 4, Issue 6, pp. 298-302.
Zinchenko et al., Substrate specificity of uridine and purine nucleoside phosphorylases of the whole cells of *Escherichia coli*, Nucleic Acids Symposium Series, 1987, vol. 18, Issue 7, pp. 137-140.
Office Action dated Oct. 8, 2013 for U.S. Appl. No. 13/236,435, filed Sep. 19, 2011.
Office Action dated Feb. 28, 2014 for U.S. Appl. No. 13/236,435, filed Sep. 19, 2011.
Opposition dated Jun. 15, 2013 for Colombian Patent Application No. 13-089868, filed Sep. 19, 2011.
Supplementary European Search Report dated Mar. 4, 2014 for European Application No. 11827318.4, filed Sep. 19, 2011.
Notification-Demand dated Oct. 30, 2013 for Georgian Application No. 13063/01, filed Sep. 19, 2011.
Notification-Demand dated Feb. 26, 2014 for Georgian Application No. 13063/01, filed Sep. 19, 2011.
Examination Report dated Aug. 19, 2013 for New Zealand Application No. 607996, filed Sep. 19, 2011.

(56) References Cited

OTHER PUBLICATIONS

Examination Report dated Nov. 15, 2013 for New Zealand Application No. 607996, filed Sep. 19, 2011.
Examination Report dated Mar. 3, 2014 for New Zealand Application No. 607996, filed Sep. 19, 2011.
International Search Report and Written Opinion, dated Nov. 17, 2011, for International Application No. PCT/US2011/052220, filed Sep. 19, 2011.
Written Opinion of the International Preliminary Examining Authority, dated Sep. 19, 2012, for International Application No. PCT/US2011/052220, filed Sep. 19, 2011.
International Preliminary Report on Patentability, dated Dec. 12, 2012, for International Application No. PCT/US11/052220, filed Sep. 19, 2011.
Feng, et al. Kinetic and mechanistic studies on the dephosphoryl reaction catalyzed in nucleoside 5'-amino acid phosphoramidates. Journal of Molecular Catalysis A: Chemical 239(2005):239-242.
Official Action dated Jul. 22, 2014 for Colombian Patent Application No. 13-089868-8, filed Apr. 5, 2013.
Notification dated May 5, 2014 for Eurasian Patent Application No. 201390230, filed Mar. 11, 2013.
Opposition dated Jun. 4, 2014 for Chilean Application No. 755-2013, filed Mar. 20, 2013.
Office Action dated Jul. 21, 2014 for Chinese Patent Application No. 201180055315.0, filed May 16, 2013.
Examination Report dated Aug. 5, 2014 for New Zealand Application No. 627730, filed Jul. 21, 2014.
Office Action dated Aug. 15, 2014 for Philippines Patent Application No. 1-2013-500629, filed Apr. 2, 2013.
Choung, S., et al., "Chemical modifications of siRNAs to improve serum stability without loss of efficacy," Biochem. Biophys. Res. Comm., vol. 342, Mo. 3 (2006), pp. 919-927.
Furrer P. et al., "Structural effect of complete [Rp]-phosphorothioate and phosphorodithioate substitutions in the DNA strand of a model antisense inhibitor-target RNA complex," J. Mol. Biol., vol. 285, No. 4, (1999) pp. 1609-1622.
McGuigan, C., et al., "The application of the phosphoramidate ProTide approach confers micromolar potency against Hepatitis C virus on inactive agent 40-azidoinosine: Kinase bypass on a dual base/sugar modified nucleoside," Bioorg. Med. Chem. Lett. vol. 19, (2009) pp. 3122-3124.
Office Action dated Jul. 13, 2015 for Japanese Application No. 2013-530217, filed Sep. 19, 2011.
Search Report and Written Opinion received Jun. 10, 2015, for Singapore Patent Application No. 2013017835, filed Sep. 19, 2011.

\* cited by examiner

Figure 2A: HCV Protease Inhibitors

| # | Name | Structure |
|---|------|-----------|
| 1001 | Telaprevir VX-950 | 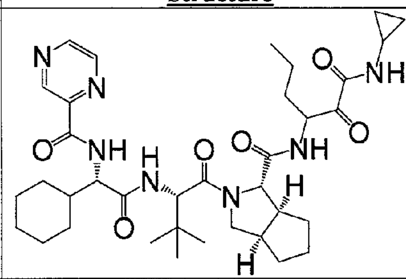 |
| 1002 | MK-5172 | 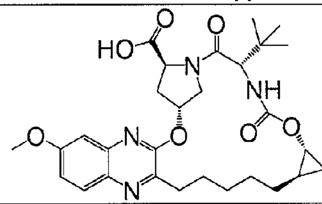 |
| 1003 | ABT-450 | |
| 1004 | BILN-2061 | 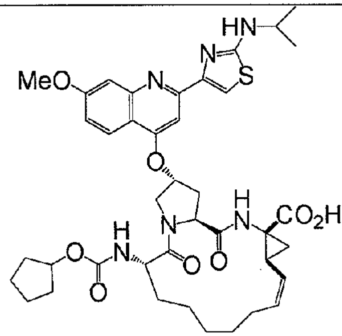 |

| # | Name | Structure |
|---|------|-----------|
| 1005 | BI-201335 | |
| 1006 | BMS-650032 | |
| 1007 | Boceprevir SCH 503034 | |

Figure 2B: HCV Protease Inhibitors
| 1008 | GS-9256 |
| 1009 | GS-9451 |
| 1010 | IDX-320 |
| 1011 | ACH-1625 |
| 1012 | ACH-2684 |
| 1013 | TMC-435<br>TMC-435350 |
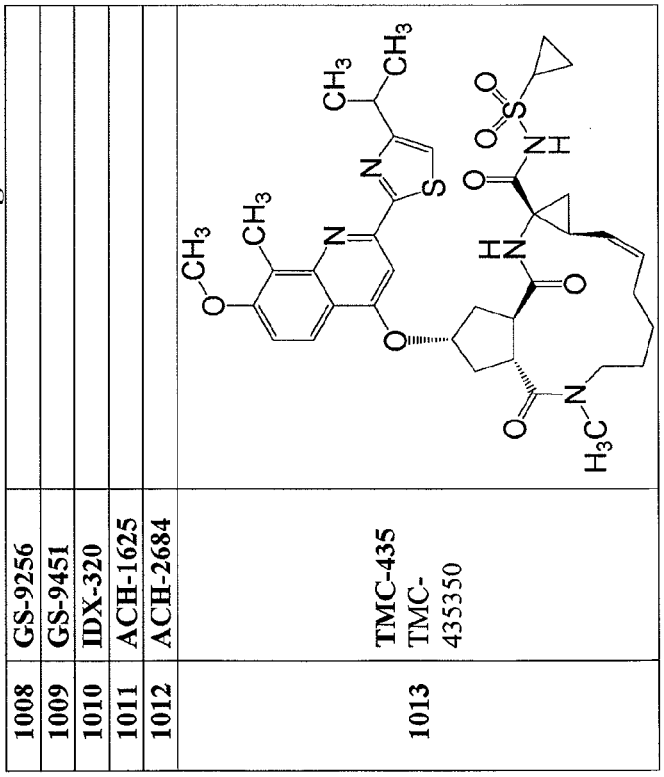
| 1014 | Danoprevir<br>ITMN-191<br>RG7227<br>RO5190591 |
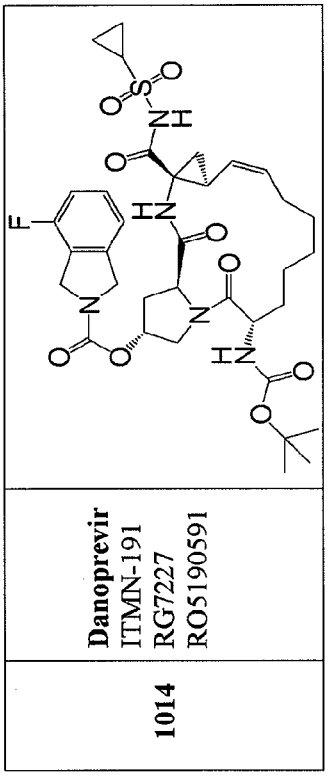

Figure 3: HCV Polymerase Inhibitors – Nucleosides, Nucleotides and Analogs Thereof

| # | Name | Structure |
|---|------|-----------|
| 2001 | RG7128 | 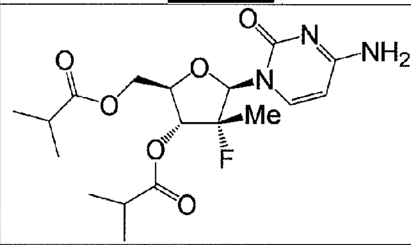 |
| 2002 | PSI-7851 | 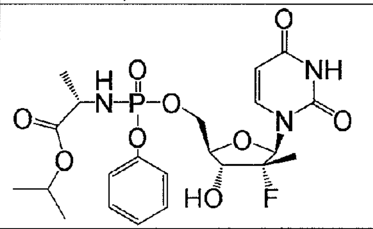 |
| 2003 | PSI-7977 | 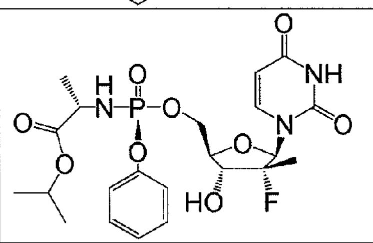 |
| 2004 | INX-189 | 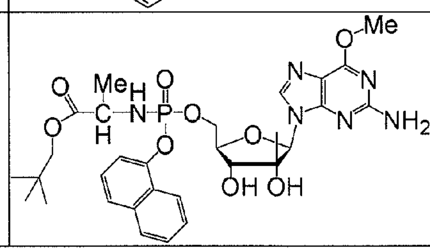 |
| 2005 | PSI-352938 | 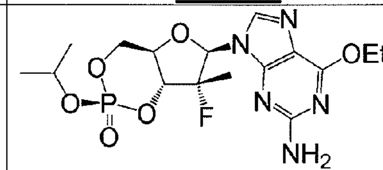 |
| 2006 | 4'-azidouridine and its prodrugs | 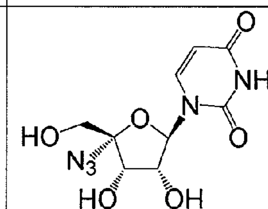 |
| 2007 | PSI-661 | |
| 2008 | GS-6620 | |
| 2009 | IDX-184 | 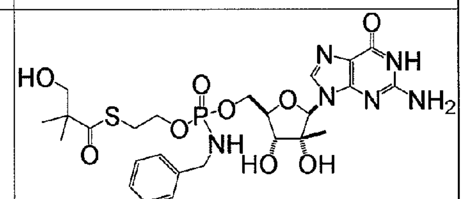 |
| 2010 | TMC649128 | |

Figure 4: HCV Polymerase Inhibitors – Non-Nucleosides

| # | Name | Structure |
|---|---|---|
| 3004 | HCV-796 | 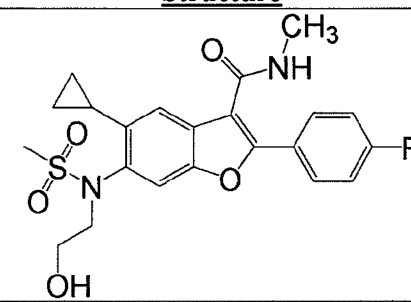 |
| 3005 | BI-207127 | |
| 3006 | GS-9190 | 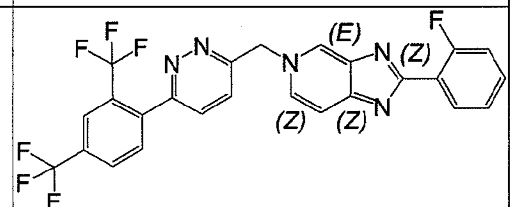 |
| 3007 | Filibuvir PF-00868554 | 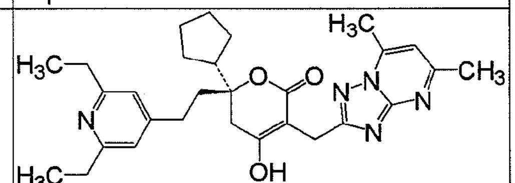 |
| 3008 | VX-497 | 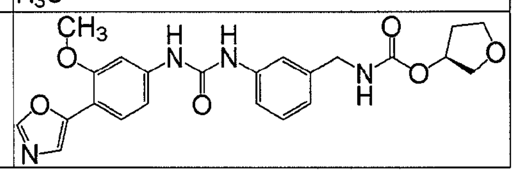 |

| # | Name | Structure |
|---|---|---|
| 3001 | ABT-333 | |
| 3002 | ANA-598 | |
| 3003 | VX-222 S1480 VCH-222 | |

Figure 5: NS5A Inhibitors

| # | Name | Structure |
|---|---|---|
| 4001 | BMS-790052 S1482 | (structure shown) |
| 4002 | PPI-461 | |
| 4003 | ACH-2928 | |
| 4004 | GS-5885 | |
| 4005 | BMS-824393 | |

Figure 6: Other Antivirals

| # | Name |
|---|---|
| 5001 | Debio-025 |
| 5002 | MIR-122 |

Figure 7A: Compounds of Formula (I)

Figure 7B: Compounds of Formula (I)

Figure 7C: Compounds of Formula (I)
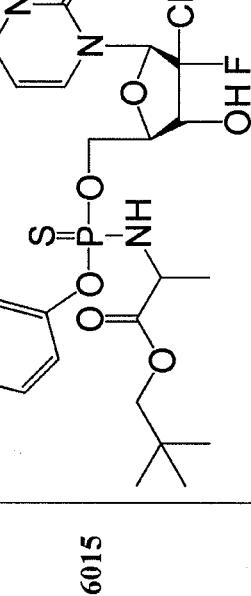

Figure 7D: Compounds of Formula (I)

Figure 7E: Compounds of Formula (I)

Figure 7F: Compounds of Formula (I)
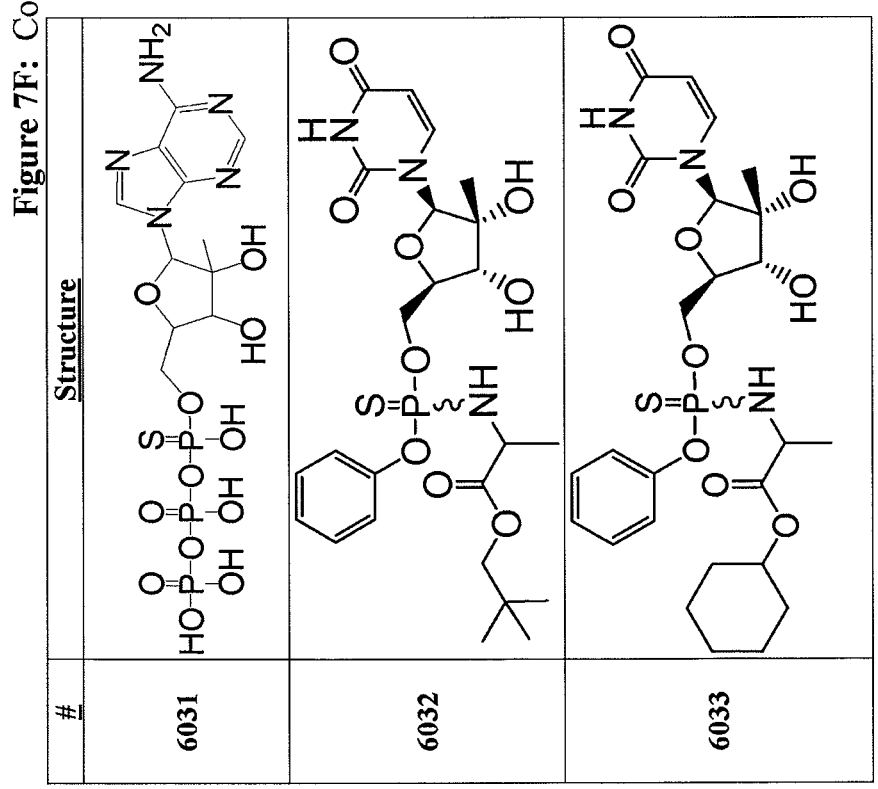
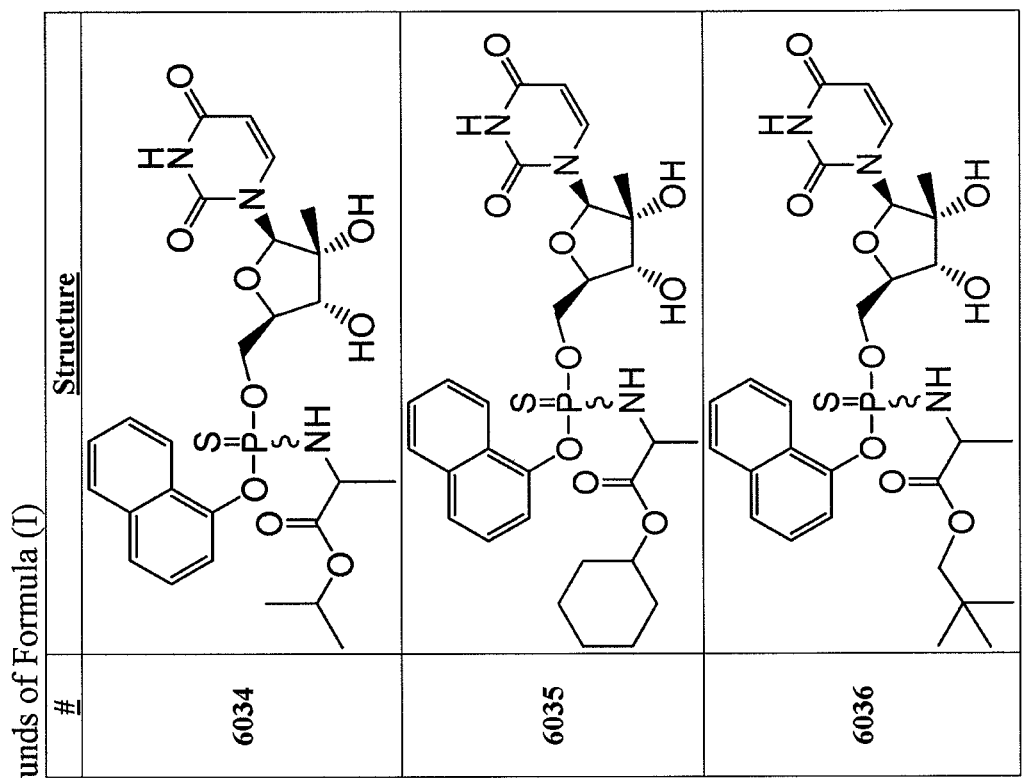

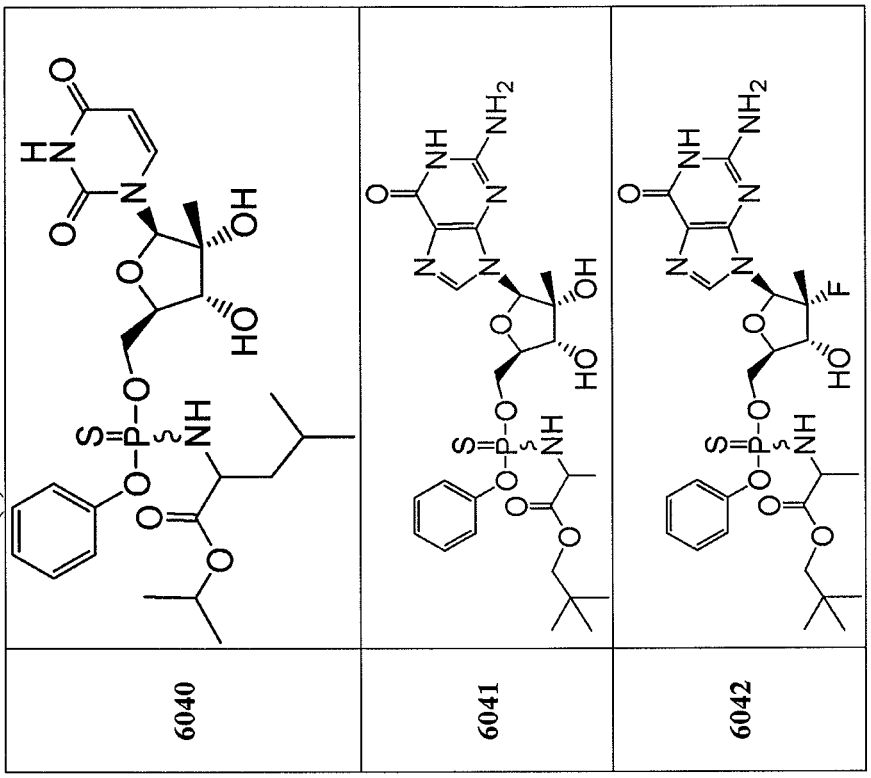
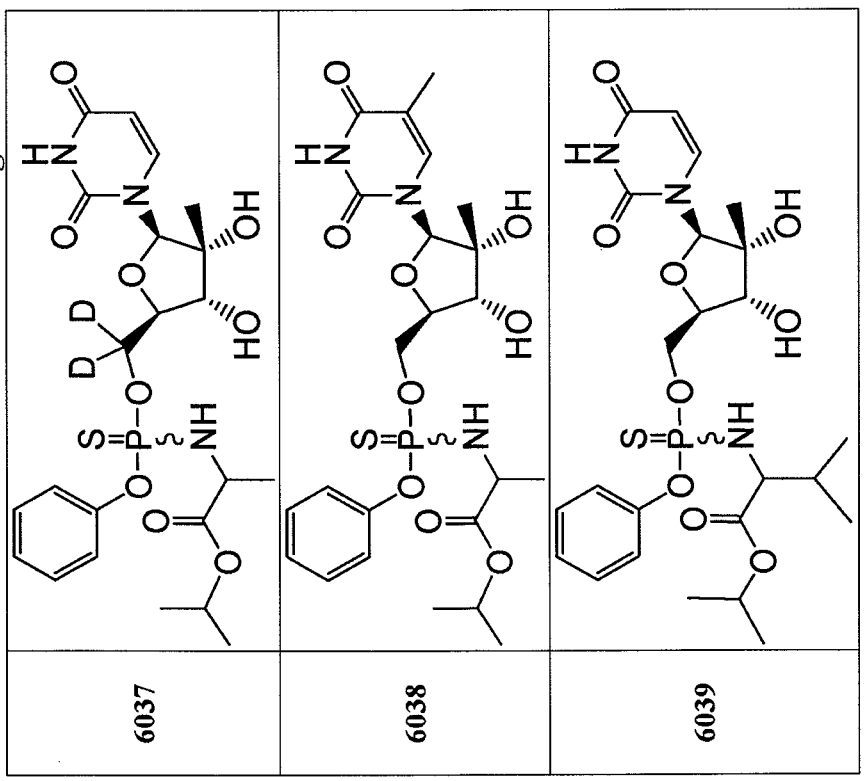
Figure 7G: Compounds of Formula (I)

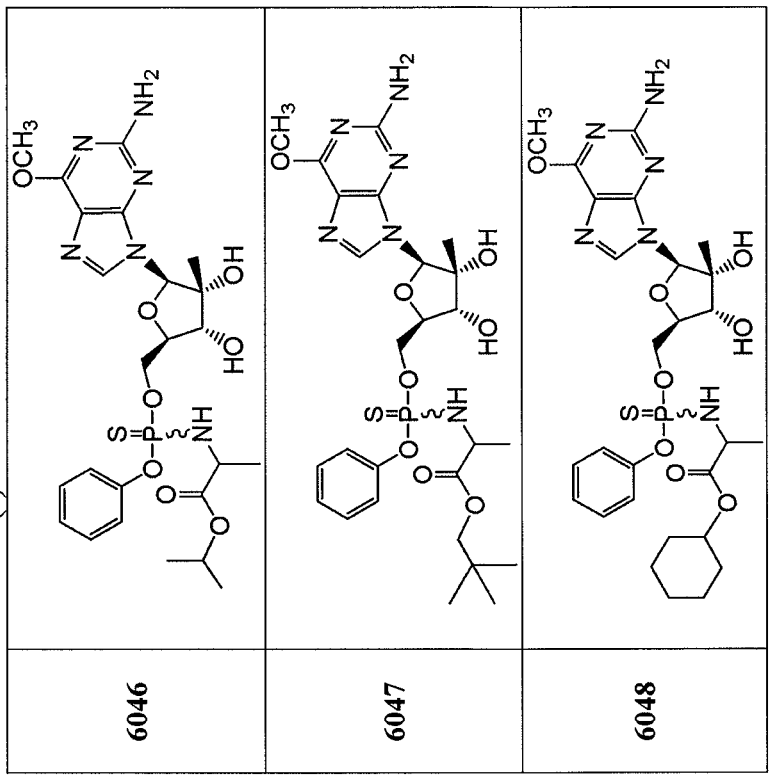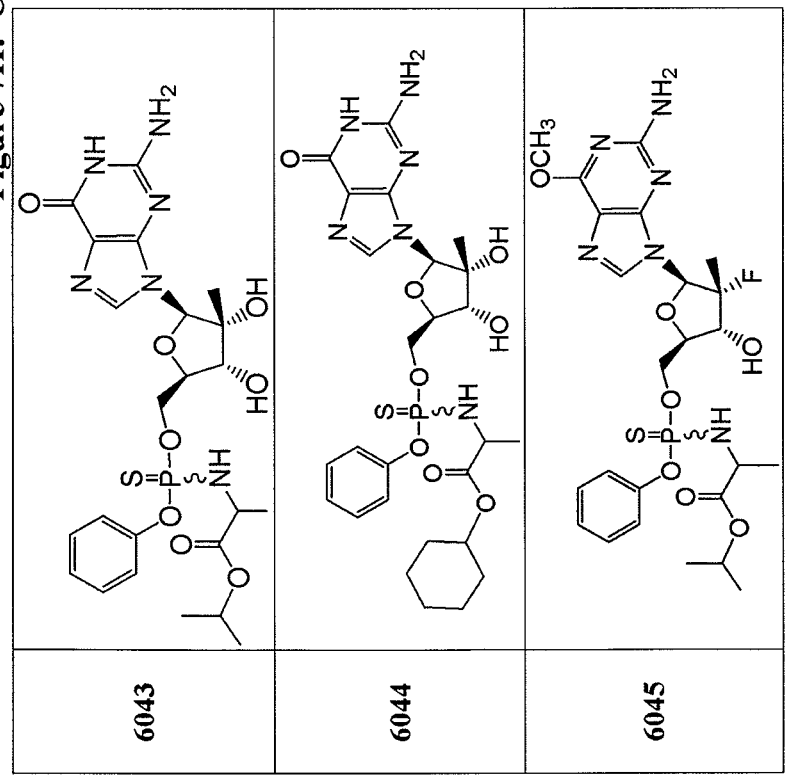
Figure 7H: Compounds of Formula (I)

Figure 7I: Compounds of Formula (I)

Figure 7J: Compounds of Formula (I)

Figure 7K: Compounds of Formula (I)

| # | Structure |
|---|---|
| 6061 | 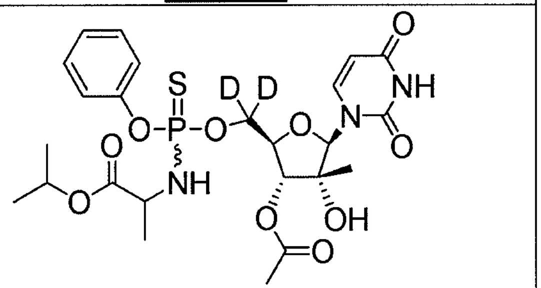 |
| 6062 | 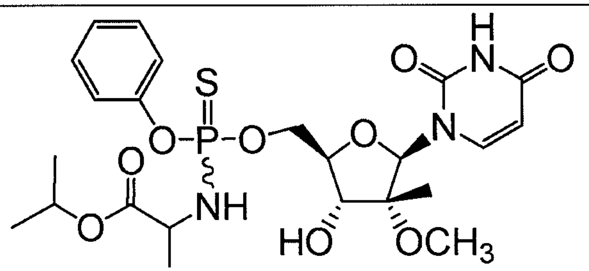 |
| 6063 | 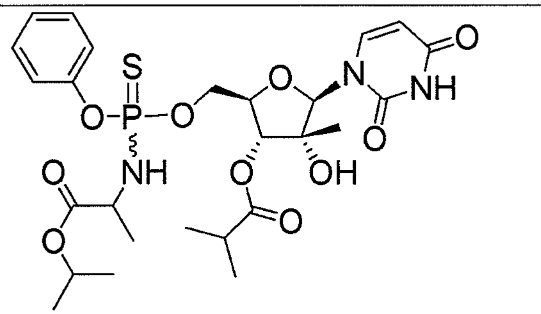 |
| 6064 | |
| 6065 | |
| 6066 | |

Figure 7L: Compounds of Formula (I)
| # | Structure |
|---|---|
| 6070 | 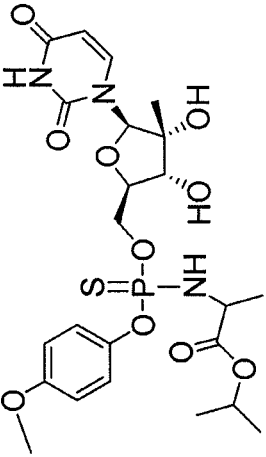 |
| 6071 | 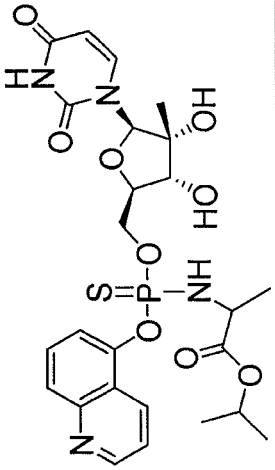 |
| 6072 | 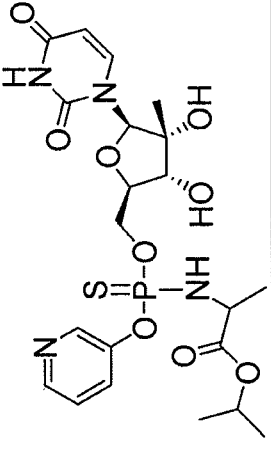 |
| # | Structure |
|---|---|
| 6067 | 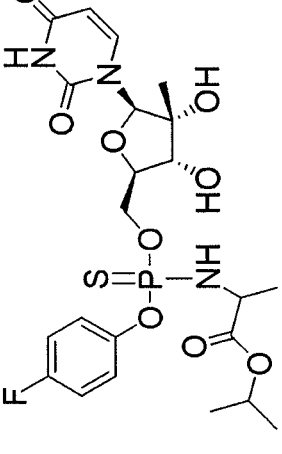 |
| 6068 | 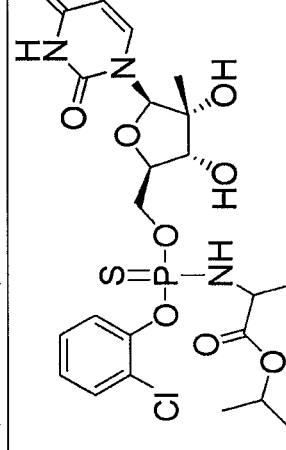 |
| 6069 | 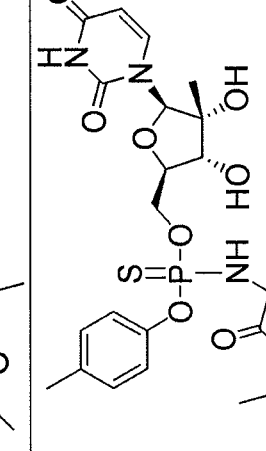 |

Figure 7M: Compounds of Formula (I)
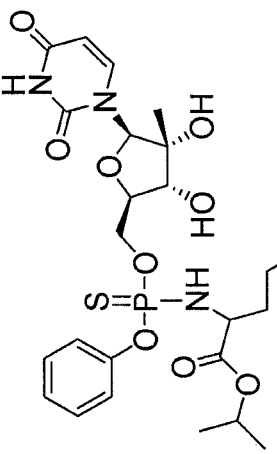

Figure 8A: Compounds of Formula (AA)
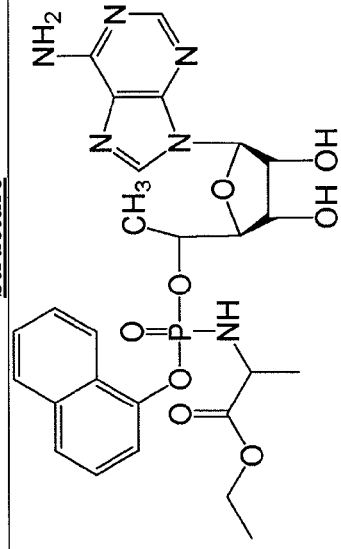

Figure 8B: Compounds of Formula (AA)

Figure 8C: Compounds of Formula (AA)
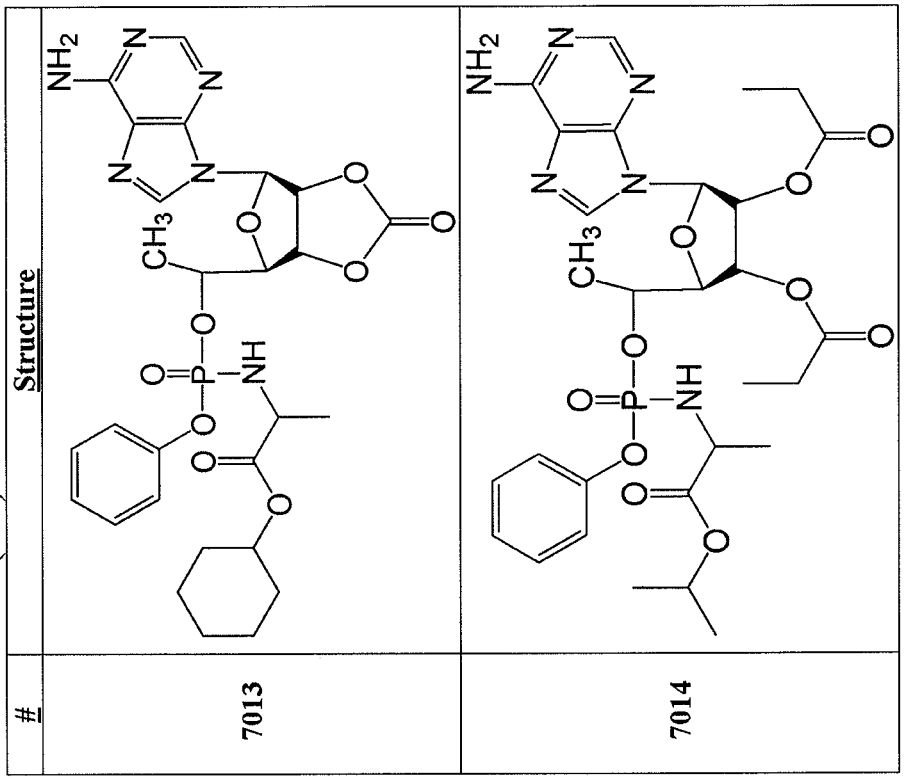
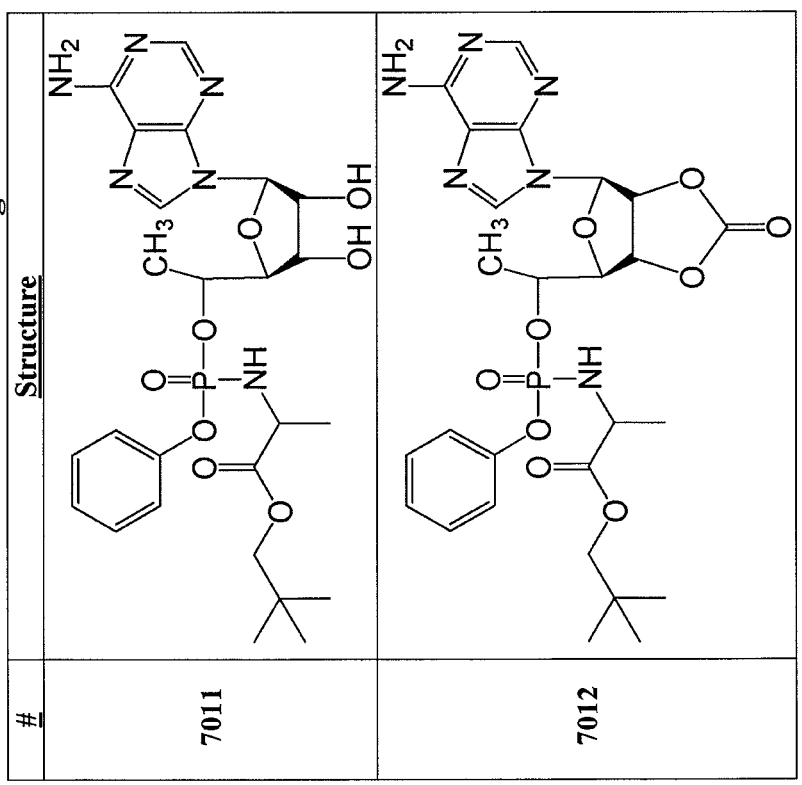

Figure 8D: Compounds of Formula (AA)
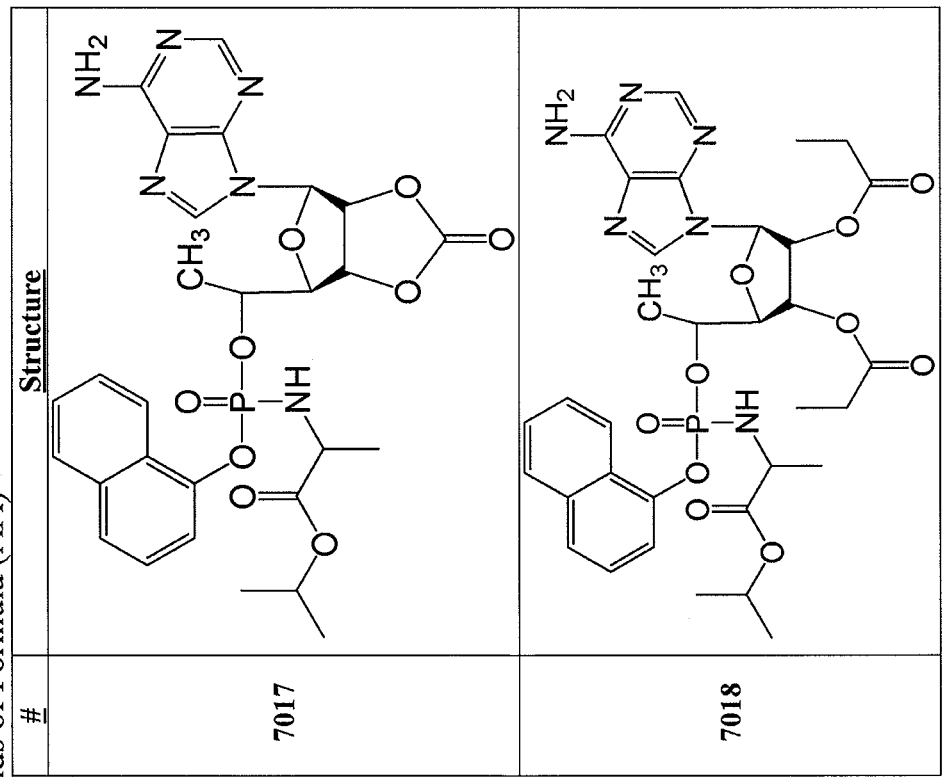
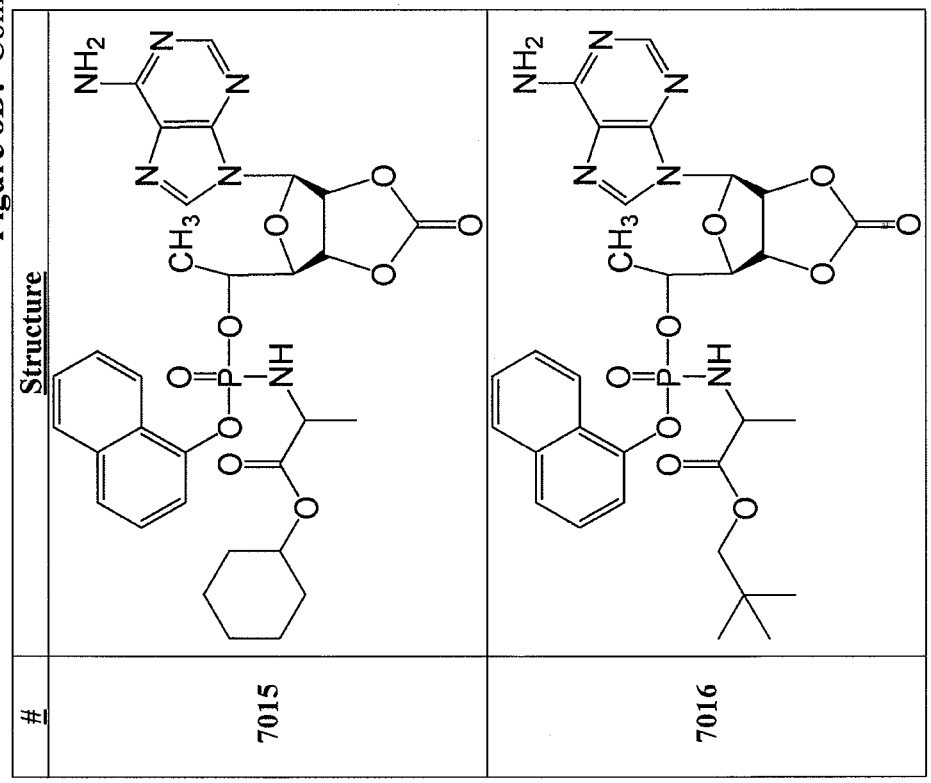

Figure 8E: Compounds of Formula (AA)
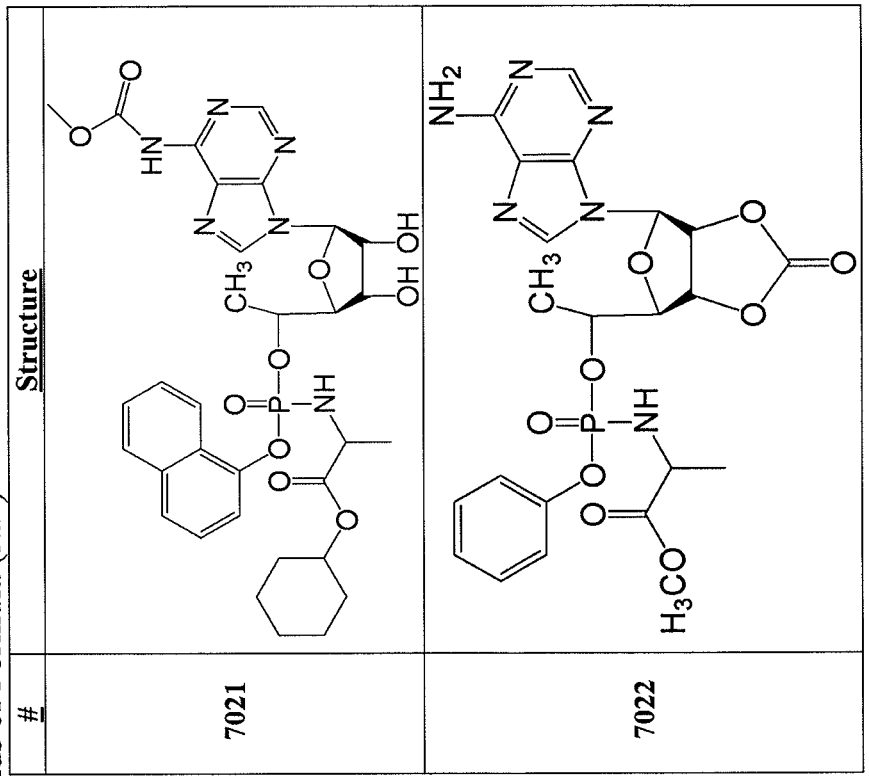
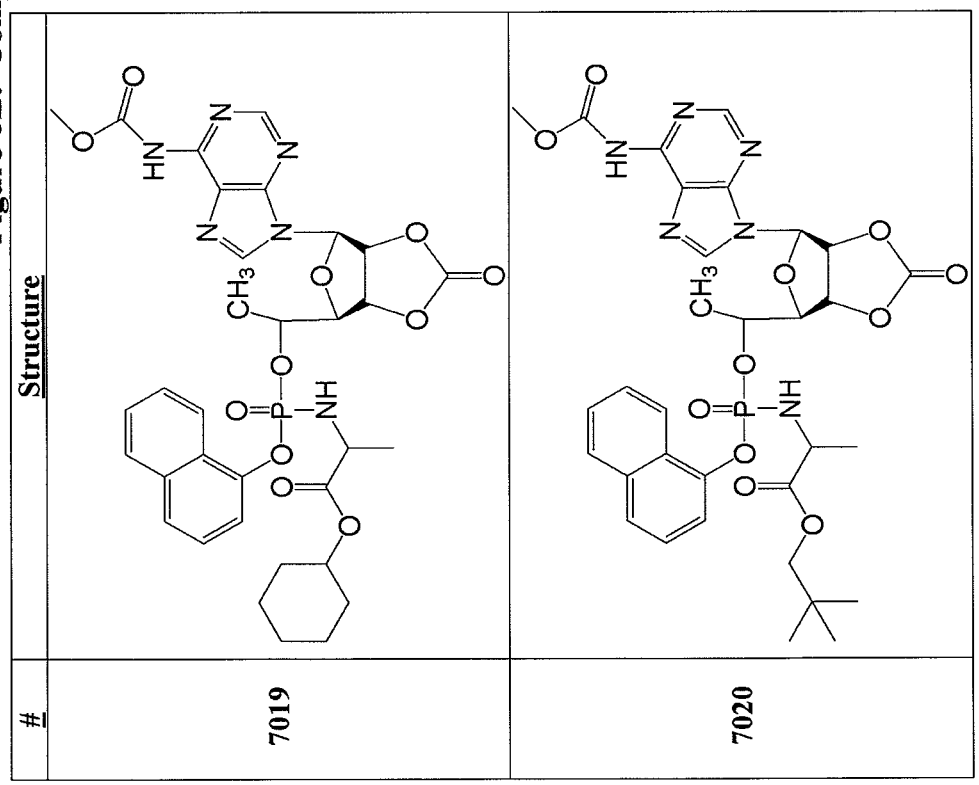

Figure 8F: Compounds of Formula (AA)
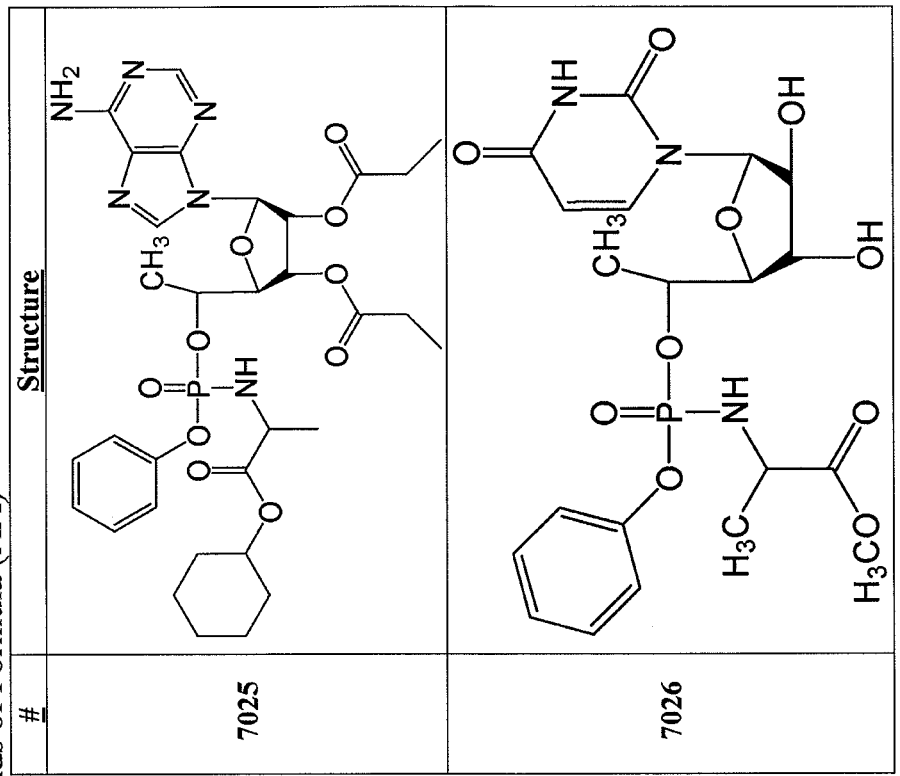
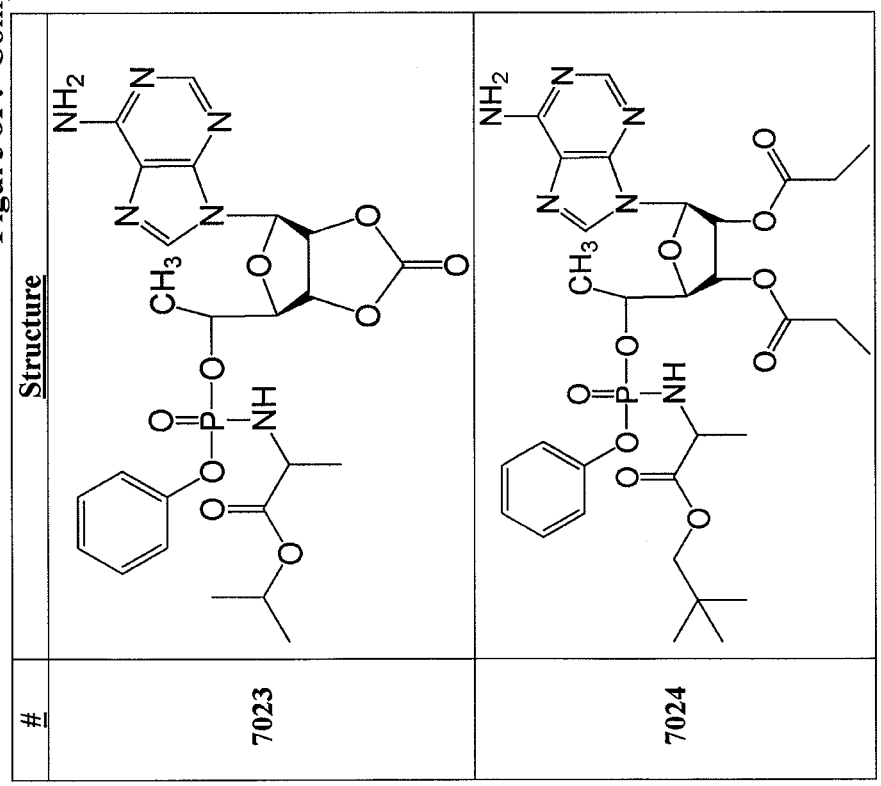

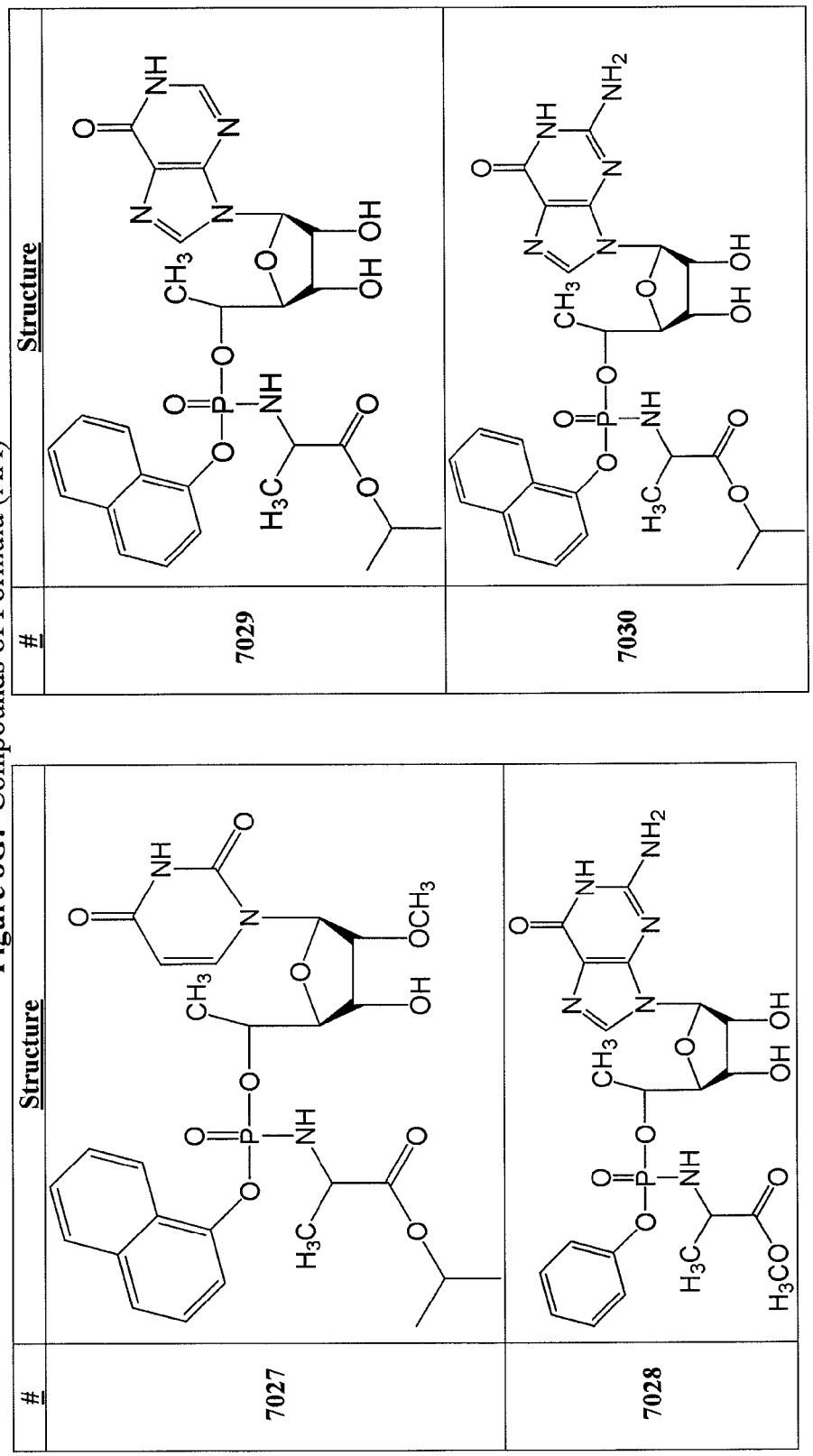
Figure 8G: Compounds of Formula (AA)

Figure 8H: Compounds of Formula (AA)

| # | Structure |
|---|---|
| 7031 | 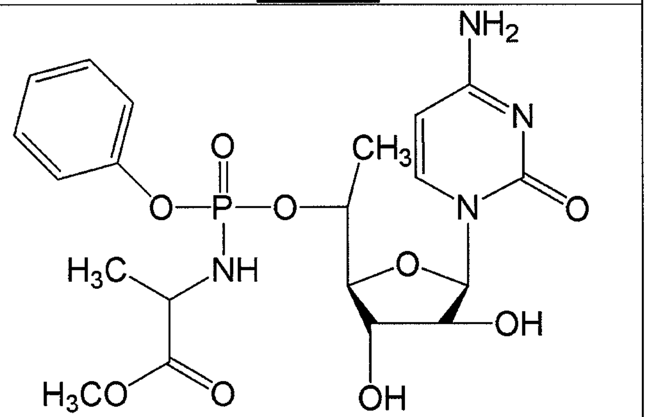 |
| 7032 | 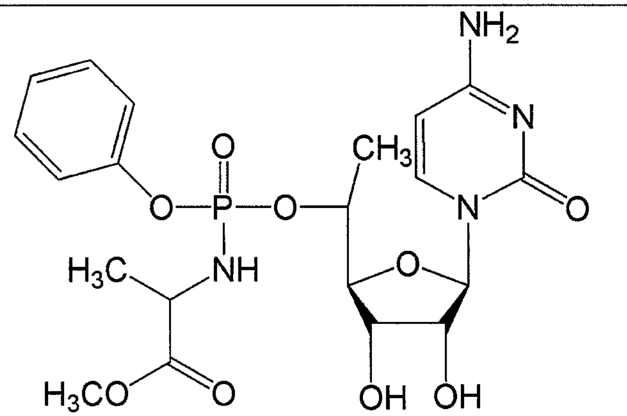 |
| 7033 | |
| 7034 | |

Figure 8I: Compounds of Formula (AA)
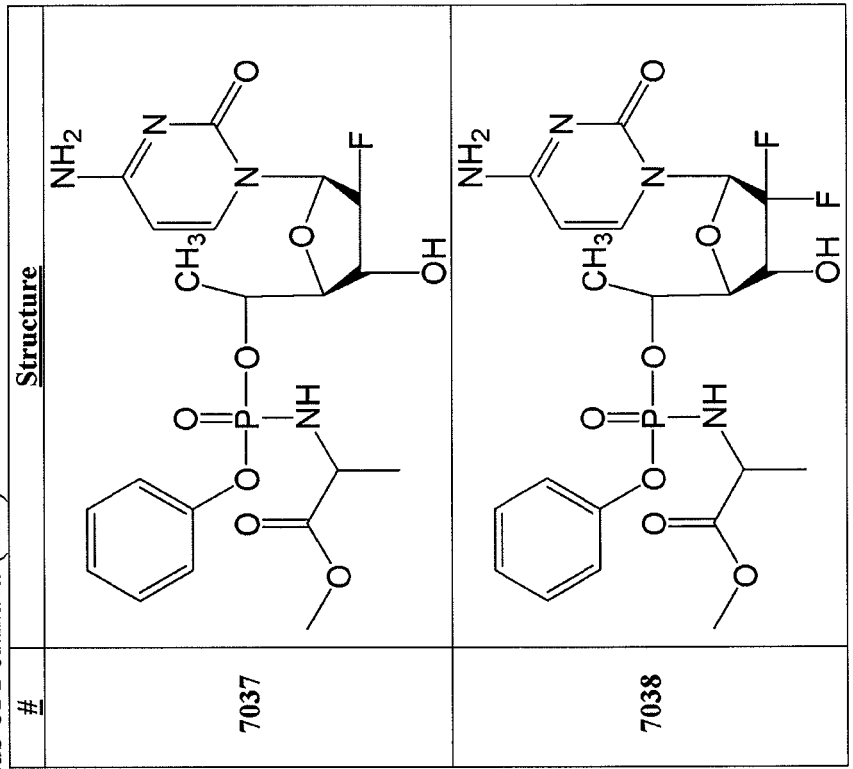
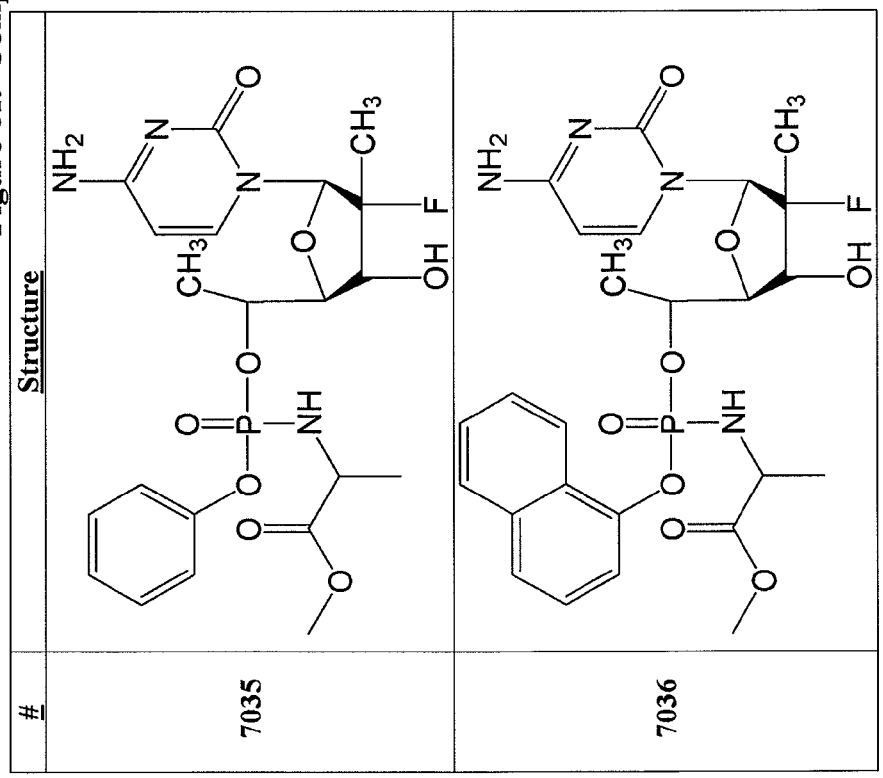

Figure 8J: Compounds of Formula (AA)
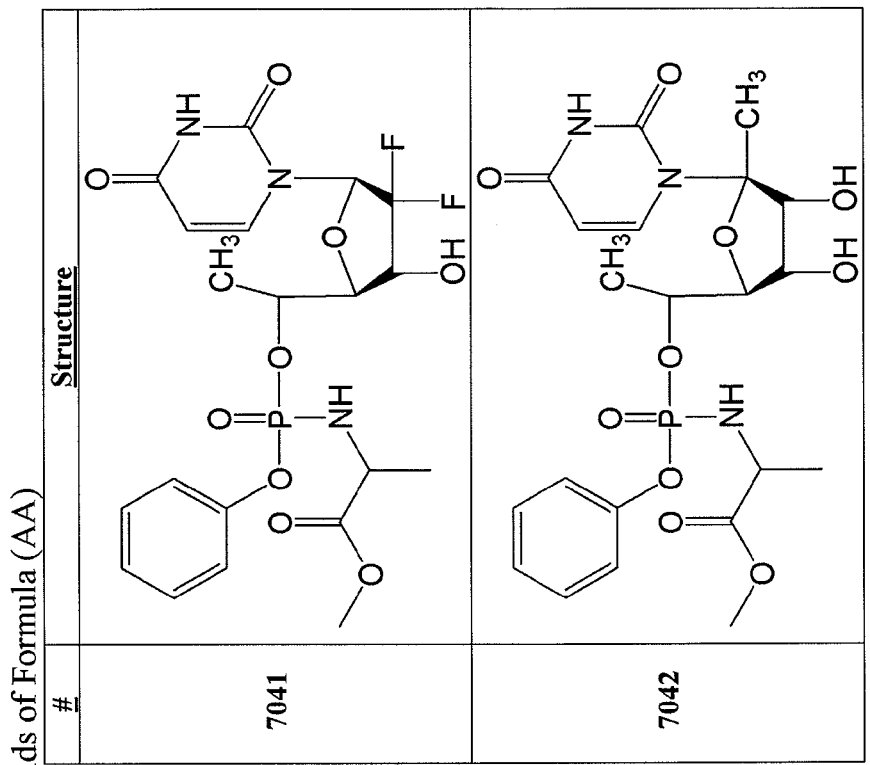
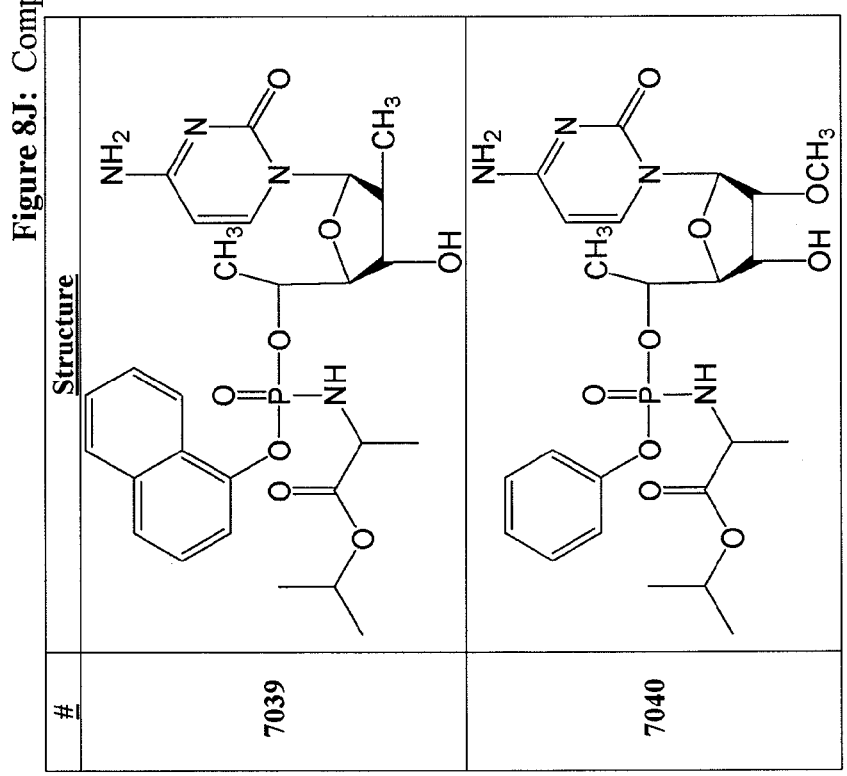

Figure 8K: Compounds of Formula (AA)

| # | Structure |
|---|---|
| 7043 | 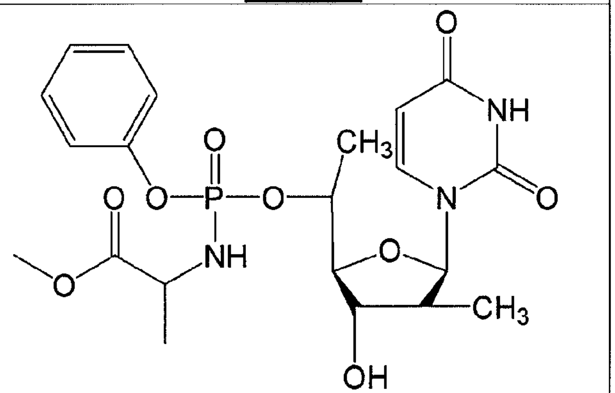 |
| 7044 | 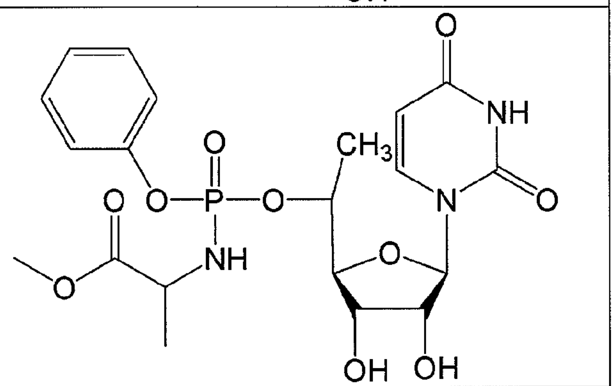 |
| 7045 | 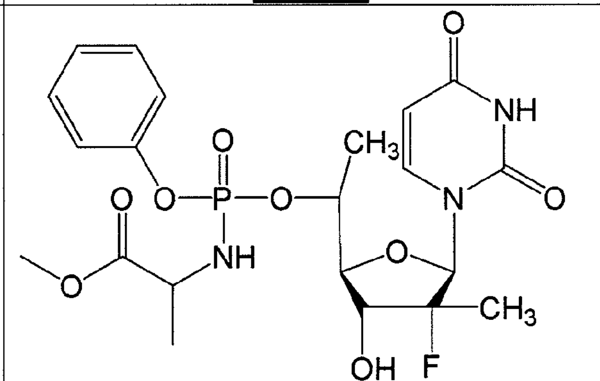 |
| 7046 | 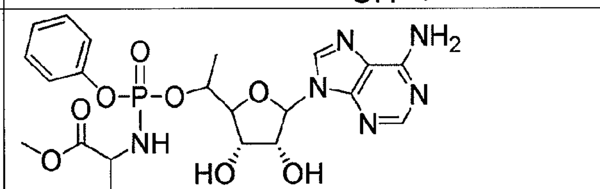 |
| 7047 | 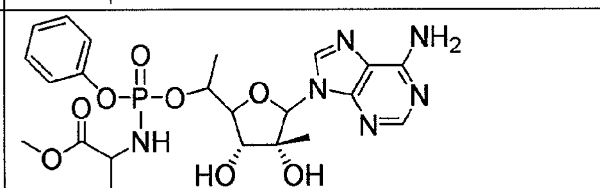 |
| 7048 | 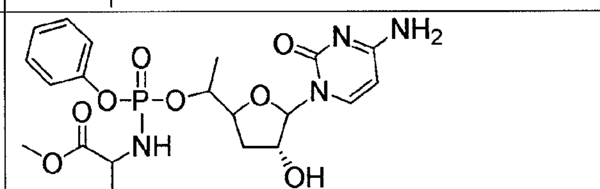 |

Figure 8L: Compounds of Formula (AA)

Figure 8M: Compounds of Formula (AA)

Figure 8N: Compounds of Formula (AA)

| # | Structure |
|---|---|
| 7065 | 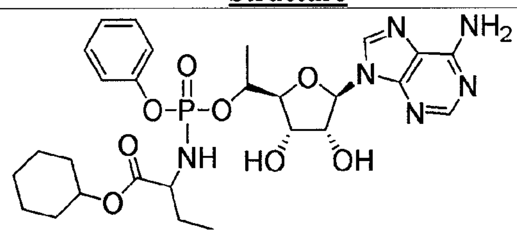 |
| 7066 | 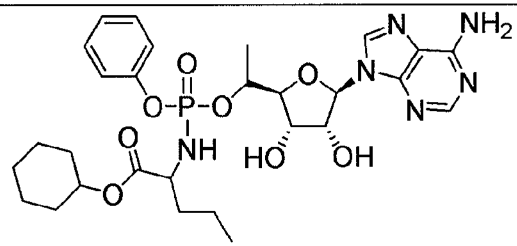 |
| 7067 | 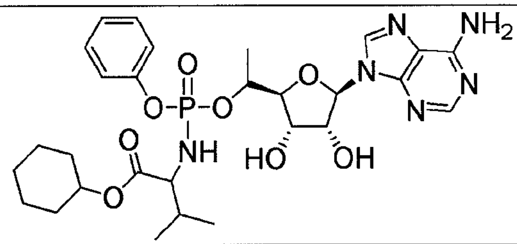 |
| 7068 | 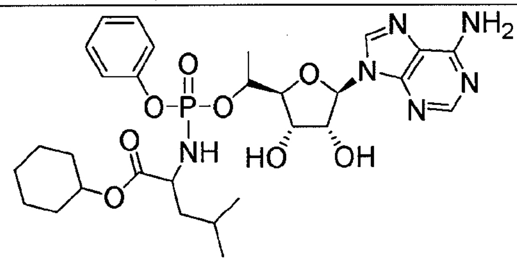 |
| 7069 | |
| 7070 | |
| 7071 | |
| 7072 | |

Figure 8O: Compounds of Formula (AA)

Figure 9A: Compounds of Formula (BB)

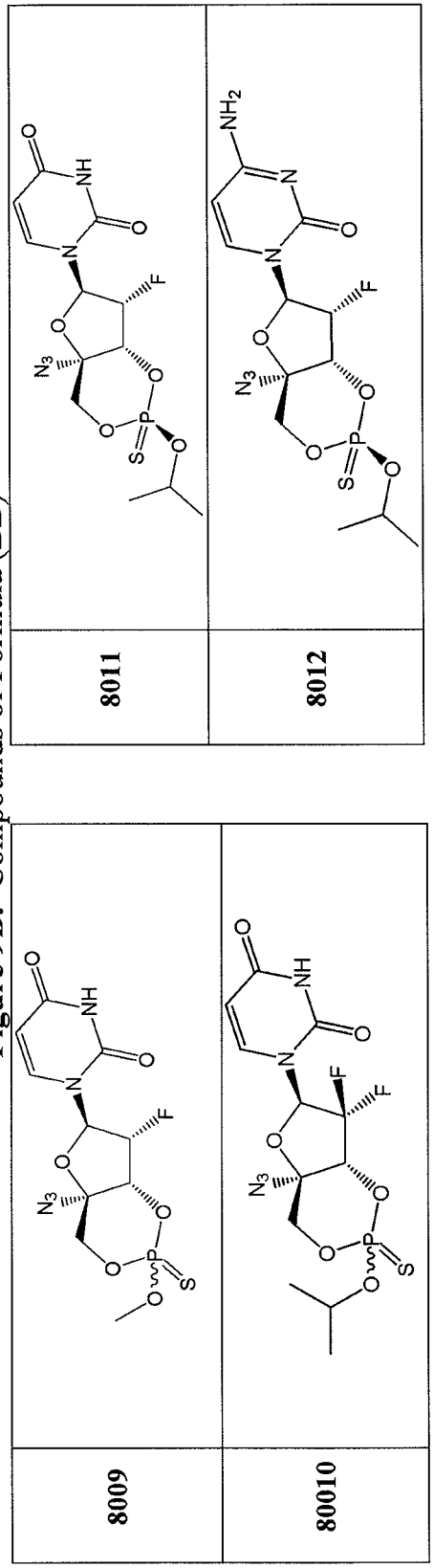
Figure 9B: Compounds of Formula (BB)
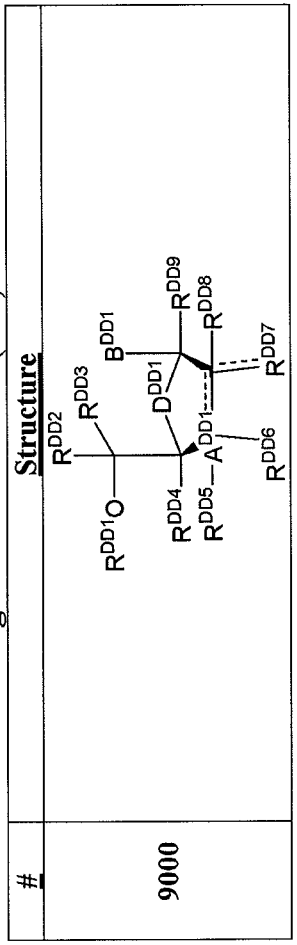
Figure 10: Formula (DD)

SUBSTITUTED NUCLEOTIDE ANALOGS

CROSS-REFERENCE TO RELATED APPLICATIONS

This application is a continuation of U.S. application Ser. No. 13/236,435, filed Sep. 19, 2011, (now U.S. Pat. No. 8,871,737) which claims the benefit of U.S. Provisional Application Nos. 61/385,363, filed Sep. 22, 2010; and 61/426,461, filed Dec. 22, 2010; all of which are incorporated herein by reference in their entirety, including any drawings.

BACKGROUND

1. Field

The present application relates to the fields of chemistry, biochemistry and medicine. More particularly, disclosed herein are phosphorothioate nucleotide analogs, pharmaceutical compositions that include one or more nucleotide analogs and methods of synthesizing the same. Also disclosed herein are methods of treating diseases and/or conditions with a phosphorothioate nucleotide analog, alone or in combination therapy with other agents.

2. Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to methods of ameliorating and/or treating a neoplastic disease that can include administering to a subject suffering from the neoplastic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a neoplastic disease. Still other embodiments described herein relate to one or more compounds of Formula (I), or a pharmaceutically acceptable salt thereof, that can be used for ameliorating and/or treating a neoplastic disease.

Some embodiments disclosed herein relate to methods of inhibiting the growth of a tumor that can include administering to a subject having a tumor a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for inhibiting the growth of a tumor. Still other embodiments described herein relate to one or more compounds of Formula (I), or a pharmaceutically acceptable salt of thereof, that can be used for inhibiting the growth of a tumor.

Some embodiments disclosed herein relate to methods of ameliorating and/or treating a viral infection that can include administering to a subject suffering from the viral infection a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a viral infection. Still other embodiments described herein relate to one or more compounds of Formula (I), or a pharmaceutically acceptable salt thereof, that can be used for ameliorating and/or treating a viral infection.

Some embodiments disclosed herein relate to methods of ameliorating and/or treating a viral infection that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of one or more compounds described herein, that can be used for ameliorating and/or treating a viral infection by contacting a cell infected with the virus with an effective amount of said compound(s).

Some embodiments disclosed herein relate to methods of inhibiting replication of a virus that can include contacting a cell infected with the virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a virus that can include contacting a cell infected with the virus with an effective amount of said compound(s). Still other embodiments described herein relate to one or more compounds described herein, or a pharmaceutically acceptable salt of one or more compounds described herein, that can be used for inhibiting replication of a virus by contacting a cell infected with the virus with an effective amount of said compound(s).

Some embodiments disclosed herein relate to methods of ameliorating and/or treating a parasitic disease that can include administering to a subject suffering from the parasitic disease a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a parasitic disease. Still other embodiments described herein relate to one or more compounds of Formula (I), or a pharmaceutically acceptable salt thereof, that can be used for ameliorating and/or treating a parasitic disease.

Some embodiments disclosed herein relate to methods of ameliorating and/or treating a viral infection that can include administering to a subject suffering from the viral infection a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, or a pharmaceutically acceptable salt of the foregoing, a compound of Formula (BB), or a pharmaceutically acceptable salt thereof, and a compound of Formula (DD), or a pharmaceutically acceptable salt thereof. Some embodiments disclosed herein relate to methods of ameliorating and/or treating a viral infection that can include contacting a cell infected with the viral infection with a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, or a pharmaceutically acceptable salt of the foregoing, a compound of Formula (BB), or a pharmaceutically acceptable salt thereof, and a compound of Formula (DD), or a pharmaceutically acceptable salt thereof. Some embodiments disclosed herein relate to methods of inhibiting replication of a virus that can include administering to a subject a therapeutically effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, or a pharmaceutically acceptable salt of the foregoing, a compound of Formula (BB), or a pharmaceutically acceptable salt thereof, and a compound of Formula (DD), or a pharmaceutically acceptable salt thereof. In some embodiments, the agent can be a compound, or a pharmaceutically acceptable salt thereof, selected from Compound 1001-1014, 2001-2010, 3001-3008, 4001-4005, 5001-5002, 7000-7077, 8000-8012 or 9000, or a pharmaceutical composition that includes one or more of the aforementioned compounds, or pharmaceutically acceptable salt thereof. In some embodiments, the method can include administering a second agent selected from an interferon, ribavirin, a HCV protease inhibitor, a HCV polymerase inhibitor, a NS5A inhibitor, an other antiviral compound, a compound of Formula (AA), a mono-, di- and/or tri-phosphate thereof, or a pharmaceutically acceptable salt of the foregoing, a compound of Formula (BB), or a pharmaceutically acceptable salt thereof and a compound of Formula (DD), or a pharmaceutically acceptable salt thereof. In some embodiments, the viral infection is HCV.

BRIEF DESCRIPTION OF THE DRAWINGS

FIGS. 2A-2B shows example HCV protease inhibitors.
FIG. 3 shows example nucleoside HCV polymerase inhibitors.
FIG. 4 shows example non-nucleoside HCV polymerase inhibitors.
FIG. 5 shows example NS5A inhibitors.
FIG. 6 shows example other antivirals.
FIGS. 7A-7M show example compounds of Formula (I).
FIGS. 8A-8O show example compounds of Formula (AA), and triphosphates thereof.
FIGS. 9A-9B show example compounds of Formula (BB).
FIG. 10 shows Formula (DD).

DETAILED DESCRIPTION

Figure 1:
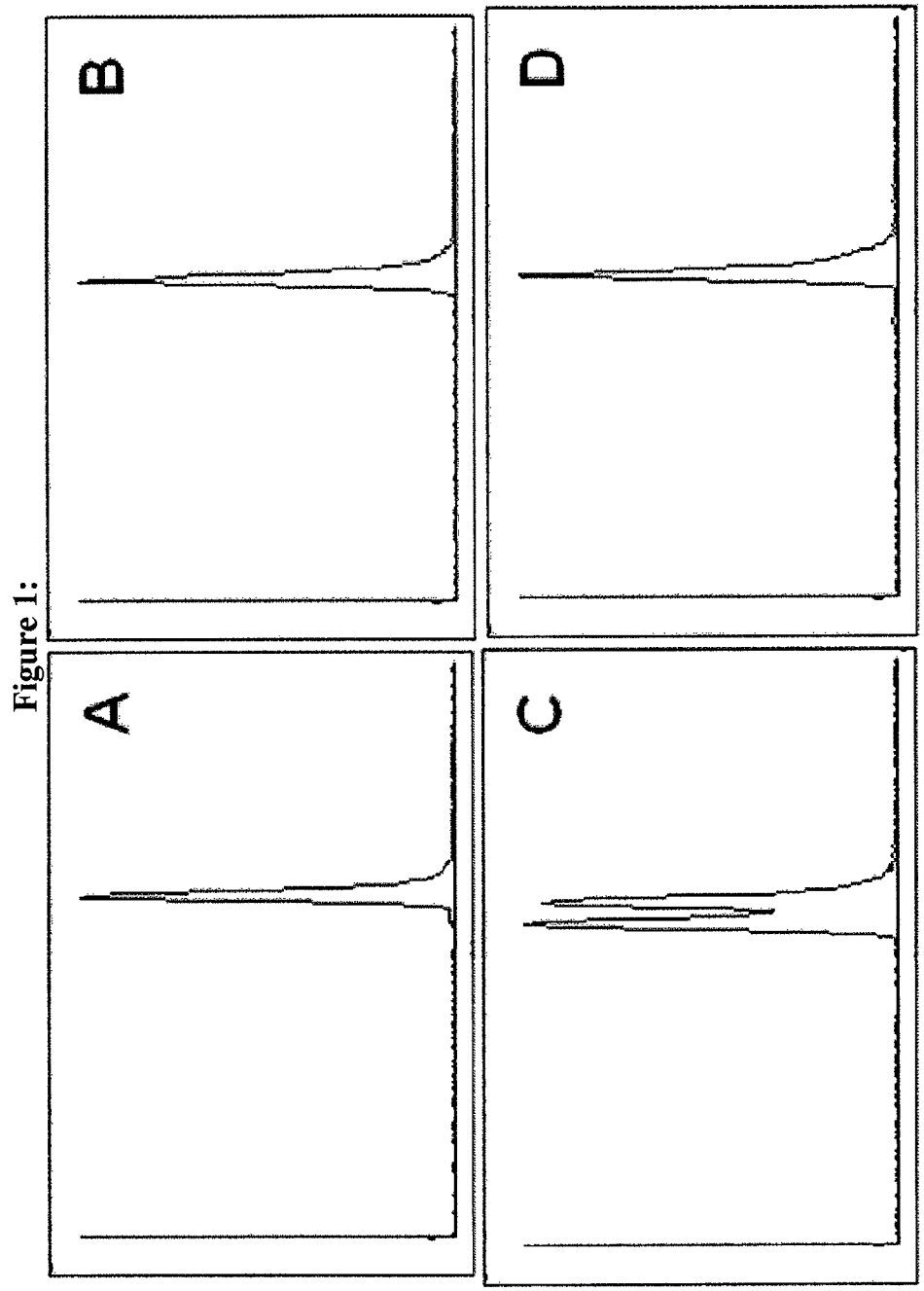
FIG. 1 illustrates four chromatograms, labeled A, B, C and D, from the results of a hepatocyte activation assay.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R, $R^1$, $R^2$, $R^{3a}$, $R^{3b}$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{1A}$, $R^{2A}$, $R^{3A}$, $R^{3B}$, $R^{4A}$, $R^{5A}$, $R^{6A}$, $R^{7A}$, $R^{8A}$, $R^{9A}$ and R" represent substituents that can be attached to the indicated atom. An R group may be substituted or unsubstituted. If two "R" groups are described as being "taken together" the R groups and the atoms they are attached to can form a cycloalkyl, aryl, heteroaryl or heterocycle. For example, without limitation, if $R^{1a}$ and $R^{1b}$ of an $NR^{1a}R^{1b}$ group are indicated to be "taken together," it means that they are covalently bonded to one another to form a ring:

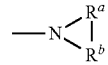

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4$,$N^4$-ethanocytosin, $N^6$,$N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but not limited to, α-amino acids, β-amino acids, γ-amino acids and ε-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include, methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, and benzyl-O—C(=O)—. N-linked amino acid ester derivatives can be substituted or unsubstituted.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5th ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

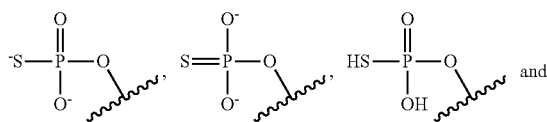

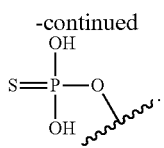

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Some embodiments disclosed herein relate to a compound of Formula (I) or a pharmaceutically acceptable salt thereof:

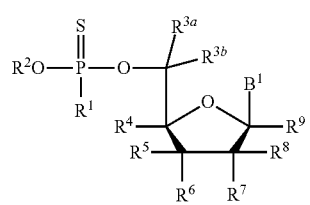

(I)

wherein: $B^1$ can be an optionally substituted heterocyclic base or an optionally substituted heterocyclic base with a protected amino group; $R^1$ can be selected from $O^-$, OH, an optionally substituted N-linked amino acid and an optionally substituted N-linked amino acid ester derivative; $R^2$ can be selected from an optionally substituted aryl, an optionally substituted heteroaryl, an optionally substituted heterocyclyl and

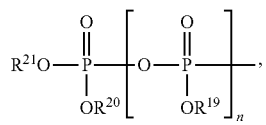

wherein $R^{19}$, $R^{20}$ and $R^{21}$ can be independently absent or hydrogen, and n can be 0 or 1; provided that when $R^1$ is $O^-$ or OH, then $R^2$ is

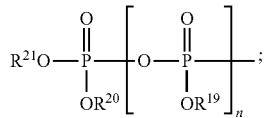

$R^{3a}$ and $R^{3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{3a}$ and $R^{3b}$ can be taken together to form an optionally substituted $C_{3-6}$ cycloalkyl; $R^4$ can be selected from hydrogen, azido, an optionally substituted $C_{1-6}$ alkyl, an optionally substituted $C_{2-6}$ alkenyl and an optionally substituted $C_{2-6}$ alkynyl; $R^5$ can be selected from hydrogen, halogen, azido, cyano, an optionally substituted $C_{1-6}$ alkyl, —$OR^{10}$ and —$OC(=O)R^{11}$; $R^6$ can be selected from hydrogen, halogen, azido, cyano, an optionally substituted $C_{1-6}$ alkyl, —$OR^{12}$ and —$OC(=O)R^{13}$; $R^7$ can be selected from hydrogen, halogen, azido, cyano, an optionally substituted $C_{1-6}$ alkyl, —$OR^{14}$ and —$OC(=O)R^{15}$; or $R^6$ and $R^7$ can be both oxygen atoms and linked together by a carbonyl group; $R^8$ can be selected from hydrogen, halogen, azido, cyano, an optionally substituted $C_{1-6}$ alkyl, —$OR^{16}$ and —$OC(=O)R^{17}$; $R^9$ can be selected from hydrogen, azido, cyano, an optionally substituted $C_{1-6}$ alkyl and —$OR^{18}$; $R^{10}$, $R^{12}$, $R^{14}$, $R^{16}$ and $R^{18}$ can be independently selected from hydrogen and an optionally substituted $C_{1-6}$ alkyl; and $R^{11}$, $R^{13}$, $R^{15}$ and $R^{17}$ can be independently selected from an optionally substituted $C_{1-6}$ alkyl and an optionally substituted $C_{3-6}$ cycloalkyl; with the proviso that when $R^{3a}$, $R^{3b}$, $R^4$, $R^5$, $R^7$, $R^8$, and $R^9$ are all hydrogen, then $R^6$ cannot be azido.

With respect to $R^2$, in some embodiments, $R^2$ can be an optionally substituted heteroaryl. In other embodiments, $R^2$ can be an optionally substituted heterocyclyl. In still other embodiments, $R^2$ can be an optionally substituted aryl. For example, $R^2$ can be an optionally substituted phenyl or an optionally substituted naphthyl. If $R^2$ is a substituted phenyl or a substituted naphthyl, the phenyl ring and the naphthyl ring(s) can be substituted one or more times. Suitable substituents that can be present on optionally substituted phenyl and an optionally substituted naphthyl include electron-donating groups and electron-withdrawing groups. In some embodiments, $R^2$ can be a para-substituted phenyl. In other embodiment, $R^2$ can be an unsubstituted phenyl or an unsubstituted naphthyl. In yet still other embodiments, $R^2$ can be

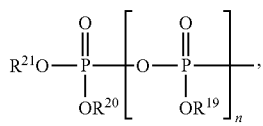

wherein $R^{19}$, $R^{20}$ and $R^{21}$ can be independently absent or hydrogen, and n can be 0 or 1. In some embodiments, n can be 0. In other embodiments, n can be 1. Those skilled in the art understand when n is 0, $R^2$ can be an α-thiodiphosphate. Similarly, those skilled in the art understand when n is 1, $R^2$ can be an α-thiotriphosphate. In some embodiments, at least one of $R^{19}$, $R^{20}$ and $R^{21}$ can be absent. In other embodiments, at least one of $R^{19}$, $R^{20}$ and $R^{21}$ can be hydrogen. In some embodiments, $R^{20}$ and $R^{21}$ can be absent. In other embodiments, $R^{20}$ and $R^{21}$ can be hydrogen. In some embodiments, $R^{19}$, $R^{20}$ and $R^{21}$ can be absent. In some embodiments, $R^{19}$, $R^{20}$ and $R^{21}$ can be hydrogen. Those skilled in the art understand that when any of $R^{19}$, $R^{20}$ and $R^{21}$ are absent the oxygen atom to which $R^{19}$, $R^{20}$ and $R^{21}$ are associated with can have a negative charge. For example, when $R^{20}$ is absent, the oxygen atom to which $R^{20}$ is associated with can be $O^-$. Depending upon the substituents attached to each phosphorus atoms, one or more phosphorus atoms can be a chiral center. For example, when n is 1, the alpha-phosphorus (the phosphorus nearest to the pentose ring) can be a chiral center. In some embodiments, the alpha-phosphorus can be a (R)-stereocenter. In other embodiments, the alpha-phosphorus can be a (S)-stereocenter.

In some embodiments, $R^1$ can be absent. In other embodiments, $R^1$ can be hydrogen. In still other embodiments, $R^1$ can be an optionally substituted N-linked α-amino acid. In yet still other embodiments, $R^1$ can be an optionally substituted N-linked α-amino acid ester derivative. Various amino acids and amino acid ester derivatives can be used, including those described herein. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional suitable amino acids include, but are not limited to, alpha-ethyl-glycine, alpha-propyl-glycine and beta-alanine. Examples of an N-linked amino acid ester derivatives include, but are not limited to, an ester derivatives of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine.

In an embodiment, $R^1$ can be an ester derivative of alanine. In an embodiment, $R^1$ can be selected from alanine methyl ester, alanine ethyl ester, alanine isopropyl ester, alanine cyclohexyl ester, alanine neopentyl ester, valine isopropyl ester and leucine isopropyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, when $R^1$ is an optionally substituted N-linked α-amino acid or an optionally substituted N-linked α-amino acid ester derivative, then $R^2$ can be selected from optionally substituted aryl, an optionally substituted heteroaryl and an optionally substituted heterocyclyl. In some embodiments, when $R^1$ is an optionally substituted N-linked α-amino acid ester derivative, then $R^2$ can be an optionally substituted aryl. In other embodiments, when $R^1$ is an optionally substituted N-linked α-amino acid ester derivative, then $R^2$ can be an optionally substituted heteroaryl. In still other embodiments, when $R^1$ is an optionally substituted N-linked α-amino acid ester derivative, then $R^2$ can be an optionally substituted heterocyclyl.

In some embodiments, $R^1$ can have the structure

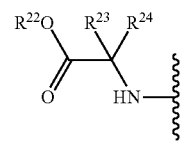

wherein $R^{22}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$ haloalkyl; and $R^{23}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{24}$ can be hydrogen or an optionally substituted $C_{1-4}$-alkyl; or $R^{23}$ and $R^{24}$ can be taken together to form an optionally substituted $C_{3-6}$ cycloalkyl.

When $R^1$ has the structure shown above, $R^{23}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{23}$ is substituted, $R^{23}$ can be substituted with one or more substituents selected from N-amido, mercapto, alkylthio, an optionally substituted aryl, hydroxy, an optionally substituted heteroaryl, O-carboxy, and amino. In some embodiment, $R^{23}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, $R^{23}$ can be methyl.

As to $R^{22}$, in some embodiments, $R^{22}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{22}$ can be methyl or isopropyl. In some embodiments, $R^{22}$ can be ethyl or neopentyl. In other embodiments, $R^{22}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{22}$ can be an optionally substituted cyclohexyl. In still other embodiments, $R^{22}$ can be an optionally substituted aryl, such as phenyl and naphthyl. In yet still other embodiments, $R^{22}$ can be an optionally substituted aryl($C_{1-6}$ alkyl). In some embodiments, $R^{22}$ can be an optionally substituted benzyl. In some embodiments, $R^{22}$ can be an optionally substituted $C_{1-6}$ haloalkyl, for example, $CF_3$.

In some embodiments, $R^{24}$ can be hydrogen. In other embodiments, $R^{24}$ can be an optionally substituted $C_{1-4}$-alkyl, such as methyl, ethyl, n-propyl, isopropyl, n-butyl, isobutyl and tert-butyl. In an embodiment, $R^{24}$ can be methyl. In some embodiments, $R^{23}$ and $R^{24}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{23}$ and $R^{24}$, the carbon to which $R^{23}$ and $R^{24}$ are attached may be a chiral center. In some embodiment, the carbon to which $R^{23}$ and $R^{24}$ are attached may be a (R)-chiral center. In other embodiments, the carbon to which $R^{23}$ and $R^{24}$ are attached may be a (S)-chiral center.

As example of a suitable

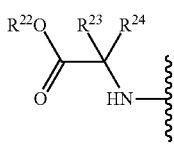

groups include the following:

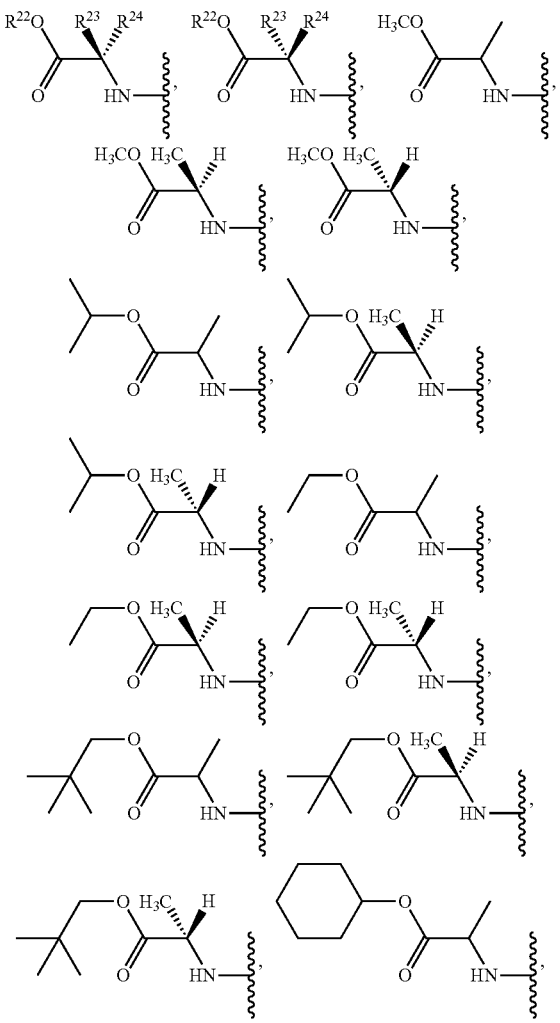

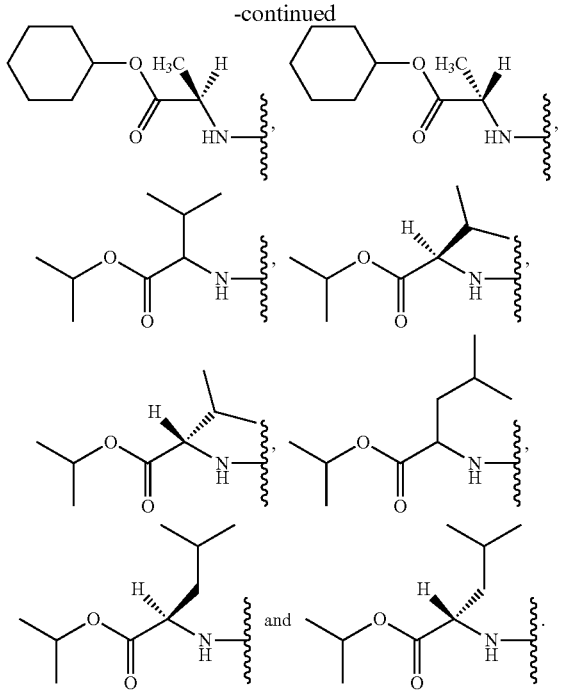

The substituents attached to the 5'-position of a compound of Formula (I) can vary. In some embodiments, $R^{3a}$ and $R^{3b}$ can be the same. In other embodiments, $R^{3a}$ and $R^{3b}$ can be different. In some embodiments, $R^{3a}$ and $R^{3b}$ can be both hydrogen. In some embodiments, at least one of $R^{3a}$ and $R^{3b}$ can be an optionally substituted $C_{1-6}$-alkyl; and the other of $R^{3a}$ and $R^{3b}$ can be hydrogen. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In an embodiment, at least one of $R^{3a}$ and $R^{3b}$ can be methyl, and the other of $R^{3a}$ and $R^{3b}$ can be hydrogen. In other embodiments, at least one of $R^{3a}$ and $R^{3b}$ can be an optionally substituted $C_{1-6}$-haloalkyl, and the other of $R^{3a}$ and $R^{3b}$ can be hydrogen. One example of a suitable optionally substituted $C_{1-6}$-haloalkyl is $CF_3$. In other still embodiments, $R^{3a}$ and $R^{3b}$ can be taken together to form an optionally substituted $C_{3-6}$ cycloalkyl. When the substituents attached to the 5'-carbon make the 5'-carbon chiral, in some embodiments, the 5'-carbon can be a (R)-stereocenter. In other embodiments, the 5'-carbon can be an (S)-stereocenter.

The substituents attached to the 4'-carbon can vary. In some embodiments, $R^4$ can be hydrogen. In other embodiments, $R^4$ can be azido. In still other embodiments, $R^4$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^4$ can be an optionally substituted $C_{2-6}$ alkenyl. In some embodiments, $R^4$ can be an optionally substituted $C_{2-6}$ alkynyl.

The substituents attached to the 2'-carbon and the 3'-carbon can also vary. In some embodiments, $R^5$ can be hydrogen. In other embodiments, $R^5$ can be halogen. In still other embodiments, $R^5$ can be azido. In yet still other embodiments, $R^5$ can be cyano. In some embodiments, $R^5$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In other embodiments, $R^5$ can be —$OR^{10}$, wherein $R^{10}$ can be hydrogen. In still other embodiments, $R^5$ can be —$OR^{10}$, wherein $R^{10}$ can be an optionally substituted $C_{1-6}$ alkyl. In yet still other embodiments, $R^5$ can be —$OC(=O)R^{11}$, wherein $R^{11}$ can be an optionally substituted $C_{1-6}$ alkyl or an optionally substituted $C_{3-6}$ cycloalkyl. Examples of suitable $C_{1-6}$ alkyls and $C_{3-6}$ cycloalkyls are described herein.

In some embodiments, $R^6$ can be hydrogen. In other embodiments, $R^6$ can be halogen. In still other embodiments, $R^6$ can be azido. In yet still other embodiments, $R^6$ can be cyano. In some embodiments, $R^6$ can be an optionally substituted $C_{1-6}$ alkyl. In other embodiments, $R^6$ can be —$OR^{12}$, wherein $R^{12}$ can be hydrogen. In still other embodiments, $R^6$ can be —$OR^{12}$, wherein $R^{12}$ can be an optionally substituted $C_{1-6}$ alkyl. A non-limiting list of examples of $R^6$ being —$OR^{12}$, wherein $R^{12}$ can be an optionally substituted $C_{1-6}$ alkyl are methoxy, ethoxy, n-propoxy, isopropoxy, n-butoxy, isobutoxy and tert-butoxy, pentoxy (straight-chained or branched) and hexoxy (straight-chained or branched). In yet still other embodiments, $R^6$ can be —$OC(=O)R^{13}$, wherein $R^{13}$ can be an optionally substituted $C_{1-6}$ alkyl or an optionally substituted $C_{3-6}$ cycloalkyl. Examples of suitable optionally substituted $C_{1-6}$ alkyls include optionally substituted variants of the following: methyl, ethyl, n-propyl, isopropyl, n-butyl, isobutyl, tert-butyl pentyl (branched and straight-chained), and hexyl (branched and straight-chained). Examples of suitable optionally substituted $C_{3-6}$ cycloalkyls include optionally substituted variants of the following: cyclopropyl, cyclobutyl, cyclopentyl and cyclohexyl.

In some embodiments, $R^7$ can be hydrogen. In other embodiments, $R^7$ can be halogen. In still other embodiments, $R^7$ can be azido. In yet still other embodiments, $R^7$ can be cyano. In some embodiments, $R^7$ can be an optionally substituted $C_{1-6}$ alkyl. In other embodiments, $R^7$ can be —$OR^{14}$. In an embodiment, when $R^{14}$ is hydrogen, $R^7$ can be a hydroxy group. In still other embodiments, when $R^{14}$ is an optionally substituted $C_{1-6}$ alkyl, $R^7$ can be an optionally substituted $C_{1-6}$ alkoxy. Examples, of $R^7$ being —$OR^{14}$, wherein $R^{14}$ can be an optionally substituted $C_{1-6}$ alkyl include, but are not limited to, are methoxy, ethoxy, n-propoxy, isopropoxy, n-butoxy, isobutoxy, tert-butoxy, pentoxy (straight-chained or branched) and hexoxy (straight-chained or branched). In yet still other embodiments, $R^7$ can be —$OC(=O)R^{15}$, wherein $R^{15}$ can be an optionally substituted $C_{1-6}$ alkyl, such as optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^7$ can be —$OC(=O)R^{15}$, wherein $R^{15}$ can be an optionally substituted $C_{3-6}$ cycloalkyl In some embodiments, $R^8$ can be hydrogen. In other embodiments, $R^8$ can be halogen. In still other embodiments, $R^8$ can be azido. In yet still other embodiments, $R^8$ can be cyano. In some embodiments, $R^8$ can be —$OR^{16}$. When $R^{16}$ is hydrogen, $R^8$ can be hydroxy. Alternatively, when $R^{16}$ is an optionally substituted $C_{1-6}$ alkyl, $R^8$ can be an optionally substituted $C_{1-6}$ alkoxy. Suitable alkoxy groups are described herein. In other embodiments, $R^8$ can be an optionally substituted $C_{1-6}$ alkyl. In still other embodiments, $R^8$ can be —$OC(=O)R^{17}$ in which $R^{17}$ is an optionally substituted $C_{1-6}$ alkyl. In yet still other embodiments, $R^8$ can be —$OC(=O)R^{17}$ in which $R^{17}$ is an optionally substituted $C_{3-6}$ cycloalkyl. Examples of suitable $C_{1-6}$ alkyl and $C_{3-6}$ cycloalkyl groups are described herein.

In some embodiments, $R^6$ and $R^7$ can both be hydroxy. In still other embodiments, $R^6$ and $R^7$ can both be both oxygen atoms and linked together by a carbonyl group, for example, —O—C(=O)—O—. In some embodiments, at least one of $R^7$ and $R^8$ can be a halogen. In some embodiments, $R^7$ and $R^8$ can both be a halogen. In other embodiments, $R^7$ can be a halogen and $R^8$ can be an optionally substituted $C_{1-6}$ alkyl, such as those described herein. In other embodiments, $R^7$ can be hydrogen and $R^8$ can be a halogen. In still other embodiments, at least one of $R^6$ and $R^7$ can be a hydroxy and $R^8$ can be an optionally substituted $C_{1-6}$ alkyl. In yet still other embodiments, $R^6$ can be hydroxy, $R^7$ can be hydroxy, H or halogen, and $R^8$ can be an optionally substituted $C_{1-6}$ alkyl. In some embodiments, $R^{3a}$, $R^{3b}$, $R^4$, $R^5$ and $R^9$ can be hydrogen in any of the embodiments described in this paragraph. In some embodiments, $B^1$ can be an optionally substituted adenine, an optionally substituted guanine, and optionally substituted thymine, optionally substituted cytosine, or an optionally substituted uracil in any of the embodiments described in this paragraph.

In some embodiments, $R^9$ can be hydrogen. In other embodiments, $R^9$ can be azido. In still other embodiments, $R^9$ can be cyano. In yet still other embodiments, $R^9$ can be an optionally substituted $C_{1-6}$ alkyl, such as those described herein. In some embodiments, $R^9$ can be —$OR^{18}$. In some embodiments, when $R^9$ is —$OR^{18}$, $R^9$ can be a hydroxy group. In other embodiments, when $R^9$ is —$OR^{18}$, $R^9$ can be an optionally substituted $C_{1-6}$ alkoxy. Examples of optionally substituted $C_{1-6}$ alkoxy include the following: methoxy, ethoxy, n-propoxy, isopropoxy, n-butoxy, isobutoxy, tert-butoxy, pentoxy (branched and straight-chained), and hexoxy (branched and straight-chained).

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

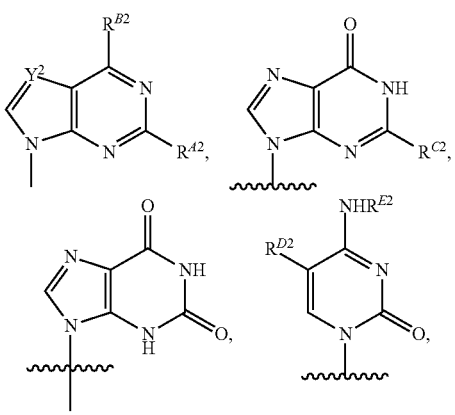

-continued

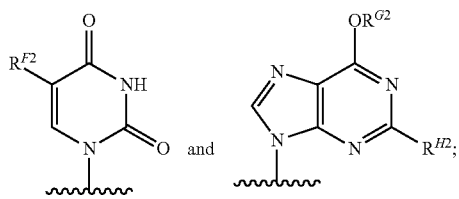

wherein: $R^{A2}$ can be selected from hydrogen, halogen and $NHR^{J2}$, wherein $R^{J2}$ can be selected from hydrogen, —C(=O)$R^{K2}$ and —C(=O)O$R^{L2}$; $R^{B2}$ can be halogen or $NHR^{W2}$, wherein $R^{W2}$ is selected from hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$; $R^{C2}$ can be hydrogen or $NHR^{O2}$, wherein $R^{O2}$ can be selected from hydrogen, —C(=O)$R^{P2}$ and —C(=O)O$R^{Q2}$; $R^{D2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, an optionally substituted $C_{1-6}$ alkyl, an optionally substituted $C_{3-8}$ cycloalkyl, —C(=O)$R^{R2}$ and —C(=O)O$R^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ can be N (nitrogen) or $CR^{T2}$, wherein $R^{T2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or $NHR^{T2}$, wherein $R^{T2}$ can be independently selected from hydrogen, —C(=O)$R^{U2}$ and —C(=O)O$R^{V2}$, and $R^{K2}$, $R^{L2}$, $R^{M2}$, $R^{N2}$, $R^{P2}$, $R^{Q2}R^{R2}$, $R_{S2}$, $R^{U2}$ and $R^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heteroalicyclyl, aryl($C_{1-6}$ alkyl), heteroaryl ($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted." Suitable optionally substituted $C_{1-6}$ alkyl groups that can be present on an optionally substituted heterocyclic base or an optionally substituted heterocyclic base with one or more protected amino groups are described herein, and include, optionally substituted variants of the following: methyl, ethyl, n-propyl, isopropyl, n-butyl, isobutyl, tert-butyl, pentyl (branched and straight-chained), and hexyl (branched and straight-chained).

In some embodiments, $B^1$ can be selected from adenine, guanine, thymine, cytosine and uracil. In some embodiments, $R^{B2}$ can be $NH_2$. In other embodiments, $R^{E2}$ can be hydrogen. In some embodiments, $B^1$ can be

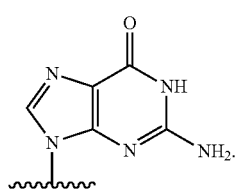 [SMILES: *n1cnc2c(=O)[nH]c(N)nc21]

In other embodiments, $B^1$ can be

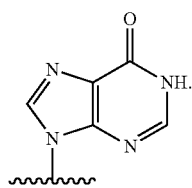 [SMILES: *n1cnc2c(=O)[nH]cnc21]

In some embodiments, $B^1$ can be

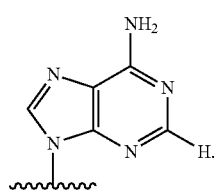

In some embodiments, $B^1$ can be

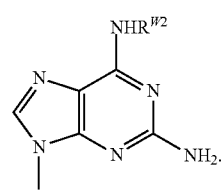

In still other embodiments, $B^1$ can be

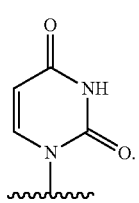

In yet still other embodiments, $B^1$ can be

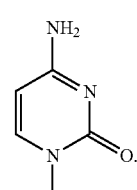

In some embodiments, $B^1$ can be

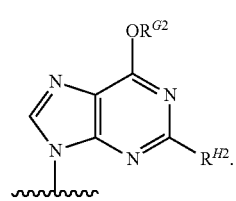

In some embodiments, when $R^2$ is a substituted or unsubstituted phenyl, then $R^1$ cannot be

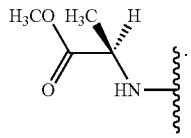

In other embodiments, when $R^2$ is a substituted or unsubstituted phenyl, then $R^1$ cannot be

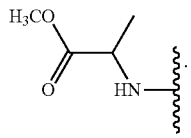

In still other embodiments, when $R^2$ is a substituted or unsubstituted phenyl and $R^1$ is

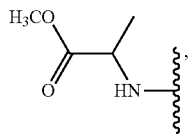

then at least one of $R^5$ and $R^6$ cannot be hydroxy.

In some embodiments, when $R^1$ is $O^-$ or OH, then $R^2$ cannot be

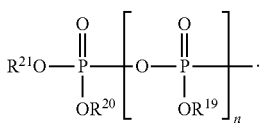

In some embodiments, at least one of $R^{3a}$ and $R^{3b}$ cannot be hydrogen. In some embodiments, $R^4$ is not azido. In some embodiments, when $R^4$ is not azido, then $R^7$ and $R^8$ are not both halogen. In some embodiments, when $R^4$ is azido, then $B^1$ is not an optionally substituted uracil, optionally substituted uracil with one or more protected amino groups, an optionally substituted cytosine or optionally substituted cytosine with one or more protected amino groups. In some embodiments, $R^6$ cannot be azido. In some embodiments, when $R^1$ is a methyl ester of glycine, alanine, valine, or phenylalanine; $R^2$ is p-chlorophenyl or p-nitrophenyl; $B^1$ is thymine; and $R^{3a}$, $R^{3b}$, $R^4$, $R^5$, $R^7$, $R^8$, and $R^9$ are all hydrogen; then $R^6$ cannot be azido. In some embodiments, at least one of $R^6$ and $R^7$ cannot be hydroxy. For example, $R^6$ cannot be hydroxy, $R^7$ cannot be hydroxy, or both of $R^6$ and $R^7$ cannot be hydroxy.

Some embodiments disclosed herein relate to a compound of Formula (I) or a pharmaceutically acceptable salt thereof, wherein: $B^1$ can be an optionally substituted heterocyclic base as described in paragraph [0106]; $R^1$ can be selected from $O^-$, OH, an optionally substituted N-linked amino acid and an optionally substituted N-linked amino acid ester derivative; $R^2$ can be selected from an optionally substituted aryl and

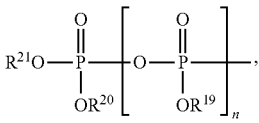

wherein $R^{19}$, $R^{20}$ and $R^{21}$ can be independently absent or hydrogen, and n can be 0 or 1; provided that when $R^1$ is $O^-$ or OH, then $R^2$ is

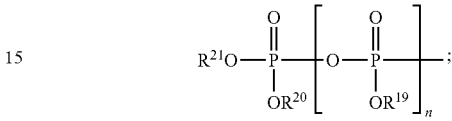

$R^{3a}$ and $R^{3b}$ can be hydrogen; $R^4$ can be hydrogen; $R^5$ can be selected from hydrogen, halogen, an optionally substituted $C_{1-6}$ alkyl and —$OR^{10}$; $R^6$ can be selected from hydrogen, halogen, optionally substituted $C_{1-6}$ alkyl, —$OR^{12}$ and —OC(=O)$R^{13}$; $R^7$ can be selected from hydrogen, halogen, azido, cyano, an optionally substituted $C_{1-6}$ alkyl, —$OR^{14}$ and —OC(=O)$R^{15}$; or $R^6$ and $R^7$ can be both oxygen atoms and linked together by a carbonyl group; $R^8$ can be selected from hydrogen, halogen, an optionally substituted $C_{1-6}$ alkyl and —$OR^{16}$; $R^9$ can be hydrogen; $R^{10}$, $R^{12}$, $R^{14}$ and $R^{16}$ can be independently selected from hydrogen and an optionally substituted $C_{1-6}$ alkyl; and $R^{13}$ and $R^{15}$ can be independently selected from an optionally substituted $C_{1-6}$ alkyl and an optionally substituted $C_{3-6}$ cycloalkyl.

Some embodiments disclosed herein relate to a compound of Formula (I) or a pharmaceutically acceptable salt thereof, wherein: $B^1$ can be an optionally substituted heterocyclic base or an optionally substituted heterocyclic base with a protected amino group selected from

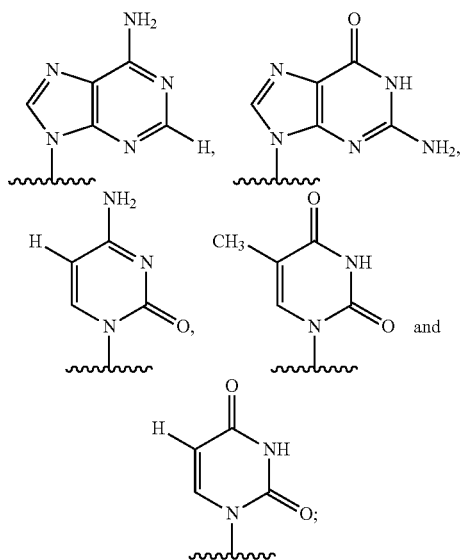

$R^1$ can be selected from $O^-$, OH, an optionally substituted N-linked amino acid and an optionally substituted N-linked amino acid ester derivative; $R^2$ can be selected from an optionally substituted aryl and

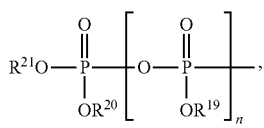

wherein $R^{19}$, $R^{20}$ and $R^{21}$ can be independently absent or hydrogen, and n can be 0 or 1; provided that when $R^1$ is $O^-$ or OH, then $R^2$ is

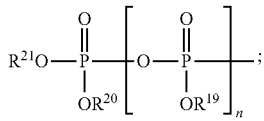

$R^{3a}$ and $R^{3b}$ can be hydrogen; $R^4$ can be hydrogen; $R^5$ can be selected from hydrogen, halogen, an optionally substituted $C_{1-6}$ alkyl and $-OR^{10}$; $R^6$ can be selected from hydrogen, halogen, optionally substituted $C_{1-6}$ alkyl, $-OR^{12}$ and $-OC(=O)R^{13}$; $R^7$ can be selected from hydrogen, halogen, azido, cyano, an optionally substituted $C_{1-6}$ alkyl, $-OR^{14}$ and $-OC(=O)R^{15}$; or $R^6$ and $R^7$ can be both oxygen atoms and linked together by a carbonyl group; $R^8$ can be selected from hydrogen, halogen, an optionally substituted $C_{1-6}$ alkyl and $-OR^{16}$; $R^9$ can be hydrogen; $R^{10}$, $R^{12}$, $R^{14}$ and $R^{16}$ can be independently selected from hydrogen and an optionally substituted $C_{1-6}$ alkyl; and $R^{13}$ and $R^{15}$ can be independently selected from an optionally substituted $C_{1-6}$ alkyl and an optionally substituted $C_{3-6}$ cycloalkyl.

In some embodiments, Formula (I) can be a compound of Formula (Iα), wherein: $B^1$ can be an optionally substituted heterocyclic base or an optionally substituted heterocyclic base with a protected amino group selected from cytosine, uridine, thymidine, guanine and adenine; $R^1$ can be selected from $O^-$, OH, and an optionally substituted N-linked amino acid ester derivative of alanine, valine, or leucine; $R^2$ can be selected from an optionally substituted phenyl, an optionally substituted naphthyl, an optionally substituted pyridyl, an optionally substituted quinolyl, and

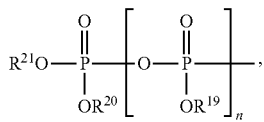

wherein $R^{19}$, $R^{20}$ and $R^{21}$ independently can be hydrogen or absent, and n can be 0 or 1; provided that when $R^1$ is $O^-$ or OH, then $R^2$ is

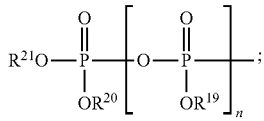

$R^{3a}$ and $R^{3b}$ can be hydrogen; $R^4$ can be hydrogen; $R^5$ can be hydrogen; $R^6$ can be $-OR^{12}$ or $-OC(=O)R^{13}$; $R^7$ can be selected from halogen, $-OR^{14}$ and $-OC(=O)R^{15}$; $R^8$ can be an optionally substituted $C_{1-6}$ alkyl; $R^9$ can be hydrogen; $R^{12}$ and $R^{14}$ can be independently hydrogen or an optionally substituted $C_{1-6}$ alkyl; and $R^{13}$ and $R^{15}$ can be independently an optionally substituted $C_{1-6}$ alkyl.

Some embodiments relate to a compound of Formula (I) or a pharmaceutically acceptable salt thereof, wherein: $B^1$ can be an optionally substituted heterocyclic base or an optionally substituted heterocyclic base with a protected amino group; $R^1$ can be selected from $O^-$, OH, an optionally substituted N-linked amino acid and an optionally substituted N-linked amino acid ester derivative; $R^2$ can be selected from an optionally substituted aryl, an optionally substituted heteroaryl, an optionally substituted heterocyclyl and

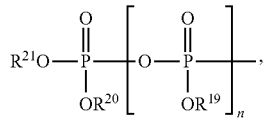

wherein $R^{19}$, $R^{20}$ and $R^{21}$ can be independently absent or hydrogen, and n can be 0 or 1; provided that when $R^1$ is $O^-$ or OH, then $R^2$ is

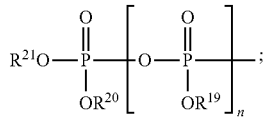

$R^{3a}$ and $R^{3b}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{3a}$ and $R^{3b}$ can be taken together to form an optionally substituted $C_{3-6}$ cycloalkyl; $R^4$ can be selected from hydrogen, azido, an optionally substituted $C_{1-6}$ alkyl, an optionally substituted $C_{2-6}$ alkenyl and an optionally substituted $C_{2-6}$ alkynyl; $R^5$ can be selected from hydrogen, halogen, azido, cyano, an optionally substituted $C_{1-6}$ alkyl, $-OR^{10}$ and $-OC(=O)R^{11}$; $R^6$ can be selected from hydrogen, halogen, azido, cyano, an optionally substituted $C_{1-6}$ alkyl, $-OR^{12}$ and $-OC(=O)R^{13}$; $R^7$ can be selected from hydrogen, halogen, azido, cyano, an optionally substituted $C_{1-6}$ alkyl, $-OR^{14}$ and $-OC(=O)R^{15}$; or $R^6$ and $R^7$ can be both oxygen atoms and linked together by a carbonyl group; $R^8$ can be selected from hydrogen, halogen, azido, cyano, an optionally substituted $C_{1-6}$ alkyl, $-OR^{16}$ and $-OC(=O)R^{17}$; $R^9$ can be selected from hydrogen, azido, cyano, an optionally substituted $C_{1-6}$ alkyl and $-OR^{18}$; $R^{10}$, $R^{12}$, $R^{14}$, $R^{16}$ and $R^{18}$ can be independently selected from hydrogen and an optionally substituted $C_{1-6}$ alkyl; and $R^{11}$, $R^{13}$, $R^{15}$ and $R^{17}$ can be independently an optionally substituted $C_{1-6}$ alkyl and an optionally substituted $C_{3-6}$ cycloalkyl.

In some embodiments, a compound of Formula (I) can be a single diastereomer. In other embodiments, a compound of Formula (I) can be a mixture of diastereomers. In some embodiments, a compound of Formula (I) can be a 1:1 mixture of two diastereomers. In some embodiments, a compound of Formula (I) can be diasteriometrically enriched (for example, one diastereomer can be present at a concentration of <55%, ≥75%, ≥80%, ≥90%, ≥95%, ≥98%, or ≥99% as compared to the total concentration of the other diastereomers).

Some embodiments of $R^1$ and $R^2$ of a compound of Formula (I), or a pharmaceutically acceptable salt thereof, are provided in Table 1. Tables 2-4 provide the structures of the variables bb01-bb12, aa01-aa11 and es01-es14, respectively. For example, the first entry in Table 1 is "bb01,aa01,es01," corresponds to a compound of Formula (I), wherein R² is

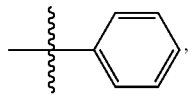

and R¹ is

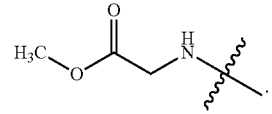

TABLE 1

| $R^2, R^1, R_\alpha$ | $R^2, R^1, R_\alpha$ | $R^2, R^1, R_\alpha$ | $R^2, R^1, R_\alpha$ | $R^2, R^1, R_\alpha$ |
|---|---|---|---|---|
| bb01,aa01,es01 | bb01,aa02,es01 | bb01,aa03,es01 | bb01,aa04,es01 | bb01,aa05,es01 |
| bb01,aa01,es02 | bb01,aa02,es02 | bb01,aa03,es02 | bb01,aa04,es02 | bb01,aa05,es02 |
| bb01,aa01,es03 | bb01,aa02,es03 | bb01,aa03,es03 | bb01,aa04,es03 | bb01,aa05,es03 |
| bb01,aa01,es04 | bb01,aa02,es04 | bb01,aa03,es04 | bb01,aa04,es04 | bb01,aa05,es04 |
| bb01,aa01,es05 | bb01,aa02,es05 | bb01,aa03,es05 | bb01,aa04,es05 | bb01,aa05,es05 |
| bb01,aa01,es06 | bb01,aa02,es06 | bb01,aa03,es06 | bb01,aa04,es06 | bb01,aa05,es06 |
| bb01,aa01,es07 | bb01,aa02,es07 | bb01,aa03,es07 | bb01,aa04,es07 | bb01,aa05,es07 |
| bb01,aa01,es08 | bb01,aa02,es08 | bb01,aa03,es08 | bb01,aa04,es08 | bb01,aa05,es08 |
| bb01,aa01,es09 | bb01,aa02,es09 | bb01,aa03,es09 | bb01,aa04,es09 | bb01,aa05,es09 |
| bb01,aa01,es10 | bb01,aa02,es10 | bb01,aa03,es10 | bb01,aa04,es10 | bb01,aa05,es10 |
| bb01,aa01,es11 | bb01,aa02,es11 | bb01,aa03,es11 | bb01,aa04,es11 | bb01,aa05,es11 |
| bb01,aa01,es12 | bb01,aa02,es12 | bb01,aa03,es12 | bb01,aa04,es12 | bb01,aa05,es12 |
| bb01,aa06,es01 | bb01,aa07,es01 | bb01,aa08,es01 | bb01,aa09,es01 | bb01,aa10,es01 |
| bb01,aa06,es02 | bb01,aa07,es02 | bb01,aa08,es02 | bb01,aa09,es02 | bb01,aa10,es02 |
| bb01,aa06,es03 | bb01,aa07,es03 | bb01,aa08,es03 | bb01,aa09,es03 | bb01,aa10,es03 |
| bb01,aa06,es04 | bb01,aa07,es04 | bb01,aa08,es04 | bb01,aa09,es04 | bb01,aa10,es04 |
| bb01,aa06,es05 | bb01,aa07,es05 | bb01,aa08,es05 | bb01,aa09,es05 | bb01,aa10,es05 |
| bb01,aa06,es06 | bb01,aa07,es06 | bb01,aa08,es06 | bb01,aa09,es06 | bb01,aa10,es06 |
| bb01,aa06,es07 | bb01,aa07,es07 | bb01,aa08,es07 | bb01,aa09,es07 | bb01,aa10,es07 |
| bb01,aa06,es08 | bb01,aa07,es08 | bb01,aa08,es08 | bb01,aa09,es08 | bb01,aa10,es08 |
| bb01,aa06,es09 | bb01,aa07,es09 | bb01,aa08,es09 | bb01,aa09,es09 | bb01,aa10,es09 |
| bb01,aa06,es10 | bb01,aa07,es10 | bb01,aa08,es10 | bb01,aa09,es10 | bb01,aa10,es10 |
| bb01,aa06,es11 | bb01,aa07,es11 | bb01,aa08,es11 | bb01,aa09,es11 | bb01,aa10,es11 |
| bb01,aa06,es12 | bb01,aa07,es12 | bb01,aa08,es12 | bb01,aa09,es12 | bb01,aa10,es12 |
| bb02,aa01,es01 | bb02,aa02,es01 | bb02,aa03,es01 | bb02,aa04,es01 | bb02,aa05,es01 |
| bb02,aa01,es02 | bb02,aa02,es02 | bb02,aa03,es02 | bb02,aa04,es02 | bb02,aa05,es02 |
| bb02,aa01,es03 | bb02,aa02,es03 | bb02,aa03,es03 | bb02,aa04,es03 | bb02,aa05,es03 |
| bb02,aa01,es04 | bb02,aa02,es04 | bb02,aa03,es04 | bb02,aa04,es04 | bb02,aa05,es04 |
| bb02,aa01,es05 | bb02,aa02,es05 | bb02,aa03,es05 | bb02,aa04,es05 | bb02,aa05,es05 |
| bb02,aa01,es06 | bb02,aa02,es06 | bb02,aa03,es06 | bb02,aa04,es06 | bb02,aa05,es06 |
| bb02,aa01,es07 | bb02,aa02,es07 | bb02,aa03,es07 | bb02,aa04,es07 | bb02,aa05,es07 |
| bb02,aa01,es08 | bb02,aa02,es08 | bb02,aa03,es08 | bb02,aa04,es08 | bb02,aa05,es08 |
| bb02,aa01,es09 | bb02,aa02,es09 | bb02,aa03,es09 | bb02,aa04,es09 | bb02,aa05,es09 |
| bb02,aa01,es10 | bb02,aa02,es10 | bb02,aa03,es10 | bb02,aa04,es10 | bb02,aa05,es10 |
| bb02,aa01,es11 | bb02,aa02,es11 | bb02,aa03,es11 | bb02,aa04,es11 | bb02,aa05,es11 |
| bb02,aa01,es12 | bb02,aa02,es12 | bb02,aa03,es12 | bb02,aa04,es12 | bb02,aa05,es12 |
| bb02,aa06,es01 | bb02,aa07,es01 | bb02,aa08,es01 | bb02,aa09,es01 | bb02,aa10,es01 |
| bb02,aa06,es02 | bb02,aa07,es02 | bb02,aa08,es02 | bb02,aa09,es02 | bb02,aa10,es02 |
| bb02,aa06,es03 | bb02,aa07,es03 | bb02,aa08,es03 | bb02,aa09,es03 | bb02,aa10,es03 |
| bb02,aa06,es04 | bb02,aa07,es04 | bb02,aa08,es04 | bb02,aa09,es04 | bb02,aa10,es04 |
| bb02,aa06,es05 | bb02,aa07,es05 | bb02,aa08,es05 | bb02,aa09,es05 | bb02,aa10,es05 |
| bb02,aa06,es06 | bb02,aa07,es06 | bb02,aa08,es06 | bb02,aa09,es06 | bb02,aa10,es06 |
| bb02,aa06,es07 | bb02,aa07,es07 | bb02,aa08,es07 | bb02,aa09,es07 | bb02,aa10,es07 |
| bb02,aa06,es08 | bb02,aa07,es08 | bb02,aa08,es08 | bb02,aa09,es08 | bb02,aa10,es08 |
| bb02,aa06,es09 | bb02,aa07,es09 | bb02,aa08,es09 | bb02,aa09,es09 | bb02,aa10,es09 |
| bb02,aa06,es10 | bb02,aa07,es10 | bb02,aa08,es10 | bb02,aa09,es10 | bb02,aa10,es10 |
| bb02,aa06,es11 | bb02,aa07,es11 | bb02,aa08,es11 | bb02,aa09,es11 | bb02,aa10,es11 |
| bb02,aa06,es12 | bb02,aa07,es12 | bb02,aa08,es12 | bb02,aa09,es12 | bb02,aa10,es12 |
| bb03,aa03,es01 | bb03,aa04,es01 | bb03,aa05,es01 | bb03,aa06,es01 | bb03,aa07,es01 |
| bb03,aa03,es02 | bb03,aa04,es02 | bb03,aa05,es02 | bb03,aa06,es02 | bb03,aa07,es02 |
| bb03,aa03,es03 | bb03,aa04,es03 | bb03,aa05,es03 | bb03,aa06,es03 | bb03,aa07,es03 |
| bb03,aa03,es04 | bb03,aa04,es04 | bb03,aa05,es04 | bb03,aa06,es04 | bb03,aa07,es04 |
| bb03,aa03,es05 | bb03,aa04,es05 | bb03,aa05,es05 | bb03,aa06,es05 | bb03,aa07,es05 |
| bb03,aa03,es06 | bb03,aa04,es06 | bb03,aa05,es06 | bb03,aa06,es06 | bb03,aa07,es06 |
| bb03,aa03,es07 | bb03,aa04,es07 | bb03,aa05,es07 | bb03,aa06,es07 | bb03,aa07,es07 |
| bb03,aa03,es08 | bb03,aa04,es08 | bb03,aa05,es08 | bb03,aa06,es08 | bb03,aa07,es08 |
| bb03,aa03,es09 | bb03,aa04,es09 | bb03,aa05,es09 | bb03,aa06,es09 | bb03,aa07,es09 |
| bb03,aa03,es10 | bb03,aa04,es10 | bb03,aa05,es10 | bb03,aa06,es10 | bb03,aa07,es10 |
| bb03,aa03,es11 | bb03,aa04,es11 | bb03,aa05,es11 | bb03,aa06,es11 | bb03,aa07,es11 |
| bb03,aa03,es12 | bb03,aa04,es12 | bb03,aa05,es12 | bb03,aa06,es12 | bb03,aa07,es12 |

TABLE 1-continued

| $R^2, R^1, R_\alpha$ | $R^2, R^1, R_\alpha$ | $R^2, R^1, R_\alpha$ | $R^2, R^1, R_\alpha$ | $R^2, R^1, R_\alpha$ |
|---|---|---|---|---|
| bb03,aa08,es01 | bb03,aa09,es01 | bb03,aa10,es01 | bb04,aa01,es01 | bb04,aa02,es01 |
| bb03,aa08,es02 | bb03,aa09,es02 | bb03,aa10,es02 | bb04,aa01,es02 | bb04,aa02,es02 |
| bb03,aa08,es03 | bb03,aa09,es03 | bb03,aa10,es03 | bb04,aa01,es03 | bb04,aa02,es03 |
| bb03,aa08,es04 | bb03,aa09,es04 | bb03,aa10,es04 | bb04,aa01,es04 | bb04,aa02,es04 |
| bb03,aa08,es05 | bb03,aa09,es05 | bb03,aa10,es05 | bb04,aa01,es05 | bb04,aa02,es05 |
| bb03,aa08,es06 | bb03,aa09,es06 | bb03,aa10,es06 | bb04,aa01,es06 | bb04,aa02,es06 |
| bb03,aa08,es07 | bb03,aa09,es07 | bb03,aa10,es07 | bb04,aa01,es07 | bb04,aa02,es07 |
| bb03,aa08,es08 | bb03,aa09,es08 | bb03,aa10,es08 | bb04,aa01,es08 | bb04,aa02,es08 |
| bb03,aa08,es09 | bb03,aa09,es09 | bb03,aa10,es09 | bb04,aa01,es09 | bb04,aa02,es09 |
| bb03,aa08,es10 | bb03,aa09,es10 | bb03,aa10,es10 | bb04,aa01,es10 | bb04,aa02,es10 |
| bb03,aa08,es11 | bb03,aa09,es11 | bb03,aa10,es11 | bb04,aa01,es11 | bb04,aa02,es11 |
| bb03,aa08,es12 | bb03,aa09,es12 | bb03,aa10,es12 | bb04,aa01,es12 | bb04,aa02,es12 |
| bb04,aa03,es01 | bb04,aa04,es01 | bb04,aa05,es01 | bb04,aa06,es01 | bb04,aa07,es01 |
| bb04,aa03,es02 | bb04,aa04,es02 | bb04,aa05,es02 | bb04,aa06,es02 | bb04,aa07,es02 |
| bb04,aa03,es03 | bb04,aa04,es03 | bb04,aa05,es03 | bb04,aa06,es03 | bb04,aa07,es03 |
| bb04,aa03,es04 | bb04,aa04,es04 | bb04,aa05,es04 | bb04,aa06,es04 | bb04,aa07,es04 |
| bb04,aa03,es05 | bb04,aa04,es05 | bb04,aa05,es05 | bb04,aa06,es05 | bb04,aa07,es05 |
| bb04,aa03,es06 | bb04,aa04,es06 | bb04,aa05,es06 | bb04,aa06,es06 | bb04,aa07,es06 |
| bb04,aa03,es07 | bb04,aa04,es07 | bb04,aa05,es07 | bb04,aa06,es07 | bb04,aa07,es07 |
| bb04,aa03,es08 | bb04,aa04,es08 | bb04,aa05,es08 | bb04,aa06,es08 | bb04,aa07,es08 |
| bb04,aa03,es09 | bb04,aa04,es09 | bb04,aa05,es09 | bb04,aa06,es09 | bb04,aa07,es09 |
| bb04,aa03,es10 | bb04,aa04,es10 | bb04,aa05,es10 | bb04,aa06,es10 | bb04,aa07,es10 |
| bb04,aa03,es11 | bb04,aa04,es11 | bb04,aa05,es11 | bb04,aa06,es11 | bb04,aa07,es11 |
| bb04,aa03,es12 | bb04,aa04,es12 | bb04,aa05,es12 | bb04,aa06,es12 | bb04,aa07,es12 |
| bb04,aa08,es01 | bb04,aa09,es01 | bb04,aa10,es01 | bb05,aa01,es01 | bb05,aa02,es01 |
| bb04,aa08,es02 | bb04,aa09,es02 | bb04,aa10,es02 | bb05,aa01,es02 | bb05,aa02,es02 |
| bb04,aa08,es03 | bb04,aa09,es03 | bb04,aa10,es03 | bb05,aa01,es03 | bb05,aa02,es03 |
| bb04,aa08,es04 | bb04,aa09,es04 | bb04,aa10,es04 | bb05,aa01,es04 | bb05,aa02,es04 |
| bb04,aa08,es05 | bb04,aa09,es05 | bb04,aa10,es05 | bb05,aa01,es05 | bb05,aa02,es05 |
| bb04,aa08,es06 | bb04,aa09,es06 | bb04,aa10,es06 | bb05,aa01,es06 | bb05,aa02,es06 |
| bb04,aa08,es07 | bb04,aa09,es07 | bb04,aa10,es07 | bb05,aa01,es07 | bb05,aa02,es07 |
| bb04,aa08,es08 | bb04,aa09,es08 | bb04,aa10,es08 | bb05,aa01,es08 | bb05,aa02,es08 |
| bb04,aa08,es09 | bb04,aa09,es09 | bb04,aa10,es09 | bb05,aa01,es09 | bb05,aa02,es09 |
| bb04,aa08,es10 | bb04,aa09,es10 | bb04,aa10,es10 | bb05,aa01,es10 | bb05,aa02,es10 |
| bb04,aa08,es11 | bb04,aa09,es11 | bb04,aa10,es11 | bb05,aa01,es11 | bb05,aa02,es11 |
| bb04,aa08,es12 | bb04,aa09,es12 | bb04,aa10,es12 | bb05,aa01,es12 | bb05,aa02,es12 |
| bb05,aa03,es01 | bb05,aa04,es01 | bb05,aa05,es01 | bb05,aa06,es01 | bb05,aa07,es01 |
| bb05,aa03,es02 | bb05,aa04,es02 | bb05,aa05,es02 | bb05,aa06,es02 | bb05,aa07,es02 |
| bb05,aa03,es03 | bb05,aa04,es03 | bb05,aa05,es03 | bb05,aa06,es03 | bb05,aa07,es03 |
| bb05,aa03,es04 | bb05,aa04,es04 | bb05,aa05,es04 | bb05,aa06,es04 | bb05,aa07,es04 |
| bb05,aa03,es05 | bb05,aa04,es05 | bb05,aa05,es05 | bb05,aa06,es05 | bb05,aa07,es05 |
| bb05,aa03,es06 | bb05,aa04,es06 | bb05,aa05,es06 | bb05,aa06,es06 | bb05,aa07,es06 |
| bb05,aa03,es07 | bb05,aa04,es07 | bb05,aa05,es07 | bb05,aa06,es07 | bb05,aa07,es07 |
| bb05,aa03,es08 | bb05,aa04,es08 | bb05,aa05,es08 | bb05,aa06,es08 | bb05,aa07,es08 |
| bb05,aa03,es09 | bb05,aa04,es09 | bb05,aa05,es09 | bb05,aa06,es09 | bb05,aa07,es09 |
| bb05,aa03,es10 | bb05,aa04,es10 | bb05,aa05,es10 | bb05,aa06,es10 | bb05,aa07,es10 |
| bb05,aa03,es11 | bb05,aa04,es11 | bb05,aa05,es11 | bb05,aa06,es11 | bb05,aa07,es11 |
| bb05,aa03,es12 | bb05,aa04,es12 | bb05,aa05,es12 | bb05,aa06,es12 | bb05,aa07,es12 |
| bb05,aa08,es01 | bb05,aa09,es01 | bb05,aa10,es01 | bb06,aa01,es01 | bb06,aa02,es01 |
| bb05,aa08,es02 | bb05,aa09,es02 | bb05,aa10,es02 | bb06,aa01,es02 | bb06,aa02,es02 |
| bb05,aa08,es03 | bb05,aa09,es03 | bb05,aa10,es03 | bb06,aa01,es03 | bb06,aa02,es03 |
| bb05,aa08,es04 | bb05,aa09,es04 | bb05,aa10,es04 | bb06,aa01,es04 | bb06,aa02,es04 |
| bb05,aa08,es05 | bb05,aa09,es05 | bb05,aa10,es05 | bb06,aa01,es05 | bb06,aa02,es05 |
| bb05,aa08,es06 | bb05,aa09,es06 | bb05,aa10,es06 | bb06,aa01,es06 | bb06,aa02,es06 |
| bb05,aa08,es07 | bb05,aa09,es07 | bb05,aa10,es07 | bb06,aa01,es07 | bb06,aa02,es07 |
| bb05,aa08,es08 | bb05,aa09,es08 | bb05,aa10,es08 | bb06,aa01,es08 | bb06,aa02,es08 |
| bb05,aa08,es09 | bb05,aa09,es09 | bb05,aa10,es09 | bb06,aa01,es09 | bb06,aa02,es09 |
| bb05,aa08,es10 | bb05,aa09,es10 | bb05,aa10,es10 | bb06,aa01,es10 | bb06,aa02,es10 |
| bb05,aa08,es11 | bb05,aa09,es11 | bb05,aa10,es11 | bb06,aa01,es11 | bb06,aa02,es11 |
| bb05,aa08,es12 | bb05,aa09,es12 | bb05,aa10,es12 | bb06,aa01,es12 | bb06,aa02,es12 |
| bb06,aa03,es01 | bb06,aa04,es01 | bb06,aa05,es01 | bb06,aa06,es01 | bb06,aa07,es01 |
| bb06,aa03,es02 | bb06,aa04,es02 | bb06,aa05,es02 | bb06,aa06,es02 | bb06,aa07,es02 |
| bb06,aa03,es03 | bb06,aa04,es03 | bb06,aa05,es03 | bb06,aa06,es03 | bb06,aa07,es03 |
| bb06,aa03,es04 | bb06,aa04,es04 | bb06,aa05,es04 | bb06,aa06,es04 | bb06,aa07,es04 |
| bb06,aa03,es05 | bb06,aa04,es05 | bb06,aa05,es05 | bb06,aa06,es05 | bb06,aa07,es05 |
| bb06,aa03,es06 | bb06,aa04,es06 | bb06,aa05,es06 | bb06,aa06,es06 | bb06,aa07,es06 |
| bb06,aa03,es07 | bb06,aa04,es07 | bb06,aa05,es07 | bb06,aa06,es07 | bb06,aa07,es07 |
| bb06,aa03,es08 | bb06,aa04,es08 | bb06,aa05,es08 | bb06,aa06,es08 | bb06,aa07,es08 |
| bb06,aa03,es09 | bb06,aa04,es09 | bb06,aa05,es09 | bb06,aa06,es09 | bb06,aa07,es09 |
| bb06,aa03,es10 | bb06,aa04,es10 | bb06,aa05,es10 | bb06,aa06,es10 | bb06,aa07,es10 |

TABLE 1-continued

| $R^2, R^1, R_\alpha$ | $R^2, R^1, R_\alpha$ | $R^2, R^1, R_\alpha$ | $R^2, R^1, R_\alpha$ | $R^2, R^1, R_\alpha$ |
|---|---|---|---|---|
| bb06,aa03,es11 | bb06,aa04,es11 | bb06,aa05,es11 | bb06,aa06,es11 | bb06,aa07,es11 |
| bb06,aa03,es12 | bb06,aa04,es12 | bb06,aa05,es12 | bb06,aa06,es12 | bb06,aa07,es12 |
| bb06,aa08,es01 | bb06,aa09,es01 | bb06,aa10,es01 | bb07,aa01,es01 | bb07,aa02,es01 |
| bb06,aa08,es02 | bb06,aa09,es02 | bb06,aa10,es02 | bb07,aa01,es02 | bb07,aa02,es02 |
| bb06,aa08,es03 | bb06,aa09,es03 | bb06,aa10,es03 | bb07,aa01,es03 | bb07,aa02,es03 |
| bb06,aa08,es04 | bb06,aa09,es04 | bb06,aa10,es04 | bb07,aa01,es04 | bb07,aa02,es04 |
| bb06,aa08,es05 | bb06,aa09,es05 | bb06,aa10,es05 | bb07,aa01,es05 | bb07,aa02,es05 |
| bb06,aa08,es06 | bb06,aa09,es06 | bb06,aa10,es06 | bb07,aa01,es06 | bb07,aa02,es06 |
| bb06,aa08,es07 | bb06,aa09,es07 | bb06,aa10,es07 | bb07,aa01,es07 | bb07,aa02,es07 |
| bb06,aa08,es08 | bb06,aa09,es08 | bb06,aa10,es08 | bb07,aa01,es08 | bb07,aa02,es08 |
| bb06,aa08,es09 | bb06,aa09,es09 | bb06,aa10,es09 | bb07,aa01,es09 | bb07,aa02,es09 |
| bb06,aa08,es10 | bb06,aa09,es10 | bb06,aa10,es10 | bb07,aa01,es10 | bb07,aa02,es10 |
| bb06,aa08,es11 | bb06,aa09,es11 | bb06,aa10,es11 | bb07,aa01,es11 | bb07,aa02,es11 |
| bb06,aa08,es12 | bb06,aa09,es12 | bb06,aa10,es12 | bb07,aa01,es12 | bb07,aa02,es12 |
| bb07,aa03,es01 | bb07,aa04,es01 | bb07,aa05,es01 | bb07,aa06,es01 | bb07,aa07,es01 |
| bb07,aa03,es02 | bb07,aa04,es02 | bb07,aa05,es02 | bb07,aa06,es02 | bb07,aa07,es02 |
| bb07,aa03,es03 | bb07,aa04,es03 | bb07,aa05,es03 | bb07,aa06,es03 | bb07,aa07,es03 |
| bb07,aa03,es04 | bb07,aa04,es04 | bb07,aa05,es04 | bb07,aa06,es04 | bb07,aa07,es04 |
| bb07,aa03,es05 | bb07,aa04,es05 | bb07,aa05,es05 | bb07,aa06,es05 | bb07,aa07,es05 |
| bb07,aa03,es06 | bb07,aa04,es06 | bb07,aa05,es06 | bb07,aa06,es06 | bb07,aa07,es06 |
| bb07,aa03,es07 | bb07,aa04,es07 | bb07,aa05,es07 | bb07,aa06,es07 | bb07,aa07,es07 |
| bb07,aa03,es08 | bb07,aa04,es08 | bb07,aa05,es08 | bb07,aa06,es08 | bb07,aa07,es08 |
| bb07,aa03,es09 | bb07,aa04,es09 | bb07,aa05,es09 | bb07,aa06,es09 | bb07,aa07,es09 |
| bb07,aa03,es10 | bb07,aa04,es10 | bb07,aa05,es10 | bb07,aa06,es10 | bb07,aa07,es10 |
| bb07,aa03,es11 | bb07,aa04,es11 | bb07,aa05,es11 | bb07,aa06,es11 | bb07,aa07,es11 |
| bb07,aa03,es12 | bb07,aa04,es12 | bb07,aa05,es12 | bb07,aa06,es12 | bb07,aa07,es12 |
| bb07,aa08,es01 | bb07,aa09,es01 | bb07,aa10,es01 | bb08,aa01,es01 | bb08,aa02,es01 |
| bb07,aa08,es02 | bb07,aa09,es02 | bb07,aa10,es02 | bb08,aa01,es02 | bb08,aa02,es02 |
| bb07,aa08,es03 | bb07,aa09,es03 | bb07,aa10,es03 | bb08,aa01,es03 | bb08,aa02,es03 |
| bb07,aa08,es04 | bb07,aa09,es04 | bb07,aa10,es04 | bb08,aa01,es04 | bb08,aa02,es04 |
| bb07,aa08,es05 | bb07,aa09,es05 | bb07,aa10,es05 | bb08,aa01,es05 | bb08,aa02,es05 |
| bb07,aa08,es06 | bb07,aa09,es06 | bb07,aa10,es06 | bb08,aa01,es06 | bb08,aa02,es06 |
| bb07,aa08,es07 | bb07,aa09,es07 | bb07,aa10,es07 | bb08,aa01,es07 | bb08,aa02,es07 |
| bb07,aa08,es08 | bb07,aa09,es08 | bb07,aa10,es08 | bb08,aa01,es08 | bb08,aa02,es08 |
| bb07,aa08,es09 | bb07,aa09,es09 | bb07,aa10,es09 | bb08,aa01,es09 | bb08,aa02,es09 |
| bb07,aa08,es10 | bb07,aa09,es10 | bb07,aa10,es10 | bb08,aa01,es10 | bb08,aa02,es10 |
| bb07,aa08,es11 | bb07,aa09,es11 | bb07,aa10,es11 | bb08,aa01,es11 | bb08,aa02,es11 |
| bb07,aa08,es12 | bb07,aa09,es12 | bb07,aa10,es12 | bb08,aa01,es12 | bb08,aa02,es12 |
| bb08,aa03,es01 | bb08,aa04,es01 | bb08,aa05,es01 | bb08,aa06,es01 | bb08,aa07,es01 |
| bb08,aa03,es02 | bb08,aa04,es02 | bb08,aa05,es02 | bb08,aa06,es02 | bb08,aa07,es02 |
| bb08,aa03,es03 | bb08,aa04,es03 | bb08,aa05,es03 | bb08,aa06,es03 | bb08,aa07,es03 |
| bb08,aa03,es04 | bb08,aa04,es04 | bb08,aa05,es04 | bb08,aa06,es04 | bb08,aa07,es04 |
| bb08,aa03,es05 | bb08,aa04,es05 | bb08,aa05,es05 | bb08,aa06,es05 | bb08,aa07,es05 |
| bb08,aa03,es06 | bb08,aa04,es06 | bb08,aa05,es06 | bb08,aa06,es06 | bb08,aa07,es06 |
| bb08,aa03,es07 | bb08,aa04,es07 | bb08,aa05,es07 | bb08,aa06,es07 | bb08,aa07,es07 |
| bb08,aa03,es08 | bb08,aa04,es08 | bb08,aa05,es08 | bb08,aa06,es08 | bb08,aa07,es08 |
| bb08,aa03,es09 | bb08,aa04,es09 | bb08,aa05,es09 | bb08,aa06,es09 | bb08,aa07,es09 |
| bb08,aa03,es10 | bb08,aa04,es10 | bb08,aa05,es10 | bb08,aa06,es10 | bb08,aa07,es10 |
| bb08,aa03,es11 | bb08,aa04,es11 | bb08,aa05,es11 | bb08,aa06,es11 | bb08,aa07,es11 |
| bb08,aa03,es12 | bb08,aa04,es12 | bb08,aa05,es12 | bb08,aa06,es12 | bb08,aa07,es12 |
| bb08,aa08,es01 | bb08,aa09,es01 | bb08,aa10,es01 | bb09,aa01,es01 | bb09,aa02,es01 |
| bb08,aa08,es02 | bb08,aa09,es02 | bb08,aa10,es02 | bb09,aa01,es02 | bb09,aa02,es02 |
| bb08,aa08,es03 | bb08,aa09,es03 | bb08,aa10,es03 | bb09,aa01,es03 | bb09,aa02,es03 |
| bb08,aa08,es04 | bb08,aa09,es04 | bb08,aa10,es04 | bb09,aa01,es04 | bb09,aa02,es04 |
| bb08,aa08,es05 | bb08,aa09,es05 | bb08,aa10,es05 | bb09,aa01,es05 | bb09,aa02,es05 |
| bb08,aa08,es06 | bb08,aa09,es06 | bb08,aa10,es06 | bb09,aa01,es06 | bb09,aa02,es06 |
| bb08,aa08,es07 | bb08,aa09,es07 | bb08,aa10,es07 | bb09,aa01,es07 | bb09,aa02,es07 |
| bb08,aa08,es08 | bb08,aa09,es08 | bb08,aa10,es08 | bb09,aa01,es08 | bb09,aa02,es08 |
| bb08,aa08,es09 | bb08,aa09,es09 | bb08,aa10,es09 | bb09,aa01,es09 | bb09,aa02,es09 |
| bb08,aa08,es10 | bb08,aa09,es10 | bb08,aa10,es10 | bb09,aa01,es10 | bb09,aa02,es10 |
| bb08,aa08,es11 | bb08,aa09,es11 | bb08,aa10,es11 | bb09,aa01,es11 | bb09,aa02,es11 |
| bb08,aa08,es12 | bb08,aa09,es12 | bb08,aa10,es12 | bb09,aa01,es12 | bb09,aa02,es12 |
| bb09,aa03,es01 | bb09,aa04,es01 | bb09,aa05,es01 | bb09,aa06,es01 | bb09,aa07,es01 |
| bb09,aa03,es02 | bb09,aa04,es02 | bb09,aa05,es02 | bb09,aa06,es02 | bb09,aa07,es02 |
| bb09,aa03,es03 | bb09,aa04,es03 | bb09,aa05,es03 | bb09,aa06,es03 | bb09,aa07,es03 |
| bb09,aa03,es04 | bb09,aa04,es04 | bb09,aa05,es04 | bb09,aa06,es04 | bb09,aa07,es04 |
| bb09,aa03,es05 | bb09,aa04,es05 | bb09,aa05,es05 | bb09,aa06,es05 | bb09,aa07,es05 |
| bb09,aa03,es06 | bb09,aa04,es06 | bb09,aa05,es06 | bb09,aa06,es06 | bb09,aa07,es06 |
| bb09,aa03,es07 | bb09,aa04,es07 | bb09,aa05,es07 | bb09,aa06,es07 | bb09,aa07,es07 |
| bb09,aa03,es08 | bb09,aa04,es08 | bb09,aa05,es08 | bb09,aa06,es08 | bb09,aa07,es08 |
| bb09,aa03,es09 | bb09,aa04,es09 | bb09,aa05,es09 | bb09,aa06,es09 | bb09,aa07,es09 |
| bb09,aa03,es10 | bb09,aa04,es10 | bb09,aa05,es10 | bb09,aa06,es10 | bb09,aa07,es10 |

TABLE 1-continued

| $R^2, R^1, R_\alpha$ | $R^2, R^1, R_\alpha$ | $R^2, R^1, R_\alpha$ | $R^2, R^1, R_\alpha$ | $R^2, R^1, R_\alpha$ |
|---|---|---|---|---|
| bb09,aa03,es11 | bb09,aa04,es11 | bb09,aa05,es11 | bb09,aa06,es11 | bb09,aa07,es11 |
| bb09,aa03,es12 | bb09,aa04,es12 | bb09,aa05,es12 | bb09,aa06,es12 | bb09,aa07,es12 |
| bb09,aa08,es01 | bb09,aa09,es01 | bb09,aa10,es01 | bb10,aa01,es01 | bb10,aa02,es01 |
| bb09,aa08,es02 | bb09,aa09,es02 | bb09,aa10,es02 | bb10,aa01,es02 | bb10,aa02,es02 |
| bb09,aa08,es03 | bb09,aa09,es03 | bb09,aa10,es03 | bb10,aa01,es03 | bb10,aa02,es03 |
| bb09,aa08,es04 | bb09,aa09,es04 | bb09,aa10,es04 | bb10,aa01,es04 | bb10,aa02,es04 |
| bb09,aa08,es05 | bb09,aa09,es05 | bb09,aa10,es05 | bb10,aa01,es05 | bb10,aa02,es05 |
| bb09,aa08,es06 | bb09,aa09,es06 | bb09,aa10,es06 | bb10,aa01,es06 | bb10,aa02,es06 |
| bb09,aa08,es07 | bb09,aa09,es07 | bb09,aa10,es07 | bb10,aa01,es07 | bb10,aa02,es07 |
| bb09,aa08,es08 | bb09,aa09,es08 | bb09,aa10,es08 | bb10,aa01,es08 | bb10,aa02,es08 |
| bb09,aa08,es09 | bb09,aa09,es09 | bb09,aa10,es09 | bb10,aa01,es09 | bb10,aa02,es09 |
| bb09,aa08,es10 | bb09,aa09,es10 | bb09,aa10,es10 | bb10,aa01,es10 | bb10,aa02,es10 |
| bb09,aa08,es11 | bb09,aa09,es11 | bb09,aa10,es11 | bb10,aa01,es11 | bb10,aa02,es11 |
| bb09,aa08,es12 | bb09,aa09,es12 | bb09,aa10,es12 | bb10,aa01,es12 | bb10,aa02,es12 |
| bb10,aa03,es01 | bb10,aa04,es01 | bb10,aa05,es01 | bb10,aa06,es01 | bb10,aa07,es01 |
| bb10,aa03,es02 | bb10,aa04,es02 | bb10,aa05,es02 | bb10,aa06,es02 | bb10,aa07,es02 |
| bb10,aa03,es03 | bb10,aa04,es03 | bb10,aa05,es03 | bb10,aa06,es03 | bb10,aa07,es03 |
| bb10,aa03,es04 | bb10,aa04,es04 | bb10,aa05,es04 | bb10,aa06,es04 | bb10,aa07,es04 |
| bb10,aa03,es05 | bb10,aa04,es05 | bb10,aa05,es05 | bb10,aa06,es05 | bb10,aa07,es05 |
| bb10,aa03,es06 | bb10,aa04,es06 | bb10,aa05,es06 | bb10,aa06,es06 | bb10,aa07,es06 |
| bb10,aa03,es07 | bb10,aa04,es07 | bb10,aa05,es07 | bb10,aa06,es07 | bb10,aa07,es07 |
| bb10,aa03,es08 | bb10,aa04,es08 | bb10,aa05,es08 | bb10,aa06,es08 | bb10,aa07,es08 |
| bb10,aa03,es09 | bb10,aa04,es09 | bb10,aa05,es09 | bb10,aa06,es09 | bb10,aa07,es09 |
| bb10,aa03,es10 | bb10,aa04,es10 | bb10,aa05,es10 | bb10,aa06,es10 | bb10,aa07,es10 |
| bb10,aa03,es11 | bb10,aa04,es11 | bb10,aa05,es11 | bb10,aa06,es11 | bb10,aa07,es11 |
| bb10,aa03,es12 | bb10,aa04,es12 | bb10,aa05,es12 | bb10,aa06,es12 | bb10,aa07,es12 |
| bb10,aa08,es01 | bb10,aa09,es01 | bb10,aa10,es01 | | |
| bb10,aa08,es02 | bb10,aa09,es02 | bb10,aa10,es02 | | |
| bb10,aa08,es03 | bb10,aa09,es03 | bb10,aa10,es03 | | |
| bb10,aa08,es04 | bb10,aa09,es04 | bb10,aa10,es04 | | |
| bb10,aa08,es05 | bb10,aa09,es05 | bb10,aa10,es05 | | |
| bb10,aa08,es06 | bb10,aa09,es06 | bb10,aa10,es06 | | |
| bb10,aa08,es07 | bb10,aa09,es07 | bb10,aa10,es07 | | |
| bb10,aa08,es08 | bb10,aa09,es08 | bb10,aa10,es08 | | |
| bb10,aa08,es09 | bb10,aa09,es09 | bb10,aa10,es09 | | |
| bb10,aa08,es10 | bb10,aa09,es10 | bb10,aa10,es10 | | |
| bb10,aa08,es11 | bb10,aa09,es11 | bb10,aa10,es11 | | |
| bb10,aa08,es12 | bb10,aa09,es12 | bb10,aa10,es12 | | |

TABLE 2

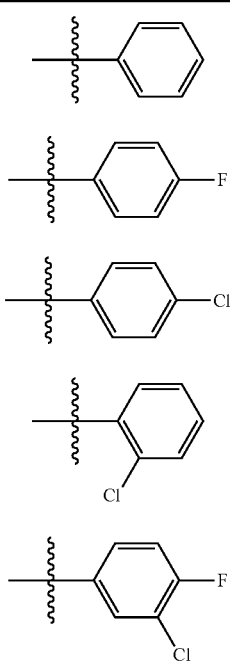
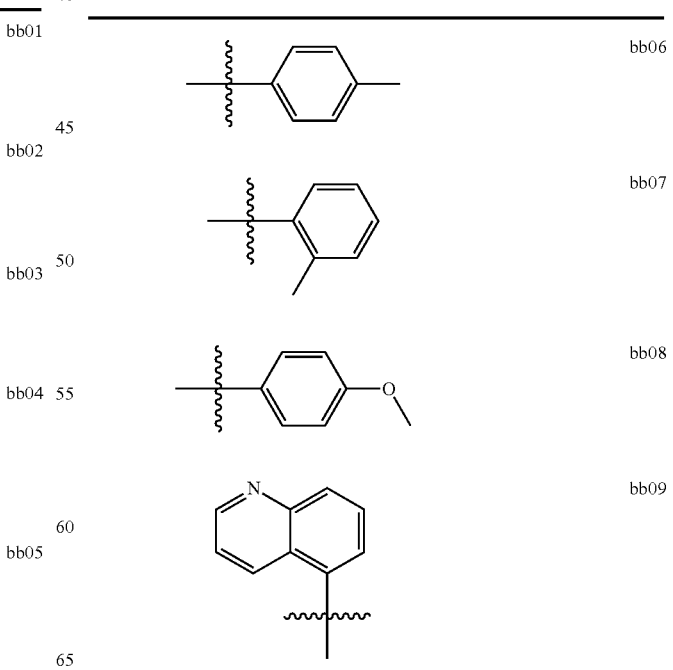

TABLE 2-continued

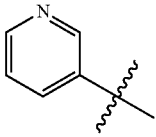 [SMILES: *c1cccnc1]
bb10

TABLE 3

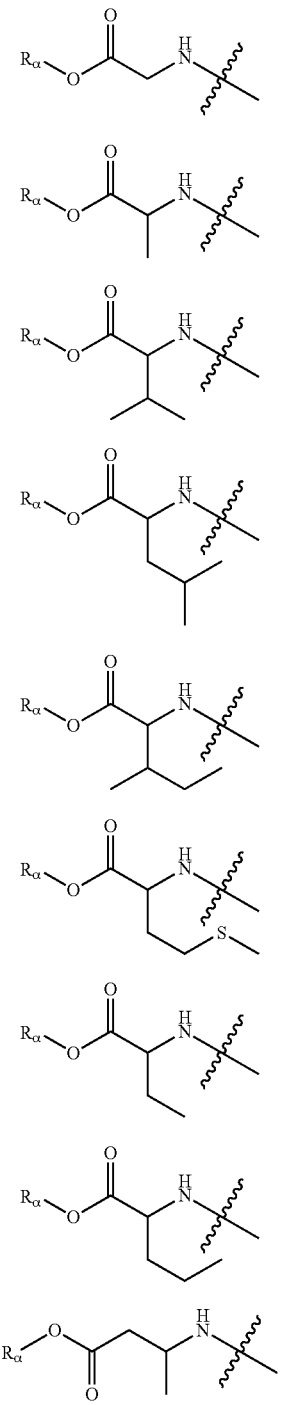

aa01
aa02
aa03
aa04
aa05
aa06
aa07
aa08
aa09

TABLE 3-continued

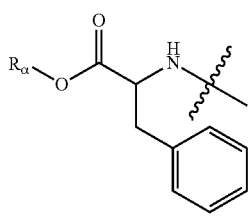
aa10

TABLE 4

| | | |
|---|---|---|
| es01 $R_\alpha$ = methyl | es02 $R_\alpha$ = ethyl | es03 $R_\alpha$ = isopropyl |
| es04 $R_\alpha$ = propyl | es05 $R_\alpha$ = cyclohexyl | es06 $R_\alpha$ = cyclopentyl |
| es07 $R_\alpha$ = cyclobutyl | es08 $R_\alpha$ = cyclopropyl | es09 $R_\alpha$ = benzyl |
| es11 $R_\alpha$ = neopentyl | es10 $R_\alpha$ = t-butyl | es12 $R_\alpha$ = hydrogen |

In some embodiments, $R^{3a}$, $R^{3b}$, $R^4$, $R^5$ and $R^9$ can be all hydrogens in any of the embodiments described in Table 1. In some embodiments, at least one of $R^6$ and $R^7$ can be OH in any of the embodiments described in Table 1. In some embodiments, $R^8$ can be a $C_{1-6}$ alkyl in any of the embodiments described in Table 1. In some embodiments, $B^1$ can be adenine, guanine, uracil, thymine or cystine in any of the embodiments described in Table 1. In some embodiments, $R^{3a}$, $R^{3b}$, $R^4$, $R^5$, $R^6$, $R^7$, $R^8$, $R^9$ and $B^1$ can be the groups provided with respect to Formula (Iα) in any of the embodiments described in Table 1.

Examples of compounds of Formula (I) include, but are not limited to the following:

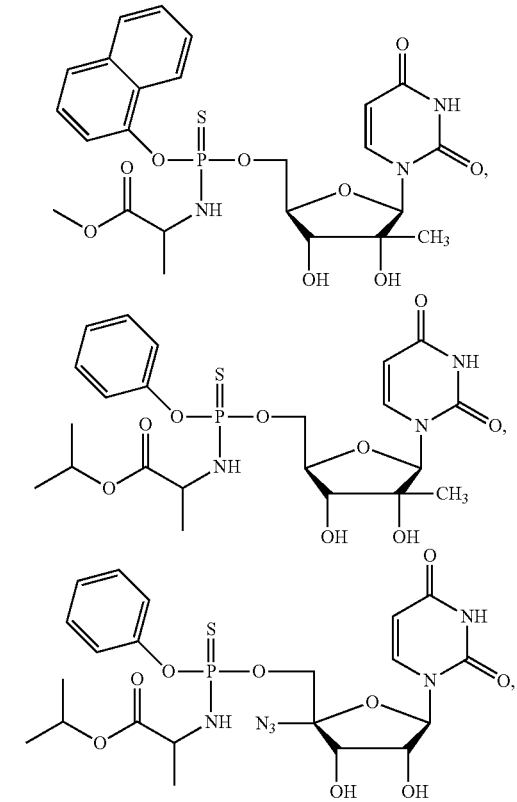

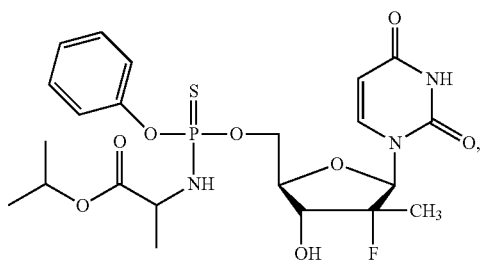
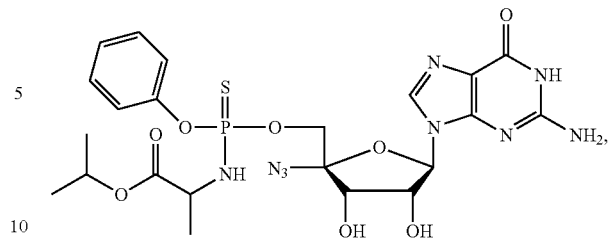
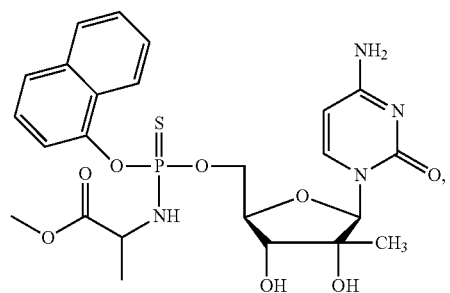
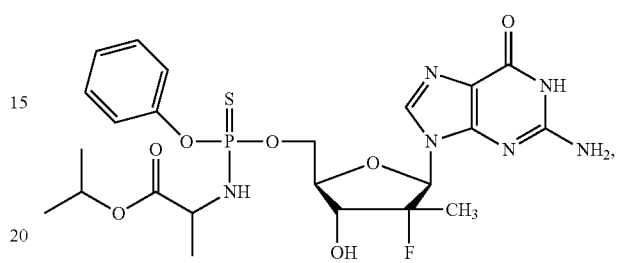
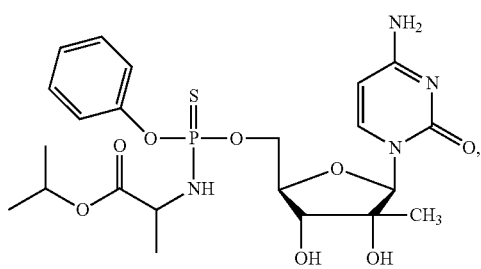
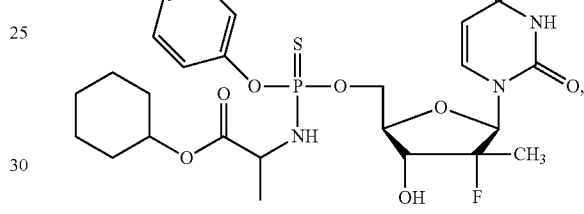
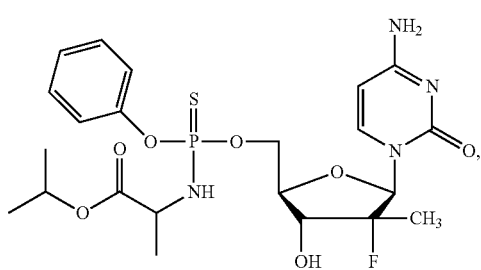
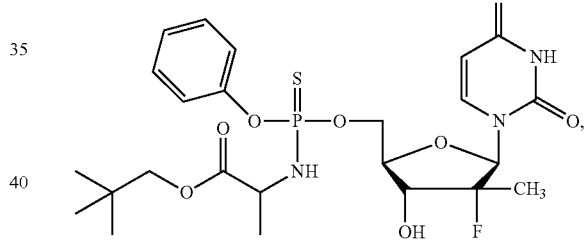
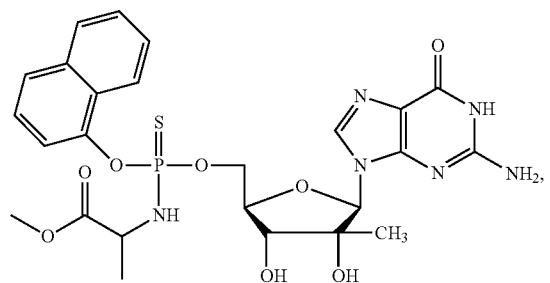
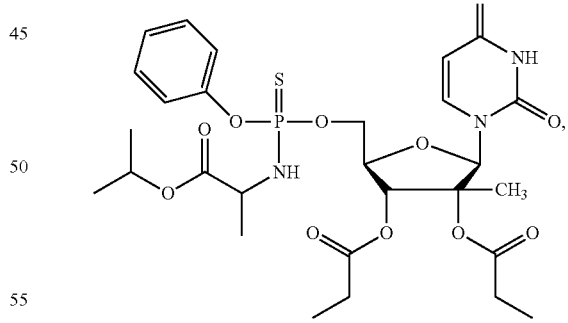
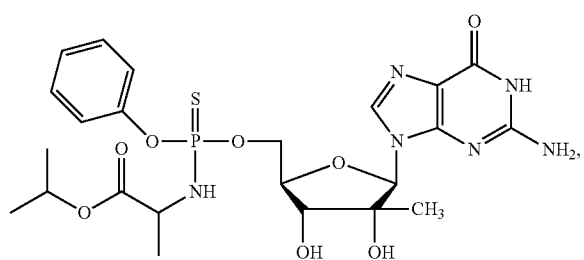
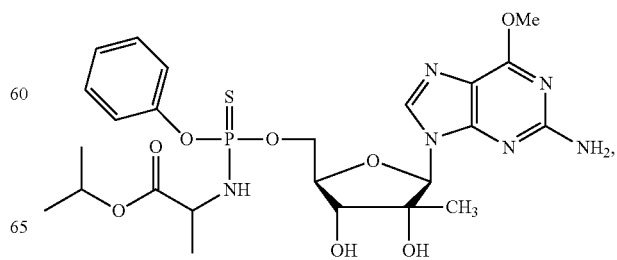

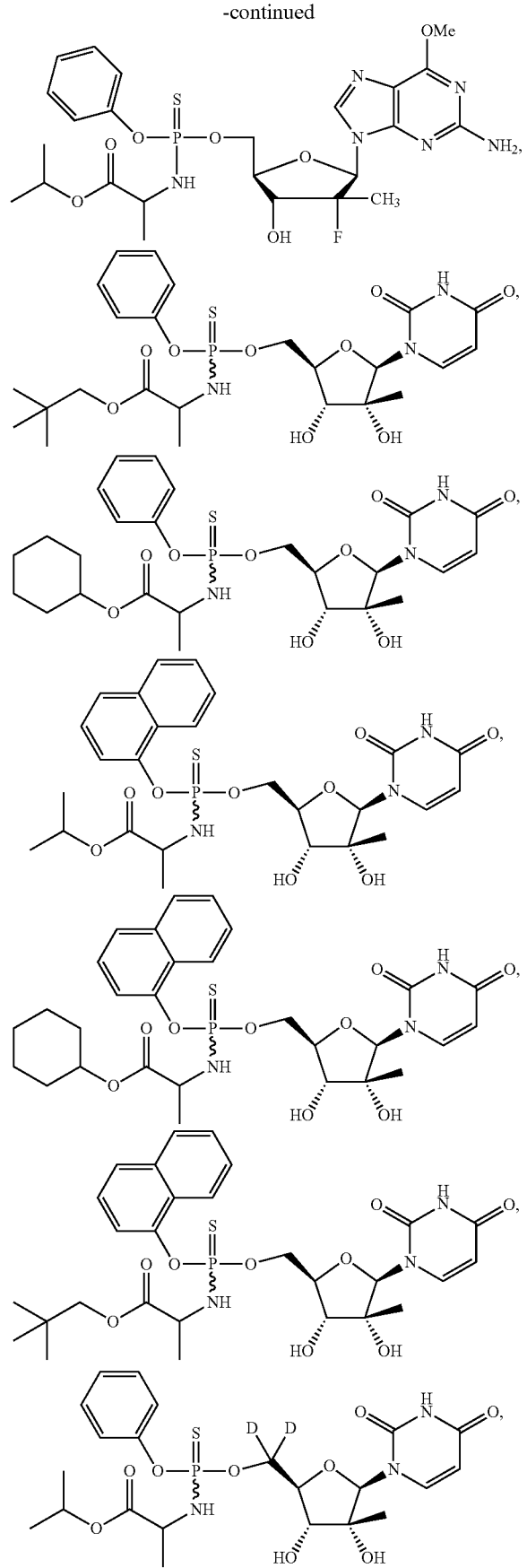
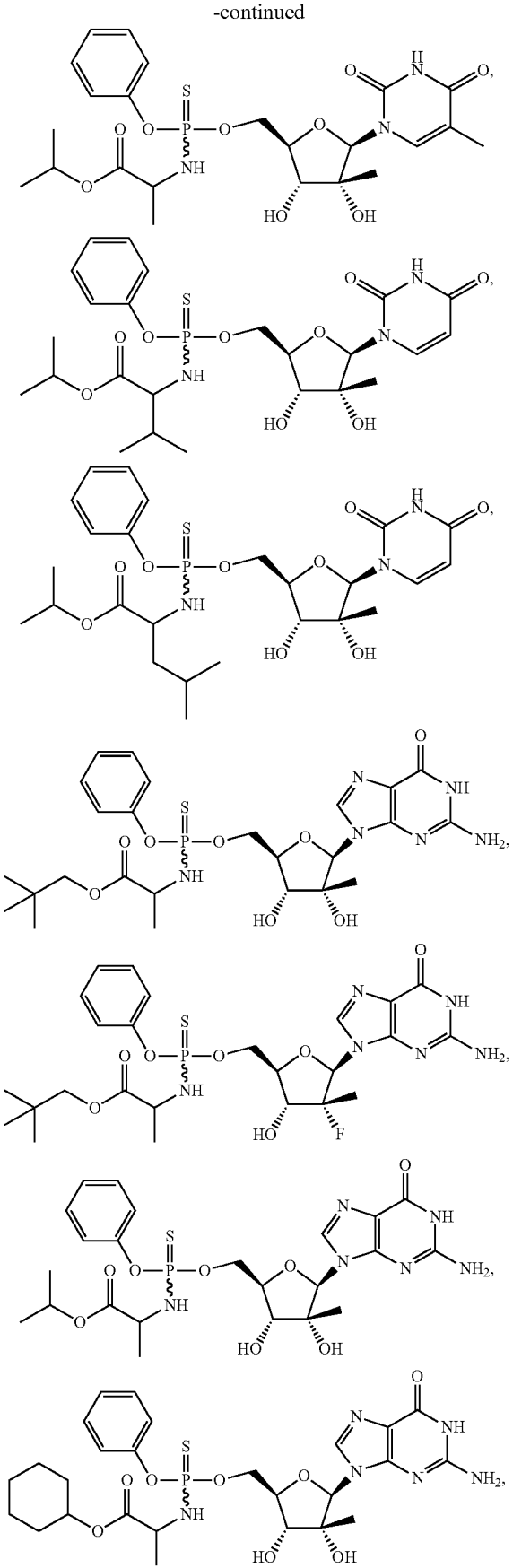

41
-continued
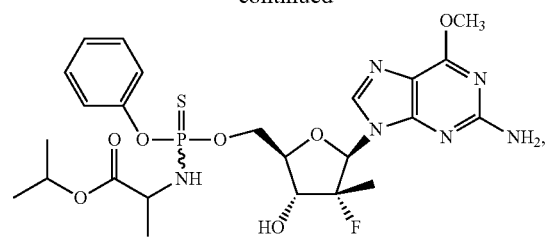
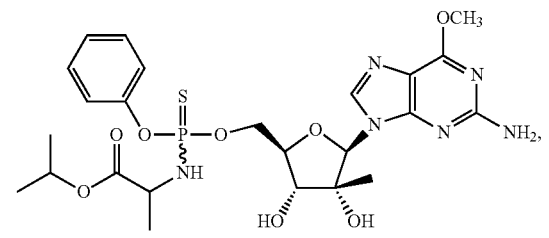
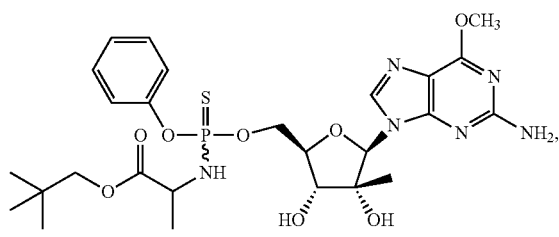
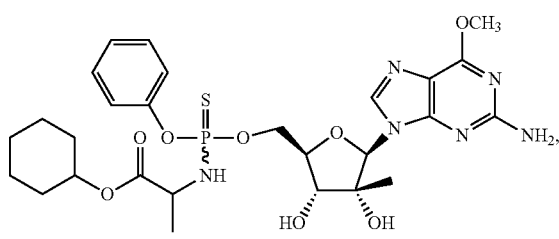
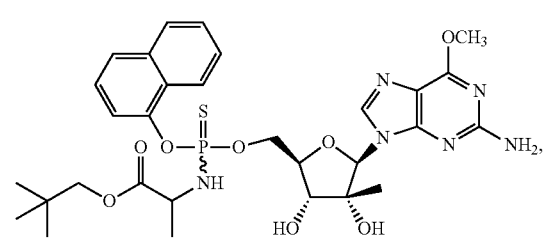
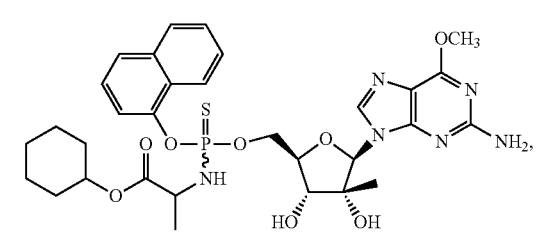
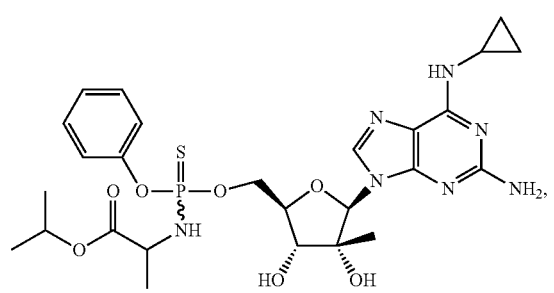
42
-continued
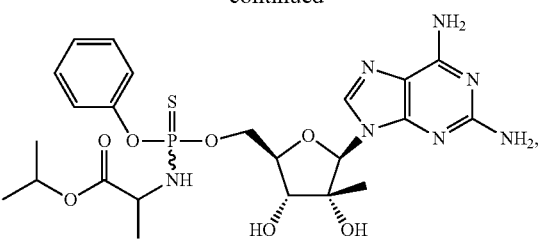
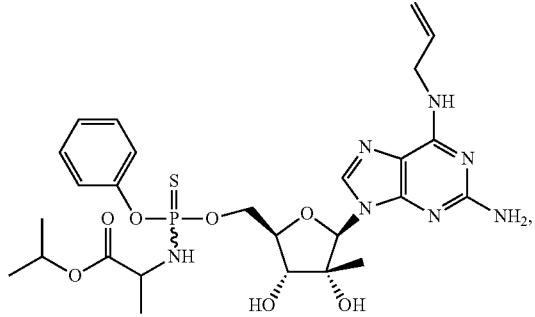
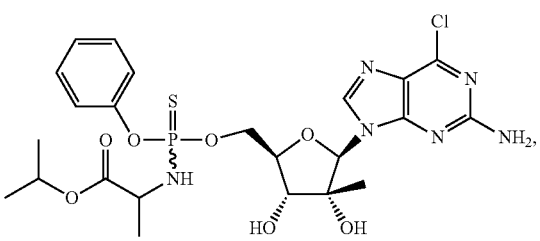
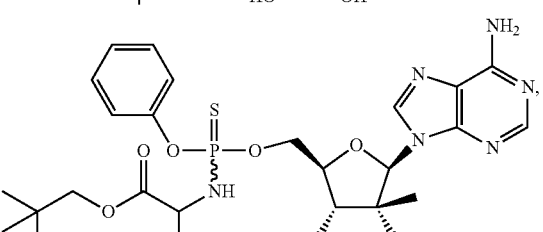
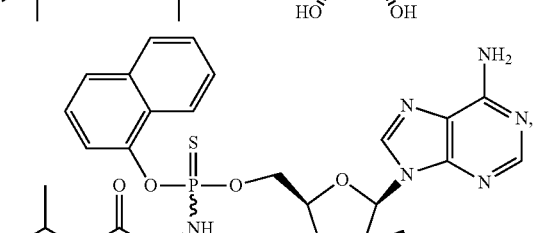
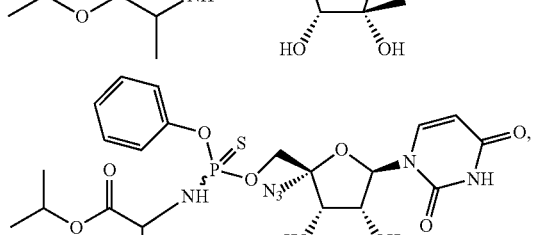
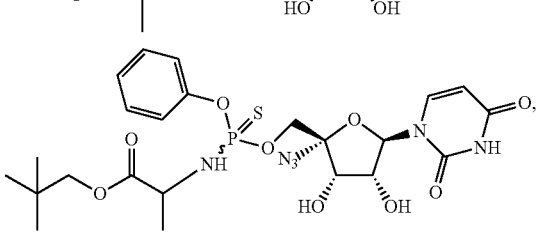

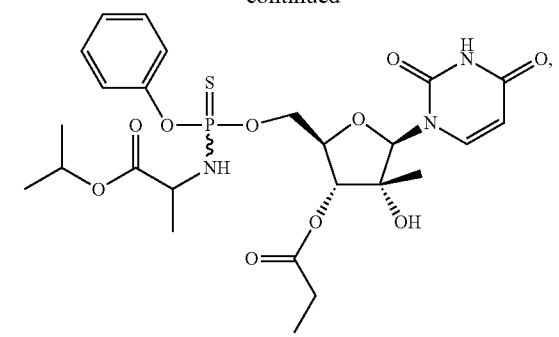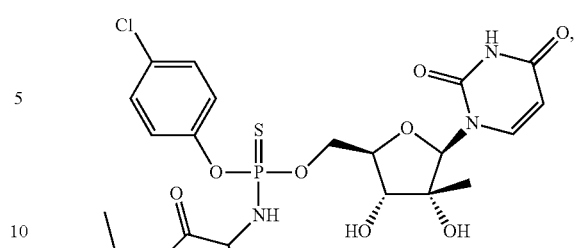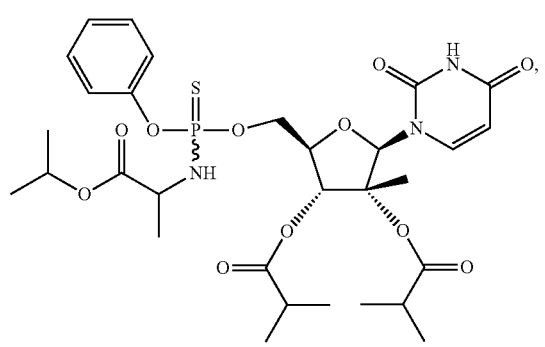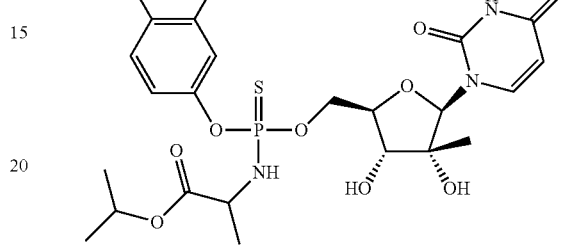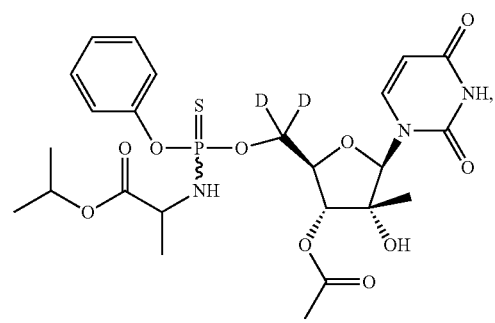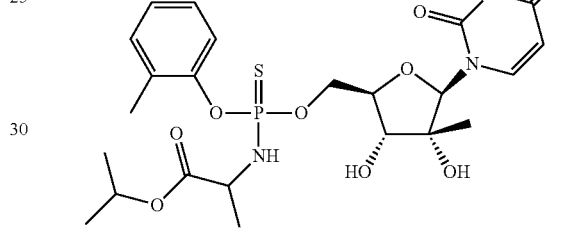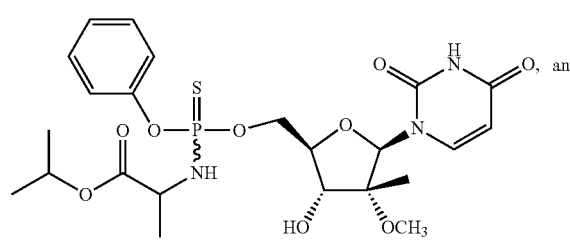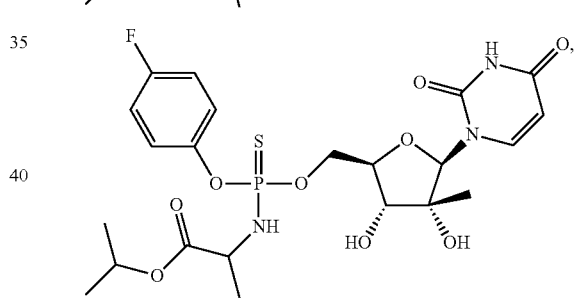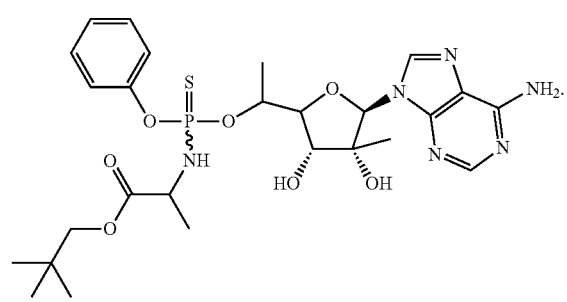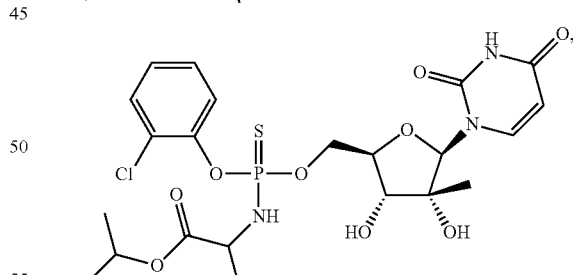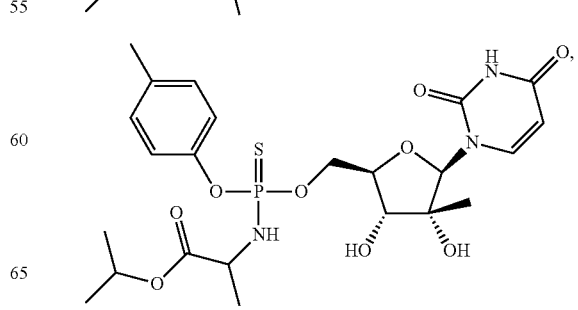
Additional examples of compounds of Formula (I) include, but are not limited to the following:

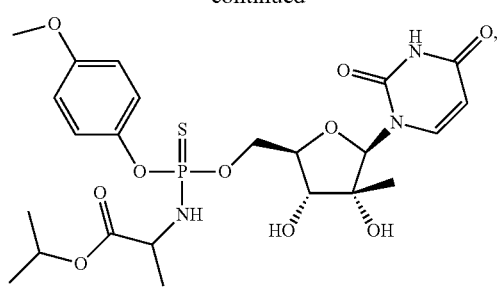
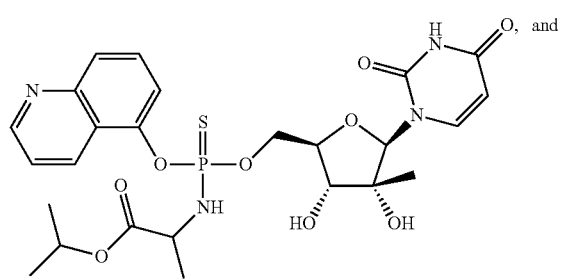
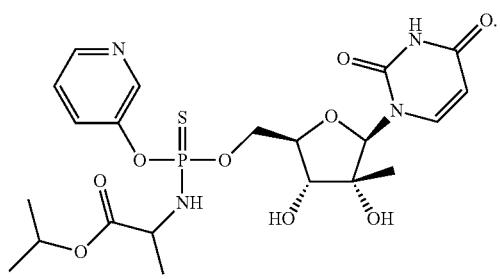
In some embodiments, the compound of Formula (I) can be the following:
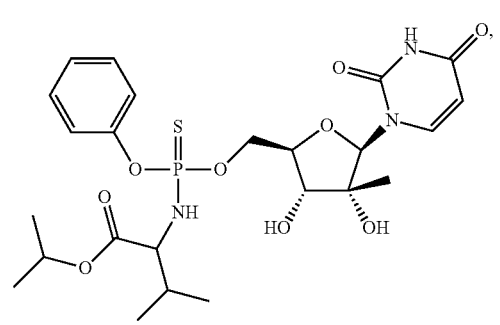
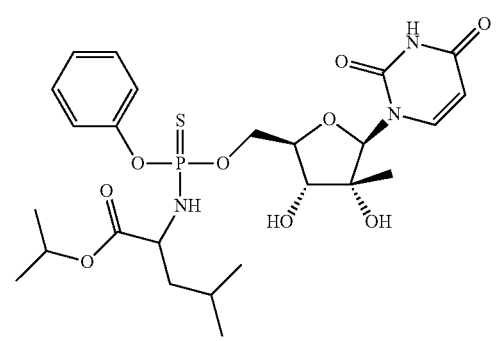
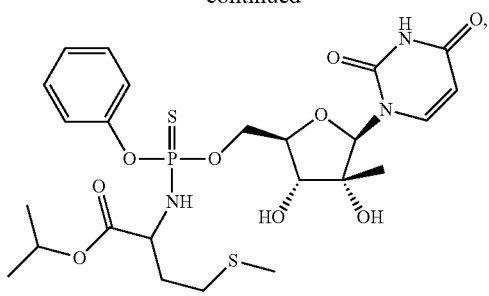
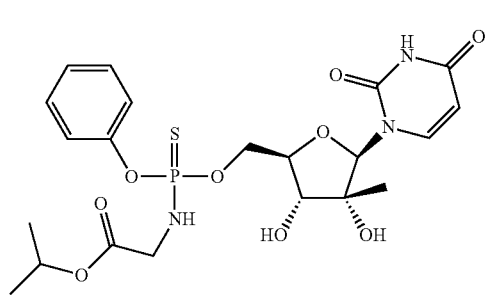
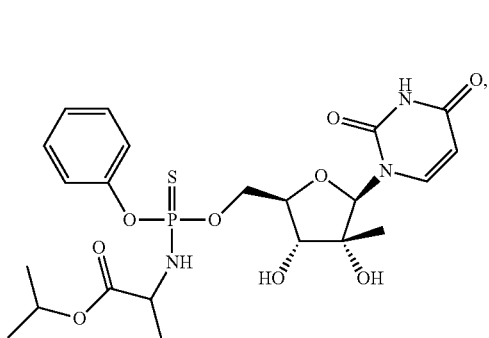
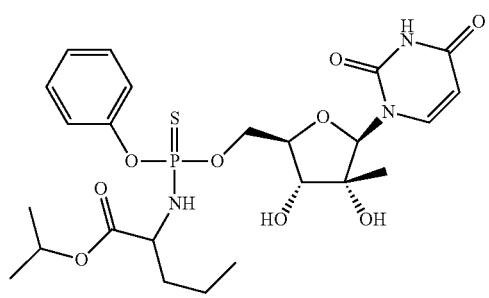
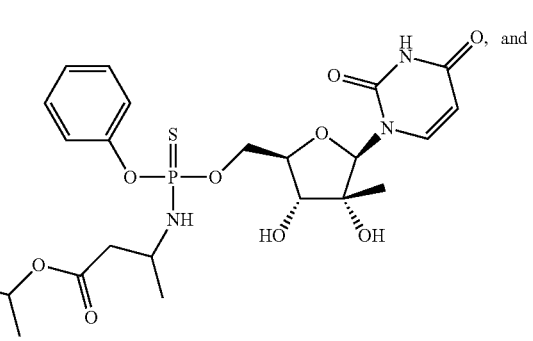

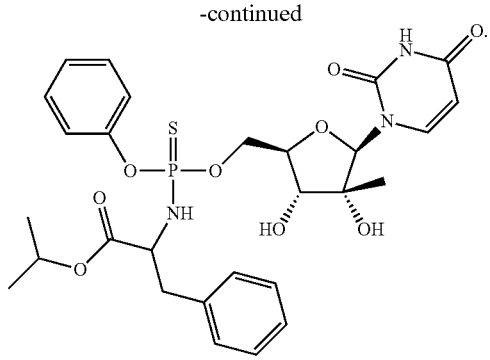

Additional examples of compounds of Formula (I) include the following:

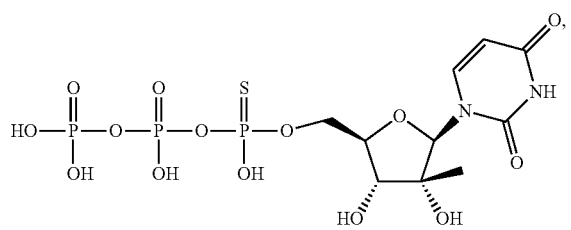

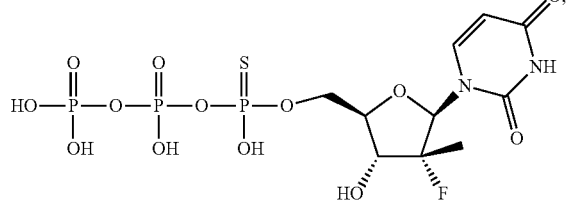

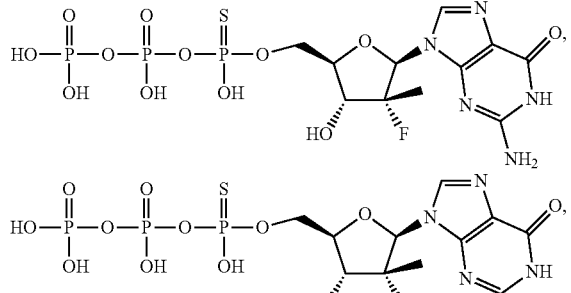

and

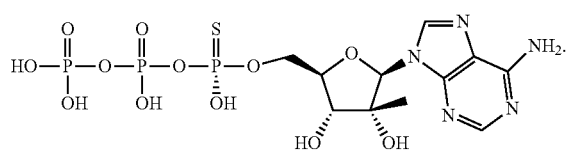

In some embodiments, neutralizing the charge on the thiophosphate group may facilitate the penetration of the cell membrane by a compound of Formula (I) (including a compound of Formula (Iα)) by making the compound more lipophilic compared to a thionucleotide having a comparable structure with one or more charges present on the phosphate. Once absorbed and taken inside the cell, the groups attached to the thiophosphate can be easily removed by esterases, proteases, or other enzymes. In some embodiments, the groups attached to the thiophosphate can be removed by simple hydrolysis. Inside the cell, the thio-monophosphate thus released may then be metabolized by cellular enzymes to the thio-diphosphate or the active thio-triphosphate. In some embodiments, the phosphorylation of a thio-monophosphate of a compound of Formula (I), or pharmaceutically acceptable salt thereof, can be stereoselective. For example, a thio-monophosphate of a compound of Formula (I) (including a compound of Formula (Iα)) can be phosphorylated to give an alpha-thiodiphosphate and/or an alpha-thiotriphosphate compound that can be enriched in the (R) or (S) diastereomer with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom. In some embodiments, phosphorylation of a compound of Formula (I), or pharmaceutically acceptable salt thereof, can result in the formation of a compound that has the (R)-configuration at the 5'-O-phosphorous atom. In some embodiments, phosphorylation of a compound of Formula (I), or pharmaceutically acceptable salt thereof, can result in formation of a compound that has the (S)-configuration at the 5'-O-phosphorous atom.

In some embodiments, a compound of Formula (I) (including a compound of Formula (Iα)), or a pharmaceutically acceptable salt thereof, can act as a chain terminator of HCV replication. For example, incorporation of a compound of Formula (I) containing a moiety at the 2'-carbon position can terminate further elongation of the RNA chain of HCV. For example, a compound of Formula (I) can contain a 2'-carbon modification when $R^8$ is a non-hydrogen group selected from halogen, azido, cyano, an optionally substituted $C_{1-6}$ alkyl, —$OR^{16}$ and —$OC(=O)R^{17}$.

In some embodiments, a compound of Formula (I) (including a compound of Formula (Iα)), or a pharmaceutically acceptable salt thereof, can have increased metabolic and/or plasma stability. In some embodiments, a compound of Formula (I) (including a compound of Formula (Iα)), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having a phosphate attached to the 5'-carbon of the ribose ring. In some embodiments, a compound of Formula (I) (including a compound of Formula (Iα)), or a pharmaceutically acceptable salt thereof, can have improved properties. In previous studies, replacing a sulfur with an oxygen on the alpha-phosphate of a nucleotide phosphoramidate has resulted in more than a 1000-fold decrease in potency. See Venkatachalam et al. *European Journal of Medicinal Chemistry* (2004) 39:665-683. A non-limiting list of example properties include, but are not limited to, increased biological half life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half life of greater than 24 hours. In some embodiments, a compound of Formula (I), or a pharmaceutically acceptable salt thereof, can have a biological half life in the range of about 40 hours to about 46 hours. In some embodiments, a compound of Formula (I), or a pharmaceutically acceptable salt thereof, can have a biological half life greater than a compound that has a phosphate attached to the 5'-carbon of the ribose ring (for example, a compound that is identical in structure but for having a phosphate attached to the 5'-carbon of the ribose ring). In some embodiments, a compound of Formula (I), or a pharmaceutically acceptable salt thereof, can have more potent antiviral activity (for example, a lower $IC_{50}$ in an HCV replicon assay) as compared to the current standard of care.

Synthesis

Compounds of Formula (I) (including compounds of Formula (Iα)), and those described herein may be prepared in various ways. General synthetic routes to the compound of Formula (I), and some examples of starting materials used to synthesize the compounds of Formula (I) are shown in Scheme 1, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

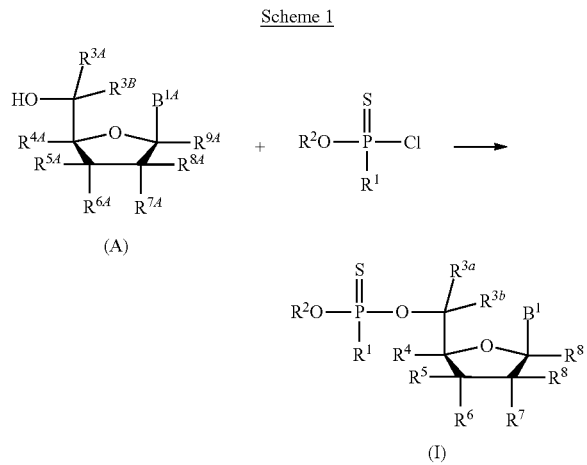

(A)

(I)

One method for forming a compound of Formula (I) is shown in Scheme 1. In Scheme 1, $R^{3A}$, $R^{3B}$, $R^{4A}$, $R^{5A}$, $R^{6A}$, $R^{7A}$, $R^{8A}$, $R^{9A}$ and $B^{1A}$ can be the same as $R^{3a}$, $R^{3b}$, $R^4$, $R^5$, $R^6$, $R^7$, $R^8$, $R^9$ and $B^1$ as described herein for Formula (I); and $R^1$ and $R^2$ can be the same as described herein for Formula (I). As shown in Scheme 1, a compound of Formula (A) can be reacted with a compound having the formula $R^2O$—P(=S)($R^1$)—Cl to form a compound of Formula (I).

To reduce the formation of side products, one or more the groups attached to the pentose ring can be protected with one or more suitable protecting groups. As an example, if $R^{6A}$ and/or $R^{7A}$ is/are hydroxy group(s), the hydroxy group(s) can be protected with suitable protecting groups, such as triarylmethyl and/or silyl groups. Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy)trityl (TBTr), 4,4',4''-tris(4,5-dichlorophthalimido)trityl (CPTr), 4,4',4''-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4''-tris-(tert-butylphenyl) methyl (TTTr) and 4,4'-di-3, 5-hexadienoxytrityl. Examples of suitable silyl groups are described herein. Alternatively, $R^{6A}$ and/or $R^{7A}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy) propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal.

If desired, any —NH and/or $NH_2$ groups present on the $B^{1A}$ can also be protected with one or more suitable protecting groups. Examples of suitable protecting groups include triarylmethyl groups and silyl groups. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl.

Suitable thiophosphorochloridates can be commercially obtained or prepared by a synthetic method described herein. An example of a general structure of a thiophosphorochloridate is shown in Scheme 1. In some embodiments, the thiophosphorochloridate can be coupled to a compound of Formula (A). In some embodiments, to facilitate the coupling, a Grignard reagent can be used. Suitable Grignard reagents are known to those skilled in the art and include, but are not limited to, alkylmagnesium chlorides and alkylmagnesium bromides. In other embodiments, the thiophosphorochloridate can be added to a compound of Formula (A) using a base. Suitable bases are known to those skilled in the art. Examples of bases include, but are not limited to, an amine base, such as an alkylamine (including mono-, di- and tri-alkylamines (e.g., triethylamine)), optionally substituted pyridines (e.g. collidine) and optionally substituted imidzoles (e.g., N-methylimidazole)).

When at least one of $R^{3a}$ and $R^{3b}$ is an optionally substituted $C_{1-6}$ alkyl or an optionally substituted $C_{1-6}$ haloalkyl, the optionally substituted $C_{1-6}$ alkyl or the optionally substituted $C_{1-6}$ haloalkyl can be added to the 5'-position using methods known to those skilled in the art. In some embodiments, the hydroxy attached to the 5'-carbon can be oxidized to an aldehyde. Suitable oxidation conditions include, but are not limited to, DMSO in combination with an activating agent (usually an acylating agent or an acid) and an amine base, Moffatt oxidation, Swern oxidation and Corey-Kim oxidation, and suitable oxidizing agents include, but are not limited to, Dess-Martin periodinane, TPAP/NMO (tetrapropylammonium perruthenate/N-methylmorpholine N-oxide), Swern oxidation reagent, PCC (pyridinium chlorochromate), and/or PDC (pyridinium dichromate), sodium periodate, Collin's reagent, ceric ammonium nitrate CAN, $Na_2Cr_2O_7$ in water, Ag$_2$CO$_3$ on celite, hot HNO$_3$ in aqueous glyme, O$_2$-pyridine CuCl, Pb(OAc)$_4$-pyridine and benzoyl peroxide-NiBr$_2$. The resulting aldehyde compound can be reacted with a Grignard reagent, an organolithium reagent or trialkylaluminum (e.g., trimethylaluminum) to form a compound of Formula (A) where at least one of R$^{3A}$ and R$^{3B}$ is an optionally substituted C$_{1-6}$ alkyl or an optionally substituted C$_{1-6}$ haloalkyl. Optionally, the alkylating reagents can be in the presence of a Lewis acid. Suitable Lewis acids are known to those skilled in the art.

The chirality of the 5'-carbon of compounds of Formulae (A) and/or (I) can be inverted using methods known to the skilled in the art. For example, the oxygen attached to the 5'-carbon can be oxidized, for example to an aldehyde, for a compound of Formula (A), or ketone, for a compound of Formula (I), using a suitable oxidizing agent. The aldehyde and/or ketone can then be reduced using a suitable reducing agent. Examples of suitable reducing agents include, but are not limited to, NaH, LiH, NaBH$_4$, LiAlH$_4$ and CaH$_2$. Suitable oxidizing and reducing agents are known to those skilled in the art. Examples of suitable oxidizing agents and conditions are described herein.

As described herein, in some embodiments, R$^6$ and R$^7$ can be both oxygen atoms linked together by a carbonyl groups. The —O—C(=O)—O— group can be formed using methods known to those skilled in the art. For example, a compound of Formula (I), wherein R$^6$ and R$^7$ are both hydroxy groups, can be treated with 1,1'-carbonyldiimidazole (CDI).

In some embodiments, R$^6$ and/or R$^7$ can be —OC(=O)R$^{13}$ and —OC(=O)R$^{15}$, respectively. The —OC(=O)R$^{13}$ and —OC(=O)R$^{15}$ groups can be formed at the 2'- and 3'-positions using various methods known to those skilled in the art. As an example, a compound of Formula (I), wherein R$^6$ and R$^7$ are both hydroxy groups, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the —OC(=O)R$^{13}$ and —OC(=O)R$^{15}$ groups can be formed at the 2'- and 3'-positions by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropylcarbodiimide (DIC) and 1-ethyl-3-(3-dimethylaminopropyl) carbodiimide (EDC).

As described herein, B$^{1A}$ can include a carbamate and/or an amide. Those skilled in the art know methods for forming a carbamate and/or an amide on B$^{1A}$. In some embodiments, the carbamate can be formed using 1,1'-carbonyldiimidazole and an alcohol.

B$^{1A}$ can be added to the pentose ring using various methods known to those skilled in the art. In some embodiments, a compound of Formula (B) can be reacted with a nitrogenous base. In some embodiments, R$^{3A}$, R$^{3B}$, R$^{4A}$, R$^{5A}$, R$^{6A}$, R$^{7A}$, R$^{8A}$, R$^{9A}$ and B$^{1A}$ of a compound of Formula (B) can be the same as disclosed herein, with respect to R$^{3a}$, R$^{3b}$, R$^4$, R$^5$, R$^6$, R$^7$, R$^8$, R$^9$ and B$^1$; and PG$^1$ can be an appropriate protecting group. In some embodiments, PG$^1$ can be p-nitrobenzyl group. In some embodiments, any hydroxy groups attached to the pentose ring can be protected with one or more suitable protecting groups. In some embodiments, any hydroxy groups attached to the pentose ring can be protected with benzoyl groups. Examples of nitrogenous bases include an optionally substituted heterocyclic bases described herein, wherein the nitrogen atom (—N) connected to the pentose ring is —NH. If desired, any —NH and/or NH$_2$ groups present on the nitrogenous base can be protected with one or more suitable protecting groups. Suitable protecting groups are described herein. In some embodiments, the nitrogenous base can be added via a coupling reaction in the presence of a Lewis acid or TMSOTf. Suitable Lewis acids are known to those skilled in the art.

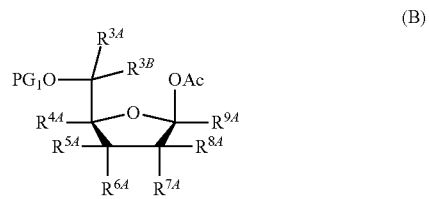

(B)

Various methods can be used to make a compound of Formula (I), wherein R$^1$ is

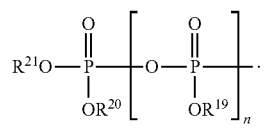

For example, a thiophosphorochloridate having the general formula of (P(=S)Cl$_3$) can be transformed into a phosphorus reagent having the general formula, P(=S)LG$_3$, wherein each LG can be amine-based leaving group. In some embodiments, each LG can be a triazole. The phosphorus reagent having the general formula, P(=S)LG$_3$, can be reacted with a compound of Formula (I). Using a suitable pyrophosphorylation reagent, the β and γ phosphates can be added. An example of a suitable pyrophosphorylation reagent is tris (tetrabutylammonium) hydrogen pyrophosphate.

During the synthesis of any of the compounds described herein, if desired, any hydroxy groups attached to the pentose ring, and any —NH and/or NH$_2$ groups present on the B$^{1A}$ can be protected with one or more suitable protecting groups. Suitable protecting groups are described herein. Those skilled in the art will appreciate that groups attached to the pentose ring and any —NH and/or NH$_2$ groups present on the B$^{1A}$ can be protected with various protecting groups, and any protecting groups present can be exchanged for other protecting groups. The selection and exchange of the protecting groups is within the skill of those of ordinary skill in the art. Any protecting group(s) can also be removed by methods known in the art, for example, with an acid (e.g., a mineral or an organic acid), a base or a fluoride source.

Pharmaceutical Compositions

Some embodiments described herein relates to a pharmaceutical composition, that can include a therapeutically effective amount of one or more compounds described herein (e.g., a compound of Formulae (I) or (Iα)), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

One embodiment disclosed herein relates to a method of treating and/or ameliorating a disease or condition that can include administering to a subject a therapeutically effective amount of one or more compounds described herein, such as a compound of Formula (I) (including compounds of Formula (Iα)), or a pharmaceutically acceptable salt thereof, or a pharmaceutical composition that includes a compound described herein.

Some embodiments disclosed herein relate to a method of ameliorating or treating a neoplastic disease that can include administering to a subject suffering from a neoplastic disease a therapeutically effective amount of one or more compounds described herein (e.g., a compound of Formulae (I) and/or (Iα), or a pharmaceutically acceptable salt thereof), or a pharmaceutical composition that includes a compound described herein). In an embodiment, the neoplastic disease can be cancer. In some embodiments, the neoplastic disease can be a tumor such as a solid tumor. In an embodiment, the neoplastic disease can be leukemia. Exemplary leukemias include, but are not limited to, acute lymphoblastic leukemia (ALL), acute myeloid leukemia (AML) and juvenile myelomonocytic leukemia (JMML).

Some embodiments disclosed herein relate to a method of inhibiting the growth of a tumor that can include administering to a subject having a tumor a therapeutically effective amount of one or more compounds described herein (for example, a compound of Formulae (I) and/or (Iα)), or a pharmaceutical composition that includes one or more compounds described herein.

Other embodiments disclosed herein relates to a method of ameliorating or treating a viral infection that can include administering to a subject suffering from a viral infection a therapeutically effective amount of one or more compounds described herein (for example, a compound of Formulae (I) and/or (Iα)), or a pharmaceutical composition that includes one or more compounds described herein. In an embodiment, the viral infection can be caused by a virus selected from an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a Paramyxoviruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxviridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae, a Togaviridae an Arenaviridae and/or a Bornaviridae. In some embodiments, the viral infection can be a hepatitis C viral (HCV) infection. In still other embodiments, the viral infection can be HIV.

Some embodiments disclosed herein relate to methods of ameliorating and/or treating a viral infection that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a viral infection that can include contacting a cell infected with the virus with an effective amount of said compound(s). Still other embodiments described herein relate to one or more compounds described herein, or a pharmaceutically acceptable salt of a compound described herein, that can be used for ameliorating and/or treating a viral infection by contacting a cell infected with the virus with an effective amount of said compound(s). In some embodiments, the compound can be a compound of Formulae (I) and/or (Iα), or a pharmaceutical acceptable salt thereof. In other embodiments, the compound can be a mono-, di- and/or tri-phosphate of a compound of Formulae (I) and/or (Iα), or a pharmaceutically acceptable salt of the foregoing. In some embodiments, the virus can be a HCV virus.

Some embodiments disclosed herein relate to methods of inhibiting replication of a virus that can include contacting a cell infected with the virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a virus that can include contacting a cell infected with the virus with an effective amount of said compound(s). Still other embodiments described herein relate to a compound described herein, or a pharmaceutically acceptable salt of a compound described herein, that can be used for inhibiting replication of a virus by contacting a cell infected with the virus with an effective amount of said compound(s). In some embodiments, the compound can be a compound of Formulae (I) and/or (Iα), or a pharmaceutical acceptable salt thereof. In other embodiments, the compound can be a mono-, di- and/or tri-phosphate of a compound of Formulae (I) and/or (Iα), or a pharmaceutically acceptable salt of the foregoing. In some embodiments, the virus can be a HCV virus.

HCV is an enveloped positive strand RNA virus in the Flaviviridae family. There are various nonstructural proteins of HCV, such as (NS2, NS3, NS4, NS4A, NS4B, NS5A, and NS5B. NS5B is believed to be an RNA-dependent RNA polymerase involved in the replication of HCV RNA.

Some embodiments described herein relate to a method of inhibiting NS5B polymerase activity can include contacting a cell (for example, a cell infected with HCV) with an effective amount of a compound of Formulae (I) and/or (Iα), or a pharmaceutical acceptable salt thereof. Some embodiments described herein relate to a method of inhibiting NS5B polymerase activity can include administering a cell (for example, a cell infected with HCV) with an effective amount of a compound of Formulae (I) and/or (Iα), or a pharmaceutical acceptable salt thereof. In some embodiments, a compound of Formula (I) (including a compound of Formula (Iα)), or a pharmaceutically acceptable salt thereof, can inhibit a RNA dependent RNA polymerase. In some embodiments, a compound of Formula (I) (including a compound of Formula (Iα)), or a pharmaceutically acceptable salt thereof, can inhibit a HCV polymerase (for example, NS5B polymerase).

Some embodiments described herein relate to a method of treating HCV infection in a subject suffering from a HCV infection that can include administering to the subject an effective amount of a compound of Formulae (I) and/or (Iα), or a pharmaceutical acceptable salt thereof, or a pharmaceutical composition that includes an effective amount of a compound of Formulae (I) and/or (Iα), or a pharmaceutical acceptable salt thereof. Some embodiments described herein relate to a method of treating a condition selected from liver fibrosis, liver cirrhosis, and liver cancer in a subject suffering from one or more of the aforementioned liver conditions that can include administering to the subject an effective amount of a compound or a pharmaceutical composition described herein (for example, a compound of Formulae (I) and/or (Iα), or a pharmaceutical acceptable salt thereof). One cause of the liver fibrosis, liver cirrhosis, and/or liver cancer can be a HCV infection. Some embodiments described herein relate to a method of increasing liver function in a subject having a HCV infection that can include administering to the subject an effective amount of a compound or a pharmaceutical composition described herein (for example, a compound of Formulae (I) and/or (Iα), or a pharmaceutical acceptable salt thereof). Also contemplated is a method for reducing or eliminating further virus-caused liver damage in a subject having an HCV infection by administering to the subject an effective amount of a compound or a pharmaceutical composition described herein (for example, a compound of Formulae (I) and/or (Iα), or a pharmaceutical acceptable salt thereof). In one embodiment, this method comprises slowing or halting the progression of liver disease. In another embodiment, the course of the disease is reversed, and stasis or improvement in liver function is contemplated.

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formulae (I) and/or (Iα), or a pharmaceutical acceptable salt thereof, or a pharmaceutical composition that includes an effective amount of a compound of Formulae (I) and/or (Iα), or a pharmaceutical acceptable salt thereof, can be effective to treat at least one genotype of HCV. In some embodiments, a compound described herein (for example, a compound of Formulae (I) and/or (Iα), or a pharmaceutical acceptable salt thereof) can be effective to treat all 11 genotypes of HCV. In some embodiments, a compound described herein (for example, a compound of Formulae (I) and/or (Iα), or a pharmaceutical acceptable salt thereof) can be effective to treat 3 or more, 5 or more, 7 or more of 9 more genotypes of HCV. In some embodiments, a compound of Formula (I) and/or (Iα), or a pharmaceutical acceptable salt thereof is more effective against a larger number of HCV genotypes than the standard of care. In some embodiments, a compound of Formula (I)

and/or (Iα), or a pharmaceutical acceptable salt thereof, is more effective against a particular HCV genotype than the standard of care (such as genotype 1, 2, 3, 4, 5 and/or 6).

Various indicators for determining the effectiveness of a method for treating a HCV infection are known to those skilled in the art. Example of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase, and/or other indicator of disease response. Similarly, successful therapy with an effective amount of a compound or a pharmaceutical composition described herein (for example, a compound of Formulae (I) and/or (Iα), or a pharmaceutical acceptable salt thereof) can reduce the incidence of liver cancer in HCV patients.

In some embodiments, an effective amount of a compound of Formulae (I) and/or (Iα), or a pharmaceutically acceptable salt thereof, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formula (I) and/or (Iα), or a pharmaceutically acceptable salt thereof, is an amount that is effective to reduce viral load compared to the viral load before administration of the compound of Formula (I) and/or (Iα), or a pharmaceutically acceptable salt thereof. For example, wherein the viral load is measured before administration of the compound of Formula (I) and/or (Iα), or a pharmaceutically acceptable salt thereof, and again after completion of the treatment regime with the compound of Formula (I) and/or (Iα), or a pharmaceutically acceptable salt thereof (for example, 1 month after completion). In some embodiments, an effective amount of a compound of Formula (I) and/or (Iα), or a pharmaceutically acceptable salt thereof, can be an amount that is effective to reduce viral load to lower than about 100 genome copies/mL serum. In some embodiments, an effective amount of a compound of Formula (I) and/or (Iα), or a pharmaceutically acceptable salt thereof, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formula (I) and/or (Iα), or a pharmaceutically acceptable salt thereof. For example, the viral load can be measured before administration of the compound of Formula (I) and/or (Iα), or a pharmaceutically acceptable salt thereof, and again after completion of the treatment regime with the compound of Formula (I) and/or (Iα), or a pharmaceutically acceptable salt thereof (for example, 1 month after completion).

In some embodiments, a compound of Formula (I) and/or (Iα), or a pharmaceutically acceptable salt thereof, can result in at least a 1, 2, 3, 4, 5, 10, 15, 20, 25, 50, 75, 100-fold or more reduction in the replication of HCV relative to pre-treatment levels in a subject, as determined after completion of the treatment regime (for example 1 month after completion). In some embodiments, a compound of Formula (I) and/or (Iα), or a pharmaceutically acceptable salt thereof, can result in a reduction of the replication of HCV relative to pre-treatment levels in the range of about 2 to about 5 fold, about 10 to about 20 fold, about 15 to about 40 fold, or about 50 to about 100 fold. In some embodiments, a compound of Formula (I) and/or (Iα), or a pharmaceutically acceptable salt thereof, can result in a reduction of HCV replication in the range of 1 to 1.5 log, 1.5 log to 2 log, 2 log to 2.5 log, 2.5 to 3 log, 3 log to 3.5 log or 3.5 to 4 log more reduction of HCV replication compared to the reduction of HCV reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I) and/or (Iα), or a pharmaceutically acceptable salt thereof, is an amount that is effective to achieve a sustained viral response, for example, non-detectable or substantially non-detectable HCV RNA (e.g., less than about 500, less than about 400, less than about 200, or less than about 100 genome copies per milliliter serum) is found in the subject's serum for a period of at least about one month, at least about two months, at least about three months, at least about four months, at least about five months, or at least about six months following cessation of therapy.

In some embodiments, a therapeutically effective amount of a compound of Formula (I) and/or (Iα), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of a markers includes measuring the levels of serum alanine aminotransferase (ALT), asparatate aminotransferacse (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I) and/or (Iα) is an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents. In some embodiments, development of resistant HCV strains is delayed when patients are treated with a compound of Formula (I), or a pharmaceutically acceptable salt thereof, compared to the development of HCV strains resistant to other HCV drugs.

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I) (including a compound of Formula (Iα)), or a pharmaceutically acceptable salt thereof, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of apetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents.

Table 5 provides some embodiments of a compound of Formula (I), or a pharmaceutically acceptable salt thereof, compared to the standard of care. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results number of side effects that is in the range of about 10% to about 30% less compared to the number of side effects experienced by a subject receiving the standard of care; and in some embodiments, a compound of Formula (I), or a pharmaceutically acceptable salt thereof, results a severity of a side effect (such as one of those described herein) that is 25% less than compared to the severity of the same side effect experienced by a subject receiving the standard of care. Methods of quantifying the severity of a side effect are known to those skilled in the art.

TABLE 5

| Percentage of non-responders | Percentage of relapsers | Percentage of resistance | Percentage of viral load rebound | Number of side effects | Severity of side effects |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

Yet still other embodiments disclosed herein relates to a method of ameliorating or treating a parasitic disease that can include administering to a subject suffering from a parasitic disease a therapeutically effective amount of one or more compounds described herein (for example, a compound of Formula (I) and/or (Iα)), or a pharmaceutical composition that includes one or more compounds described herein. In an embodiment, the parasite disease can be Chagas' disease.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I) (including a compound of Formula (Iα)), or a pharmaceutically acceptable salt thereof, can be administered less frequently compared to the frequency of administration of an agent within the standard of care. In some embodiments, a compound of Formula (I) (including a compound of Formula (Iα)), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I) (including a compound of Formula (Iα)), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I) (including compounds of Formula (Iα)), or a pharmaceutically acceptable salt thereof, or a pharmaceutical composition that includes a compound described herein, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, compounds of Formula (AA) (including mono-, di, and/or tri-phosphates of Formula (AA), pharmaceutically acceptable salts and pharmaceutical compositions that can include a compound of Formula (AA), mono-, di- and/or tri-phosphates thereof, or a pharmaceutically acceptable salt of the foregoing), compounds of Formula (BB) (including pharmaceutically acceptable salts and pharmaceutical compositions that can include a compound of Formula (BB), or a pharmaceutically acceptable salt thereof), compounds of Formula (DD) (including pharmaceutically acceptable salts and pharmaceutical compositions that can include a compound of Formula (DD), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein. A non-limiting list of examples of combinations of a compound of Formula (I), or a pharmaceutically acceptable salt thereof, or a pharmaceutical composition that includes a compound of Formula (I), or a pharmaceutically acceptable salt thereof, is provided in Tables A, B, C and D.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, or Pegylated interferon-alpha-2b (brand name PEG-INTRON®) and ribavirin. As another example, a compound disclosed herein can be used in combination with oseltamivir (TAMIFLU®) or zanamivin (RELENZA®) for treating an influenza infection.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. A non-limiting list of example HCV protease inhibitors includes the compounds numbered 1001-1014 in FIG. 2.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-184, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2010 in FIG. 3. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3008 in FIG. 4.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. A non-limiting list of example NS5A inhibitors include BMS-790052, PPI-461, ACH-2928, GS-5885, BMS-824393 and/or combinations thereof. A non-limiting list of example NS5A inhibitors includes the compounds numbered 4001-4005 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122 and/or combinations thereof. A non-limiting list of example other antiviral compounds includes the compounds numbered 5001-5002 in FIG. 6.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (AA), mono-, di- and/or tri-phosphate thereof, or a pharmaceutically acceptable salt of the foregoing, or a pharmaceutical composition that includes a compound of Formula (AA), mono-, di- and/or tri-phosphate thereof, or a pharmaceutically acceptable salt of the foregoing (see, U.S. Provisional Application Nos. 61/385,425, filed Sep. 22, 2010, and 61/426,467, filed Dec. 22, 2010, the contents of which are incorporated by reference in its entirety):

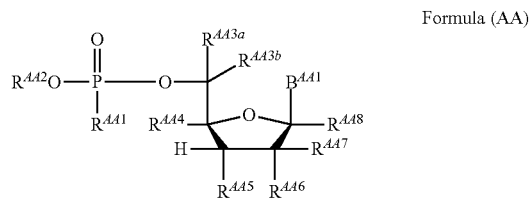

Formula (AA)

wherein $B^{AA1}$ can be an optionally substituted heterocyclic base or an optionally substituted heterocyclic base with a protected amino group; $R^{AA1}$ can be an optionally substituted N-linked amino acid or an optionally substituted N-linked amino acid ester derivative; $R^{AA2}$ can be selected from an optionally substituted aryl, an optionally substituted heteroaryl and an optionally substituted heterocyclyl; $R^{AA3a}$ and $R^{AA3b}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl), provided that at least one of $R^{AA3a}$ and $R^{AA3b}$ is not hydrogen; or $R^{AA3a}$ and $R^{AA3b}$ can be taken together to form a group selected from an optionally substituted $C_{3-6}$ cycloalkyl, an optionally substituted $C_{3-6}$ cycloalkenyl, an optionally substituted $C_{3-6}$ aryl, and an optionally substituted $C_{3-6}$ heteroaryl; $R^{AA4}$ can be hydrogen; $R^{AA5}$ be selected from hydrogen, $-OR^{AA9}$ and $-OC(=O)R^{AA10}$; $R^{AA6}$ can be selected from hydrogen, halogen, $-OR^{AA11}$ and $-OC(=O)R^{AA12}$; or $R^{AA5}$ and $R^{AA6}$ can be both oxygen atoms and linked together by a carbonyl group; $R^{AA7}$ can be selected from hydrogen, halogen, an optionally substituted $C_{1-6}$ alkyl, $-OR^{AA13}$ and $-OC(=O)R^{AA14}$; $R^{AA8}$ can be hydrogen or an optionally substituted $C_{1-6}$ alkyl; $R^{AA9}$, $R^{AA11}$ and $R^{AA13}$ can be independently selected from hydrogen and an optionally substituted $C_{1-6}$ alkyl; and $R^{AA10}$, $R^{AA12}$ and $R^{AA14}$ can be independently selected from an optionally substituted $C_{1-6}$ alkyl and an optionally substituted $C_{3-6}$ cycloalkyl. A non-limiting list of examples of compounds of Formula (AA), and phosphates thereof, includes the compounds numbered 7000-7077 in FIGS. 8A-8I. In some embodiments, Formula (AA) cannot be compound 7044, 7045, 7046, 7047, 7048, 7049, 7050, 7072, 7073, 7074, 7075, 7076 or 7077.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Provisional Application No. 61/426,471, filed Dec. 22, 2010, the contents of which are incorporated by reference in its entirety):

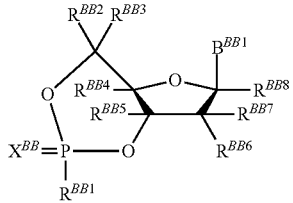

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $-Z^{BB}-R^{BB9}$, an optionally substituted N-linked amino acid and an optionally substituted N-linked amino acid ester derivative; $Z^{BB}$ can be selected from O (oxygen), S (sulfur) and N($R^{BB10}$); $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $-OR^{BB11}$ and $-OC(=O)R^{BB12}$; $R^{BB7}$ can be selected from hydrogen, halogen, azido, cyano, an optionally substituted $C_{1-6}$ alkyl, $-OR^{BB13}$ and $-OC(=O)R^{BB14}$; $R^{BB8}$ can be selected from hydrogen, halogen, azido, cyano, an optionally substituted $C_{1-6}$ alkyl, $-OR^{BB15}$ and $-OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl ($C_{1-6}$alkyl) and an optionally substituted heterocyclyl ($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl ($C_{1-6}$alkyl) and an optionally substituted heterocyclyl ($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8000-8012 in FIGS. 9A-9B.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (DD), or a pharmaceutically acceptable salt thereof, or a pharmaceutical composition that includes a compound of Formula (DD), or a pharmaceutically acceptable salt thereof (see, U.S. Publication No. 2010-0249068, filed Mar. 19, 2010, the contents of which are incorporated by reference in its entirety):

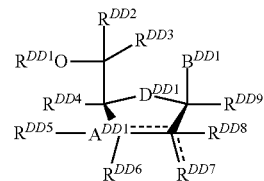

Formula (DD)

wherein each ----- can be independently a double or single bond; $A^{DD1}$ can be selected from C (carbon), O (oxygen) and S (sulfur); $B^{DD1}$ can be an optionally substituted heterocyclic base or a derivative thereof; $D^{DD1}$ can be selected from $C=CH_2$, $CH_2$, O (oxygen), S (sulfur), CHF, and $CF_2$; $R^{DD1}$ can be hydrogen, an optionally substituted alkyl, an optionally substituted cycloalkyl, an optionally substituted aralkyl, dialkylaminoalkylene, alkyl-C(=O)—, aryl-C(=O)—, alkoxyalkyl-C(=O)—, aryloxyalkyl-C(=O)—, alkylsulfonyl, arylsulfonyl, aralkylsulfonyl,

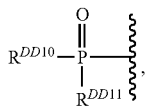

an —O-linked amino acid, diphosphate, triphosphate or derivatives thereof; $R^{DD2}$ and $R^{DD3}$ can be each independently selected from hydrogen, an optionally substituted $C_{1-6}$ alkyl, an optionally substituted $C_{2-6}$ alkenyl, an optionally substituted $C_{2-6}$ alkynyl and an optionally substituted $C_{1-6}$ haloalkyl, provided that at least one of $R^{DD2}$ and $R^{DD3}$ cannot be hydrogen; or $R^{DD2}$ and $R^{DD3}$ are taken together to form a group selected from among $C_{3-6}$ cycloalkyl, $C_{3-6}$ cycloalkenyl, $C_{3-6}$ aryl, and a $C_{3-6}$ heteroaryl; $R^{DD4}$ and $R^{DD9}$ can be independently selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$, —C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, —N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted $C_{1-6}$ alkyl, an optionally substituted $C_{2-6}$ alkenyl, an optionally substituted $C_{2-6}$ alkynyl, an optionally substituted aralkyl and an —O-linked amino acid; $R^{DD5}$, $R^{DD6}$ and $R^{DD7}$ can be independently absent or selected from hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$)—NR$^{DDa1}$R$^{DDb1}$, —N(R$^{DDc1}$)—OR$^{DDa1}$, —S—SR$^{DDa1}$, —C(=O)R$^{DDa1}$, —C(=O)OR$^{DDa1}$—C(=O)NR$^{DDa1}$R$^{DDb1}$, —O—(C=O)R$^{DDa1}$, —O—C(=O)OR$^{DDa1}$, —O—C(=O)NR$^{DDa1}$R$^{DDb1}$, N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, —N(R$^{DDc1}$)—S(=O)$_2$NR$^{DDa1}$R$^{DDb1}$, an optionally substituted $C_{1-6}$ alkyl, an optionally substituted $C_{2-6}$ alkenyl, an optionally substituted $C_{2-6}$ alkynyl, an optionally substituted aralkyl and an —O-linked amino acid; or $R^{DD6}$ and $R^{DD7}$ taken together form —O—C(=O)—O—; $R^{DD8}$ can be absent or selected from the group consisting of hydrogen, halogen, —NH$_2$, —NHR$^{DDa1}$, NR$^{DDa1}$R$^{DDb1}$, —OR$^{DDa1}$, —SR$^{DDa1}$, —CN, —NC, —N$_3$, —NO$_2$, —N(R$^{DDc1}$) NR$^{DDa1}$R$^{DDb1}$, N(R$^{DDc1}$)—OR$^{DDa1}$, —S—SR$^{DDa1}$, —C(=O)R$^{DDa1}$, —C(=O)OR$^{DDa1}$, —C(=O) NR$^{DDa1}$R$^{DDb1}$, O—C(=O)OR$^{DDa1}$, —O—C(=O) NR$^{DDa1}$R$^{DDb1}$, N(R$^{DDc1}$)—C(=O)NR$^{DDa1}$R$^{DDb1}$, —S(=O)R$^{DDa1}$, S(=O)$_2$R$^{DDa1}$, —O—S(=O)$_2$NR$^{DDa1}$R$^{DDb1}$, N(R$^{DDc1}$)—S(=O)$_2$NR$^{DDa1}$R$^{DDb1}$, an optionally substituted $C_{1-6}$ alkyl, an optionally substituted $C_{2-6}$ alkenyl, an optionally substituted $C_{2-6}$ alkynyl, an optionally substituted haloalkyl, an optionally substituted hydroxyalkyl and an —O-linked amino acid, or when the bond to $R^{DD7}$ indicated by ----- is a double bond, then $R^{DD7}$ is a $C_{2-6}$ alkylidene and $R^{DD8}$ is absent; $R^{DDa1}$, $R^{DDb1}$ and $R^{DDc1}$ can be each independently selected from hydrogen, an optionally substituted alkyl, an optionally substituted alkenyl, an optionally substituted alkynyl, an optionally substituted aryl, an optionally substituted heteroaryl, an optionally substituted aralkyl and an optionally substituted heteroaryl($C_{1-6}$ alkyl); $R^{DD10}$ can be selected from O⁻, —OH, an optionally substituted aryloxy or aryl-O—,

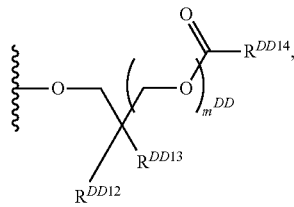

alkyl-C(=O)—O—CH$_2$—O—, alkyl-C(=O)—S—CH$_2$CH$_2$—O— and an —N-linked amino acid; $R^{DD11}$ can be selected from O⁻, —OH, an optionally substituted aryloxy or aryl-O—,

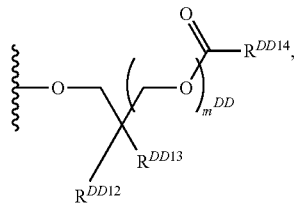

alkyl-C(=O)—O—CH$_2$—O—, alkyl-C(=O)—S—CH$_2$CH$_2$—O— and an —N-linked amino acid; each $R^{DD12}$ and each $R^{DD13}$ can be independently —C≡N or an optionally substituted substituent selected from $C_{1-8}$ organylcarbonyl, $C_{1-8}$ alkoxycarbonyl and $C_{1-8}$ organylaminocarbonyl; each $R^{DD14}$ can be hydrogen or an optionally substituted $C_{1-6}$-alkyl; each m$^{DD}$ can be independently 1 or 2, and if both $R^{DD10}$ and $R^{DD11}$ are

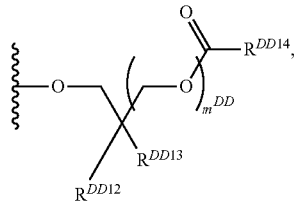

each $R^{DD12}$, each $R^{DD13}$, each $R^{DD14}$ and each m$^{DD}$ can be the same or different. In some embodiments, $R^{DD8}$ can be halogen, —OR$^{DDa1}$, an optionally substituted $C_{1-6}$ alkyl, an optionally substituted $C_{2-6}$ alkenyl, an optionally substituted $C_{2-6}$ alkynyl and an optionally substituted $C_{1-6}$ haloalkyl.

Some embodiments described herein relate to a method of ameliorating or treating a viral infection that can include contacting a cell infected with the viral infection with a therapeutically effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (BB), and a compound of Formula (DD), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (BB), and a compound of Formula (DD), or a pharmaceutically acceptable salt of any of the aforementioned compounds.

Some embodiments described herein relate to a method of inhibiting viral replication of a virus that can include contacting a cell infected with the virus with an effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a mono-, di, and/or tri-phosphate thereof, a compound of Formula (BB), and a compound of Formula (DD), or a pharmaceutically acceptable salt of any of the aforementioned compounds.

Some embodiments described herein relate to a method of ameliorating or treating a viral infection that can include contacting a cell infected with the viral infection with a therapeutically effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), and a compound of Formula (DD), or a pharmaceutically acceptable salt of any of the aforementioned compounds.

Some embodiments described herein relate to a method of ameliorating or treating a viral infection that can include administering to a subject suffering from the viral infection a therapeutically effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), and a compound of Formula (DD), or a pharmaceutically acceptable salt of any of the aforementioned compounds.

Some embodiments described herein relate to a method of inhibiting viral replication of a virus that can include contacting a cell infected with the virus with an effective amount of a compound of Formula (I) (including a compound of Formula (Iα)), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB), and a compound of Formula (DD), or a pharmaceutically acceptable salt of any of the aforementioned compounds.

In some embodiments, a compound of Formula (I) (including a compound of Formula (Iα)), or a pharmaceutically acceptable salt thereof, can be administered with one or more additional agent(s) together in a single pharmaceutical composition. In some embodiments, a compound of Formula (I) (including a compound of Formula (Iα)), or a pharmaceutically acceptable salt the thereof, can be administered with one or more additional agent(s) as two or more separate pharmaceutical compositions. For example, a compound of Formula (I) (including a compound of Formula (Iα)), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I) (including a compound of Formula (Iα)), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I) (including a compound of Formula (Iα)), or a pharmaceutically acceptable salt thereof, can be administered prior to all additional agents. In other embodiments, a compound of Formula (I) (including a compound of Formula (Iα)), or a pharmaceutically acceptable salt thereof, can be administered prior to at least one additional agent. In still other embodiments, a compound of Formula (I) (including a compound of Formula (Iα)), or a pharmaceutically acceptable salt thereof, can be administered concomitantly with one or more additional agent(s). In yet still other embodiments, a compound of Formula (I) (including a compound of Formula (Iα)), or a pharmaceutically acceptable salt thereof, can be administered subsequent to the administration of at least one additional agent. In some embodiments, a compound of Formula (I) (including a compound of Formula (Iα)), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 2-6 and 8-10 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 2-6 and 8-10 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 2-6 and 8-10 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 2-6 and 8-10 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 2-6 and 8-10 (including pharmaceutically acceptable salts and prodrugs thereof) may be a reduction in the required amount(s) of one or more compounds of FIGS. 2-6 and 8-10 (including pharmaceutically acceptable salts and prodrugs thereof) that is effective in treating a disease condition disclosed herein (for example, HCV), as compared to the amount required to achieve same therapeutic result when one or more compounds of FIGS. 2-6 and 8-10 (including pharmaceutically acceptable salts and prodrugs thereof) are administered without a compound of Formula (I), or a pharmaceutically acceptable salt thereof. For example, the amount of a compound in FIGS. 2-6 and 8-10 (including a pharmaceutically acceptable salt and prodrug thereof), can be less compared to the amount of the compound in FIGS. 2-6 and 8-10 (including a pharmaceutically acceptable salt and prodrug thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 2-6 and 8-10 (including pharmaceutically acceptable salts and prodrugs thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 2-6 and 8-10 (including pharmaceutically acceptable salts and prodrugs thereof) may include little to no cross resistance between a compound of Formula (I), or a pharmaceutically acceptable salt thereof, and one or more additional agent(s) in FIGS. 2-6 and 8-10 (including pharmaceutically acceptable salts and prodrugs thereof) thereof; different routes for elimination of a compound of Formula (I), or a pharmaceutically acceptable salt thereof, and one or more additional agent(s) in FIGS. 2-6 and 8-10 (including pharmaceutically acceptable salts and prodrugs thereof); little to no overlapping toxicities between a compound of Formula (I), or a pharmaceutically acceptable salt thereof, and one or more additional agent(s) in FIGS. 2-6 and 8-10 (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) in FIGS. 2-6 and 8-10 (including pharmaceutically acceptable salts and prodrugs thereof).

A non-limiting list of example combination of compounds of Formula (I), or a pharmaceutically acceptable salt thereof, or a pharmaceutical composition that includes a compound described herein, with one or more additional agent(s) are provided in Tables A, B, C and D. Each numbered X and Y compound in Tables A, B, C and D has a corresponding name and/or structure provided in FIGS. 2 to 10. The numbered compounds in Tables A, B, C and D includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C and D are designated by the formula X:Y, which represents a combination of a compound X with a compound Y. For example, the combination designated as 1001:6001 in Table A represents a combination of compound 1001 with compound 6001, including pharmaceutically acceptable salts of compound 1001 and/or 6001, and pharmaceutical compositions including compound 1001 and 6001 (including pharmaceutical compositions that include pharmaceutically acceptable salts of compound 1001 and/or compound 6001). Thus, the combination designated as 1001:6001 in Table A represents the combination of Telaprevir (compound 1001, as shown in FIG. 2) and

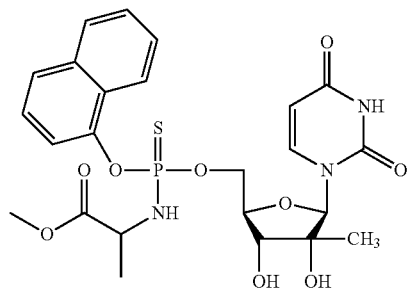

Figure 7A:
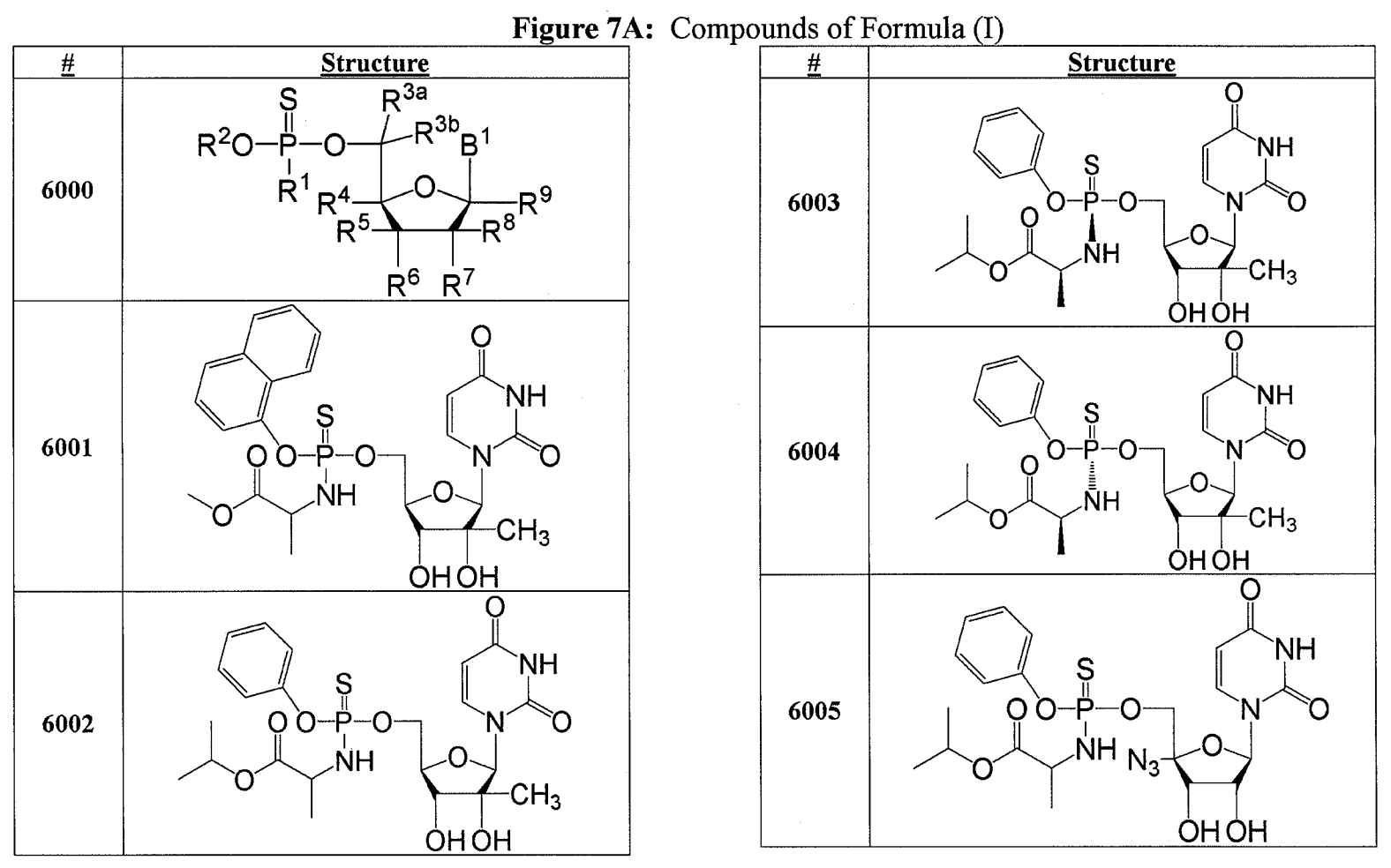
Figure 7B:
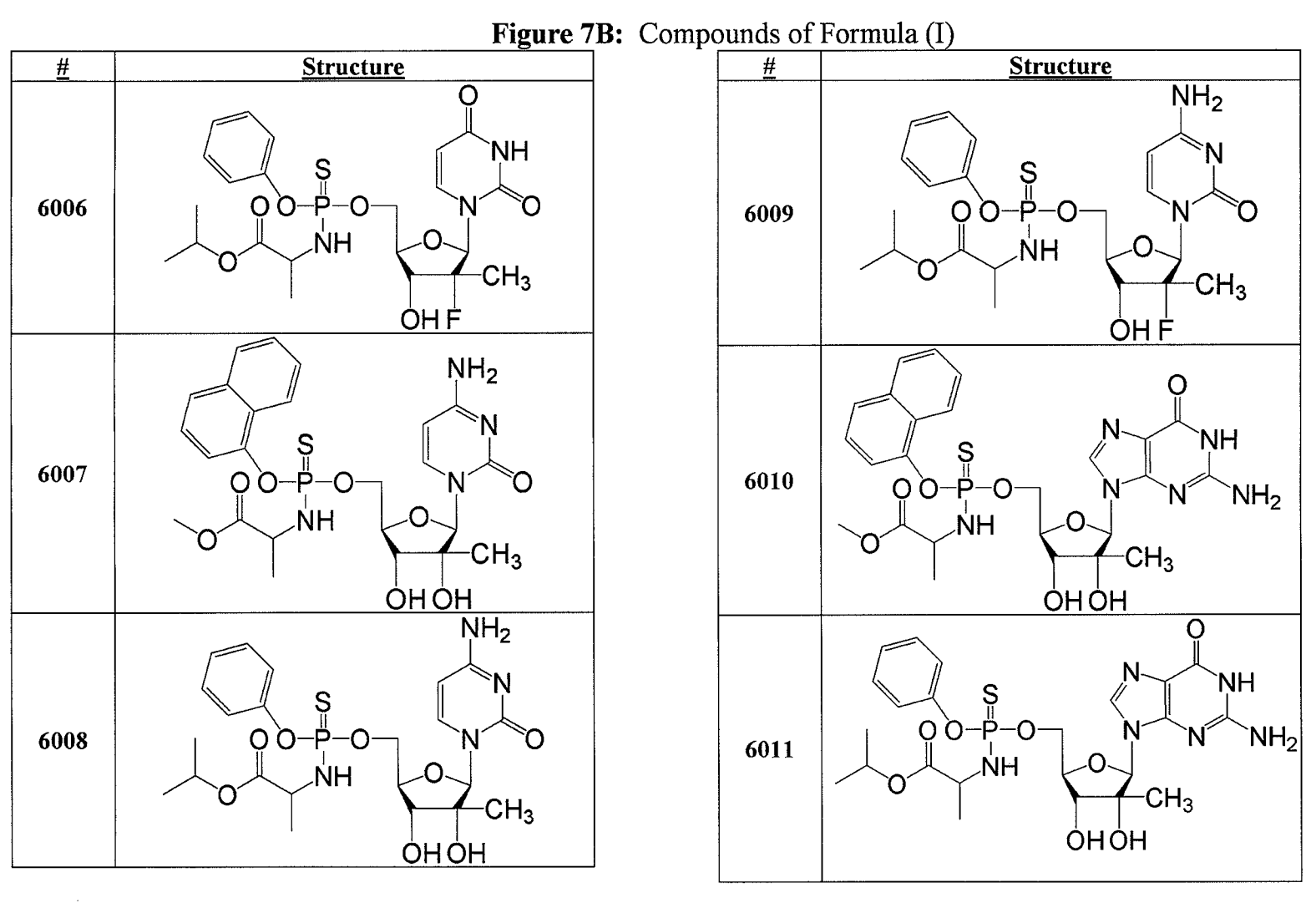
Figure 7D:
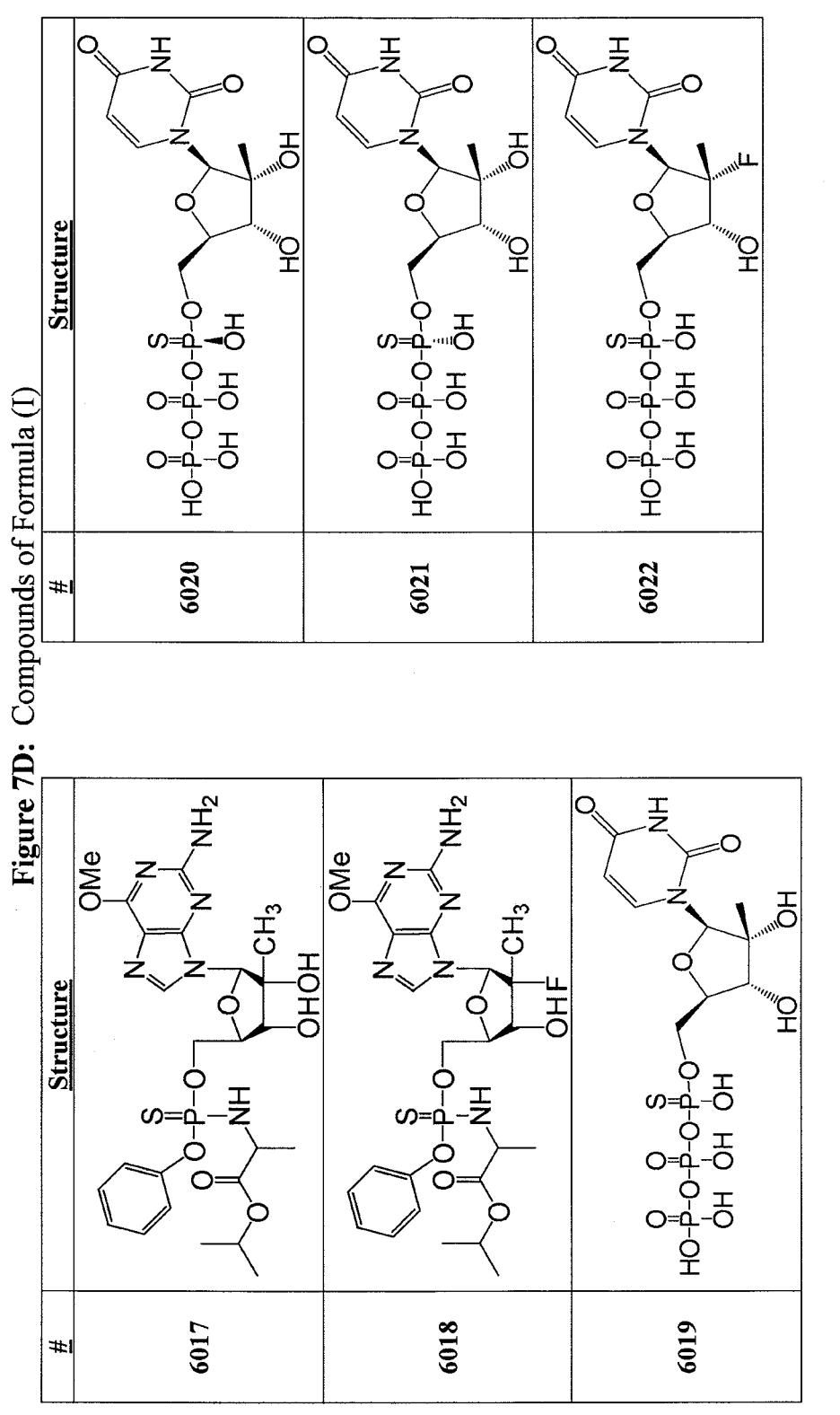
Figure 7E:
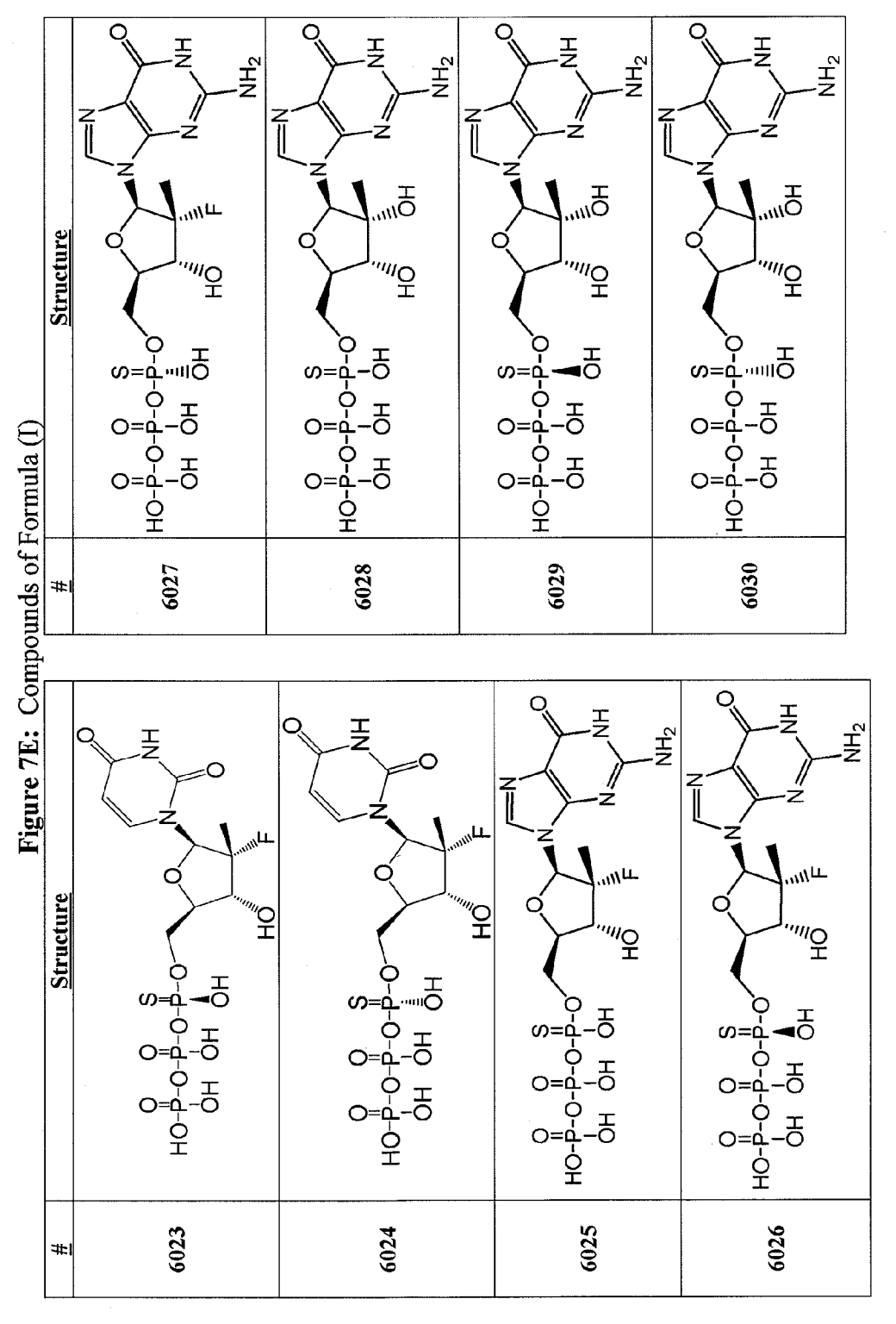
Figure 7I:
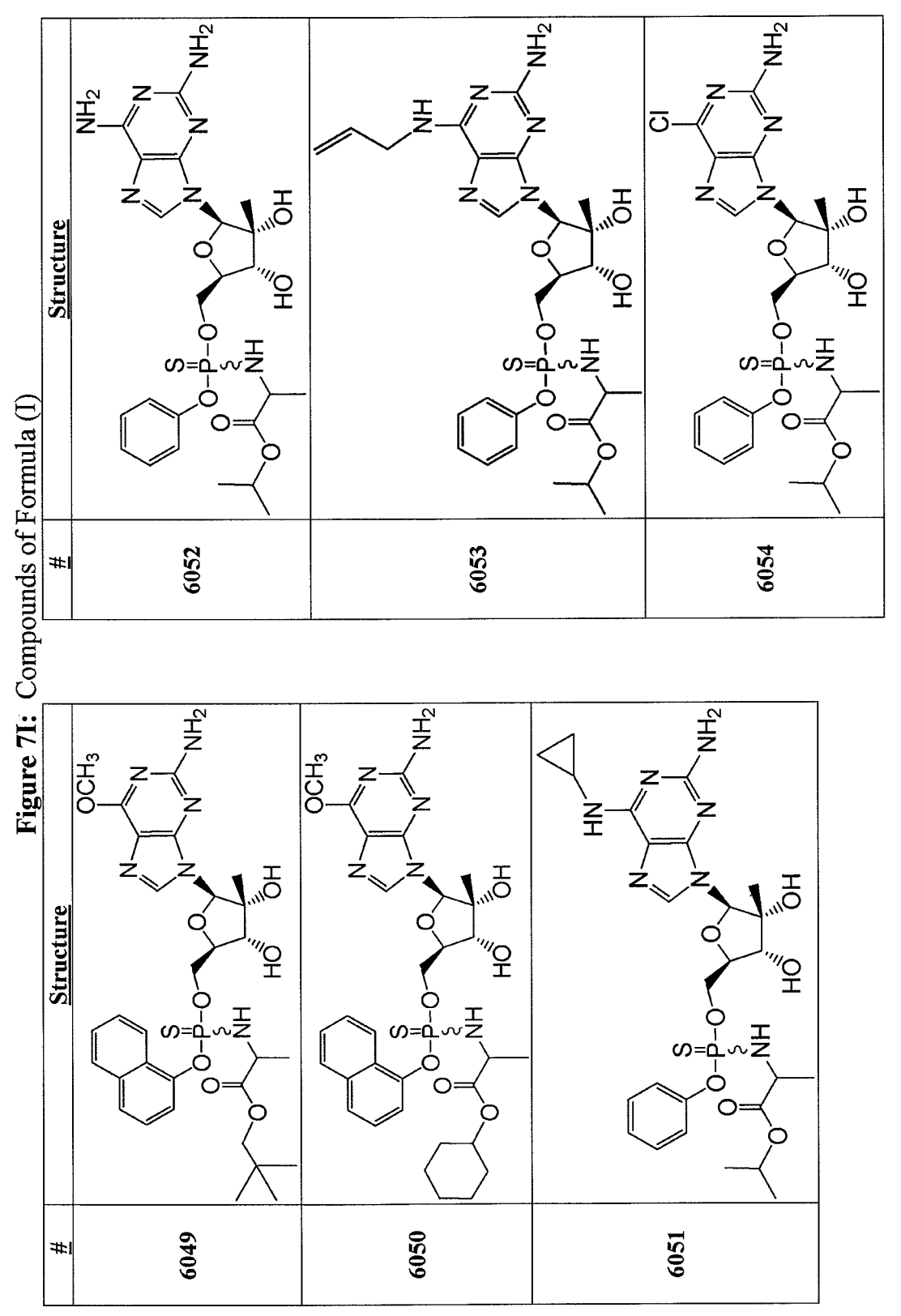
Figure 7J:
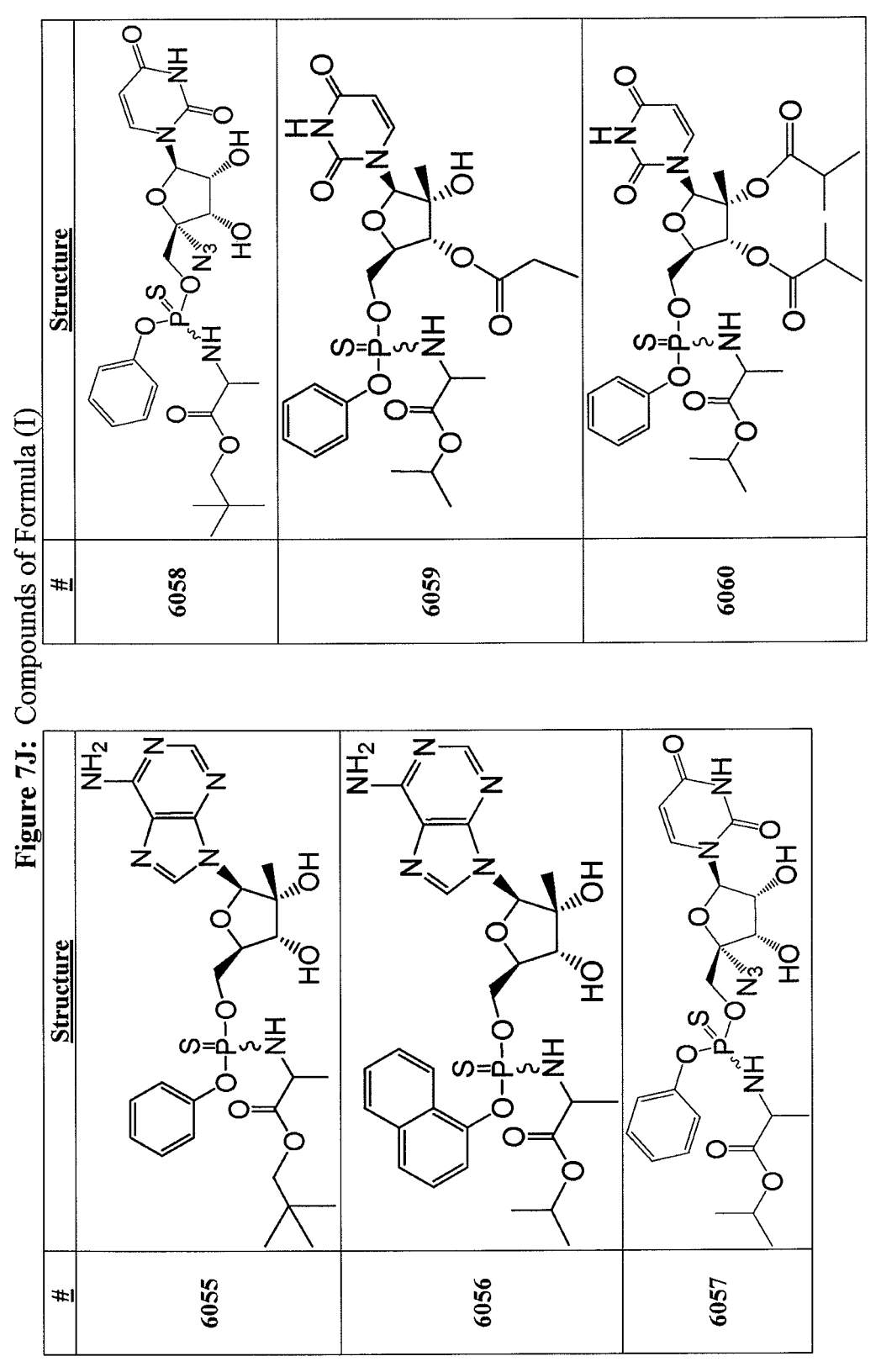

(compound 6001, as shown in FIG. 7A), including pharmaceutically acceptable salts of compound 1001 and/or 6001, and pharmaceutical compositions including compound 1001 and 6001 (including pharmaceutical compositions that include pharmaceutically acceptable salts of compound 1001 and/or compound 6001). Each of the combinations provided in Tables A, B, C and D can be used with one, two, three or more additional agents described herein. In some embodiments, embodiments described herein, the combination of agents can be used to treat, amerliorate and/or inhibit a virus and/or a viral infection, wherein the virus can be HCV and the viral infection can be an HCV viral infection.

TABLE A

| Example combinations of a compound X with a compound Y. | | | | | | |
|---|---|---|---|---|---|---|
| X:Y | X:Y | X:Y | X:Y | X:Y | X:Y | X:Y |
| 1001:6000 | 1001:6001 | 1001:6002 | 1001:6003 | 1001:6004 | 1001:6005 | 1001:6006 |
| 1002:6000 | 1002:6001 | 1002:6002 | 1002:6003 | 1002:6004 | 1002:6005 | 1002:6006 |
| 1003:6000 | 1003:6001 | 1003:6002 | 1003:6003 | 1003:6004 | 1003:6005 | 1003:6006 |
| 1004:6000 | 1004:6001 | 1004:6002 | 1004:6003 | 1004:6004 | 1004:6005 | 1004:6006 |
| 1005:6000 | 1005:6001 | 1005:6002 | 1005:6003 | 1005:6004 | 1005:6005 | 1005:6006 |

TABLE A-continued

Example combinations of a compound X with a compound Y.

| X:Y | X:Y | X:Y | X:Y | X:Y | X:Y | X:Y |
|---|---|---|---|---|---|---|
| 1006:6000 | 1006:6001 | 1006:6002 | 1006:6003 | 1006:6004 | 1006:6005 | 1006:6006 |
| 1007:6000 | 1007:6001 | 1007:6002 | 1007:6003 | 1007:6004 | 1007:6005 | 1007:6006 |
| 1008:6000 | 1008:6001 | 1008:6002 | 1008:6003 | 1008:6004 | 1008:6005 | 1008:6006 |
| 1009:6000 | 1009:6001 | 1009:6002 | 1009:6003 | 1009:6004 | 1009:6005 | 1009:6006 |
| 1010:6000 | 1010:6001 | 1010:6002 | 1010:6003 | 1010:6004 | 1010:6005 | 1010:6006 |
| 1011:6000 | 1011:6001 | 1011:6002 | 1011:6003 | 1011:6004 | 1011:6005 | 1011:6006 |
| 1012:6000 | 1012:6001 | 1012:6002 | 1012:6003 | 1012:6004 | 1012:6005 | 1012:6006 |
| 1013:6000 | 1013:6001 | 1013:6002 | 1013:6003 | 1013:6004 | 1013:6005 | 1013:6006 |
| 1014:6000 | 1014:6001 | 1014:6002 | 1014:6003 | 1014:6004 | 1014:6005 | 1014:6006 |
| 2001:6000 | 2001:6001 | 2001:6002 | 2001:6003 | 2001:6004 | 2001:6005 | 2001:6006 |
| 2002:6000 | 2002:6001 | 2002:6002 | 2002:6003 | 2002:6004 | 2002:6005 | 2002:6006 |
| 2003:6000 | 2003:6001 | 2003:6002 | 2003:6003 | 2003:6004 | 2003:6005 | 2003:6006 |
| 2004:6000 | 2004:6001 | 2004:6002 | 2004:6003 | 2004:6004 | 2004:6005 | 2004:6006 |
| 2005:6000 | 2005:6001 | 2005:6002 | 2005:6003 | 2005:6004 | 2005:6005 | 2005:6006 |
| 2006:6000 | 2006:6001 | 2006:6002 | 2006:6003 | 2006:6004 | 2006:6005 | 2006:6006 |
| 2007:6000 | 2007:6001 | 2007:6002 | 2007:6003 | 2007:6004 | 2007:6005 | 2007:6006 |
| 2008:6000 | 2008:6001 | 2008:6002 | 2008:6003 | 2008:6004 | 2008:6005 | 2008:6006 |
| 2009:6000 | 2009:6001 | 2009:6002 | 2009:6003 | 2009:6004 | 2009:6005 | 2009:6006 |
| 2010:6000 | 2010:6001 | 2010:6002 | 2010:6003 | 2010:6004 | 2010:6005 | 2010:6006 |
| 3001:6000 | 3001:6001 | 3001:6002 | 3001:6003 | 3001:6004 | 3001:6005 | 3001:6006 |
| 3002:6000 | 3002:6001 | 3002:6002 | 3002:6003 | 3002:6004 | 3002:6005 | 3002:6006 |
| 3003:6000 | 3003:6001 | 3003:6002 | 3003:6003 | 3003:6004 | 3003:6005 | 3003:6006 |
| 3004:6000 | 3004:6001 | 3004:6002 | 3004:6003 | 3004:6004 | 3004:6005 | 3004:6006 |
| 3005:6000 | 3005:6001 | 3005:6002 | 3005:6003 | 3005:6004 | 3005:6005 | 3005:6006 |
| 3006:6000 | 3006:6001 | 3006:6002 | 3006:6003 | 3006:6004 | 3006:6005 | 3006:6006 |
| 3007:6000 | 3007:6001 | 3007:6002 | 3007:6003 | 3007:6004 | 3007:6005 | 3007:6006 |
| 3008:6000 | 3008:6001 | 3008:6002 | 3008:6003 | 3008:6004 | 3008:6005 | 3008:6006 |
| 4001:6000 | 4001:6001 | 4001:6002 | 4001:6003 | 4001:6004 | 4001:6005 | 4001:6006 |
| 4002:6000 | 4002:6001 | 4002:6002 | 4002:6003 | 4002:6004 | 4002:6005 | 4002:6006 |
| 4003:6000 | 4003:6001 | 4003:6002 | 4003:6003 | 4003:6004 | 4003:6005 | 4003:6006 |
| 4004:6000 | 4004:6001 | 4004:6002 | 4004:6003 | 4004:6004 | 4004:6005 | 4004:6006 |
| 4005:6000 | 4005:6001 | 4005:6002 | 4005:6003 | 4005:6004 | 4005:6005 | 4005:6006 |
| 5001:6000 | 5001:6001 | 5001:6002 | 5001:6003 | 5001:6004 | 5001:6005 | 5001:6006 |
| 5002:6000 | 5002:6001 | 5002:6002 | 5002:6003 | 5002:6004 | 5002:6005 | 5002:6006 |
| 1001:6007 | 1001:6008 | 1001:6009 | 1001:6010 | 1001:6011 | 1001:6012 | 1001:6013 |
| 1002:6007 | 1002:6008 | 1002:6009 | 1002:6010 | 1002:6011 | 1002:6012 | 1002:6013 |
| 1003:6007 | 1003:6008 | 1003:6009 | 1003:6010 | 1003:6011 | 1003:6012 | 1003:6013 |
| 1004:6007 | 1004:6008 | 1004:6009 | 1004:6010 | 1004:6011 | 1004:6012 | 1004:6013 |
| 1005:6007 | 1005:6008 | 1005:6009 | 1005:6010 | 1005:6011 | 1005:6012 | 1005:6013 |
| 1006:6007 | 1006:6008 | 1006:6009 | 1006:6010 | 1006:6011 | 1006:6012 | 1006:6013 |
| 1007:6007 | 1007:6008 | 1007:6009 | 1007:6010 | 1007:6011 | 1007:6012 | 1007:6013 |
| 1008:6007 | 1008:6008 | 1008:6009 | 1008:6010 | 1008:6011 | 1008:6012 | 1008:6013 |
| 1009:6007 | 1009:6008 | 1009:6009 | 1009:6010 | 1009:6011 | 1009:6012 | 1009:6013 |
| 1010:6007 | 1010:6008 | 1010:6009 | 1010:6010 | 1010:6011 | 1010:6012 | 1010:6013 |
| 1011:6007 | 1011:6008 | 1011:6009 | 1011:6010 | 1011:6011 | 1011:6012 | 1011:6013 |
| 1012:6007 | 1012:6008 | 1012:6009 | 1012:6010 | 1012:6011 | 1012:6012 | 1012:6013 |
| 1013:6007 | 1013:6008 | 1013:6009 | 1013:6010 | 1013:6011 | 1013:6012 | 1013:6013 |
| 1014:6007 | 1014:6008 | 1014:6009 | 1014:6010 | 1014:6011 | 1014:6012 | 1014:6013 |
| 2001:6007 | 2001:6008 | 2001:6009 | 2001:6010 | 2001:6011 | 2001:6012 | 2001:6013 |
| 2002:6007 | 2002:6008 | 2002:6009 | 2002:6010 | 2002:6011 | 2002:6012 | 2002:6013 |
| 2003:6007 | 2003:6008 | 2003:6009 | 2003:6010 | 2003:6011 | 2003:6012 | 2003:6013 |
| 2004:6007 | 2004:6008 | 2004:6009 | 2004:6010 | 2004:6011 | 2004:6012 | 2004:6013 |
| 2005:6007 | 2005:6008 | 2005:6009 | 2005:6010 | 2005:6011 | 2005:6012 | 2005:6013 |
| 2006:6007 | 2006:6008 | 2006:6009 | 2006:6010 | 2006:6011 | 2006:6012 | 2006:6013 |
| 2007:6007 | 2007:6008 | 2007:6009 | 2007:6010 | 2007:6011 | 2007:6012 | 2007:6013 |
| 2008:6007 | 2008:6008 | 2008:6009 | 2008:6010 | 2008:6011 | 2008:6012 | 2008:6013 |
| 2009:6007 | 2009:6008 | 2009:6009 | 2009:6010 | 2009:6011 | 2009:6012 | 2009:6013 |
| 2010:6007 | 2010:6008 | 2010:6009 | 2010:6010 | 2010:6011 | 2010:6012 | 2010:6013 |
| 3001:6007 | 3001:6008 | 3001:6009 | 3001:6010 | 3001:6011 | 3001:6012 | 3001:6013 |
| 3002:6007 | 3002:6008 | 3002:6009 | 3002:6010 | 3002:6011 | 3002:6012 | 3002:6013 |
| 3003:6007 | 3003:6008 | 3003:6009 | 3003:6010 | 3003:6011 | 3003:6012 | 3003:6013 |
| 3004:6007 | 3004:6008 | 3004:6009 | 3004:6010 | 3004:6011 | 3004:6012 | 3004:6013 |
| 3005:6007 | 3005:6008 | 3005:6009 | 3005:6010 | 3005:6011 | 3005:6012 | 3005:6013 |
| 3006:6007 | 3006:6008 | 3006:6009 | 3006:6010 | 3006:6011 | 3006:6012 | 3006:6013 |
| 3007:6007 | 3007:6008 | 3007:6009 | 3007:6010 | 3007:6011 | 3007:6012 | 3007:6013 |
| 3008:6007 | 3008:6008 | 3008:6009 | 3008:6010 | 3008:6011 | 3008:6012 | 3008:6013 |
| 4001:6007 | 4001:6008 | 4001:6009 | 4001:6010 | 4001:6011 | 4001:6012 | 4001:6013 |
| 4002:6007 | 4002:6008 | 4002:6009 | 4002:6010 | 4002:6011 | 4002:6012 | 4002:6013 |
| 4003:6007 | 4003:6008 | 4003:6009 | 4003:6010 | 4003:6011 | 4003:6012 | 4003:6013 |
| 4004:6007 | 4004:6008 | 4004:6009 | 4004:6010 | 4004:6011 | 4004:6012 | 4004:6013 |
| 4005:6007 | 4005:6008 | 4005:6009 | 4005:6010 | 4005:6011 | 4005:6012 | 4005:6013 |
| 5001:6007 | 5001:6008 | 5001:6009 | 5001:6010 | 5001:6011 | 5001:6012 | 5001:6013 |
| 5002:6007 | 5002:6008 | 5002:6009 | 5002:6010 | 5002:6011 | 5002:6012 | 5002:6013 |

TABLE A-continued

Example combinations of a compound X with a compound Y.

| X:Y | X:Y | X:Y | X:Y | X:Y | X:Y | X:Y |
|---|---|---|---|---|---|---|
| 1001:6014 | 1001:6015 | 1001:6016 | 1001:6017 | 1001:6018 | 1001:6019 | 1001:6020 |
| 1002:6014 | 1002:6015 | 1002:6016 | 1002:6017 | 1002:6018 | 1002:6019 | 1002:6020 |
| 1003:6014 | 1003:6015 | 1003:6016 | 1003:6017 | 1003:6018 | 1003:6019 | 1003:6020 |
| 1004:6014 | 1004:6015 | 1004:6016 | 1004:6017 | 1004:6018 | 1004:6019 | 1004:6020 |
| 1005:6014 | 1005:6015 | 1005:6016 | 1005:6017 | 1005:6018 | 1005:6019 | 1005:6020 |
| 1006:6014 | 1006:6015 | 1006:6016 | 1006:6017 | 1006:6018 | 1006:6019 | 1006:6020 |
| 1007:6014 | 1007:6015 | 1007:6016 | 1007:6017 | 1007:6018 | 1007:6019 | 1007:6020 |
| 1008:6014 | 1008:6015 | 1008:6016 | 1008:6017 | 1008:6018 | 1008:6019 | 1008:6020 |
| 1009:6014 | 1009:6015 | 1009:6016 | 1009:6017 | 1009:6018 | 1009:6019 | 1009:6020 |
| 1010:6014 | 1010:6015 | 1010:6016 | 1010:6017 | 1010:6018 | 1010:6019 | 1010:6020 |
| 1011:6014 | 1011:6015 | 1011:6016 | 1011:6017 | 1011:6018 | 1011:6019 | 1011:6020 |
| 1012:6014 | 1012:6015 | 1012:6016 | 1012:6017 | 1012:6018 | 1012:6019 | 1012:6020 |
| 1013:6014 | 1013:6015 | 1013:6016 | 1013:6017 | 1013:6018 | 1013:6019 | 1013:6020 |
| 1014:6014 | 1014:6015 | 1014:6016 | 1014:6017 | 1014:6018 | 1014:6019 | 1014:6020 |
| 2001:6014 | 2001:6015 | 2001:6016 | 2001:6017 | 2001:6018 | 2001:6019 | 2001:6020 |
| 2002:6014 | 2002:6015 | 2002:6016 | 2002:6017 | 2002:6018 | 2002:6019 | 2002:6020 |
| 2003:6014 | 2003:6015 | 2003:6016 | 2003:6017 | 2003:6018 | 2003:6019 | 2003:6020 |
| 2004:6014 | 2004:6015 | 2004:6016 | 2004:6017 | 2004:6018 | 2004:6019 | 2004:6020 |
| 2005:6014 | 2005:6015 | 2005:6016 | 2005:6017 | 2005:6018 | 2005:6019 | 2005:6020 |
| 2006:6014 | 2006:6015 | 2006:6016 | 2006:6017 | 2006:6018 | 2006:6019 | 2006:6020 |
| 2007:6014 | 2007:6015 | 2007:6016 | 2007:6017 | 2007:6018 | 2007:6019 | 2007:6020 |
| 2008:6014 | 2008:6015 | 2008:6016 | 2008:6017 | 2008:6018 | 2008:6019 | 2008:6020 |
| 2009:6014 | 2009:6015 | 2009:6016 | 2009:6017 | 2009:6018 | 2009:6019 | 2009:6020 |
| 2010:6014 | 2010:6015 | 2010:6016 | 2010:6017 | 2010:6018 | 2010:6019 | 2010:6020 |
| 3001:6014 | 3001:6015 | 3001:6016 | 3001:6017 | 3001:6018 | 3001:6019 | 3001:6020 |
| 3002:6014 | 3002:6015 | 3002:6016 | 3002:6017 | 3002:6018 | 3002:6019 | 3002:6020 |
| 3003:6014 | 3003:6015 | 3003:6016 | 3003:6017 | 3003:6018 | 3003:6019 | 3003:6020 |
| 3004:6014 | 3004:6015 | 3004:6016 | 3004:6017 | 3004:6018 | 3004:6019 | 3004:6020 |
| 3005:6014 | 3005:6015 | 3005:6016 | 3005:6017 | 3005:6018 | 3005:6019 | 3005:6020 |
| 3006:6014 | 3006:6015 | 3006:6016 | 3006:6017 | 3006:6018 | 3006:6019 | 3006:6020 |
| 3007:6014 | 3007:6015 | 3007:6016 | 3007:6017 | 3007:6018 | 3007:6019 | 3007:6020 |
| 3008:6014 | 3008:6015 | 3008:6016 | 3008:6017 | 3008:6018 | 3008:6019 | 3008:6020 |
| 4001:6014 | 4001:6015 | 4001:6016 | 4001:6017 | 4001:6018 | 4001:6019 | 4001:6020 |
| 4002:6014 | 4002:6015 | 4002:6016 | 4002:6017 | 4002:6018 | 4002:6019 | 4002:6020 |
| 4003:6014 | 4003:6015 | 4003:6016 | 4003:6017 | 4003:6018 | 4003:6019 | 4003:6020 |
| 4004:6014 | 4004:6015 | 4004:6016 | 4004:6017 | 4004:6018 | 4004:6019 | 4004:6020 |
| 4005:6014 | 4005:6015 | 4005:6016 | 4005:6017 | 4005:6018 | 4005:6019 | 4005:6020 |
| 5001:6014 | 5001:6015 | 5001:6016 | 5001:6017 | 5001:6018 | 5001:6019 | 5001:6020 |
| 5002:6014 | 5002:6015 | 5002:6016 | 5002:6017 | 5002:6018 | 5002:6019 | 5002:6020 |
| 1001:6021 | 1001:6022 | 1001:6023 | 1001:6024 | 1001:6025 | 1001:6026 | 1001:6027 |
| 1002:6021 | 1002:6022 | 1002:6023 | 1002:6024 | 1002:6025 | 1002:6026 | 1002:6027 |
| 1003:6021 | 1003:6022 | 1003:6023 | 1003:6024 | 1003:6025 | 1003:6026 | 1003:6027 |
| 1004:6021 | 1004:6022 | 1004:6023 | 1004:6024 | 1004:6025 | 1004:6026 | 1004:6027 |
| 1005:6021 | 1005:6022 | 1005:6023 | 1005:6024 | 1005:6025 | 1005:6026 | 1005:6027 |
| 1006:6021 | 1006:6022 | 1006:6023 | 1006:6024 | 1006:6025 | 1006:6026 | 1006:6027 |
| 1007:6021 | 1007:6022 | 1007:6023 | 1007:6024 | 1007:6025 | 1007:6026 | 1007:6027 |
| 1008:6021 | 1008:6022 | 1008:6023 | 1008:6024 | 1008:6025 | 1008:6026 | 1008:6027 |
| 1009:6021 | 1009:6022 | 1009:6023 | 1009:6024 | 1009:6025 | 1009:6026 | 1009:6027 |
| 1010:6021 | 1010:6022 | 1010:6023 | 1010:6024 | 1010:6025 | 1010:6026 | 1010:6027 |
| 1011:6021 | 1011:6022 | 1011:6023 | 1011:6024 | 1011:6025 | 1011:6026 | 1011:6027 |
| 1012:6021 | 1012:6022 | 1012:6023 | 1012:6024 | 1012:6025 | 1012:6026 | 1012:6027 |
| 1013:6021 | 1013:6022 | 1013:6023 | 1013:6024 | 1013:6025 | 1013:6026 | 1013:6027 |
| 1014:6021 | 1014:6022 | 1014:6023 | 1014:6024 | 1014:6025 | 1014:6026 | 1014:6027 |
| 2001:6021 | 2001:6022 | 2001:6023 | 2001:6024 | 2001:6025 | 2001:6026 | 2001:6027 |
| 2002:6021 | 2002:6022 | 2002:6023 | 2002:6024 | 2002:6025 | 2002:6026 | 2002:6027 |
| 2003:6021 | 2003:6022 | 2003:6023 | 2003:6024 | 2003:6025 | 2003:6026 | 2003:6027 |
| 2004:6021 | 2004:6022 | 2004:6023 | 2004:6024 | 2004:6025 | 2004:6026 | 2004:6027 |
| 2005:6021 | 2005:6022 | 2005:6023 | 2005:6024 | 2005:6025 | 2005:6026 | 2005:6027 |
| 2006:6021 | 2006:6022 | 2006:6023 | 2006:6024 | 2006:6025 | 2006:6026 | 2006:6027 |
| 2007:6021 | 2007:6022 | 2007:6023 | 2007:6024 | 2007:6025 | 2007:6026 | 2007:6027 |
| 2008:6021 | 2008:6022 | 2008:6023 | 2008:6024 | 2008:6025 | 2008:6026 | 2008:6027 |
| 2009:6021 | 2009:6022 | 2009:6023 | 2009:6024 | 2009:6025 | 2009:6026 | 2009:6027 |
| 2010:6021 | 2010:6022 | 2010:6023 | 2010:6024 | 2010:6025 | 2010:6026 | 2010:6027 |
| 3001:6021 | 3001:6022 | 3001:6023 | 3001:6024 | 3001:6025 | 3001:6026 | 3001:6027 |
| 3002:6021 | 3002:6022 | 3002:6023 | 3002:6024 | 3002:6025 | 3002:6026 | 3002:6027 |
| 3003:6021 | 3003:6022 | 3003:6023 | 3003:6024 | 3003:6025 | 3003:6026 | 3003:6027 |
| 3004:6021 | 3004:6022 | 3004:6023 | 3004:6024 | 3004:6025 | 3004:6026 | 3004:6027 |
| 3005:6021 | 3005:6022 | 3005:6023 | 3005:6024 | 3005:6025 | 3005:6026 | 3005:6027 |
| 3006:6021 | 3006:6022 | 3006:6023 | 3006:6024 | 3006:6025 | 3006:6026 | 3006:6027 |
| 3007:6021 | 3007:6022 | 3007:6023 | 3007:6024 | 3007:6025 | 3007:6026 | 3007:6027 |
| 3008:6021 | 3008:6022 | 3008:6023 | 3008:6024 | 3008:6025 | 3008:6026 | 3008:6027 |
| 4001:6021 | 4001:6022 | 4001:6023 | 4001:6024 | 4001:6025 | 4001:6026 | 4001:6027 |
| 4002:6021 | 4002:6022 | 4002:6023 | 4002:6024 | 4002:6025 | 4002:6026 | 4002:6027 |
| 4003:6021 | 4003:6022 | 4003:6023 | 4003:6024 | 4003:6025 | 4003:6026 | 4003:6027 |
| 4004:6021 | 4004:6022 | 4004:6023 | 4004:6024 | 4004:6025 | 4004:6026 | 4004:6027 |

TABLE A-continued

Example combinations of a compound X with a compound Y.

| X:Y | X:Y | X:Y | X:Y | X:Y | X:Y | X:Y |
|---|---|---|---|---|---|---|
| 4005:6021 | 4005:6022 | 4005:6023 | 4005:6024 | 4005:6025 | 4005:6026 | 4005:6027 |
| 5001:6021 | 5001:6022 | 5001:6023 | 5001:6024 | 5001:6025 | 5001:6026 | 5001:6027 |
| 5002:6021 | 5002:6022 | 5002:6023 | 5002:6024 | 5002:6025 | 5002:6026 | 5002:6027 |
| 1001:6028 | 1001:6029 | 1001:6030 | 1001:6031 | 1001:6032 | 1001:6033 | 1001:6034 |
| 1002:6028 | 1002:6029 | 1002:6030 | 1002:6031 | 1002:6032 | 1002:6033 | 1002:6034 |
| 1003:6028 | 1003:6029 | 1003:6030 | 1003:6031 | 1003:6032 | 1003:6033 | 1003:6034 |
| 1004:6028 | 1004:6029 | 1004:6030 | 1004:6031 | 1004:6032 | 1004:6033 | 1004:6034 |
| 1005:6028 | 1005:6029 | 1005:6030 | 1005:6031 | 1005:6032 | 1005:6033 | 1005:6034 |
| 1006:6028 | 1006:6029 | 1006:6030 | 1006:6031 | 1006:6032 | 1006:6033 | 1006:6034 |
| 1007:6028 | 1007:6029 | 1007:6030 | 1007:6031 | 1007:6032 | 1007:6033 | 1007:6034 |
| 1008:6028 | 1008:6029 | 1008:6030 | 1008:6031 | 1008:6032 | 1008:6033 | 1008:6034 |
| 1009:6028 | 1009:6029 | 1009:6030 | 1009:6031 | 1009:6032 | 1009:6033 | 1009:6034 |
| 1010:6028 | 1010:6029 | 1010:6030 | 1010:6031 | 1010:6032 | 1010:6033 | 1010:6034 |
| 1011:6028 | 1011:6029 | 1011:6030 | 1011:6031 | 1011:6032 | 1011:6033 | 1011:6034 |
| 1012:6028 | 1012:6029 | 1012:6030 | 1012:6031 | 1012:6032 | 1012:6033 | 1012:6034 |
| 1013:6028 | 1013:6029 | 1013:6030 | 1013:6031 | 1013:6032 | 1013:6033 | 1013:6034 |
| 1014:6028 | 1014:6029 | 1014:6030 | 1014:6031 | 1014:6032 | 1014:6033 | 1014:6034 |
| 2001:6028 | 2001:6029 | 2001:6030 | 2001:6031 | 2001:6032 | 2001:6033 | 2001:6034 |
| 2002:6028 | 2002:6029 | 2002:6030 | 2002:6031 | 2002:6032 | 2002:6033 | 2002:6034 |
| 2003:6028 | 2003:6029 | 2003:6030 | 2003:6031 | 2003:6032 | 2003:6033 | 2003:6034 |
| 2004:6028 | 2004:6029 | 2004:6030 | 2004:6031 | 2004:6032 | 2004:6033 | 2004:6034 |
| 2005:6028 | 2005:6029 | 2005:6030 | 2005:6031 | 2005:6032 | 2005:6033 | 2005:6034 |
| 2006:6028 | 2006:6029 | 2006:6030 | 2006:6031 | 2006:6032 | 2006:6033 | 2006:6034 |
| 2007:6028 | 2007:6029 | 2007:6030 | 2007:6031 | 2007:6032 | 2007:6033 | 2007:6034 |
| 2008:6028 | 2008:6029 | 2008:6030 | 2008:6031 | 2008:6032 | 2008:6033 | 2008:6034 |
| 2009:6028 | 2009:6029 | 2009:6030 | 2009:6031 | 2009:6032 | 2009:6033 | 2009:6034 |
| 2010:6028 | 2010:6029 | 2010:6030 | 2010:6031 | 2010:6032 | 2010:6033 | 2010:6034 |
| 3001:6028 | 3001:6029 | 3001:6030 | 3001:6031 | 3001:6032 | 3001:6033 | 3001:6034 |
| 3002:6028 | 3002:6029 | 3002:6030 | 3002:6031 | 3002:6032 | 3002:6033 | 3002:6034 |
| 3003:6028 | 3003:6029 | 3003:6030 | 3003:6031 | 3003:6032 | 3003:6033 | 3003:6034 |
| 3004:6028 | 3004:6029 | 3004:6030 | 3004:6031 | 3004:6032 | 3004:6033 | 3004:6034 |
| 3005:6028 | 3005:6029 | 3005:6030 | 3005:6031 | 3005:6032 | 3005:6033 | 3005:6034 |
| 3006:6028 | 3006:6029 | 3006:6030 | 3006:6031 | 3006:6032 | 3006:6033 | 3006:6034 |
| 3007:6028 | 3007:6029 | 3007:6030 | 3007:6031 | 3007:6032 | 3007:6033 | 3007:6034 |
| 3008:6028 | 3008:6029 | 3008:6030 | 3008:6031 | 3008:6032 | 3008:6033 | 3008:6034 |
| 4001:6028 | 4001:6029 | 4001:6030 | 4001:6031 | 4001:6032 | 4001:6033 | 4001:6034 |
| 4002:6028 | 4002:6029 | 4002:6030 | 4002:6031 | 4002:6032 | 4002:6033 | 4002:6034 |
| 4003:6028 | 4003:6029 | 4003:6030 | 4003:6031 | 4003:6032 | 4003:6033 | 4003:6034 |
| 4004:6028 | 4004:6029 | 4004:6030 | 4004:6031 | 4004:6032 | 4004:6033 | 4004:6034 |
| 4005:6028 | 4005:6029 | 4005:6030 | 4005:6031 | 4005:6032 | 4005:6033 | 4005:6034 |
| 5001:6028 | 5001:6029 | 5001:6030 | 5001:6031 | 5001:6032 | 5001:6033 | 5001:6034 |
| 5002:6028 | 5002:6029 | 5002:6030 | 5002:6031 | 5002:6032 | 5002:6033 | 5002:6034 |
| 1001:6035 | 1001:6036 | 1001:6037 | 1001:6038 | 1001:6039 | 1001:6040 | 1001:6041 |
| 1002:6035 | 1002:6036 | 1002:6037 | 1002:6038 | 1002:6039 | 1002:6040 | 1002:6041 |
| 1003:6035 | 1003:6036 | 1003:6037 | 1003:6038 | 1003:6039 | 1003:6040 | 1003:6041 |
| 1004:6035 | 1004:6036 | 1004:6037 | 1004:6038 | 1004:6039 | 1004:6040 | 1004:6041 |
| 1005:6035 | 1005:6036 | 1005:6037 | 1005:6038 | 1005:6039 | 1005:6040 | 1005:6041 |
| 1006:6035 | 1006:6036 | 1006:6037 | 1006:6038 | 1006:6039 | 1006:6040 | 1006:6041 |
| 1007:6035 | 1007:6036 | 1007:6037 | 1007:6038 | 1007:6039 | 1007:6040 | 1007:6041 |
| 1008:6035 | 1008:6036 | 1008:6037 | 1008:6038 | 1008:6039 | 1008:6040 | 1008:6041 |
| 1009:6035 | 1009:6036 | 1009:6037 | 1009:6038 | 1009:6039 | 1009:6040 | 1009:6041 |
| 1010:6035 | 1010:6036 | 1010:6037 | 1010:6038 | 1010:6039 | 1010:6040 | 1010:6041 |
| 1011:6035 | 1011:6036 | 1011:6037 | 1011:6038 | 1011:6039 | 1011:6040 | 1011:6041 |
| 1012:6035 | 1012:6036 | 1012:6037 | 1012:6038 | 1012:6039 | 1012:6040 | 1012:6041 |
| 1013:6035 | 1013:6036 | 1013:6037 | 1013:6038 | 1013:6039 | 1013:6040 | 1013:6041 |
| 1014:6035 | 1014:6036 | 1014:6037 | 1014:6038 | 1014:6039 | 1014:6040 | 1014:6041 |
| 2001:6035 | 2001:6036 | 2001:6037 | 2001:6038 | 2001:6039 | 2001:6040 | 2001:6041 |
| 2002:6035 | 2002:6036 | 2002:6037 | 2002:6038 | 2002:6039 | 2002:6040 | 2002:6041 |
| 2003:6035 | 2003:6036 | 2003:6037 | 2003:6038 | 2003:6039 | 2003:6040 | 2003:6041 |
| 2004:6035 | 2004:6036 | 2004:6037 | 2004:6038 | 2004:6039 | 2004:6040 | 2004:6041 |
| 2005:6035 | 2005:6036 | 2005:6037 | 2005:6038 | 2005:6039 | 2005:6040 | 2005:6041 |
| 2006:6035 | 2006:6036 | 2006:6037 | 2006:6038 | 2006:6039 | 2006:6040 | 2006:6041 |
| 2007:6035 | 2007:6036 | 2007:6037 | 2007:6038 | 2007:6039 | 2007:6040 | 2007:6041 |
| 2008:6035 | 2008:6036 | 2008:6037 | 2008:6038 | 2008:6039 | 2008:6040 | 2008:6041 |
| 2009:6035 | 2009:6036 | 2009:6037 | 2009:6038 | 2009:6039 | 2009:6040 | 2009:6041 |
| 2010:6035 | 2010:6036 | 2010:6037 | 2010:6038 | 2010:6039 | 2010:6040 | 2010:6041 |
| 3001:6035 | 3001:6036 | 3001:6037 | 3001:6038 | 3001:6039 | 3001:6040 | 3001:6041 |
| 3002:6035 | 3002:6036 | 3002:6037 | 3002:6038 | 3002:6039 | 3002:6040 | 3002:6041 |
| 3003:6035 | 3003:6036 | 3003:6037 | 3003:6038 | 3003:6039 | 3003:6040 | 3003:6041 |
| 3004:6035 | 3004:6036 | 3004:6037 | 3004:6038 | 3004:6039 | 3004:6040 | 3004:6041 |
| 3005:6035 | 3005:6036 | 3005:6037 | 3005:6038 | 3005:6039 | 3005:6040 | 3005:6041 |
| 3006:6035 | 3006:6036 | 3006:6037 | 3006:6038 | 3006:6039 | 3006:6040 | 3006:6041 |
| 3007:6035 | 3007:6036 | 3007:6037 | 3007:6038 | 3007:6039 | 3007:6040 | 3007:6041 |
| 3008:6035 | 3008:6036 | 3008:6037 | 3008:6038 | 3008:6039 | 3008:6040 | 3008:6041 |

TABLE A-continued

Example combinations of a compound X with a compound Y.

| X:Y | X:Y | X:Y | X:Y | X:Y | X:Y | X:Y |
|---|---|---|---|---|---|---|
| 4001:6035 | 4001:6036 | 4001:6037 | 4001:6038 | 4001:6039 | 4001:6040 | 4001:6041 |
| 4002:6035 | 4002:6036 | 4002:6037 | 4002:6038 | 4002:6039 | 4002:6040 | 4002:6041 |
| 4003:6035 | 4003:6036 | 4003:6037 | 4003:6038 | 4003:6039 | 4003:6040 | 4003:6041 |
| 4004:6035 | 4004:6036 | 4004:6037 | 4004:6038 | 4004:6039 | 4004:6040 | 4004:6041 |
| 4005:6035 | 4005:6036 | 4005:6037 | 4005:6038 | 4005:6039 | 4005:6040 | 4005:6041 |
| 5001:6035 | 5001:6036 | 5001:6037 | 5001:6038 | 5001:6039 | 5001:6040 | 5001:6041 |
| 5002:6035 | 5002:6036 | 5002:6037 | 5002:6038 | 5002:6039 | 5002:6040 | 5002:6041 |
| 1001:6042 | 1001:6043 | 1001:6044 | 1001:6045 | 1001:6046 | 1001:6047 | 1001:6048 |
| 1002:6042 | 1002:6043 | 1002:6044 | 1002:6045 | 1002:6046 | 1002:6047 | 1002:6048 |
| 1003:6042 | 1003:6043 | 1003:6044 | 1003:6045 | 1003:6046 | 1003:6047 | 1003:6048 |
| 1004:6042 | 1004:6043 | 1004:6044 | 1004:6045 | 1004:6046 | 1004:6047 | 1004:6048 |
| 1005:6042 | 1005:6043 | 1005:6044 | 1005:6045 | 1005:6046 | 1005:6047 | 1005:6048 |
| 1006:6042 | 1006:6043 | 1006:6044 | 1006:6045 | 1006:6046 | 1006:6047 | 1006:6048 |
| 1007:6042 | 1007:6043 | 1007:6044 | 1007:6045 | 1007:6046 | 1007:6047 | 1007:6048 |
| 1008:6042 | 1008:6043 | 1008:6044 | 1008:6045 | 1008:6046 | 1008:6047 | 1008:6048 |
| 1009:6042 | 1009:6043 | 1009:6044 | 1009:6045 | 1009:6046 | 1009:6047 | 1009:6048 |
| 1010:6042 | 1010:6043 | 1010:6044 | 1010:6045 | 1010:6046 | 1010:6047 | 1010:6048 |
| 1011:6042 | 1011:6043 | 1011:6044 | 1011:6045 | 1011:6046 | 1011:6047 | 1011:6048 |
| 1012:6042 | 1012:6043 | 1012:6044 | 1012:6045 | 1012:6046 | 1012:6047 | 1012:6048 |
| 1013:6042 | 1013:6043 | 1013:6044 | 1013:6045 | 1013:6046 | 1013:6047 | 1013:6048 |
| 1014:6042 | 1014:6043 | 1014:6044 | 1014:6045 | 1014:6046 | 1014:6047 | 1014:6048 |
| 2001:6042 | 2001:6043 | 2001:6044 | 2001:6045 | 2001:6046 | 2001:6047 | 2001:6048 |
| 2002:6042 | 2002:6043 | 2002:6044 | 2002:6045 | 2002:6046 | 2002:6047 | 2002:6048 |
| 2003:6042 | 2003:6043 | 2003:6044 | 2003:6045 | 2003:6046 | 2003:6047 | 2003:6048 |
| 2004:6042 | 2004:6043 | 2004:6044 | 2004:6045 | 2004:6046 | 2004:6047 | 2004:6048 |
| 2005:6042 | 2005:6043 | 2005:6044 | 2005:6045 | 2005:6046 | 2005:6047 | 2005:6048 |
| 2006:6042 | 2006:6043 | 2006:6044 | 2006:6045 | 2006:6046 | 2006:6047 | 2006:6048 |
| 2007:6042 | 2007:6043 | 2007:6044 | 2007:6045 | 2007:6046 | 2007:6047 | 2007:6048 |
| 2008:6042 | 2008:6043 | 2008:6044 | 2008:6045 | 2008:6046 | 2008:6047 | 2008:6048 |
| 2009:6042 | 2009:6043 | 2009:6044 | 2009:6045 | 2009:6046 | 2009:6047 | 2009:6048 |
| 2010:6042 | 2010:6043 | 2010:6044 | 2010:6045 | 2010:6046 | 2010:6047 | 2010:6048 |
| 3001:6042 | 3001:6043 | 3001:6044 | 3001:6045 | 3001:6046 | 3001:6047 | 3001:6048 |
| 3002:6042 | 3002:6043 | 3002:6044 | 3002:6045 | 3002:6046 | 3002:6047 | 3002:6048 |
| 3003:6042 | 3003:6043 | 3003:6044 | 3003:6045 | 3003:6046 | 3003:6047 | 3003:6048 |
| 3004:6042 | 3004:6043 | 3004:6044 | 3004:6045 | 3004:6046 | 3004:6047 | 3004:6048 |
| 3005:6042 | 3005:6043 | 3005:6044 | 3005:6045 | 3005:6046 | 3005:6047 | 3005:6048 |
| 3006:6042 | 3006:6043 | 3006:6044 | 3006:6045 | 3006:6046 | 3006:6047 | 3006:6048 |
| 3007:6042 | 3007:6043 | 3007:6044 | 3007:6045 | 3007:6046 | 3007:6047 | 3007:6048 |
| 3008:6042 | 3008:6043 | 3008:6044 | 3008:6045 | 3008:6046 | 3008:6047 | 3008:6048 |
| 4001:6042 | 4001:6043 | 4001:6044 | 4001:6045 | 4001:6046 | 4001:6047 | 4001:6048 |
| 4002:6042 | 4002:6043 | 4002:6044 | 4002:6045 | 4002:6046 | 4002:6047 | 4002:6048 |
| 4003:6042 | 4003:6043 | 4003:6044 | 4003:6045 | 4003:6046 | 4003:6047 | 4003:6048 |
| 4004:6042 | 4004:6043 | 4004:6044 | 4004:6045 | 4004:6046 | 4004:6047 | 4004:6048 |
| 4005:6042 | 4005:6043 | 4005:6044 | 4005:6045 | 4005:6046 | 4005:6047 | 4005:6048 |
| 5001:6042 | 5001:6043 | 5001:6044 | 5001:6045 | 5001:6046 | 5001:6047 | 5001:6048 |
| 5002:6042 | 5002:6043 | 5002:6044 | 5002:6045 | 5002:6046 | 5002:6047 | 5002:6048 |
| 1001:6049 | 1001:6050 | 1001:6051 | 1001:6052 | 1001:6053 | 1001:6054 | 1001:6055 |
| 1002:6049 | 1002:6050 | 1002:6051 | 1002:6052 | 1002:6053 | 1002:6054 | 1002:6055 |
| 1003:6049 | 1003:6050 | 1003:6051 | 1003:6052 | 1003:6053 | 1003:6054 | 1003:6055 |
| 1004:6049 | 1004:6050 | 1004:6051 | 1004:6052 | 1004:6053 | 1004:6054 | 1004:6055 |
| 1005:6049 | 1005:6050 | 1005:6051 | 1005:6052 | 1005:6053 | 1005:6054 | 1005:6055 |
| 1006:6049 | 1006:6050 | 1006:6051 | 1006:6052 | 1006:6053 | 1006:6054 | 1006:6055 |
| 1007:6049 | 1007:6050 | 1007:6051 | 1007:6052 | 1007:6053 | 1007:6054 | 1007:6055 |
| 1008:6049 | 1008:6050 | 1008:6051 | 1008:6052 | 1008:6053 | 1008:6054 | 1008:6055 |
| 1009:6049 | 1009:6050 | 1009:6051 | 1009:6052 | 1009:6053 | 1009:6054 | 1009:6055 |
| 1010:6049 | 1010:6050 | 1010:6051 | 1010:6052 | 1010:6053 | 1010:6054 | 1010:6055 |
| 1011:6049 | 1011:6050 | 1011:6051 | 1011:6052 | 1011:6053 | 1011:6054 | 1011:6055 |
| 1012:6049 | 1012:6050 | 1012:6051 | 1012:6052 | 1012:6053 | 1012:6054 | 1012:6055 |
| 1013:6049 | 1013:6050 | 1013:6051 | 1013:6052 | 1013:6053 | 1013:6054 | 1013:6055 |
| 1014:6049 | 1014:6050 | 1014:6051 | 1014:6052 | 1014:6053 | 1014:6054 | 1014:6055 |
| 2001:6049 | 2001:6050 | 2001:6051 | 2001:6052 | 2001:6053 | 2001:6054 | 2001:6055 |
| 2002:6049 | 2002:6050 | 2002:6051 | 2002:6052 | 2002:6053 | 2002:6054 | 2002:6055 |
| 2003:6049 | 2003:6050 | 2003:6051 | 2003:6052 | 2003:6053 | 2003:6054 | 2003:6055 |
| 2004:6049 | 2004:6050 | 2004:6051 | 2004:6052 | 2004:6053 | 2004:6054 | 2004:6055 |
| 2005:6049 | 2005:6050 | 2005:6051 | 2005:6052 | 2005:6053 | 2005:6054 | 2005:6055 |
| 2006:6049 | 2006:6050 | 2006:6051 | 2006:6052 | 2006:6053 | 2006:6054 | 2006:6055 |
| 2007:6049 | 2007:6050 | 2007:6051 | 2007:6052 | 2007:6053 | 2007:6054 | 2007:6055 |
| 2008:6049 | 2008:6050 | 2008:6051 | 2008:6052 | 2008:6053 | 2008:6054 | 2008:6055 |
| 2009:6049 | 2009:6050 | 2009:6051 | 2009:6052 | 2009:6053 | 2009:6054 | 2009:6055 |
| 2010:6049 | 2010:6050 | 2010:6051 | 2010:6052 | 2010:6053 | 2010:6054 | 2010:6055 |
| 3001:6049 | 3001:6050 | 3001:6051 | 3001:6052 | 3001:6053 | 3001:6054 | 3001:6055 |
| 3002:6049 | 3002:6050 | 3002:6051 | 3002:6052 | 3002:6053 | 3002:6054 | 3002:6055 |
| 3003:6049 | 3003:6050 | 3003:6051 | 3003:6052 | 3003:6053 | 3003:6054 | 3003:6055 |
| 3004:6049 | 3004:6050 | 3004:6051 | 3004:6052 | 3004:6053 | 3004:6054 | 3004:6055 |

TABLE A-continued

Example combinations of a compound X with a compound Y.

| X:Y | X:Y | X:Y | X:Y | X:Y | X:Y | X:Y |
|---|---|---|---|---|---|---|
| 3005:6049 | 3005:6050 | 3005:6051 | 3005:6052 | 3005:6053 | 3005:6054 | 3005:6055 |
| 3006:6049 | 3006:6050 | 3006:6051 | 3006:6052 | 3006:6053 | 3006:6054 | 3006:6055 |
| 3007:6049 | 3007:6050 | 3007:6051 | 3007:6052 | 3007:6053 | 3007:6054 | 3007:6055 |
| 3008:6049 | 3008:6050 | 3008:6051 | 3008:6052 | 3008:6053 | 3008:6054 | 3008:6055 |
| 4001:6049 | 4001:6050 | 4001:6051 | 4001:6052 | 4001:6053 | 4001:6054 | 4001:6055 |
| 4002:6049 | 4002:6050 | 4002:6051 | 4002:6052 | 4002:6053 | 4002:6054 | 4002:6055 |
| 4003:6049 | 4003:6050 | 4003:6051 | 4003:6052 | 4003:6053 | 4003:6054 | 4003:6055 |
| 4004:6049 | 4004:6050 | 4004:6051 | 4004:6052 | 4004:6053 | 4004:6054 | 4004:6055 |
| 4005:6049 | 4005:6050 | 4005:6051 | 4005:6052 | 4005:6053 | 4005:6054 | 4005:6055 |
| 5001:6049 | 5001:6050 | 5001:6051 | 5001:6052 | 5001:6053 | 5001:6054 | 5001:6055 |
| 5002:6049 | 5002:6050 | 5002:6051 | 5002:6052 | 5002:6053 | 5002:6054 | 5002:6055 |
| 1001:6056 | 1001:6057 | 1001:6058 | 1001:6059 | 1001:6060 | 1001:6061 | 1001:6062 |
| 1002:6056 | 1002:6057 | 1002:6058 | 1002:6059 | 1002:6060 | 1002:6061 | 1002:6062 |
| 1003:6056 | 1003:6057 | 1003:6058 | 1003:6059 | 1003:6060 | 1003:6061 | 1003:6062 |
| 1004:6056 | 1004:6057 | 1004:6058 | 1004:6059 | 1004:6060 | 1004:6061 | 1004:6062 |
| 1005:6056 | 1005:6057 | 1005:6058 | 1005:6059 | 1005:6060 | 1005:6061 | 1005:6062 |
| 1006:6056 | 1006:6057 | 1006:6058 | 1006:6059 | 1006:6060 | 1006:6061 | 1006:6062 |
| 1007:6056 | 1007:6057 | 1007:6058 | 1007:6059 | 1007:6060 | 1007:6061 | 1007:6062 |
| 1008:6056 | 1008:6057 | 1008:6058 | 1008:6059 | 1008:6060 | 1008:6061 | 1008:6062 |
| 1009:6056 | 1009:6057 | 1009:6058 | 1009:6059 | 1009:6060 | 1009:6061 | 1009:6062 |
| 1010:6056 | 1010:6057 | 1010:6058 | 1010:6059 | 1010:6060 | 1010:6061 | 1010:6062 |
| 1011:6056 | 1011:6057 | 1011:6058 | 1011:6059 | 1011:6060 | 1011:6061 | 1011:6062 |
| 1012:6056 | 1012:6057 | 1012:6058 | 1012:6059 | 1012:6060 | 1012:6061 | 1012:6062 |
| 1013:6056 | 1013:6057 | 1013:6058 | 1013:6059 | 1013:6060 | 1013:6061 | 1013:6062 |
| 1014:6056 | 1014:6057 | 1014:6058 | 1014:6059 | 1014:6060 | 1014:6061 | 1014:6062 |
| 2001:6056 | 2001:6057 | 2001:6058 | 2001:6059 | 2001:6060 | 2001:6061 | 2001:6062 |
| 2002:6056 | 2002:6057 | 2002:6058 | 2002:6059 | 2002:6060 | 2002:6061 | 2002:6062 |
| 2003:6056 | 2003:6057 | 2003:6058 | 2003:6059 | 2003:6060 | 2003:6061 | 2003:6062 |
| 2004:6056 | 2004:6057 | 2004:6058 | 2004:6059 | 2004:6060 | 2004:6061 | 2004:6062 |
| 2005:6056 | 2005:6057 | 2005:6058 | 2005:6059 | 2005:6060 | 2005:6061 | 2005:6062 |
| 2006:6056 | 2006:6057 | 2006:6058 | 2006:6059 | 2006:6060 | 2006:6061 | 2006:6062 |
| 2007:6056 | 2007:6057 | 2007:6058 | 2007:6059 | 2007:6060 | 2007:6061 | 2007:6062 |
| 2008:6056 | 2008:6057 | 2008:6058 | 2008:6059 | 2008:6060 | 2008:6061 | 2008:6062 |
| 2009:6056 | 2009:6057 | 2009:6058 | 2009:6059 | 2009:6060 | 2009:6061 | 2009:6062 |
| 2010:6056 | 2010:6057 | 2010:6058 | 2010:6059 | 2010:6060 | 2010:6061 | 2010:6062 |
| 3001:6056 | 3001:6057 | 3001:6058 | 3001:6059 | 3001:6060 | 3001:6061 | 3001:6062 |
| 3002:6056 | 3002:6057 | 3002:6058 | 3002:6059 | 3002:6060 | 3002:6061 | 3002:6062 |
| 3003:6056 | 3003:6057 | 3003:6058 | 3003:6059 | 3003:6060 | 3003:6061 | 3003:6062 |
| 3004:6056 | 3004:6057 | 3004:6058 | 3004:6059 | 3004:6060 | 3004:6061 | 3004:6062 |
| 3005:6056 | 3005:6057 | 3005:6058 | 3005:6059 | 3005:6060 | 3005:6061 | 3005:6062 |
| 3006:6056 | 3006:6057 | 3006:6058 | 3006:6059 | 3006:6060 | 3006:6061 | 3006:6062 |
| 3007:6056 | 3007:6057 | 3007:6058 | 3007:6059 | 3007:6060 | 3007:6061 | 3007:6062 |
| 3008:6056 | 3008:6057 | 3008:6058 | 3008:6059 | 3008:6060 | 3008:6061 | 3008:6062 |
| 4001:6056 | 4001:6057 | 4001:6058 | 4001:6059 | 4001:6060 | 4001:6061 | 4001:6062 |
| 4002:6056 | 4002:6057 | 4002:6058 | 4002:6059 | 4002:6060 | 4002:6061 | 4002:6062 |
| 4003:6056 | 4003:6057 | 4003:6058 | 4003:6059 | 4003:6060 | 4003:6061 | 4003:6062 |
| 4004:6056 | 4004:6057 | 4004:6058 | 4004:6059 | 4004:6060 | 4004:6061 | 4004:6062 |
| 4005:6056 | 4005:6057 | 4005:6058 | 4005:6059 | 4005:6060 | 4005:6061 | 4005:6062 |
| 5001:6056 | 5001:6057 | 5001:6058 | 5001:6059 | 5001:6060 | 5001:6061 | 5001:6062 |
| 5002:6056 | 5002:6057 | 5002:6058 | 5002:6059 | 5002:6060 | 5002:6061 | 5002:6062 |
| 1001:6063 | 1001:6064 | 1001:6065 | 1001:6066 | 1001:6067 | 1001:6068 | 1001:6069 |
| 1002:6063 | 1002:6064 | 1002:6065 | 1002:6066 | 1002:6067 | 1002:6068 | 1002:6069 |
| 1003:6063 | 1003:6064 | 1003:6065 | 1003:6066 | 1003:6067 | 1003:6068 | 1003:6069 |
| 1004:6063 | 1004:6064 | 1004:6065 | 1004:6066 | 1004:6067 | 1004:6068 | 1004:6069 |
| 1005:6063 | 1005:6064 | 1005:6065 | 1005:6066 | 1005:6067 | 1005:6068 | 1005:6069 |
| 1006:6063 | 1006:6064 | 1006:6065 | 1006:6066 | 1006:6067 | 1006:6068 | 1006:6069 |
| 1007:6063 | 1007:6064 | 1007:6065 | 1007:6066 | 1007:6067 | 1007:6068 | 1007:6069 |
| 1008:6063 | 1008:6064 | 1008:6065 | 1008:6066 | 1008:6067 | 1008:6068 | 1008:6069 |
| 1009:6063 | 1009:6064 | 1009:6065 | 1009:6066 | 1009:6067 | 1009:6068 | 1009:6069 |
| 1010:6063 | 1010:6064 | 1010:6065 | 1010:6066 | 1010:6067 | 1010:6068 | 1010:6069 |
| 1011:6063 | 1011:6064 | 1011:6065 | 1011:6066 | 1011:6067 | 1011:6068 | 1011:6069 |
| 1012:6063 | 1012:6064 | 1012:6065 | 1012:6066 | 1012:6067 | 1012:6068 | 1012:6069 |
| 1013:6063 | 1013:6064 | 1013:6065 | 1013:6066 | 1013:6067 | 1013:6068 | 1013:6069 |
| 1014:6063 | 1014:6064 | 1014:6065 | 1014:6066 | 1014:6067 | 1014:6068 | 1014:6069 |
| 2001:6063 | 2001:6064 | 2001:6065 | 2001:6066 | 2001:6067 | 2001:6068 | 2001:6069 |
| 2002:6063 | 2002:6064 | 2002:6065 | 2002:6066 | 2002:6067 | 2002:6068 | 2002:6069 |
| 2003:6063 | 2003:6064 | 2003:6065 | 2003:6066 | 2003:6067 | 2003:6068 | 2003:6069 |
| 2004:6063 | 2004:6064 | 2004:6065 | 2004:6066 | 2004:6067 | 2004:6068 | 2004:6069 |
| 2005:6063 | 2005:6064 | 2005:6065 | 2005:6066 | 2005:6067 | 2005:6068 | 2005:6069 |
| 2006:6063 | 2006:6064 | 2006:6065 | 2006:6066 | 2006:6067 | 2006:6068 | 2006:6069 |
| 2007:6063 | 2007:6064 | 2007:6065 | 2007:6066 | 2007:6067 | 2007:6068 | 2007:6069 |
| 2008:6063 | 2008:6064 | 2008:6065 | 2008:6066 | 2008:6067 | 2008:6068 | 2008:6069 |
| 2009:6063 | 2009:6064 | 2009:6065 | 2009:6066 | 2009:6067 | 2009:6068 | 2009:6069 |
| 2010:6063 | 2010:6064 | 2010:6065 | 2010:6066 | 2010:6067 | 2010:6068 | 2010:6069 |

TABLE A-continued

Example combinations of a compound X with a compound Y.

| X:Y | X:Y | X:Y | X:Y | X:Y | X:Y | X:Y |
|---|---|---|---|---|---|---|
| 3001:6063 | 3001:6064 | 3001:6065 | 3001:6066 | 3001:6067 | 3001:6068 | 3001:6069 |
| 3002:6063 | 3002:6064 | 3002:6065 | 3002:6066 | 3002:6067 | 3002:6068 | 3002:6069 |
| 3003:6063 | 3003:6064 | 3003:6065 | 3003:6066 | 3003:6067 | 3003:6068 | 3003:6069 |
| 3004:6063 | 3004:6064 | 3004:6065 | 3004:6066 | 3004:6067 | 3004:6068 | 3004:6069 |
| 3005:6063 | 3005:6064 | 3005:6065 | 3005:6066 | 3005:6067 | 3005:6068 | 3005:6069 |
| 3006:6063 | 3006:6064 | 3006:6065 | 3006:6066 | 3006:6067 | 3006:6068 | 3006:6069 |
| 3007:6063 | 3007:6064 | 3007:6065 | 3007:6066 | 3007:6067 | 3007:6068 | 3007:6069 |
| 3008:6063 | 3008:6064 | 3008:6065 | 3008:6066 | 3008:6067 | 3008:6068 | 3008:6069 |
| 4001:6063 | 4001:6064 | 4001:6065 | 4001:6066 | 4001:6067 | 4001:6068 | 4001:6069 |
| 4002:6063 | 4002:6064 | 4002:6065 | 4002:6066 | 4002:6067 | 4002:6068 | 4002:6069 |
| 4003:6063 | 4003:6064 | 4003:6065 | 4003:6066 | 4003:6067 | 4003:6068 | 4003:6069 |
| 4004:6063 | 4004:6064 | 4004:6065 | 4004:6066 | 4004:6067 | 4004:6068 | 4004:6069 |
| 4005:6063 | 4005:6064 | 4005:6065 | 4005:6066 | 4005:6067 | 4005:6068 | 4005:6069 |
| 5001:6063 | 5001:6064 | 5001:6065 | 5001:6066 | 5001:6067 | 5001:6068 | 5001:6069 |
| 5002:6063 | 5002:6064 | 5002:6065 | 5002:6066 | 5002:6067 | 5002:6068 | 5002:6069 |
| 1001:6070 | 1001:6071 | 1001:6072 | 1001:6073 | 1001:6074 | 1001:6075 | 1001:6076 |
| 1002:6070 | 1002:6071 | 1002:6072 | 1002:6073 | 1002:6074 | 1002:6075 | 1002:6076 |
| 1003:6070 | 1003:6071 | 1003:6072 | 1003:6073 | 1003:6074 | 1003:6075 | 1003:6076 |
| 1004:6070 | 1004:6071 | 1004:6072 | 1004:6073 | 1004:6074 | 1004:6075 | 1004:6076 |
| 1005:6070 | 1005:6071 | 1005:6072 | 1005:6073 | 1005:6074 | 1005:6075 | 1005:6076 |
| 1006:6070 | 1006:6071 | 1006:6072 | 1006:6073 | 1006:6074 | 1006:6075 | 1006:6076 |
| 1007:6070 | 1007:6071 | 1007:6072 | 1007:6073 | 1007:6074 | 1007:6075 | 1007:6076 |
| 1008:6070 | 1008:6071 | 1008:6072 | 1008:6073 | 1008:6074 | 1008:6075 | 1008:6076 |
| 1009:6070 | 1009:6071 | 1009:6072 | 1009:6073 | 1009:6074 | 1009:6075 | 1009:6076 |
| 1010:6070 | 1010:6071 | 1010:6072 | 1010:6073 | 1010:6074 | 1010:6075 | 1010:6076 |
| 1011:6070 | 1011:6071 | 1011:6072 | 1011:6073 | 1011:6074 | 1011:6075 | 1011:6076 |
| 1012:6070 | 1012:6071 | 1012:6072 | 1012:6073 | 1012:6074 | 1012:6075 | 1012:6076 |
| 1013:6070 | 1013:6071 | 1013:6072 | 1013:6073 | 1013:6074 | 1013:6075 | 1013:6076 |
| 1014:6070 | 1014:6071 | 1014:6072 | 1014:6073 | 1014:6074 | 1014:6075 | 1014:6076 |
| 2001:6070 | 2001:6071 | 2001:6072 | 2001:6073 | 2001:6074 | 2001:6075 | 2001:6076 |
| 2002:6070 | 2002:6071 | 2002:6072 | 2002:6073 | 2002:6074 | 2002:6075 | 2002:6076 |
| 2003:6070 | 2003:6071 | 2003:6072 | 2003:6073 | 2003:6074 | 2003:6075 | 2003:6076 |
| 2004:6070 | 2004:6071 | 2004:6072 | 2004:6073 | 2004:6074 | 2004:6075 | 2004:6076 |
| 2005:6070 | 2005:6071 | 2005:6072 | 2005:6073 | 2005:6074 | 2005:6075 | 2005:6076 |
| 2006:6070 | 2006:6071 | 2006:6072 | 2006:6073 | 2006:6074 | 2006:6075 | 2006:6076 |
| 2007:6070 | 2007:6071 | 2007:6072 | 2007:6073 | 2007:6074 | 2007:6075 | 2007:6076 |
| 2008:6070 | 2008:6071 | 2008:6072 | 2008:6073 | 2008:6074 | 2008:6075 | 2008:6076 |
| 2009:6070 | 2009:6071 | 2009:6072 | 2009:6073 | 2009:6074 | 2009:6075 | 2009:6076 |
| 2010:6070 | 2010:6071 | 2010:6072 | 2010:6073 | 2010:6074 | 2010:6075 | 2010:6076 |
| 3001:6070 | 3001:6071 | 3001:6072 | 3001:6073 | 3001:6074 | 3001:6075 | 3001:6076 |
| 3002:6070 | 3002:6071 | 3002:6072 | 3002:6073 | 3002:6074 | 3002:6075 | 3002:6076 |
| 3003:6070 | 3003:6071 | 3003:6072 | 3003:6073 | 3003:6074 | 3003:6075 | 3003:6076 |
| 3004:6070 | 3004:6071 | 3004:6072 | 3004:6073 | 3004:6074 | 3004:6075 | 3004:6076 |
| 3005:6070 | 3005:6071 | 3005:6072 | 3005:6073 | 3005:6074 | 3005:6075 | 3005:6076 |
| 3006:6070 | 3006:6071 | 3006:6072 | 3006:6073 | 3006:6074 | 3006:6075 | 3006:6076 |
| 3007:6070 | 3007:6071 | 3007:6072 | 3007:6073 | 3007:6074 | 3007:6075 | 3007:6076 |
| 3008:6070 | 3008:6071 | 3008:6072 | 3008:6073 | 3008:6074 | 3008:6075 | 3008:6076 |
| 4001:6070 | 4001:6071 | 4001:6072 | 4001:6073 | 4001:6074 | 4001:6075 | 4001:6076 |
| 4002:6070 | 4002:6071 | 4002:6072 | 4002:6073 | 4002:6074 | 4002:6075 | 4002:6076 |
| 4003:6070 | 4003:6071 | 4003:6072 | 4003:6073 | 4003:6074 | 4003:6075 | 4003:6076 |
| 4004:6070 | 4004:6071 | 4004:6072 | 4004:6073 | 4004:6074 | 4004:6075 | 4004:6076 |
| 4005:6070 | 4005:6071 | 4005:6072 | 4005:6073 | 4005:6074 | 4005:6075 | 4005:6076 |
| 5001:6070 | 5001:6071 | 5001:6072 | 5001:6073 | 5001:6074 | 5001:6075 | 5001:6076 |
| 5002:6070 | 5002:6071 | 5002:6072 | 5002:6073 | 5002:6074 | 5002:6075 | 5002:6076 |
| 1001:6077 | 1001:6078 | — | | | | |
| 1002:6077 | 1002:6078 | | | | | |
| 1003:6077 | 1003:6078 | | | | | |
| 1004:6077 | 1004:6078 | | | | | |
| 1005:6077 | 1005:6078 | | | | | |
| 1006:6077 | 1006:6078 | | | | | |
| 1007:6077 | 1007:6078 | | | | | |
| 1008:6077 | 1008:6078 | | | | | |
| 1009:6077 | 1009:6078 | | | | | |
| 1010:6077 | 1010:6078 | | | | | |
| 1011:6077 | 1011:6078 | | | | | |
| 1012:6077 | 1012:6078 | | | | | |
| 1013:6077 | 1013:6078 | | | | | |
| 1014:6077 | 1014:6078 | | | | | |
| 2001:6077 | 2001:6078 | | | | | |
| 2002:6077 | 2002:6078 | | | | | |
| 2003:6077 | 2003:6078 | | | | | |
| 2004:6077 | 2004:6078 | | | | | |
| 2005:6077 | 2005:6078 | | | | | |
| 2006:6077 | 2006:6078 | | | | | |

TABLE A-continued

Example combinations of a compound X with a compound Y.

| X:Y | X:Y | X:Y | X:Y | X:Y | X:Y | X:Y |
|---|---|---|---|---|---|---|
| 2007:6077 | 2007:6078 | | | | | |
| 2008:6077 | 2008:6078 | | | | | |
| 2009:6077 | 2009:6078 | | | | | |
| 2010:6077 | 2010:6078 | | | | | |
| 3001:6077 | 3001:6078 | | | | | |
| 3002:6077 | 3002:6078 | | | | | |
| 3003:6077 | 3003:6078 | | | | | |
| 3004:6077 | 3004:6078 | | | | | |
| 3005:6077 | 3005:6078 | | | | | |
| 3006:6077 | 3006:6078 | | | | | |
| 3007:6077 | 3007:6078 | | | | | |
| 3008:6077 | 3008:6078 | | | | | |
| 4001:6077 | 4001:6078 | | | | | |
| 4002:6077 | 4002:6078 | | | | | |
| 4003:6077 | 4003:6078 | | | | | |
| 4004:6077 | 4004:6078 | | | | | |
| 4005:6077 | 4005:6078 | | | | | |
| 5001:6077 | 5001:6078 | | | | | |
| 5002:6077 | 5002:6078 | | | | | |

TABLE B

Example combinations of a compound X with a compound Y.

| X:Y | X:Y | X:Y | X:Y | X:Y | X:Y | X:Y |
|---|---|---|---|---|---|---|
| 6000:7000 | 6000:7001 | 6000:7002 | 6000:7003 | 6000:7004 | 6000:7005 | 6000:7006 |
| 6001:7000 | 6001:7001 | 6001:7002 | 6001:7003 | 6001:7004 | 6001:7005 | 6001:7006 |
| 6002:7000 | 6002:7001 | 6002:7002 | 6002:7003 | 6002:7004 | 6002:7005 | 6002:7006 |
| 6003:7000 | 6003:7001 | 6003:7002 | 6003:7003 | 6003:7004 | 6003:7005 | 6003:7006 |
| 6004:7000 | 6004:7001 | 6004:7002 | 6004:7003 | 6004:7004 | 6004:7005 | 6004:7006 |
| 6005:7000 | 6005:7001 | 6005:7002 | 6005:7003 | 6005:7004 | 6005:7005 | 6005:7006 |
| 6006:7000 | 6006:7001 | 6006:7002 | 6006:7003 | 6006:7004 | 6006:7005 | 6006:7006 |
| 6007:7000 | 6007:7001 | 6007:7002 | 6007:7003 | 6007:7004 | 6007:7005 | 6007:7006 |
| 6008:7000 | 6008:7001 | 6008:7002 | 6008:7003 | 6008:7004 | 6008:7005 | 6008:7006 |
| 6009:7000 | 6009:7001 | 6009:7002 | 6009:7003 | 6009:7004 | 6009:7005 | 6009:7006 |
| 6010:7000 | 6010:7001 | 6010:7002 | 6010:7003 | 6010:7004 | 6010:7005 | 6010:7006 |
| 6011:7000 | 6011:7001 | 6011:7002 | 6011:7003 | 6011:7004 | 6011:7005 | 6011:7006 |
| 6012:7000 | 6012:7001 | 6012:7002 | 6012:7003 | 6012:7004 | 6012:7005 | 6012:7006 |
| 6013:7000 | 6013:7001 | 6013:7002 | 6013:7003 | 6013:7004 | 6013:7005 | 6013:7006 |
| 6014:7000 | 6014:7001 | 6014:7002 | 6014:7003 | 6014:7004 | 6014:7005 | 6014:7006 |
| 6015:7000 | 6015:7001 | 6015:7002 | 6015:7003 | 6015:7004 | 6015:7005 | 6015:7006 |
| 6016:7000 | 6016:7001 | 6016:7002 | 6016:7003 | 6016:7004 | 6016:7005 | 6016:7006 |
| 6017:7000 | 6017:7001 | 6017:7002 | 6017:7003 | 6017:7004 | 6017:7005 | 6017:7006 |
| 6018:7000 | 6018:7001 | 6018:7002 | 6018:7003 | 6018:7004 | 6018:7005 | 6018:7006 |
| 6019:7000 | 6019:7001 | 6019:7002 | 6019:7003 | 6019:7004 | 6019:7005 | 6019:7006 |
| 6020:7000 | 6020:7001 | 6020:7002 | 6020:7003 | 6020:7004 | 6020:7005 | 6020:7006 |
| 6000:7007 | 6000:7008 | 6000:7009 | 6000:7010 | 6000:7011 | 6000:7012 | 6000:7013 |
| 6001:7007 | 6001:7008 | 6001:7009 | 6001:7010 | 6001:7011 | 6001:7012 | 6001:7013 |
| 6002:7007 | 6002:7008 | 6002:7009 | 6002:7010 | 6002:7011 | 6002:7012 | 6002:7013 |
| 6003:7007 | 6003:7008 | 6003:7009 | 6003:7010 | 6003:7011 | 6003:7012 | 6003:7013 |
| 6004:7007 | 6004:7008 | 6004:7009 | 6004:7010 | 6004:7011 | 6004:7012 | 6004:7013 |
| 6005:7007 | 6005:7008 | 6005:7009 | 6005:7010 | 6005:7011 | 6005:7012 | 6005:7013 |
| 6006:7007 | 6006:7008 | 6006:7009 | 6006:7010 | 6006:7011 | 6006:7012 | 6006:7013 |
| 6007:7007 | 6007:7008 | 6007:7009 | 6007:7010 | 6007:7011 | 6007:7012 | 6007:7013 |
| 6008:7007 | 6008:7008 | 6008:7009 | 6008:7010 | 6008:7011 | 6008:7012 | 6008:7013 |
| 6009:7007 | 6009:7008 | 6009:7009 | 6009:7010 | 6009:7011 | 6009:7012 | 6009:7013 |
| 6010:7007 | 6010:7008 | 6010:7009 | 6010:7010 | 6010:7011 | 6010:7012 | 6010:7013 |
| 6011:7007 | 6011:7008 | 6011:7009 | 6011:7010 | 6011:7011 | 6011:7012 | 6011:7013 |
| 6012:7007 | 6012:7008 | 6012:7009 | 6012:7010 | 6012:7011 | 6012:7012 | 6012:7013 |
| 6013:7007 | 6013:7008 | 6013:7009 | 6013:7010 | 6013:7011 | 6013:7012 | 6013:7013 |
| 6014:7007 | 6014:7008 | 6014:7009 | 6014:7010 | 6014:7011 | 6014:7012 | 6014:7013 |
| 6015:7007 | 6015:7008 | 6015:7009 | 6015:7010 | 6015:7011 | 6015:7012 | 6015:7013 |
| 6016:7007 | 6016:7008 | 6016:7009 | 6016:7010 | 6016:7011 | 6016:7012 | 6016:7013 |
| 6017:7007 | 6017:7008 | 6017:7009 | 6017:7010 | 6017:7011 | 6017:7012 | 6017:7013 |
| 6018:7007 | 6018:7008 | 6018:7009 | 6018:7010 | 6018:7011 | 6018:7012 | 6018:7013 |
| 6019:7007 | 6019:7008 | 6019:7009 | 6019:7010 | 6019:7011 | 6019:7012 | 6019:7013 |
| 6020:7007 | 6020:7008 | 6020:7009 | 6020:7010 | 6020:7011 | 6020:7012 | 6020:7013 |
| 6000:7014 | 6000:7015 | 6000:7016 | 6000:7017 | 6000:7018 | 6000:7019 | 6000:7020 |
| 6001:7014 | 6001:7015 | 6001:7016 | 6001:7017 | 6001:7018 | 6001:7019 | 6001:7020 |
| 6002:7014 | 6002:7015 | 6002:7016 | 6002:7017 | 6002:7018 | 6002:7019 | 6002:7020 |

TABLE B-continued

Example combinations of a compound X with a compound Y.

| X:Y | X:Y | X:Y | X:Y | X:Y | X:Y | X:Y |
|---|---|---|---|---|---|---|
| 6003:7014 | 6003:7015 | 6003:7016 | 6003:7017 | 6003:7018 | 6003:7019 | 6003:7020 |
| 6004:7014 | 6004:7015 | 6004:7016 | 6004:7017 | 6004:7018 | 6004:7019 | 6004:7020 |
| 6005:7014 | 6005:7015 | 6005:7016 | 6005:7017 | 6005:7018 | 6005:7019 | 6005:7020 |
| 6006:7014 | 6006:7015 | 6006:7016 | 6006:7017 | 6006:7018 | 6006:7019 | 6006:7020 |
| 6007:7014 | 6007:7015 | 6007:7016 | 6007:7017 | 6007:7018 | 6007:7019 | 6007:7020 |
| 6008:7014 | 6008:7015 | 6008:7016 | 6008:7017 | 6008:7018 | 6008:7019 | 6008:7020 |
| 6009:7014 | 6009:7015 | 6009:7016 | 6009:7017 | 6009:7018 | 6009:7019 | 6009:7020 |
| 6010:7014 | 6010:7015 | 6010:7016 | 6010:7017 | 6010:7018 | 6010:7019 | 6010:7020 |
| 6011:7014 | 6011:7015 | 6011:7016 | 6011:7017 | 6011:7018 | 6011:7019 | 6011:7020 |
| 6012:7014 | 6012:7015 | 6012:7016 | 6012:7017 | 6012:7018 | 6012:7019 | 6012:7020 |
| 6013:7014 | 6013:7015 | 6013:7016 | 6013:7017 | 6013:7018 | 6013:7019 | 6013:7020 |
| 6014:7014 | 6014:7015 | 6014:7016 | 6014:7017 | 6014:7018 | 6014:7019 | 6014:7020 |
| 6015:7014 | 6015:7015 | 6015:7016 | 6015:7017 | 6015:7018 | 6015:7019 | 6015:7020 |
| 6016:7014 | 6016:7015 | 6016:7016 | 6016:7017 | 6016:7018 | 6016:7019 | 6016:7020 |
| 6017:7014 | 6017:7015 | 6017:7016 | 6017:7017 | 6017:7018 | 6017:7019 | 6017:7020 |
| 6018:7014 | 6018:7015 | 6018:7016 | 6018:7017 | 6018:7018 | 6018:7019 | 6018:7020 |
| 6019:7014 | 6019:7015 | 6019:7016 | 6019:7017 | 6019:7018 | 6019:7019 | 6019:7020 |
| 6020:7014 | 6020:7015 | 6020:7016 | 6020:7017 | 6020:7018 | 6020:7019 | 6020:7020 |
| 6000:7021 | 6000:7022 | 6000:7023 | 6000:7024 | 6000:7025 | 6000:7026 | 6000:7027 |
| 6001:7021 | 6001:7022 | 6001:7023 | 6001:7024 | 6001:7025 | 6001:7026 | 6001:7027 |
| 6002:7021 | 6002:7022 | 6002:7023 | 6002:7024 | 6002:7025 | 6002:7026 | 6002:7027 |
| 6003:7021 | 6003:7022 | 6003:7023 | 6003:7024 | 6003:7025 | 6003:7026 | 6003:7027 |
| 6004:7021 | 6004:7022 | 6004:7023 | 6004:7024 | 6004:7025 | 6004:7026 | 6004:7027 |
| 6005:7021 | 6005:7022 | 6005:7023 | 6005:7024 | 6005:7025 | 6005:7026 | 6005:7027 |
| 6006:7021 | 6006:7022 | 6006:7023 | 6006:7024 | 6006:7025 | 6006:7026 | 6006:7027 |
| 6007:7021 | 6007:7022 | 6007:7023 | 6007:7024 | 6007:7025 | 6007:7026 | 6007:7027 |
| 6008:7021 | 6008:7022 | 6008:7023 | 6008:7024 | 6008:7025 | 6008:7026 | 6008:7027 |
| 6009:7021 | 6009:7022 | 6009:7023 | 6009:7024 | 6009:7025 | 6009:7026 | 6009:7027 |
| 6010:7021 | 6010:7022 | 6010:7023 | 6010:7024 | 6010:7025 | 6010:7026 | 6010:7027 |
| 6011:7021 | 6011:7022 | 6011:7023 | 6011:7024 | 6011:7025 | 6011:7026 | 6011:7027 |
| 6012:7021 | 6012:7022 | 6012:7023 | 6012:7024 | 6012:7025 | 6012:7026 | 6012:7027 |
| 6013:7021 | 6013:7022 | 6013:7023 | 6013:7024 | 6013:7025 | 6013:7026 | 6013:7027 |
| 6014:7021 | 6014:7022 | 6014:7023 | 6014:7024 | 6014:7025 | 6014:7026 | 6014:7027 |
| 6015:7021 | 6015:7022 | 6015:7023 | 6015:7024 | 6015:7025 | 6015:7026 | 6015:7027 |
| 6016:7021 | 6016:7022 | 6016:7023 | 6016:7024 | 6016:7025 | 6016:7026 | 6016:7027 |
| 6017:7021 | 6017:7022 | 6017:7023 | 6017:7024 | 6017:7025 | 6017:7026 | 6017:7027 |
| 6018:7021 | 6018:7022 | 6018:7023 | 6018:7024 | 6018:7025 | 6018:7026 | 6018:7027 |
| 6019:7021 | 6019:7022 | 6019:7023 | 6019:7024 | 6019:7025 | 6019:7026 | 6019:7027 |
| 6020:7021 | 6020:7022 | 6020:7023 | 6020:7024 | 6020:7025 | 6020:7026 | 6020:7027 |
| 6000:7028 | 6000:7029 | 6000:7030 | 6000:7031 | 6000:7032 | 6000:7033 | 6000:7034 |
| 6001:7028 | 6001:7029 | 6001:7030 | 6001:7031 | 6001:7032 | 6001:7033 | 6001:7034 |
| 6002:7028 | 6002:7029 | 6002:7030 | 6002:7031 | 6002:7032 | 6002:7033 | 6002:7034 |
| 6003:7028 | 6003:7029 | 6003:7030 | 6003:7031 | 6003:7032 | 6003:7033 | 6003:7034 |
| 6004:7028 | 6004:7029 | 6004:7030 | 6004:7031 | 6004:7032 | 6004:7033 | 6004:7034 |
| 6005:7028 | 6005:7029 | 6005:7030 | 6005:7031 | 6005:7032 | 6005:7033 | 6005:7034 |
| 6006:7028 | 6006:7029 | 6006:7030 | 6006:7031 | 6006:7032 | 6006:7033 | 6006:7034 |
| 6007:7028 | 6007:7029 | 6007:7030 | 6007:7031 | 6007:7032 | 6007:7033 | 6007:7034 |
| 6008:7028 | 6008:7029 | 6008:7030 | 6008:7031 | 6008:7032 | 6008:7033 | 6008:7034 |
| 6009:7028 | 6009:7029 | 6009:7030 | 6009:7031 | 6009:7032 | 6009:7033 | 6009:7034 |
| 6010:7028 | 6010:7029 | 6010:7030 | 6010:7031 | 6010:7032 | 6010:7033 | 6010:7034 |
| 6011:7028 | 6011:7029 | 6011:7030 | 6011:7031 | 6011:7032 | 6011:7033 | 6011:7034 |
| 6012:7028 | 6012:7029 | 6012:7030 | 6012:7031 | 6012:7032 | 6012:7033 | 6012:7034 |
| 6013:7028 | 6013:7029 | 6013:7030 | 6013:7031 | 6013:7032 | 6013:7033 | 6013:7034 |
| 6014:7028 | 6014:7029 | 6014:7030 | 6014:7031 | 6014:7032 | 6014:7033 | 6014:7034 |
| 6015:7028 | 6015:7029 | 6015:7030 | 6015:7031 | 6015:7032 | 6015:7033 | 6015:7034 |
| 6016:7028 | 6016:7029 | 6016:7030 | 6016:7031 | 6016:7032 | 6016:7033 | 6016:7034 |
| 6017:7028 | 6017:7029 | 6017:7030 | 6017:7031 | 6017:7032 | 6017:7033 | 6017:7034 |
| 6018:7028 | 6018:7029 | 6018:7030 | 6018:7031 | 6018:7032 | 6018:7033 | 6018:7034 |
| 6019:7028 | 6019:7029 | 6019:7030 | 6019:7031 | 6019:7032 | 6019:7033 | 6019:7034 |
| 6020:7028 | 6020:7029 | 6020:7030 | 6020:7031 | 6020:7032 | 6020:7033 | 6020:7034 |
| 6000:7035 | 6000:7036 | 6000:7037 | 6000:7038 | 6000:7039 | 6000:7040 | 6000:7041 |
| 6001:7035 | 6001:7036 | 6001:7037 | 6001:7038 | 6001:7039 | 6001:7040 | 6001:7041 |
| 6002:7035 | 6002:7036 | 6002:7037 | 6002:7038 | 6002:7039 | 6002:7040 | 6002:7041 |
| 6003:7035 | 6003:7036 | 6003:7037 | 6003:7038 | 6003:7039 | 6003:7040 | 6003:7041 |
| 6004:7035 | 6004:7036 | 6004:7037 | 6004:7038 | 6004:7039 | 6004:7040 | 6004:7041 |
| 6005:7035 | 6005:7036 | 6005:7037 | 6005:7038 | 6005:7039 | 6005:7040 | 6005:7041 |
| 6006:7035 | 6006:7036 | 6006:7037 | 6006:7038 | 6006:7039 | 6006:7040 | 6006:7041 |
| 6007:7035 | 6007:7036 | 6007:7037 | 6007:7038 | 6007:7039 | 6007:7040 | 6007:7041 |
| 6008:7035 | 6008:7036 | 6008:7037 | 6008:7038 | 6008:7039 | 6008:7040 | 6008:7041 |
| 6009:7035 | 6009:7036 | 6009:7037 | 6009:7038 | 6009:7039 | 6009:7040 | 6009:7041 |
| 6010:7035 | 6010:7036 | 6010:7037 | 6010:7038 | 6010:7039 | 6010:7040 | 6010:7041 |
| 6011:7035 | 6011:7036 | 6011:7037 | 6011:7038 | 6011:7039 | 6011:7040 | 6011:7041 |
| 6012:7035 | 6012:7036 | 6012:7037 | 6012:7038 | 6012:7039 | 6012:7040 | 6012:7041 |

TABLE B-continued

Example combinations of a compound X with a compound Y.

| X:Y | X:Y | X:Y | X:Y | X:Y | X:Y | X:Y |
|---|---|---|---|---|---|---|
| 6013:7035 | 6013:7036 | 6013:7037 | 6013:7038 | 6013:7039 | 6013:7040 | 6013:7041 |
| 6014:7035 | 6014:7036 | 6014:7037 | 6014:7038 | 6014:7039 | 6014:7040 | 6014:7041 |
| 6015:7035 | 6015:7036 | 6015:7037 | 6015:7038 | 6015:7039 | 6015:7040 | 6015:7041 |
| 6016:7035 | 6016:7036 | 6016:7037 | 6016:7038 | 6016:7039 | 6016:7040 | 6016:7041 |
| 6017:7035 | 6017:7036 | 6017:7037 | 6017:7038 | 6017:7039 | 6017:7040 | 6017:7041 |
| 6018:7035 | 6018:7036 | 6018:7037 | 6018:7038 | 6018:7039 | 6018:7040 | 6018:7041 |
| 6019:7035 | 6019:7036 | 6019:7037 | 6019:7038 | 6019:7039 | 6019:7040 | 6019:7041 |
| 6020:7035 | 6020:7036 | 6020:7037 | 6020:7038 | 6020:7039 | 6020:7040 | 6020:7041 |
| 6000:7042 | 6000:7043 | 6000:7044 | 6000:7045 | 6000:7046 | 6000:7047 | 6000:7048 |
| 6001:7042 | 6001:7043 | 6001:7044 | 6001:7045 | 6001:7046 | 6001:7047 | 6001:7048 |
| 6002:7042 | 6002:7043 | 6002:7044 | 6002:7045 | 6002:7046 | 6002:7047 | 6002:7048 |
| 6003:7042 | 6003:7043 | 6003:7044 | 6003:7045 | 6003:7046 | 6003:7047 | 6003:7048 |
| 6004:7042 | 6004:7043 | 6004:7044 | 6004:7045 | 6004:7046 | 6004:7047 | 6004:7048 |
| 6005:7042 | 6005:7043 | 6005:7044 | 6005:7045 | 6005:7046 | 6005:7047 | 6005:7048 |
| 6006:7042 | 6006:7043 | 6006:7044 | 6006:7045 | 6006:7046 | 6006:7047 | 6006:7048 |
| 6007:7042 | 6007:7043 | 6007:7044 | 6007:7045 | 6007:7046 | 6007:7047 | 6007:7048 |
| 6008:7042 | 6008:7043 | 6008:7044 | 6008:7045 | 6008:7046 | 6008:7047 | 6008:7048 |
| 6009:7042 | 6009:7043 | 6009:7044 | 6009:7045 | 6009:7046 | 6009:7047 | 6009:7048 |
| 6010:7042 | 6010:7043 | 6010:7044 | 6010:7045 | 6010:7046 | 6010:7047 | 6010:7048 |
| 6011:7042 | 6011:7043 | 6011:7044 | 6011:7045 | 6011:7046 | 6011:7047 | 6011:7048 |
| 6012:7042 | 6012:7043 | 6012:7044 | 6012:7045 | 6012:7046 | 6012:7047 | 6012:7048 |
| 6013:7042 | 6013:7043 | 6013:7044 | 6013:7045 | 6013:7046 | 6013:7047 | 6013:7048 |
| 6014:7042 | 6014:7043 | 6014:7044 | 6014:7045 | 6014:7046 | 6014:7047 | 6014:7048 |
| 6015:7042 | 6015:7043 | 6015:7044 | 6015:7045 | 6015:7046 | 6015:7047 | 6015:7048 |
| 6016:7042 | 6016:7043 | 6016:7044 | 6016:7045 | 6016:7046 | 6016:7047 | 6016:7048 |
| 6017:7042 | 6017:7043 | 6017:7044 | 6017:7045 | 6017:7046 | 6017:7047 | 6017:7048 |
| 6018:7042 | 6018:7043 | 6018:7044 | 6018:7045 | 6018:7046 | 6018:7047 | 6018:7048 |
| 6019:7042 | 6019:7043 | 6019:7044 | 6019:7045 | 6019:7046 | 6019:7047 | 6019:7048 |
| 6020:7042 | 6020:7043 | 6020:7044 | 6020:7045 | 6020:7046 | 6020:7047 | 6020:7048 |
| 6000:7049 | 6000:7050 | 6000:7051 | 6000:7052 | 6000:7053 | 6000:7054 | 6000:7055 |
| 6001:7049 | 6001:7050 | 6001:7051 | 6001:7052 | 6001:7053 | 6001:7054 | 6001:7055 |
| 6002:7049 | 6002:7050 | 6002:7051 | 6002:7052 | 6002:7053 | 6002:7054 | 6002:7055 |
| 6003:7049 | 6003:7050 | 6003:7051 | 6003:7052 | 6003:7053 | 6003:7054 | 6003:7055 |
| 6004:7049 | 6004:7050 | 6004:7051 | 6004:7052 | 6004:7053 | 6004:7054 | 6004:7055 |
| 6005:7049 | 6005:7050 | 6005:7051 | 6005:7052 | 6005:7053 | 6005:7054 | 6005:7055 |
| 6006:7049 | 6006:7050 | 6006:7051 | 6006:7052 | 6006:7053 | 6006:7054 | 6006:7055 |
| 6007:7049 | 6007:7050 | 6007:7051 | 6007:7052 | 6007:7053 | 6007:7054 | 6007:7055 |
| 6008:7049 | 6008:7050 | 6008:7051 | 6008:7052 | 6008:7053 | 6008:7054 | 6008:7055 |
| 6009:7049 | 6009:7050 | 6009:7051 | 6009:7052 | 6009:7053 | 6009:7054 | 6009:7055 |
| 6010:7049 | 6010:7050 | 6010:7051 | 6010:7052 | 6010:7053 | 6010:7054 | 6010:7055 |
| 6011:7049 | 6011:7050 | 6011:7051 | 6011:7052 | 6011:7053 | 6011:7054 | 6011:7055 |
| 6012:7049 | 6012:7050 | 6012:7051 | 6012:7052 | 6012:7053 | 6012:7054 | 6012:7055 |
| 6013:7049 | 6013:7050 | 6013:7051 | 6013:7052 | 6013:7053 | 6013:7054 | 6013:7055 |
| 6014:7049 | 6014:7050 | 6014:7051 | 6014:7052 | 6014:7053 | 6014:7054 | 6014:7055 |
| 6015:7049 | 6015:7050 | 6015:7051 | 6015:7052 | 6015:7053 | 6015:7054 | 6015:7055 |
| 6016:7049 | 6016:7050 | 6016:7051 | 6016:7052 | 6016:7053 | 6016:7054 | 6016:7055 |
| 6017:7049 | 6017:7050 | 6017:7051 | 6017:7052 | 6017:7053 | 6017:7054 | 6017:7055 |
| 6018:7049 | 6018:7050 | 6018:7051 | 6018:7052 | 6018:7053 | 6018:7054 | 6018:7055 |
| 6019:7049 | 6019:7050 | 6019:7051 | 6019:7052 | 6019:7053 | 6019:7054 | 6019:7055 |
| 6020:7049 | 6020:7050 | 6020:7051 | 6020:7052 | 6020:7053 | 6020:7054 | 6020:7055 |
| 6000:7056 | 6000:7057 | 6000:7058 | 6000:7059 | 6000:7060 | 6000:7061 | 6000:7062 |
| 6001:7056 | 6001:7057 | 6001:7058 | 6001:7059 | 6001:7060 | 6001:7061 | 6001:7062 |
| 6002:7056 | 6002:7057 | 6002:7058 | 6002:7059 | 6002:7060 | 6002:7061 | 6002:7062 |
| 6003:7056 | 6003:7057 | 6003:7058 | 6003:7059 | 6003:7060 | 6003:7061 | 6003:7062 |
| 6004:7056 | 6004:7057 | 6004:7058 | 6004:7059 | 6004:7060 | 6004:7061 | 6004:7062 |
| 6005:7056 | 6005:7057 | 6005:7058 | 6005:7059 | 6005:7060 | 6005:7061 | 6005:7062 |
| 6006:7056 | 6006:7057 | 6006:7058 | 6006:7059 | 6006:7060 | 6006:7061 | 6006:7062 |
| 6007:7056 | 6007:7057 | 6007:7058 | 6007:7059 | 6007:7060 | 6007:7061 | 6007:7062 |
| 6008:7056 | 6008:7057 | 6008:7058 | 6008:7059 | 6008:7060 | 6008:7061 | 6008:7062 |
| 6009:7056 | 6009:7057 | 6009:7058 | 6009:7059 | 6009:7060 | 6009:7061 | 6009:7062 |
| 6010:7056 | 6010:7057 | 6010:7058 | 6010:7059 | 6010:7060 | 6010:7061 | 6010:7062 |
| 6011:7056 | 6011:7057 | 6011:7058 | 6011:7059 | 6011:7060 | 6011:7061 | 6011:7062 |
| 6012:7056 | 6012:7057 | 6012:7058 | 6012:7059 | 6012:7060 | 6012:7061 | 6012:7062 |
| 6013:7056 | 6013:7057 | 6013:7058 | 6013:7059 | 6013:7060 | 6013:7061 | 6013:7062 |
| 6014:7056 | 6014:7057 | 6014:7058 | 6014:7059 | 6014:7060 | 6014:7061 | 6014:7062 |
| 6015:7056 | 6015:7057 | 6015:7058 | 6015:7059 | 6015:7060 | 6015:7061 | 6015:7062 |
| 6016:7056 | 6016:7057 | 6016:7058 | 6016:7059 | 6016:7060 | 6016:7061 | 6016:7062 |
| 6017:7056 | 6017:7057 | 6017:7058 | 6017:7059 | 6017:7060 | 6017:7061 | 6017:7062 |
| 6018:7056 | 6018:7057 | 6018:7058 | 6018:7059 | 6018:7060 | 6018:7061 | 6018:7062 |
| 6019:7056 | 6019:7057 | 6019:7058 | 6019:7059 | 6019:7060 | 6019:7061 | 6019:7062 |
| 6020:7056 | 6020:7057 | 6020:7058 | 6020:7059 | 6020:7060 | 6020:7061 | 6020:7062 |

TABLE B-continued

Example combinations of a compound X with a compound Y.

| X:Y | X:Y | X:Y | X:Y | X:Y | X:Y | X:Y |
|---|---|---|---|---|---|---|
| 6000:7063 | 6000:7064 | 6000:7065 | 6000:7066 | 6000:7067 | 6000:7068 | 6000:7069 |
| 6001:7063 | 6001:7064 | 6001:7065 | 6001:7066 | 6001:7067 | 6001:7068 | 6001:7069 |
| 6002:7063 | 6002:7064 | 6002:7065 | 6002:7066 | 6002:7067 | 6002:7068 | 6002:7069 |
| 6003:7063 | 6003:7064 | 6003:7065 | 6003:7066 | 6003:7067 | 6003:7068 | 6003:7069 |
| 6004:7063 | 6004:7064 | 6004:7065 | 6004:7066 | 6004:7067 | 6004:7068 | 6004:7069 |
| 6005:7063 | 6005:7064 | 6005:7065 | 6005:7066 | 6005:7067 | 6005:7068 | 6005:7069 |
| 6006:7063 | 6006:7064 | 6006:7065 | 6006:7066 | 6006:7067 | 6006:7068 | 6006:7069 |
| 6007:7063 | 6007:7064 | 6007:7065 | 6007:7066 | 6007:7067 | 6007:7068 | 6007:7069 |
| 6008:7063 | 6008:7064 | 6008:7065 | 6008:7066 | 6008:7067 | 6008:7068 | 6008:7069 |
| 6009:7063 | 6009:7064 | 6009:7065 | 6009:7066 | 6009:7067 | 6009:7068 | 6009:7069 |
| 6010:7063 | 6010:7064 | 6010:7065 | 6010:7066 | 6010:7067 | 6010:7068 | 6010:7069 |
| 6011:7063 | 6011:7064 | 6011:7065 | 6011:7066 | 6011:7067 | 6011:7068 | 6011:7069 |
| 6012:7063 | 6012:7064 | 6012:7065 | 6012:7066 | 6012:7067 | 6012:7068 | 6012:7069 |
| 6013:7063 | 6013:7064 | 6013:7065 | 6013:7066 | 6013:7067 | 6013:7068 | 6013:7069 |
| 6014:7063 | 6014:7064 | 6014:7065 | 6014:7066 | 6014:7067 | 6014:7068 | 6014:7069 |
| 6015:7063 | 6015:7064 | 6015:7065 | 6015:7066 | 6015:7067 | 6015:7068 | 6015:7069 |
| 6016:7063 | 6016:7064 | 6016:7065 | 6016:7066 | 6016:7067 | 6016:7068 | 6016:7069 |
| 6017:7063 | 6017:7064 | 6017:7065 | 6017:7066 | 6017:7067 | 6017:7068 | 6017:7069 |
| 6018:7063 | 6018:7064 | 6018:7065 | 6018:7066 | 6018:7067 | 6018:7068 | 6018:7069 |
| 6019:7063 | 6019:7064 | 6019:7065 | 6019:7066 | 6019:7067 | 6019:7068 | 6019:7069 |
| 6020:7063 | 6020:7064 | 6020:7065 | 6020:7066 | 6020:7067 | 6020:7068 | 6020:7069 |
| 6000:7070 | 6000:7071 | 6000:7072 | 6000:7073 | 6000:7074 | 6000:7075 | 6000:7076 |
| 6001:7070 | 6001:7071 | 6001:7072 | 6001:7073 | 6001:7074 | 6001:7075 | 6001:7076 |
| 6002:7070 | 6002:7071 | 6002:7072 | 6002:7073 | 6002:7074 | 6002:7075 | 6002:7076 |
| 6003:7070 | 6003:7071 | 6003:7072 | 6003:7073 | 6003:7074 | 6003:7075 | 6003:7076 |
| 6004:7070 | 6004:7071 | 6004:7072 | 6004:7073 | 6004:7074 | 6004:7075 | 6004:7076 |
| 6005:7070 | 6005:7071 | 6005:7072 | 6005:7073 | 6005:7074 | 6005:7075 | 6005:7076 |
| 6006:7070 | 6006:7071 | 6006:7072 | 6006:7073 | 6006:7074 | 6006:7075 | 6006:7076 |
| 6007:7070 | 6007:7071 | 6007:7072 | 6007:7073 | 6007:7074 | 6007:7075 | 6007:7076 |
| 6008:7070 | 6008:7071 | 6008:7072 | 6008:7073 | 6008:7074 | 6008:7075 | 6008:7076 |
| 6009:7070 | 6009:7071 | 6009:7072 | 6009:7073 | 6009:7074 | 6009:7075 | 6009:7076 |
| 6010:7070 | 6010:7071 | 6010:7072 | 6010:7073 | 6010:7074 | 6010:7075 | 6010:7076 |
| 6011:7070 | 6011:7071 | 6011:7072 | 6011:7073 | 6011:7074 | 6011:7075 | 6011:7076 |
| 6012:7070 | 6012:7071 | 6012:7072 | 6012:7073 | 6012:7074 | 6012:7075 | 6012:7076 |
| 6013:7070 | 6013:7071 | 6013:7072 | 6013:7073 | 6013:7074 | 6013:7075 | 6013:7076 |
| 6014:7070 | 6014:7071 | 6014:7072 | 6014:7073 | 6014:7074 | 6014:7075 | 6014:7076 |
| 6015:7070 | 6015:7071 | 6015:7072 | 6015:7073 | 6015:7074 | 6015:7075 | 6015:7076 |
| 6016:7070 | 6016:7071 | 6016:7072 | 6016:7073 | 6016:7074 | 6016:7075 | 6016:7076 |
| 6017:7070 | 6017:7071 | 6017:7072 | 6017:7073 | 6017:7074 | 6017:7075 | 6017:7076 |
| 6018:7070 | 6018:7071 | 6018:7072 | 6018:7073 | 6018:7074 | 6018:7075 | 6018:7076 |
| 6019:7070 | 6019:7071 | 6019:7072 | 6019:7073 | 6019:7074 | 6019:7075 | 6019:7076 |
| 6020:7070 | 6020:7071 | 6020:7072 | 6020:7073 | 6020:7074 | 6020:7075 | 6020:7076 |
| 6000:7077 | 6021:7000 | 6021:7001 | 6021:7002 | 6021:7003 | 6021:7004 | 6021:7005 |
| 6001:7077 | 6022:7000 | 6022:7001 | 6022:7002 | 6022:7003 | 6022:7004 | 6022:7005 |
| 6002:7077 | 6023:7000 | 6023:7001 | 6023:7002 | 6023:7003 | 6023:7004 | 6023:7005 |
| 6003:7077 | 6024:7000 | 6024:7001 | 6024:7002 | 6024:7003 | 6024:7004 | 6024:7005 |
| 6004:7077 | 6025:7000 | 6025:7001 | 6025:7002 | 6025:7003 | 6025:7004 | 6025:7005 |
| 6005:7077 | 6026:7000 | 6026:7001 | 6026:7002 | 6026:7003 | 6026:7004 | 6026:7005 |
| 6006:7077 | 6027:7000 | 6027:7001 | 6027:7002 | 6027:7003 | 6027:7004 | 6027:7005 |
| 6007:7077 | 6028:7000 | 6028:7001 | 6028:7002 | 6028:7003 | 6028:7004 | 6028:7005 |
| 6008:7077 | 6029:7000 | 6029:7001 | 6029:7002 | 6029:7003 | 6029:7004 | 6029:7005 |
| 6009:7077 | 6030:7000 | 6030:7001 | 6030:7002 | 6030:7003 | 6030:7004 | 6030:7005 |
| 6010:7077 | 6031:7000 | 6031:7001 | 6031:7002 | 6031:7003 | 6031:7004 | 6031:7005 |
| 6011:7077 | 6032:7000 | 6032:7001 | 6032:7002 | 6032:7003 | 6032:7004 | 6032:7005 |
| 6012:7077 | 6033:7000 | 6033:7001 | 6033:7002 | 6033:7003 | 6033:7004 | 6033:7005 |
| 6013:7077 | 6034:7000 | 6034:7001 | 6034:7002 | 6034:7003 | 6034:7004 | 6034:7005 |
| 6014:7077 | 6035:7000 | 6035:7001 | 6035:7002 | 6035:7003 | 6035:7004 | 6035:7005 |
| 6015:7077 | 6036:7000 | 6036:7001 | 6036:7002 | 6036:7003 | 6036:7004 | 6036:7005 |
| 6016:7077 | 6037:7000 | 6037:7001 | 6037:7002 | 6037:7003 | 6037:7004 | 6037:7005 |
| 6017:7077 | 6038:7000 | 6038:7001 | 6038:7002 | 6038:7003 | 6038:7004 | 6038:7005 |
| 6018:7077 | 6039:7000 | 6039:7001 | 6039:7002 | 6039:7003 | 6039:7004 | 6039:7005 |
| 6019:7077 | 6040:7000 | 6040:7001 | 6040:7002 | 6040:7003 | 6040:7004 | 6040:7005 |
| 6020:7077 | | | | | | |
| 6021:7006 | 6021:7007 | 6021:7008 | 6021:7009 | 6021:7010 | 6021:7011 | 6021:7012 |
| 6022:7006 | 6022:7007 | 6022:7008 | 6022:7009 | 6022:7010 | 6022:7011 | 6022:7012 |
| 6023:7006 | 6023:7007 | 6023:7008 | 6023:7009 | 6023:7010 | 6023:7011 | 6023:7012 |
| 6024:7006 | 6024:7007 | 6024:7008 | 6024:7009 | 6024:7010 | 6024:7011 | 6024:7012 |
| 6025:7006 | 6025:7007 | 6025:7008 | 6025:7009 | 6025:7010 | 6025:7011 | 6025:7012 |
| 6026:7006 | 6026:7007 | 6026:7008 | 6026:7009 | 6026:7010 | 6026:7011 | 6026:7012 |
| 6027:7006 | 6027:7007 | 6027:7008 | 6027:7009 | 6027:7010 | 6027:7011 | 6027:7012 |
| 6028:7006 | 6028:7007 | 6028:7008 | 6028:7009 | 6028:7010 | 6028:7011 | 6028:7012 |
| 6029:7006 | 6029:7007 | 6029:7008 | 6029:7009 | 6029:7010 | 6029:7011 | 6029:7012 |
| 6030:7006 | 6030:7007 | 6030:7008 | 6030:7009 | 6030:7010 | 6030:7011 | 6030:7012 |

TABLE B-continued

Example combinations of a compound X with a compound Y.

| X:Y | X:Y | X:Y | X:Y | X:Y | X:Y | X:Y |
|---|---|---|---|---|---|---|
| 6031:7006 | 6031:7007 | 6031:7008 | 6031:7009 | 6031:7010 | 6031:7011 | 6031:7012 |
| 6032:7006 | 6032:7007 | 6032:7008 | 6032:7009 | 6032:7010 | 6032:7011 | 6032:7012 |
| 6033:7006 | 6033:7007 | 6033:7008 | 6033:7009 | 6033:7010 | 6033:7011 | 6033:7012 |
| 6034:7006 | 6034:7007 | 6034:7008 | 6034:7009 | 6034:7010 | 6034:7011 | 6034:7012 |
| 6035:7006 | 6035:7007 | 6035:7008 | 6035:7009 | 6035:7010 | 6035:7011 | 6035:7012 |
| 6036:7006 | 6036:7007 | 6036:7008 | 6036:7009 | 6036:7010 | 6036:7011 | 6036:7012 |
| 6037:7006 | 6037:7007 | 6037:7008 | 6037:7009 | 6037:7010 | 6037:7011 | 6037:7012 |
| 6038:7006 | 6038:7007 | 6038:7008 | 6038:7009 | 6038:7010 | 6038:7011 | 6038:7012 |
| 6039:7006 | 6039:7007 | 6039:7008 | 6039:7009 | 6039:7010 | 6039:7011 | 6039:7012 |
| 6040:7006 | 6040:7007 | 6040:7008 | 6040:7009 | 6040:7010 | 6040:7011 | 6040:7012 |
| 6021:7013 | 6021:7014 | 6021:7015 | 6021:7016 | 6021:7017 | 6021:7018 | 6021:7019 |
| 6022:7013 | 6022:7014 | 6022:7015 | 6022:7016 | 6022:7017 | 6022:7018 | 6022:7019 |
| 6023:7013 | 6023:7014 | 6023:7015 | 6023:7016 | 6023:7017 | 6023:7018 | 6023:7019 |
| 6024:7013 | 6024:7014 | 6024:7015 | 6024:7016 | 6024:7017 | 6024:7018 | 6024:7019 |
| 6025:7013 | 6025:7014 | 6025:7015 | 6025:7016 | 6025:7017 | 6025:7018 | 6025:7019 |
| 6026:7013 | 6026:7014 | 6026:7015 | 6026:7016 | 6026:7017 | 6026:7018 | 6026:7019 |
| 6027:7013 | 6027:7014 | 6027:7015 | 6027:7016 | 6027:7017 | 6027:7018 | 6027:7019 |
| 6028:7013 | 6028:7014 | 6028:7015 | 6028:7016 | 6028:7017 | 6028:7018 | 6028:7019 |
| 6029:7013 | 6029:7014 | 6029:7015 | 6029:7016 | 6029:7017 | 6029:7018 | 6029:7019 |
| 6030:7013 | 6030:7014 | 6030:7015 | 6030:7016 | 6030:7017 | 6030:7018 | 6030:7019 |
| 6031:7013 | 6031:7014 | 6031:7015 | 6031:7016 | 6031:7017 | 6031:7018 | 6031:7019 |
| 6032:7013 | 6032:7014 | 6032:7015 | 6032:7016 | 6032:7017 | 6032:7018 | 6032:7019 |
| 6033:7013 | 6033:7014 | 6033:7015 | 6033:7016 | 6033:7017 | 6033:7018 | 6033:7019 |
| 6034:7013 | 6034:7014 | 6034:7015 | 6034:7016 | 6034:7017 | 6034:7018 | 6034:7019 |
| 6035:7013 | 6035:7014 | 6035:7015 | 6035:7016 | 6035:7017 | 6035:7018 | 6035:7019 |
| 6036:7013 | 6036:7014 | 6036:7015 | 6036:7016 | 6036:7017 | 6036:7018 | 6036:7019 |
| 6037:7013 | 6037:7014 | 6037:7015 | 6037:7016 | 6037:7017 | 6037:7018 | 6037:7019 |
| 6038:7013 | 6038:7014 | 6038:7015 | 6038:7016 | 6038:7017 | 6038:7018 | 6038:7019 |
| 6039:7013 | 6039:7014 | 6039:7015 | 6039:7016 | 6039:7017 | 6039:7018 | 6039:7019 |
| 6040:7013 | 6040:7014 | 6040:7015 | 6040:7016 | 6040:7017 | 6040:7018 | 6040:7019 |
| 6021:7020 | 6021:7021 | 6021:7022 | 6021:7023 | 6021:7024 | 6021:7025 | 6021:7026 |
| 6022:7020 | 6022:7021 | 6022:7022 | 6022:7023 | 6022:7024 | 6022:7025 | 6022:7026 |
| 6023:7020 | 6023:7021 | 6023:7022 | 6023:7023 | 6023:7024 | 6023:7025 | 6023:7026 |
| 6024:7020 | 6024:7021 | 6024:7022 | 6024:7023 | 6024:7024 | 6024:7025 | 6024:7026 |
| 6025:7020 | 6025:7021 | 6025:7022 | 6025:7023 | 6025:7024 | 6025:7025 | 6025:7026 |
| 6026:7020 | 6026:7021 | 6026:7022 | 6026:7023 | 6026:7024 | 6026:7025 | 6026:7026 |
| 6027:7020 | 6027:7021 | 6027:7022 | 6027:7023 | 6027:7024 | 6027:7025 | 6027:7026 |
| 6028:7020 | 6028:7021 | 6028:7022 | 6028:7023 | 6028:7024 | 6028:7025 | 6028:7026 |
| 6029:7020 | 6029:7021 | 6029:7022 | 6029:7023 | 6029:7024 | 6029:7025 | 6029:7026 |
| 6030:7020 | 6030:7021 | 6030:7022 | 6030:7023 | 6030:7024 | 6030:7025 | 6030:7026 |
| 6031:7020 | 6031:7021 | 6031:7022 | 6031:7023 | 6031:7024 | 6031:7025 | 6031:7026 |
| 6032:7020 | 6032:7021 | 6032:7022 | 6032:7023 | 6032:7024 | 6032:7025 | 6032:7026 |
| 6033:7020 | 6033:7021 | 6033:7022 | 6033:7023 | 6033:7024 | 6033:7025 | 6033:7026 |
| 6034:7020 | 6034:7021 | 6034:7022 | 6034:7023 | 6034:7024 | 6034:7025 | 6034:7026 |
| 6035:7020 | 6035:7021 | 6035:7022 | 6035:7023 | 6035:7024 | 6035:7025 | 6035:7026 |
| 6036:7020 | 6036:7021 | 6036:7022 | 6036:7023 | 6036:7024 | 6036:7025 | 6036:7026 |
| 6037:7020 | 6037:7021 | 6037:7022 | 6037:7023 | 6037:7024 | 6037:7025 | 6037:7026 |
| 6038:7020 | 6038:7021 | 6038:7022 | 6038:7023 | 6038:7024 | 6038:7025 | 6038:7026 |
| 6039:7020 | 6039:7021 | 6039:7022 | 6039:7023 | 6039:7024 | 6039:7025 | 6039:7026 |
| 6040:7020 | 6040:7021 | 6040:7022 | 6040:7023 | 6040:7024 | 6040:7025 | 6040:7026 |
| 6021:7027 | 6021:7028 | 6021:7029 | 6021:7030 | 6021:7031 | 6021:7032 | 6021:7033 |
| 6022:7027 | 6022:7028 | 6022:7029 | 6022:7030 | 6022:7031 | 6022:7032 | 6022:7033 |
| 6023:7027 | 6023:7028 | 6023:7029 | 6023:7030 | 6023:7031 | 6023:7032 | 6023:7033 |
| 6024:7027 | 6024:7028 | 6024:7029 | 6024:7030 | 6024:7031 | 6024:7032 | 6024:7033 |
| 6025:7027 | 6025:7028 | 6025:7029 | 6025:7030 | 6025:7031 | 6025:7032 | 6025:7033 |
| 6026:7027 | 6026:7028 | 6026:7029 | 6026:7030 | 6026:7031 | 6026:7032 | 6026:7033 |
| 6027:7027 | 6027:7028 | 6027:7029 | 6027:7030 | 6027:7031 | 6027:7032 | 6027:7033 |
| 6028:7027 | 6028:7028 | 6028:7029 | 6028:7030 | 6028:7031 | 6028:7032 | 6028:7033 |
| 6029:7027 | 6029:7028 | 6029:7029 | 6029:7030 | 6029:7031 | 6029:7032 | 6029:7033 |
| 6030:7027 | 6030:7028 | 6030:7029 | 6030:7030 | 6030:7031 | 6030:7032 | 6030:7033 |
| 6031:7027 | 6031:7028 | 6031:7029 | 6031:7030 | 6031:7031 | 6031:7032 | 6031:7033 |
| 6032:7027 | 6032:7028 | 6032:7029 | 6032:7030 | 6032:7031 | 6032:7032 | 6032:7033 |
| 6033:7027 | 6033:7028 | 6033:7029 | 6033:7030 | 6033:7031 | 6033:7032 | 6033:7033 |
| 6034:7027 | 6034:7028 | 6034:7029 | 6034:7030 | 6034:7031 | 6034:7032 | 6034:7033 |
| 6035:7027 | 6035:7028 | 6035:7029 | 6035:7030 | 6035:7031 | 6035:7032 | 6035:7033 |
| 6036:7027 | 6036:7028 | 6036:7029 | 6036:7030 | 6036:7031 | 6036:7032 | 6036:7033 |
| 6037:7027 | 6037:7028 | 6037:7029 | 6037:7030 | 6037:7031 | 6037:7032 | 6037:7033 |
| 6038:7027 | 6038:7028 | 6038:7029 | 6038:7030 | 6038:7031 | 6038:7032 | 6038:7033 |
| 6039:7027 | 6039:7028 | 6039:7029 | 6039:7030 | 6039:7031 | 6039:7032 | 6039:7033 |
| 6040:7027 | 6040:7028 | 6040:7029 | 6040:7030 | 6040:7031 | 6040:7032 | 6040:7033 |
| 6021:7034 | 6021:7035 | 6021:7036 | 6021:7037 | 6021:7038 | 6021:7039 | 6021:7040 |
| 6022:7034 | 6022:7035 | 6022:7036 | 6022:7037 | 6022:7038 | 6022:7039 | 6022:7040 |

TABLE B-continued

Example combinations of a compound X with a compound Y.

| X:Y | X:Y | X:Y | X:Y | X:Y | X:Y | X:Y |
|---|---|---|---|---|---|---|
| 6023:7034 | 6023:7035 | 6023:7036 | 6023:7037 | 6023:7038 | 6023:7039 | 6023:7040 |
| 6024:7034 | 6024:7035 | 6024:7036 | 6024:7037 | 6024:7038 | 6024:7039 | 6024:7040 |
| 6025:7034 | 6025:7035 | 6025:7036 | 6025:7037 | 6025:7038 | 6025:7039 | 6025:7040 |
| 6026:7034 | 6026:7035 | 6026:7036 | 6026:7037 | 6026:7038 | 6026:7039 | 6026:7040 |
| 6027:7034 | 6027:7035 | 6027:7036 | 6027:7037 | 6027:7038 | 6027:7039 | 6027:7040 |
| 6028:7034 | 6028:7035 | 6028:7036 | 6028:7037 | 6028:7038 | 6028:7039 | 6028:7040 |
| 6029:7034 | 6029:7035 | 6029:7036 | 6029:7037 | 6029:7038 | 6029:7039 | 6029:7040 |
| 6030:7034 | 6030:7035 | 6030:7036 | 6030:7037 | 6030:7038 | 6030:7039 | 6030:7040 |
| 6031:7034 | 6031:7035 | 6031:7036 | 6031:7037 | 6031:7038 | 6031:7039 | 6031:7040 |
| 6032:7034 | 6032:7035 | 6032:7036 | 6032:7037 | 6032:7038 | 6032:7039 | 6032:7040 |
| 6033:7034 | 6033:7035 | 6033:7036 | 6033:7037 | 6033:7038 | 6033:7039 | 6033:7040 |
| 6034:7034 | 6034:7035 | 6034:7036 | 6034:7037 | 6034:7038 | 6034:7039 | 6034:7040 |
| 6035:7034 | 6035:7035 | 6035:7036 | 6035:7037 | 6035:7038 | 6035:7039 | 6035:7040 |
| 6036:7034 | 6036:7035 | 6036:7036 | 6036:7037 | 6036:7038 | 6036:7039 | 6036:7040 |
| 6037:7034 | 6037:7035 | 6037:7036 | 6037:7037 | 6037:7038 | 6037:7039 | 6037:7040 |
| 6038:7034 | 6038:7035 | 6038:7036 | 6038:7037 | 6038:7038 | 6038:7039 | 6038:7040 |
| 6039:7034 | 6039:7035 | 6039:7036 | 6039:7037 | 6039:7038 | 6039:7039 | 6039:7040 |
| 6040:7034 | 6040:7035 | 6040:7036 | 6040:7037 | 6040:7038 | 6040:7039 | 6040:7040 |
| 6021:7041 | 6021:7042 | 6021:7043 | 6021:7044 | 6021:7045 | 6021:7046 | 6021:7047 |
| 6022:7041 | 6022:7042 | 6022:7043 | 6022:7044 | 6022:7045 | 6022:7046 | 6022:7047 |
| 6023:7041 | 6023:7042 | 6023:7043 | 6023:7044 | 6023:7045 | 6023:7046 | 6023:7047 |
| 6024:7041 | 6024:7042 | 6024:7043 | 6024:7044 | 6024:7045 | 6024:7046 | 6024:7047 |
| 6025:7041 | 6025:7042 | 6025:7043 | 6025:7044 | 6025:7045 | 6025:7046 | 6025:7047 |
| 6026:7041 | 6026:7042 | 6026:7043 | 6026:7044 | 6026:7045 | 6026:7046 | 6026:7047 |
| 6027:7041 | 6027:7042 | 6027:7043 | 6027:7044 | 6027:7045 | 6027:7046 | 6027:7047 |
| 6028:7041 | 6028:7042 | 6028:7043 | 6028:7044 | 6028:7045 | 6028:7046 | 6028:7047 |
| 6029:7041 | 6029:7042 | 6029:7043 | 6029:7044 | 6029:7045 | 6029:7046 | 6029:7047 |
| 6030:7041 | 6030:7042 | 6030:7043 | 6030:7044 | 6030:7045 | 6030:7046 | 6030:7047 |
| 6031:7041 | 6031:7042 | 6031:7043 | 6031:7044 | 6031:7045 | 6031:7046 | 6031:7047 |
| 6032:7041 | 6032:7042 | 6032:7043 | 6032:7044 | 6032:7045 | 6032:7046 | 6032:7047 |
| 6033:7041 | 6033:7042 | 6033:7043 | 6033:7044 | 6033:7045 | 6033:7046 | 6033:7047 |
| 6034:7041 | 6034:7042 | 6034:7043 | 6034:7044 | 6034:7045 | 6034:7046 | 6034:7047 |
| 6035:7041 | 6035:7042 | 6035:7043 | 6035:7044 | 6035:7045 | 6035:7046 | 6035:7047 |
| 6036:7041 | 6036:7042 | 6036:7043 | 6036:7044 | 6036:7045 | 6036:7046 | 6036:7047 |
| 6037:7041 | 6037:7042 | 6037:7043 | 6037:7044 | 6037:7045 | 6037:7046 | 6037:7047 |
| 6038:7041 | 6038:7042 | 6038:7043 | 6038:7044 | 6038:7045 | 6038:7046 | 6038:7047 |
| 6039:7041 | 6039:7042 | 6039:7043 | 6039:7044 | 6039:7045 | 6039:7046 | 6039:7047 |
| 6040:7041 | 6040:7042 | 6040:7043 | 6040:7044 | 6040:7045 | 6040:7046 | 6040:7047 |
| 6021:7048 | 6021:7049 | 6021:7050 | 6021:7051 | 6021:7052 | 6021:7053 | 6021:7054 |
| 6022:7048 | 6022:7049 | 6022:7050 | 6022:7051 | 6022:7052 | 6022:7053 | 6022:7054 |
| 6023:7048 | 6023:7049 | 6023:7050 | 6023:7051 | 6023:7052 | 6023:7053 | 6023:7054 |
| 6024:7048 | 6024:7049 | 6024:7050 | 6024:7051 | 6024:7052 | 6024:7053 | 6024:7054 |
| 6025:7048 | 6025:7049 | 6025:7050 | 6025:7051 | 6025:7052 | 6025:7053 | 6025:7054 |
| 6026:7048 | 6026:7049 | 6026:7050 | 6026:7051 | 6026:7052 | 6026:7053 | 6026:7054 |
| 6027:7048 | 6027:7049 | 6027:7050 | 6027:7051 | 6027:7052 | 6027:7053 | 6027:7054 |
| 6028:7048 | 6028:7049 | 6028:7050 | 6028:7051 | 6028:7052 | 6028:7053 | 6028:7054 |
| 6029:7048 | 6029:7049 | 6029:7050 | 6029:7051 | 6029:7052 | 6029:7053 | 6029:7054 |
| 6030:7048 | 6030:7049 | 6030:7050 | 6030:7051 | 6030:7052 | 6030:7053 | 6030:7054 |
| 6031:7048 | 6031:7049 | 6031:7050 | 6031:7051 | 6031:7052 | 6031:7053 | 6031:7054 |
| 6032:7048 | 6032:7049 | 6032:7050 | 6032:7051 | 6032:7052 | 6032:7053 | 6032:7054 |
| 6033:7048 | 6033:7049 | 6033:7050 | 6033:7051 | 6033:7052 | 6033:7053 | 6033:7054 |
| 6034:7048 | 6034:7049 | 6034:7050 | 6034:7051 | 6034:7052 | 6034:7053 | 6034:7054 |
| 6035:7048 | 6035:7049 | 6035:7050 | 6035:7051 | 6035:7052 | 6035:7053 | 6035:7054 |
| 6036:7048 | 6036:7049 | 6036:7050 | 6036:7051 | 6036:7052 | 6036:7053 | 6036:7054 |
| 6037:7048 | 6037:7049 | 6037:7050 | 6037:7051 | 6037:7052 | 6037:7053 | 6037:7054 |
| 6038:7048 | 6038:7049 | 6038:7050 | 6038:7051 | 6038:7052 | 6038:7053 | 6038:7054 |
| 6039:7048 | 6039:7049 | 6039:7050 | 6039:7051 | 6039:7052 | 6039:7053 | 6039:7054 |
| 6040:7048 | 6040:7049 | 6040:7050 | 6040:7051 | 6040:7052 | 6040:7053 | 6040:7054 |
| 6021:7055 | 6021:7056 | 6021:7057 | 6021:7058 | 6021:7059 | 6021:7060 | 6021:7061 |
| 6022:7055 | 6022:7056 | 6022:7057 | 6022:7058 | 6022:7059 | 6022:7060 | 6022:7061 |
| 6023:7055 | 6023:7056 | 6023:7057 | 6023:7058 | 6023:7059 | 6023:7060 | 6023:7061 |
| 6024:7055 | 6024:7056 | 6024:7057 | 6024:7058 | 6024:7059 | 6024:7060 | 6024:7061 |
| 6025:7055 | 6025:7056 | 6025:7057 | 6025:7058 | 6025:7059 | 6025:7060 | 6025:7061 |
| 6026:7055 | 6026:7056 | 6026:7057 | 6026:7058 | 6026:7059 | 6026:7060 | 6026:7061 |
| 6027:7055 | 6027:7056 | 6027:7057 | 6027:7058 | 6027:7059 | 6027:7060 | 6027:7061 |
| 6028:7055 | 6028:7056 | 6028:7057 | 6028:7058 | 6028:7059 | 6028:7060 | 6028:7061 |
| 6029:7055 | 6029:7056 | 6029:7057 | 6029:7058 | 6029:7059 | 6029:7060 | 6029:7061 |
| 6030:7055 | 6030:7056 | 6030:7057 | 6030:7058 | 6030:7059 | 6030:7060 | 6030:7061 |
| 6031:7055 | 6031:7056 | 6031:7057 | 6031:7058 | 6031:7059 | 6031:7060 | 6031:7061 |
| 6032:7055 | 6032:7056 | 6032:7057 | 6032:7058 | 6032:7059 | 6032:7060 | 6032:7061 |
| 6033:7055 | 6033:7056 | 6033:7057 | 6033:7058 | 6033:7059 | 6033:7060 | 6033:7061 |
| 6034:7055 | 6034:7056 | 6034:7057 | 6034:7058 | 6034:7059 | 6034:7060 | 6034:7061 |
| 6035:7055 | 6035:7056 | 6035:7057 | 6035:7058 | 6035:7059 | 6035:7060 | 6035:7061 |

TABLE B-continued

Example combinations of a compound X with a compound Y.

| X:Y | X:Y | X:Y | X:Y | X:Y | X:Y | X:Y |
|---|---|---|---|---|---|---|
| 6036:7055 | 6036:7056 | 6036:7057 | 6036:7058 | 6036:7059 | 6036:7060 | 6036:7061 |
| 6037:7055 | 6037:7056 | 6037:7057 | 6037:7058 | 6037:7059 | 6037:7060 | 6037:7061 |
| 6038:7055 | 6038:7056 | 6038:7057 | 6038:7058 | 6038:7059 | 6038:7060 | 6038:7061 |
| 6039:7055 | 6039:7056 | 6039:7057 | 6039:7058 | 6039:7059 | 6039:7060 | 6039:7061 |
| 6040:7055 | 6040:7056 | 6040:7057 | 6040:7058 | 6040:7059 | 6040:7060 | 6040:7061 |
| 6021:7062 | 6021:7063 | 6021:7064 | 6021:7065 | 6021:7066 | 6021:7067 | 6021:7068 |
| 6022:7062 | 6022:7063 | 6022:7064 | 6022:7065 | 6022:7066 | 6022:7067 | 6022:7068 |
| 6023:7062 | 6023:7063 | 6023:7064 | 6023:7065 | 6023:7066 | 6023:7067 | 6023:7068 |
| 6024:7062 | 6024:7063 | 6024:7064 | 6024:7065 | 6024:7066 | 6024:7067 | 6024:7068 |
| 6025:7062 | 6025:7063 | 6025:7064 | 6025:7065 | 6025:7066 | 6025:7067 | 6025:7068 |
| 6026:7062 | 6026:7063 | 6026:7064 | 6026:7065 | 6026:7066 | 6026:7067 | 6026:7068 |
| 6027:7062 | 6027:7063 | 6027:7064 | 6027:7065 | 6027:7066 | 6027:7067 | 6027:7068 |
| 6028:7062 | 6028:7063 | 6028:7064 | 6028:7065 | 6028:7066 | 6028:7067 | 6028:7068 |
| 6029:7062 | 6029:7063 | 6029:7064 | 6029:7065 | 6029:7066 | 6029:7067 | 6029:7068 |
| 6030:7062 | 6030:7063 | 6030:7064 | 6030:7065 | 6030:7066 | 6030:7067 | 6030:7068 |
| 6031:7062 | 6031:7063 | 6031:7064 | 6031:7065 | 6031:7066 | 6031:7067 | 6031:7068 |
| 6032:7062 | 6032:7063 | 6032:7064 | 6032:7065 | 6032:7066 | 6032:7067 | 6032:7068 |
| 6033:7062 | 6033:7063 | 6033:7064 | 6033:7065 | 6033:7066 | 6033:7067 | 6033:7068 |
| 6034:7062 | 6034:7063 | 6034:7064 | 6034:7065 | 6034:7066 | 6034:7067 | 6034:7068 |
| 6035:7062 | 6035:7063 | 6035:7064 | 6035:7065 | 6035:7066 | 6035:7067 | 6035:7068 |
| 6036:7062 | 6036:7063 | 6036:7064 | 6036:7065 | 6036:7066 | 6036:7067 | 6036:7068 |
| 6037:7062 | 6037:7063 | 6037:7064 | 6037:7065 | 6037:7066 | 6037:7067 | 6037:7068 |
| 6038:7062 | 6038:7063 | 6038:7064 | 6038:7065 | 6038:7066 | 6038:7067 | 6038:7068 |
| 6039:7062 | 6039:7063 | 6039:7064 | 6039:7065 | 6039:7066 | 6039:7067 | 6039:7068 |
| 6040:7062 | 6040:7063 | 6040:7064 | 6040:7065 | 6040:7066 | 6040:7067 | 6040:7068 |
| 6021:7069 | 6021:7070 | 6021:7071 | 6021:7072 | 6021:7073 | 6021:7074 | 6021:7075 |
| 6022:7069 | 6022:7070 | 6022:7071 | 6022:7072 | 6022:7073 | 6022:7074 | 6022:7075 |
| 6023:7069 | 6023:7070 | 6023:7071 | 6023:7072 | 6023:7073 | 6023:7074 | 6023:7075 |
| 6024:7069 | 6024:7070 | 6024:7071 | 6024:7072 | 6024:7073 | 6024:7074 | 6024:7075 |
| 6025:7069 | 6025:7070 | 6025:7071 | 6025:7072 | 6025:7073 | 6025:7074 | 6025:7075 |
| 6026:7069 | 6026:7070 | 6026:7071 | 6026:7072 | 6026:7073 | 6026:7074 | 6026:7075 |
| 6027:7069 | 6027:7070 | 6027:7071 | 6027:7072 | 6027:7073 | 6027:7074 | 6027:7075 |
| 6028:7069 | 6028:7070 | 6028:7071 | 6028:7072 | 6028:7073 | 6028:7074 | 6028:7075 |
| 6029:7069 | 6029:7070 | 6029:7071 | 6029:7072 | 6029:7073 | 6029:7074 | 6029:7075 |
| 6030:7069 | 6030:7070 | 6030:7071 | 6030:7072 | 6030:7073 | 6030:7074 | 6030:7075 |
| 6031:7069 | 6031:7070 | 6031:7071 | 6031:7072 | 6031:7073 | 6031:7074 | 6031:7075 |
| 6032:7069 | 6032:7070 | 6032:7071 | 6032:7072 | 6032:7073 | 6032:7074 | 6032:7075 |
| 6033:7069 | 6033:7070 | 6033:7071 | 6033:7072 | 6033:7073 | 6033:7074 | 6033:7075 |
| 6034:7069 | 6034:7070 | 6034:7071 | 6034:7072 | 6034:7073 | 6034:7074 | 6034:7075 |
| 6035:7069 | 6035:7070 | 6035:7071 | 6035:7072 | 6035:7073 | 6035:7074 | 6035:7075 |
| 6036:7069 | 6036:7070 | 6036:7071 | 6036:7072 | 6036:7073 | 6036:7074 | 6036:7075 |
| 6037:7069 | 6037:7070 | 6037:7071 | 6037:7072 | 6037:7073 | 6037:7074 | 6037:7075 |
| 6038:7069 | 6038:7070 | 6038:7071 | 6038:7072 | 6038:7073 | 6038:7074 | 6038:7075 |
| 6039:7069 | 6039:7070 | 6039:7071 | 6039:7072 | 6039:7073 | 6039:7074 | 6039:7075 |
| 6040:7069 | 6040:7070 | 6040:7071 | 6040:7072 | 6040:7073 | 6040:7074 | 6040:7075 |
| 6021:7076 | 6021:7077 | 6041:7000 | 6041:7001 | 6041:7002 | 6041:7003 | 6041:7004 |
| 6022:7076 | 6022:7077 | 6042:7000 | 6042:7001 | 6042:7002 | 6042:7003 | 6042:7004 |
| 6023:7076 | 6023:7077 | 6043:7000 | 6043:7001 | 6043:7002 | 6043:7003 | 6043:7004 |
| 6024:7076 | 6024:7077 | 6044:7000 | 6044:7001 | 6044:7002 | 6044:7003 | 6044:7004 |
| 6025:7076 | 6025:7077 | 6045:7000 | 6045:7001 | 6045:7002 | 6045:7003 | 6045:7004 |
| 6026:7076 | 6026:7077 | 6046:7000 | 6046:7001 | 6046:7002 | 6046:7003 | 6046:7004 |
| 6027:7076 | 6027:7077 | 6047:7000 | 6047:7001 | 6047:7002 | 6047:7003 | 6047:7004 |
| 6028:7076 | 6028:7077 | 6048:7000 | 6048:7001 | 6048:7002 | 6048:7003 | 6048:7004 |
| 6029:7076 | 6029:7077 | 6049:7000 | 6049:7001 | 6049:7002 | 6049:7003 | 6049:7004 |
| 6030:7076 | 6030:7077 | 6050:7000 | 6050:7001 | 6050:7002 | 6050:7003 | 6050:7004 |
| 6031:7076 | 6031:7077 | 6051:7000 | 6051:7001 | 6051:7002 | 6051:7003 | 6051:7004 |
| 6032:7076 | 6032:7077 | 6052:7000 | 6052:7001 | 6052:7002 | 6052:7003 | 6052:7004 |
| 6033:7076 | 6033:7077 | 6053:7000 | 6053:7001 | 6053:7002 | 6053:7003 | 6053:7004 |
| 6034:7076 | 6034:7077 | 6054:7000 | 6054:7001 | 6054:7002 | 6054:7003 | 6054:7004 |
| 6035:7076 | 6035:7077 | 6055:7000 | 6055:7001 | 6055:7002 | 6055:7003 | 6055:7004 |
| 6036:7076 | 6036:7077 | 6056:7000 | 6056:7001 | 6056:7002 | 6056:7003 | 6056:7004 |
| 6037:7076 | 6037:7077 | 6057:7000 | 6057:7001 | 6057:7002 | 6057:7003 | 6057:7004 |
| 6038:7076 | 6038:7077 | 6058:7000 | 6058:7001 | 6058:7002 | 6058:7003 | 6058:7004 |
| 6039:7076 | 6039:7077 | 6059:7000 | 6059:7001 | 6059:7002 | 6059:7003 | 6059:7004 |
| 6040:7076 | 6040:7077 | 6060:7000 | 6060:7001 | 6060:7002 | 6060:7003 | 6060:7004 |
| 6041:7005 | 6041:7006 | 6041:7007 | 6041:7008 | 6041:7009 | 6041:7010 | 6041:7011 |
| 6042:7005 | 6042:7006 | 6042:7007 | 6042:7008 | 6042:7009 | 6042:7010 | 6042:7011 |
| 6043:7005 | 6043:7006 | 6043:7007 | 6043:7008 | 6043:7009 | 6043:7010 | 6043:7011 |
| 6044:7005 | 6044:7006 | 6044:7007 | 6044:7008 | 6044:7009 | 6044:7010 | 6044:7011 |
| 6045:7005 | 6045:7006 | 6045:7007 | 6045:7008 | 6045:7009 | 6045:7010 | 6045:7011 |
| 6046:7005 | 6046:7006 | 6046:7007 | 6046:7008 | 6046:7009 | 6046:7010 | 6046:7011 |
| 6047:7005 | 6047:7006 | 6047:7007 | 6047:7008 | 6047:7009 | 6047:7010 | 6047:7011 |

TABLE B-continued

Example combinations of a compound X with a compound Y.

| X:Y | X:Y | X:Y | X:Y | X:Y | X:Y | X:Y |
|---|---|---|---|---|---|---|
| 6048:7005 | 6048:7006 | 6048:7007 | 6048:7008 | 6048:7009 | 6048:7010 | 6048:7011 |
| 6049:7005 | 6049:7006 | 6049:7007 | 6049:7008 | 6049:7009 | 6049:7010 | 6049:7011 |
| 6050:7005 | 6050:7006 | 6050:7007 | 6050:7008 | 6050:7009 | 6050:7010 | 6050:7011 |
| 6051:7005 | 6051:7006 | 6051:7007 | 6051:7008 | 6051:7009 | 6051:7010 | 6051:7011 |
| 6052:7005 | 6052:7006 | 6052:7007 | 6052:7008 | 6052:7009 | 6052:7010 | 6052:7011 |
| 6053:7005 | 6053:7006 | 6053:7007 | 6053:7008 | 6053:7009 | 6053:7010 | 6053:7011 |
| 6054:7005 | 6054:7006 | 6054:7007 | 6054:7008 | 6054:7009 | 6054:7010 | 6054:7011 |
| 6055:7005 | 6055:7006 | 6055:7007 | 6055:7008 | 6055:7009 | 6055:7010 | 6055:7011 |
| 6056:7005 | 6056:7006 | 6056:7007 | 6056:7008 | 6056:7009 | 6056:7010 | 6056:7011 |
| 6057:7005 | 6057:7006 | 6057:7007 | 6057:7008 | 6057:7009 | 6057:7010 | 6057:7011 |
| 6058:7005 | 6058:7006 | 6058:7007 | 6058:7008 | 6058:7009 | 6058:7010 | 6058:7011 |
| 6059:7005 | 6059:7006 | 6059:7007 | 6059:7008 | 6059:7009 | 6059:7010 | 6059:7011 |
| 6060:7005 | 6060:7006 | 6060:7007 | 6060:7008 | 6060:7009 | 6060:7010 | 6060:7011 |
| 6041:7012 | 6041:7013 | 6041:7014 | 6041:7015 | 6041:7016 | 6041:7017 | 6041:7018 |
| 6042:7012 | 6042:7013 | 6042:7014 | 6042:7015 | 6042:7016 | 6042:7017 | 6042:7018 |
| 6043:7012 | 6043:7013 | 6043:7014 | 6043:7015 | 6043:7016 | 6043:7017 | 6043:7018 |
| 6044:7012 | 6044:7013 | 6044:7014 | 6044:7015 | 6044:7016 | 6044:7017 | 6044:7018 |
| 6045:7012 | 6045:7013 | 6045:7014 | 6045:7015 | 6045:7016 | 6045:7017 | 6045:7018 |
| 6046:7012 | 6046:7013 | 6046:7014 | 6046:7015 | 6046:7016 | 6046:7017 | 6046:7018 |
| 6047:7012 | 6047:7013 | 6047:7014 | 6047:7015 | 6047:7016 | 6047:7017 | 6047:7018 |
| 6048:7012 | 6048:7013 | 6048:7014 | 6048:7015 | 6048:7016 | 6048:7017 | 6048:7018 |
| 6049:7012 | 6049:7013 | 6049:7014 | 6049:7015 | 6049:7016 | 6049:7017 | 6049:7018 |
| 6050:7012 | 6050:7013 | 6050:7014 | 6050:7015 | 6050:7016 | 6050:7017 | 6050:7018 |
| 6051:7012 | 6051:7013 | 6051:7014 | 6051:7015 | 6051:7016 | 6051:7017 | 6051:7018 |
| 6052:7012 | 6052:7013 | 6052:7014 | 6052:7015 | 6052:7016 | 6052:7017 | 6052:7018 |
| 6053:7012 | 6053:7013 | 6053:7014 | 6053:7015 | 6053:7016 | 6053:7017 | 6053:7018 |
| 6054:7012 | 6054:7013 | 6054:7014 | 6054:7015 | 6054:7016 | 6054:7017 | 6054:7018 |
| 6055:7012 | 6055:7013 | 6055:7014 | 6055:7015 | 6055:7016 | 6055:7017 | 6055:7018 |
| 6056:7012 | 6056:7013 | 6056:7014 | 6056:7015 | 6056:7016 | 6056:7017 | 6056:7018 |
| 6057:7012 | 6057:7013 | 6057:7014 | 6057:7015 | 6057:7016 | 6057:7017 | 6057:7018 |
| 6058:7012 | 6058:7013 | 6058:7014 | 6058:7015 | 6058:7016 | 6058:7017 | 6058:7018 |
| 6059:7012 | 6059:7013 | 6059:7014 | 6059:7015 | 6059:7016 | 6059:7017 | 6059:7018 |
| 6060:7012 | 6060:7013 | 6060:7014 | 6060:7015 | 6060:7016 | 6060:7017 | 6060:7018 |
| 6041:7019 | 6041:7020 | 6041:7021 | 6041:7022 | 6041:7023 | 6041:7024 | 6041:7025 |
| 6042:7019 | 6042:7020 | 6042:7021 | 6042:7022 | 6042:7023 | 6042:7024 | 6042:7025 |
| 6043:7019 | 6043:7020 | 6043:7021 | 6043:7022 | 6043:7023 | 6043:7024 | 6043:7025 |
| 6044:7019 | 6044:7020 | 6044:7021 | 6044:7022 | 6044:7023 | 6044:7024 | 6044:7025 |
| 6045:7019 | 6045:7020 | 6045:7021 | 6045:7022 | 6045:7023 | 6045:7024 | 6045:7025 |
| 6046:7019 | 6046:7020 | 6046:7021 | 6046:7022 | 6046:7023 | 6046:7024 | 6046:7025 |
| 6047:7019 | 6047:7020 | 6047:7021 | 6047:7022 | 6047:7023 | 6047:7024 | 6047:7025 |
| 6048:7019 | 6048:7020 | 6048:7021 | 6048:7022 | 6048:7023 | 6048:7024 | 6048:7025 |
| 6049:7019 | 6049:7020 | 6049:7021 | 6049:7022 | 6049:7023 | 6049:7024 | 6049:7025 |
| 6050:7019 | 6050:7020 | 6050:7021 | 6050:7022 | 6050:7023 | 6050:7024 | 6050:7025 |
| 6051:7019 | 6051:7020 | 6051:7021 | 6051:7022 | 6051:7023 | 6051:7024 | 6051:7025 |
| 6052:7019 | 6052:7020 | 6052:7021 | 6052:7022 | 6052:7023 | 6052:7024 | 6052:7025 |
| 6053:7019 | 6053:7020 | 6053:7021 | 6053:7022 | 6053:7023 | 6053:7024 | 6053:7025 |
| 6054:7019 | 6054:7020 | 6054:7021 | 6054:7022 | 6054:7023 | 6054:7024 | 6054:7025 |
| 6055:7019 | 6055:7020 | 6055:7021 | 6055:7022 | 6055:7023 | 6055:7024 | 6055:7025 |
| 6056:7019 | 6056:7020 | 6056:7021 | 6056:7022 | 6056:7023 | 6056:7024 | 6056:7025 |
| 6057:7019 | 6057:7020 | 6057:7021 | 6057:7022 | 6057:7023 | 6057:7024 | 6057:7025 |
| 6058:7019 | 6058:7020 | 6058:7021 | 6058:7022 | 6058:7023 | 6058:7024 | 6058:7025 |
| 6059:7019 | 6059:7020 | 6059:7021 | 6059:7022 | 6059:7023 | 6059:7024 | 6059:7025 |
| 6060:7019 | 6060:7020 | 6060:7021 | 6060:7022 | 6060:7023 | 6060:7024 | 6060:7025 |
| 6041:7026 | 6041:7027 | 6041:7028 | 6041:7029 | 6041:7030 | 6041:7031 | 6041:7032 |
| 6042:7026 | 6042:7027 | 6042:7028 | 6042:7029 | 6042:7030 | 6042:7031 | 6042:7032 |
| 6043:7026 | 6043:7027 | 6043:7028 | 6043:7029 | 6043:7030 | 6043:7031 | 6043:7032 |
| 6044:7026 | 6044:7027 | 6044:7028 | 6044:7029 | 6044:7030 | 6044:7031 | 6044:7032 |
| 6045:7026 | 6045:7027 | 6045:7028 | 6045:7029 | 6045:7030 | 6045:7031 | 6045:7032 |
| 6046:7026 | 6046:7027 | 6046:7028 | 6046:7029 | 6046:7030 | 6046:7031 | 6046:7032 |
| 6047:7026 | 6047:7027 | 6047:7028 | 6047:7029 | 6047:7030 | 6047:7031 | 6047:7032 |
| 6048:7026 | 6048:7027 | 6048:7028 | 6048:7029 | 6048:7030 | 6048:7031 | 6048:7032 |
| 6049:7026 | 6049:7027 | 6049:7028 | 6049:7029 | 6049:7030 | 6049:7031 | 6049:7032 |
| 6050:7026 | 6050:7027 | 6050:7028 | 6050:7029 | 6050:7030 | 6050:7031 | 6050:7032 |
| 6051:7026 | 6051:7027 | 6051:7028 | 6051:7029 | 6051:7030 | 6051:7031 | 6051:7032 |
| 6052:7026 | 6052:7027 | 6052:7028 | 6052:7029 | 6052:7030 | 6052:7031 | 6052:7032 |
| 6053:7026 | 6053:7027 | 6053:7028 | 6053:7029 | 6053:7030 | 6053:7031 | 6053:7032 |
| 6054:7026 | 6054:7027 | 6054:7028 | 6054:7029 | 6054:7030 | 6054:7031 | 6054:7032 |
| 6055:7026 | 6055:7027 | 6055:7028 | 6055:7029 | 6055:7030 | 6055:7031 | 6055:7032 |
| 6056:7026 | 6056:7027 | 6056:7028 | 6056:7029 | 6056:7030 | 6056:7031 | 6056:7032 |
| 6057:7026 | 6057:7027 | 6057:7028 | 6057:7029 | 6057:7030 | 6057:7031 | 6057:7032 |
| 6058:7026 | 6058:7027 | 6058:7028 | 6058:7029 | 6058:7030 | 6058:7031 | 6058:7032 |

TABLE B-continued

Example combinations of a compound X with a compound Y.

| X:Y | X:Y | X:Y | X:Y | X:Y | X:Y | X:Y |
|---|---|---|---|---|---|---|
| 6059:7026 | 6059:7027 | 6059:7028 | 6059:7029 | 6059:7030 | 6059:7031 | 6059:7032 |
| 6060:7026 | 6060:7027 | 6060:7028 | 6060:7029 | 6060:7030 | 6060:7031 | 6060:7032 |
| 6041:7033 | 6041:7034 | 6041:7035 | 6041:7036 | 6041:7037 | 6041:7038 | 6041:7039 |
| 6042:7033 | 6042:7034 | 6042:7035 | 6042:7036 | 6042:7037 | 6042:7038 | 6042:7039 |
| 6043:7033 | 6043:7034 | 6043:7035 | 6043:7036 | 6043:7037 | 6043:7038 | 6043:7039 |
| 6044:7033 | 6044:7034 | 6044:7035 | 6044:7036 | 6044:7037 | 6044:7038 | 6044:7039 |
| 6045:7033 | 6045:7034 | 6045:7035 | 6045:7036 | 6045:7037 | 6045:7038 | 6045:7039 |
| 6046:7033 | 6046:7034 | 6046:7035 | 6046:7036 | 6046:7037 | 6046:7038 | 6046:7039 |
| 6047:7033 | 6047:7034 | 6047:7035 | 6047:7036 | 6047:7037 | 6047:7038 | 6047:7039 |
| 6048:7033 | 6048:7034 | 6048:7035 | 6048:7036 | 6048:7037 | 6048:7038 | 6048:7039 |
| 6049:7033 | 6049:7034 | 6049:7035 | 6049:7036 | 6049:7037 | 6049:7038 | 6049:7039 |
| 6050:7033 | 6050:7034 | 6050:7035 | 6050:7036 | 6050:7037 | 6050:7038 | 6050:7039 |
| 6051:7033 | 6051:7034 | 6051:7035 | 6051:7036 | 6051:7037 | 6051:7038 | 6051:7039 |
| 6052:7033 | 6052:7034 | 6052:7035 | 6052:7036 | 6052:7037 | 6052:7038 | 6052:7039 |
| 6053:7033 | 6053:7034 | 6053:7035 | 6053:7036 | 6053:7037 | 6053:7038 | 6053:7039 |
| 6054:7033 | 6054:7034 | 6054:7035 | 6054:7036 | 6054:7037 | 6054:7038 | 6054:7039 |
| 6055:7033 | 6055:7034 | 6055:7035 | 6055:7036 | 6055:7037 | 6055:7038 | 6055:7039 |
| 6056:7033 | 6056:7034 | 6056:7035 | 6056:7036 | 6056:7037 | 6056:7038 | 6056:7039 |
| 6057:7033 | 6057:7034 | 6057:7035 | 6057:7036 | 6057:7037 | 6057:7038 | 6057:7039 |
| 6058:7033 | 6058:7034 | 6058:7035 | 6058:7036 | 6058:7037 | 6058:7038 | 6058:7039 |
| 6059:7033 | 6059:7034 | 6059:7035 | 6059:7036 | 6059:7037 | 6059:7038 | 6059:7039 |
| 6060:7033 | 6060:7034 | 6060:7035 | 6060:7036 | 6060:7037 | 6060:7038 | 6060:7039 |
| 6041:7040 | 6041:7041 | 6041:7042 | 6041:7043 | 6041:7044 | 6041:7045 | 6041:7046 |
| 6042:7040 | 6042:7041 | 6042:7042 | 6042:7043 | 6042:7044 | 6042:7045 | 6042:7046 |
| 6043:7040 | 6043:7041 | 6043:7042 | 6043:7043 | 6043:7044 | 6043:7045 | 6043:7046 |
| 6044:7040 | 6044:7041 | 6044:7042 | 6044:7043 | 6044:7044 | 6044:7045 | 6044:7046 |
| 6045:7040 | 6045:7041 | 6045:7042 | 6045:7043 | 6045:7044 | 6045:7045 | 6045:7046 |
| 6046:7040 | 6046:7041 | 6046:7042 | 6046:7043 | 6046:7044 | 6046:7045 | 6046:7046 |
| 6047:7040 | 6047:7041 | 6047:7042 | 6047:7043 | 6047:7044 | 6047:7045 | 6047:7046 |
| 6048:7040 | 6048:7041 | 6048:7042 | 6048:7043 | 6048:7044 | 6048:7045 | 6048:7046 |
| 6049:7040 | 6049:7041 | 6049:7042 | 6049:7043 | 6049:7044 | 6049:7045 | 6049:7046 |
| 6050:7040 | 6050:7041 | 6050:7042 | 6050:7043 | 6050:7044 | 6050:7045 | 6050:7046 |
| 6051:7040 | 6051:7041 | 6051:7042 | 6051:7043 | 6051:7044 | 6051:7045 | 6051:7046 |
| 6052:7040 | 6052:7041 | 6052:7042 | 6052:7043 | 6052:7044 | 6052:7045 | 6052:7046 |
| 6053:7040 | 6053:7041 | 6053:7042 | 6053:7043 | 6053:7044 | 6053:7045 | 6053:7046 |
| 6054:7040 | 6054:7041 | 6054:7042 | 6054:7043 | 6054:7044 | 6054:7045 | 6054:7046 |
| 6055:7040 | 6055:7041 | 6055:7042 | 6055:7043 | 6055:7044 | 6055:7045 | 6055:7046 |
| 6056:7040 | 6056:7041 | 6056:7042 | 6056:7043 | 6056:7044 | 6056:7045 | 6056:7046 |
| 6057:7040 | 6057:7041 | 6057:7042 | 6057:7043 | 6057:7044 | 6057:7045 | 6057:7046 |
| 6058:7040 | 6058:7041 | 6058:7042 | 6058:7043 | 6058:7044 | 6058:7045 | 6058:7046 |
| 6059:7040 | 6059:7041 | 6059:7042 | 6059:7043 | 6059:7044 | 6059:7045 | 6059:7046 |
| 6060:7040 | 6060:7041 | 6060:7042 | 6060:7043 | 6060:7044 | 6060:7045 | 6060:7046 |
| 6041:7047 | 6041:7048 | 6041:7049 | 6041:7050 | 6041:7051 | 6041:7052 | 6041:7053 |
| 6042:7047 | 6042:7048 | 6042:7049 | 6042:7050 | 6042:7051 | 6042:7052 | 6042:7053 |
| 6043:7047 | 6043:7048 | 6043:7049 | 6043:7050 | 6043:7051 | 6043:7052 | 6043:7053 |
| 6044:7047 | 6044:7048 | 6044:7049 | 6044:7050 | 6044:7051 | 6044:7052 | 6044:7053 |
| 6045:7047 | 6045:7048 | 6045:7049 | 6045:7050 | 6045:7051 | 6045:7052 | 6045:7053 |
| 6046:7047 | 6046:7048 | 6046:7049 | 6046:7050 | 6046:7051 | 6046:7052 | 6046:7053 |
| 6047:7047 | 6047:7048 | 6047:7049 | 6047:7050 | 6047:7051 | 6047:7052 | 6047:7053 |
| 6048:7047 | 6048:7048 | 6048:7049 | 6048:7050 | 6048:7051 | 6048:7052 | 6048:7053 |
| 6049:7047 | 6049:7048 | 6049:7049 | 6049:7050 | 6049:7051 | 6049:7052 | 6049:7053 |
| 6050:7047 | 6050:7048 | 6050:7049 | 6050:7050 | 6050:7051 | 6050:7052 | 6050:7053 |
| 6051:7047 | 6051:7048 | 6051:7049 | 6051:7050 | 6051:7051 | 6051:7052 | 6051:7053 |
| 6052:7047 | 6052:7048 | 6052:7049 | 6052:7050 | 6052:7051 | 6052:7052 | 6052:7053 |
| 6053:7047 | 6053:7048 | 6053:7049 | 6053:7050 | 6053:7051 | 6053:7052 | 6053:7053 |
| 6054:7047 | 6054:7048 | 6054:7049 | 6054:7050 | 6054:7051 | 6054:7052 | 6054:7053 |
| 6055:7047 | 6055:7048 | 6055:7049 | 6055:7050 | 6055:7051 | 6055:7052 | 6055:7053 |
| 6056:7047 | 6056:7048 | 6056:7049 | 6056:7050 | 6056:7051 | 6056:7052 | 6056:7053 |
| 6057:7047 | 6057:7048 | 6057:7049 | 6057:7050 | 6057:7051 | 6057:7052 | 6057:7053 |
| 6058:7047 | 6058:7048 | 6058:7049 | 6058:7050 | 6058:7051 | 6058:7052 | 6058:7053 |
| 6059:7047 | 6059:7048 | 6059:7049 | 6059:7050 | 6059:7051 | 6059:7052 | 6059:7053 |
| 6060:7047 | 6060:7048 | 6060:7049 | 6060:7050 | 6060:7051 | 6060:7052 | 6060:7053 |
| 6041:7054 | 6041:7055 | 6041:7056 | 6041:7057 | 6041:7058 | 6041:7059 | 6041:7060 |
| 6042:7054 | 6042:7055 | 6042:7056 | 6042:7057 | 6042:7058 | 6042:7059 | 6042:7060 |
| 6043:7054 | 6043:7055 | 6043:7056 | 6043:7057 | 6043:7058 | 6043:7059 | 6043:7060 |
| 6044:7054 | 6044:7055 | 6044:7056 | 6044:7057 | 6044:7058 | 6044:7059 | 6044:7060 |
| 6045:7054 | 6045:7055 | 6045:7056 | 6045:7057 | 6045:7058 | 6045:7059 | 6045:7060 |
| 6046:7054 | 6046:7055 | 6046:7056 | 6046:7057 | 6046:7058 | 6046:7059 | 6046:7060 |
| 6047:7054 | 6047:7055 | 6047:7056 | 6047:7057 | 6047:7058 | 6047:7059 | 6047:7060 |
| 6048:7054 | 6048:7055 | 6048:7056 | 6048:7057 | 6048:7058 | 6048:7059 | 6048:7060 |
| 6049:7054 | 6049:7055 | 6049:7056 | 6049:7057 | 6049:7058 | 6049:7059 | 6049:7060 |
| 6050:7054 | 6050:7055 | 6050:7056 | 6050:7057 | 6050:7058 | 6050:7059 | 6050:7060 |

TABLE B-continued

Example combinations of a compound X with a compound Y.

| X:Y | X:Y | X:Y | X:Y | X:Y | X:Y | X:Y |
|---|---|---|---|---|---|---|
| 6051:7054 | 6051:7055 | 6051:7056 | 6051:7057 | 6051:7058 | 6051:7059 | 6051:7060 |
| 6052:7054 | 6052:7055 | 6052:7056 | 6052:7057 | 6052:7058 | 6052:7059 | 6052:7060 |
| 6053:7054 | 6053:7055 | 6053:7056 | 6053:7057 | 6053:7058 | 6053:7059 | 6053:7060 |
| 6054:7054 | 6054:7055 | 6054:7056 | 6054:7057 | 6054:7058 | 6054:7059 | 6054:7060 |
| 6055:7054 | 6055:7055 | 6055:7056 | 6055:7057 | 6055:7058 | 6055:7059 | 6055:7060 |
| 6056:7054 | 6056:7055 | 6056:7056 | 6056:7057 | 6056:7058 | 6056:7059 | 6056:7060 |
| 6057:7054 | 6057:7055 | 6057:7056 | 6057:7057 | 6057:7058 | 6057:7059 | 6057:7060 |
| 6058:7054 | 6058:7055 | 6058:7056 | 6058:7057 | 6058:7058 | 6058:7059 | 6058:7060 |
| 6059:7054 | 6059:7055 | 6059:7056 | 6059:7057 | 6059:7058 | 6059:7059 | 6059:7060 |
| 6060:7054 | 6060:7055 | 6060:7056 | 6060:7057 | 6060:7058 | 6060:7059 | 6060:7060 |
| 6041:7061 | 6041:7062 | 6041:7063 | 6041:7064 | 6041:7065 | 6041:7066 | 6041:7067 |
| 6042:7061 | 6042:7062 | 6042:7063 | 6042:7064 | 6042:7065 | 6042:7066 | 6042:7067 |
| 6043:7061 | 6043:7062 | 6043:7063 | 6043:7064 | 6043:7065 | 6043:7066 | 6043:7067 |
| 6044:7061 | 6044:7062 | 6044:7063 | 6044:7064 | 6044:7065 | 6044:7066 | 6044:7067 |
| 6045:7061 | 6045:7062 | 6045:7063 | 6045:7064 | 6045:7065 | 6045:7066 | 6045:7067 |
| 6046:7061 | 6046:7062 | 6046:7063 | 6046:7064 | 6046:7065 | 6046:7066 | 6046:7067 |
| 6047:7061 | 6047:7062 | 6047:7063 | 6047:7064 | 6047:7065 | 6047:7066 | 6047:7067 |
| 6048:7061 | 6048:7062 | 6048:7063 | 6048:7064 | 6048:7065 | 6048:7066 | 6048:7067 |
| 6049:7061 | 6049:7062 | 6049:7063 | 6049:7064 | 6049:7065 | 6049:7066 | 6049:7067 |
| 6050:7061 | 6050:7062 | 6050:7063 | 6050:7064 | 6050:7065 | 6050:7066 | 6050:7067 |
| 6051:7061 | 6051:7062 | 6051:7063 | 6051:7064 | 6051:7065 | 6051:7066 | 6051:7067 |
| 6052:7061 | 6052:7062 | 6052:7063 | 6052:7064 | 6052:7065 | 6052:7066 | 6052:7067 |
| 6053:7061 | 6053:7062 | 6053:7063 | 6053:7064 | 6053:7065 | 6053:7066 | 6053:7067 |
| 6054:7061 | 6054:7062 | 6054:7063 | 6054:7064 | 6054:7065 | 6054:7066 | 6054:7067 |
| 6055:7061 | 6055:7062 | 6055:7063 | 6055:7064 | 6055:7065 | 6055:7066 | 6055:7067 |
| 6056:7061 | 6056:7062 | 6056:7063 | 6056:7064 | 6056:7065 | 6056:7066 | 6056:7067 |
| 6057:7061 | 6057:7062 | 6057:7063 | 6057:7064 | 6057:7065 | 6057:7066 | 6057:7067 |
| 6058:7061 | 6058:7062 | 6058:7063 | 6058:7064 | 6058:7065 | 6058:7066 | 6058:7067 |
| 6059:7061 | 6059:7062 | 6059:7063 | 6059:7064 | 6059:7065 | 6059:7066 | 6059:7067 |
| 6060:7061 | 6060:7062 | 6060:7063 | 6060:7064 | 6060:7065 | 6060:7066 | 6060:7067 |
| 6041:7068 | 6041:7069 | 6041:7070 | 6041:7071 | 6041:7072 | 6041:7073 | 6041:7074 |
| 6042:7068 | 6042:7069 | 6042:7070 | 6042:7071 | 6042:7072 | 6042:7073 | 6042:7074 |
| 6043:7068 | 6043:7069 | 6043:7070 | 6043:7071 | 6043:7072 | 6043:7073 | 6043:7074 |
| 6044:7068 | 6044:7069 | 6044:7070 | 6044:7071 | 6044:7072 | 6044:7073 | 6044:7074 |
| 6045:7068 | 6045:7069 | 6045:7070 | 6045:7071 | 6045:7072 | 6045:7073 | 6045:7074 |
| 6046:7068 | 6046:7069 | 6046:7070 | 6046:7071 | 6046:7072 | 6046:7073 | 6046:7074 |
| 6047:7068 | 6047:7069 | 6047:7070 | 6047:7071 | 6047:7072 | 6047:7073 | 6047:7074 |
| 6048:7068 | 6048:7069 | 6048:7070 | 6048:7071 | 6048:7072 | 6048:7073 | 6048:7074 |
| 6049:7068 | 6049:7069 | 6049:7070 | 6049:7071 | 6049:7072 | 6049:7073 | 6049:7074 |
| 6050:7068 | 6050:7069 | 6050:7070 | 6050:7071 | 6050:7072 | 6050:7073 | 6050:7074 |
| 6051:7068 | 6051:7069 | 6051:7070 | 6051:7071 | 6051:7072 | 6051:7073 | 6051:7074 |
| 6052:7068 | 6052:7069 | 6052:7070 | 6052:7071 | 6052:7072 | 6052:7073 | 6052:7074 |
| 6053:7068 | 6053:7069 | 6053:7070 | 6053:7071 | 6053:7072 | 6053:7073 | 6053:7074 |
| 6054:7068 | 6054:7069 | 6054:7070 | 6054:7071 | 6054:7072 | 6054:7073 | 6054:7074 |
| 6055:7068 | 6055:7069 | 6055:7070 | 6055:7071 | 6055:7072 | 6055:7073 | 6055:7074 |
| 6056:7068 | 6056:7069 | 6056:7070 | 6056:7071 | 6056:7072 | 6056:7073 | 6056:7074 |
| 6057:7068 | 6057:7069 | 6057:7070 | 6057:7071 | 6057:7072 | 6057:7073 | 6057:7074 |
| 6058:7068 | 6058:7069 | 6058:7070 | 6058:7071 | 6058:7072 | 6058:7073 | 6058:7074 |
| 6059:7068 | 6059:7069 | 6059:7070 | 6059:7071 | 6059:7072 | 6059:7073 | 6059:7074 |
| 6060:7068 | 6060:7069 | 6060:7070 | 6060:7071 | 6060:7072 | 6060:7073 | 6060:7074 |
| 6041:7075 | 6041:7076 | 6041:7077 | 6061:7000 | 6061:7001 | 6061:7002 | 6061:7003 |
| 6042:7075 | 6042:7076 | 6042:7077 | 6062:7000 | 6062:7001 | 6062:7002 | 6062:7003 |
| 6043:7075 | 6043:7076 | 6043:7077 | 6063:7000 | 6063:7001 | 6063:7002 | 6063:7003 |
| 6044:7075 | 6044:7076 | 6044:7077 | 6064:7000 | 6064:7001 | 6064:7002 | 6064:7003 |
| 6045:7075 | 6045:7076 | 6045:7077 | 6065:7000 | 6065:7001 | 6065:7002 | 6065:7003 |
| 6046:7075 | 6046:7076 | 6046:7077 | 6066:7000 | 6066:7001 | 6066:7002 | 6066:7003 |
| 6047:7075 | 6047:7076 | 6047:7077 | 6067:7000 | 6067:7001 | 6067:7002 | 6067:7003 |
| 6048:7075 | 6048:7076 | 6048:7077 | 6068:7000 | 6068:7001 | 6068:7002 | 6068:7003 |
| 6049:7075 | 6049:7076 | 6049:7077 | 6069:7000 | 6069:7001 | 6069:7002 | 6069:7003 |
| 6050:7075 | 6050:7076 | 6050:7077 | 6070:7000 | 6070:7001 | 6070:7002 | 6070:7003 |
| 6051:7075 | 6051:7076 | 6051:7077 | 6071:7000 | 6071:7001 | 6071:7002 | 6071:7003 |
| 6052:7075 | 6052:7076 | 6052:7077 | 6072:7000 | 6072:7001 | 6072:7002 | 6072:7003 |
| 6053:7075 | 6053:7076 | 6053:7077 | 6073:7000 | 6073:7001 | 6073:7002 | 6073:7003 |
| 6054:7075 | 6054:7076 | 6054:7077 | 6074:7000 | 6074:7001 | 6074:7002 | 6074:7003 |
| 6055:7075 | 6055:7076 | 6055:7077 | 6075:7000 | 6075:7001 | 6075:7002 | 6075:7003 |
| 6056:7075 | 6056:7076 | 6056:7077 | 6076:7000 | 6076:7001 | 6076:7002 | 6076:7003 |
| 6057:7075 | 6057:7076 | 6057:7077 | 6077:7000 | 6077:7001 | 6077:7002 | 6077:7003 |
| 6058:7075 | 6058:7076 | 6058:7077 | 6078:7000 | 6078:7001 | 6078:7002 | 6078:7003 |
| 6059:7075 | 6059:7076 | 6059:7077 | | | | |
| 6060:7075 | 6060:7076 | 6060:7077 | | | | |
| 6061:7004 | 6061:7005 | 6061:7006 | 6061:7007 | 6061:7008 | 6061:7009 | 6061:7010 |
| 6062:7004 | 6062:7005 | 6062:7006 | 6062:7007 | 6062:7008 | 6062:7009 | 6062:7010 |

TABLE B-continued

Example combinations of a compound X with a compound Y.

| X:Y | X:Y | X:Y | X:Y | X:Y | X:Y | X:Y |
|---|---|---|---|---|---|---|
| 6063:7004 | 6063:7005 | 6063:7006 | 6063:7007 | 6063:7008 | 6063:7009 | 6063:7010 |
| 6064:7004 | 6064:7005 | 6064:7006 | 6064:7007 | 6064:7008 | 6064:7009 | 6064:7010 |
| 6065:7004 | 6065:7005 | 6065:7006 | 6065:7007 | 6065:7008 | 6065:7009 | 6065:7010 |
| 6066:7004 | 6066:7005 | 6066:7006 | 6066:7007 | 6066:7008 | 6066:7009 | 6066:7010 |
| 6067:7004 | 6067:7005 | 6067:7006 | 6067:7007 | 6067:7008 | 6067:7009 | 6067:7010 |
| 6068:7004 | 6068:7005 | 6068:7006 | 6068:7007 | 6068:7008 | 6068:7009 | 6068:7010 |
| 6069:7004 | 6069:7005 | 6069:7006 | 6069:7007 | 6069:7008 | 6069:7009 | 6069:7010 |
| 6070:7004 | 6070:7005 | 6070:7006 | 6070:7007 | 6070:7008 | 6070:7009 | 6070:7010 |
| 6071:7004 | 6071:7005 | 6071:7006 | 6071:7007 | 6071:7008 | 6071:7009 | 6071:7010 |
| 6072:7004 | 6072:7005 | 6072:7006 | 6072:7007 | 6072:7008 | 6072:7009 | 6072:7010 |
| 6073:7004 | 6073:7005 | 6073:7006 | 6073:7007 | 6073:7008 | 6073:7009 | 6073:7010 |
| 6074:7004 | 6074:7005 | 6074:7006 | 6074:7007 | 6074:7008 | 6074:7009 | 6074:7010 |
| 6075:7004 | 6075:7005 | 6075:7006 | 6075:7007 | 6075:7008 | 6075:7009 | 6075:7010 |
| 6076:7004 | 6076:7005 | 6076:7006 | 6076:7007 | 6076:7008 | 6076:7009 | 6076:7010 |
| 6077:7004 | 6077:7005 | 6077:7006 | 6077:7007 | 6077:7008 | 6077:7009 | 6077:7010 |
| 6078:7004 | 6078:7005 | 6078:7006 | 6078:7007 | 6078:7008 | 6078:7009 | 6078:7010 |
| 6061:7011 | 6061:7012 | 6061:7013 | 6061:7014 | 6061:7015 | 6061:7016 | 6061:7017 |
| 6062:7011 | 6062:7012 | 6062:7013 | 6062:7014 | 6062:7015 | 6062:7016 | 6062:7017 |
| 6063:7011 | 6063:7012 | 6063:7013 | 6063:7014 | 6063:7015 | 6063:7016 | 6063:7017 |
| 6064:7011 | 6064:7012 | 6064:7013 | 6064:7014 | 6064:7015 | 6064:7016 | 6064:7017 |
| 6065:7011 | 6065:7012 | 6065:7013 | 6065:7014 | 6065:7015 | 6065:7016 | 6065:7017 |
| 6066:7011 | 6066:7012 | 6066:7013 | 6066:7014 | 6066:7015 | 6066:7016 | 6066:7017 |
| 6067:7011 | 6067:7012 | 6067:7013 | 6067:7014 | 6067:7015 | 6067:7016 | 6067:7017 |
| 6068:7011 | 6068:7012 | 6068:7013 | 6068:7014 | 6068:7015 | 6068:7016 | 6068:7017 |
| 6069:7011 | 6069:7012 | 6069:7013 | 6069:7014 | 6069:7015 | 6069:7016 | 6069:7017 |
| 6070:7011 | 6070:7012 | 6070:7013 | 6070:7014 | 6070:7015 | 6070:7016 | 6070:7017 |
| 6071:7011 | 6071:7012 | 6071:7013 | 6071:7014 | 6071:7015 | 6071:7016 | 6071:7017 |
| 6072:7011 | 6072:7012 | 6072:7013 | 6072:7014 | 6072:7015 | 6072:7016 | 6072:7017 |
| 6073:7011 | 6073:7012 | 6073:7013 | 6073:7014 | 6073:7015 | 6073:7016 | 6073:7017 |
| 6074:7011 | 6074:7012 | 6074:7013 | 6074:7014 | 6074:7015 | 6074:7016 | 6074:7017 |
| 6075:7011 | 6075:7012 | 6075:7013 | 6075:7014 | 6075:7015 | 6075:7016 | 6075:7017 |
| 6076:7011 | 6076:7012 | 6076:7013 | 6076:7014 | 6076:7015 | 6076:7016 | 6076:7017 |
| 6077:7011 | 6077:7012 | 6077:7013 | 6077:7014 | 6077:7015 | 6077:7016 | 6077:7017 |
| 6078:7011 | 6078:7012 | 6078:7013 | 6078:7014 | 6078:7015 | 6078:7016 | 6078:7017 |
| 6061:7018 | 6061:7019 | 6061:7020 | 6061:7021 | 6061:7022 | 6061:7023 | 6061:7024 |
| 6062:7018 | 6062:7019 | 6062:7020 | 6062:7021 | 6062:7022 | 6062:7023 | 6062:7024 |
| 6063:7018 | 6063:7019 | 6063:7020 | 6063:7021 | 6063:7022 | 6063:7023 | 6063:7024 |
| 6064:7018 | 6064:7019 | 6064:7020 | 6064:7021 | 6064:7022 | 6064:7023 | 6064:7024 |
| 6065:7018 | 6065:7019 | 6065:7020 | 6065:7021 | 6065:7022 | 6065:7023 | 6065:7024 |
| 6066:7018 | 6066:7019 | 6066:7020 | 6066:7021 | 6066:7022 | 6066:7023 | 6066:7024 |
| 6067:7018 | 6067:7019 | 6067:7020 | 6067:7021 | 6067:7022 | 6067:7023 | 6067:7024 |
| 6068:7018 | 6068:7019 | 6068:7020 | 6068:7021 | 6068:7022 | 6068:7023 | 6068:7024 |
| 6069:7018 | 6069:7019 | 6069:7020 | 6069:7021 | 6069:7022 | 6069:7023 | 6069:7024 |
| 6070:7018 | 6070:7019 | 6070:7020 | 6070:7021 | 6070:7022 | 6070:7023 | 6070:7024 |
| 6071:7018 | 6071:7019 | 6071:7020 | 6071:7021 | 6071:7022 | 6071:7023 | 6071:7024 |
| 6072:7018 | 6072:7019 | 6072:7020 | 6072:7021 | 6072:7022 | 6072:7023 | 6072:7024 |
| 6073:7018 | 6073:7019 | 6073:7020 | 6073:7021 | 6073:7022 | 6073:7023 | 6073:7024 |
| 6074:7018 | 6074:7019 | 6074:7020 | 6074:7021 | 6074:7022 | 6074:7023 | 6074:7024 |
| 6075:7018 | 6075:7019 | 6075:7020 | 6075:7021 | 6075:7022 | 6075:7023 | 6075:7024 |
| 6076:7018 | 6076:7019 | 6076:7020 | 6076:7021 | 6076:7022 | 6076:7023 | 6076:7024 |
| 6077:7018 | 6077:7019 | 6077:7020 | 6077:7021 | 6077:7022 | 6077:7023 | 6077:7024 |
| 6078:7018 | 6078:7019 | 6078:7020 | 6078:7021 | 6078:7022 | 6078:7023 | 6078:7024 |
| 6061:7025 | 6061:7026 | 6061:7027 | 6061:7028 | 6061:7029 | 6061:7030 | 6061:7031 |
| 6062:7025 | 6062:7026 | 6062:7027 | 6062:7028 | 6062:7029 | 6062:7030 | 6062:7031 |
| 6063:7025 | 6063:7026 | 6063:7027 | 6063:7028 | 6063:7029 | 6063:7030 | 6063:7031 |
| 6064:7025 | 6064:7026 | 6064:7027 | 6064:7028 | 6064:7029 | 6064:7030 | 6064:7031 |
| 6065:7025 | 6065:7026 | 6065:7027 | 6065:7028 | 6065:7029 | 6065:7030 | 6065:7031 |
| 6066:7025 | 6066:7026 | 6066:7027 | 6066:7028 | 6066:7029 | 6066:7030 | 6066:7031 |
| 6067:7025 | 6067:7026 | 6067:7027 | 6067:7028 | 6067:7029 | 6067:7030 | 6067:7031 |
| 6068:7025 | 6068:7026 | 6068:7027 | 6068:7028 | 6068:7029 | 6068:7030 | 6068:7031 |
| 6069:7025 | 6069:7026 | 6069:7027 | 6069:7028 | 6069:7029 | 6069:7030 | 6069:7031 |
| 6070:7025 | 6070:7026 | 6070:7027 | 6070:7028 | 6070:7029 | 6070:7030 | 6070:7031 |
| 6071:7025 | 6071:7026 | 6071:7027 | 6071:7028 | 6071:7029 | 6071:7030 | 6071:7031 |
| 6072:7025 | 6072:7026 | 6072:7027 | 6072:7028 | 6072:7029 | 6072:7030 | 6072:7031 |
| 6073:7025 | 6073:7026 | 6073:7027 | 6073:7028 | 6073:7029 | 6073:7030 | 6073:7031 |
| 6074:7025 | 6074:7026 | 6074:7027 | 6074:7028 | 6074:7029 | 6074:7030 | 6074:7031 |
| 6075:7025 | 6075:7026 | 6075:7027 | 6075:7028 | 6075:7029 | 6075:7030 | 6075:7031 |
| 6076:7025 | 6076:7026 | 6076:7027 | 6076:7028 | 6076:7029 | 6076:7030 | 6076:7031 |
| 6077:7025 | 6077:7026 | 6077:7027 | 6077:7028 | 6077:7029 | 6077:7030 | 6077:7031 |
| 6078:7025 | 6078:7026 | 6078:7027 | 6078:7028 | 6078:7029 | 6078:7030 | 6078:7031 |
| 6061:7032 | 6061:7033 | 6061:7034 | 6061:7035 | 6061:7036 | 6061:7037 | 6061:7038 |
| 6062:7032 | 6062:7033 | 6062:7034 | 6062:7035 | 6062:7036 | 6062:7037 | 6062:7038 |

TABLE B-continued

Example combinations of a compound X with a compound Y.

| X:Y | X:Y | X:Y | X:Y | X:Y | X:Y | X:Y |
|---|---|---|---|---|---|---|
| 6063:7032 | 6063:7033 | 6063:7034 | 6063:7035 | 6063:7036 | 6063:7037 | 6063:7038 |
| 6064:7032 | 6064:7033 | 6064:7034 | 6064:7035 | 6064:7036 | 6064:7037 | 6064:7038 |
| 6065:7032 | 6065:7033 | 6065:7034 | 6065:7035 | 6065:7036 | 6065:7037 | 6065:7038 |
| 6066:7032 | 6066:7033 | 6066:7034 | 6066:7035 | 6066:7036 | 6066:7037 | 6066:7038 |
| 6067:7032 | 6067:7033 | 6067:7034 | 6067:7035 | 6067:7036 | 6067:7037 | 6067:7038 |
| 6068:7032 | 6068:7033 | 6068:7034 | 6068:7035 | 6068:7036 | 6068:7037 | 6068:7038 |
| 6069:7032 | 6069:7033 | 6069:7034 | 6069:7035 | 6069:7036 | 6069:7037 | 6069:7038 |
| 6070:7032 | 6070:7033 | 6070:7034 | 6070:7035 | 6070:7036 | 6070:7037 | 6070:7038 |
| 6071:7032 | 6071:7033 | 6071:7034 | 6071:7035 | 6071:7036 | 6071:7037 | 6071:7038 |
| 6072:7032 | 6072:7033 | 6072:7034 | 6072:7035 | 6072:7036 | 6072:7037 | 6072:7038 |
| 6073:7032 | 6073:7033 | 6073:7034 | 6073:7035 | 6073:7036 | 6073:7037 | 6073:7038 |
| 6074:7032 | 6074:7033 | 6074:7034 | 6074:7035 | 6074:7036 | 6074:7037 | 6074:7038 |
| 6075:7032 | 6075:7033 | 6075:7034 | 6075:7035 | 6075:7036 | 6075:7037 | 6075:7038 |
| 6076:7032 | 6076:7033 | 6076:7034 | 6076:7035 | 6076:7036 | 6076:7037 | 6076:7038 |
| 6077:7032 | 6077:7033 | 6077:7034 | 6077:7035 | 6077:7036 | 6077:7037 | 6077:7038 |
| 6078:7032 | 6078:7033 | 6078:7034 | 6078:7035 | 6078:7036 | 6078:7037 | 6078:7038 |
| 6061:7039 | 6061:7040 | 6061:7041 | 6061:7042 | 6061:7043 | 6061:7044 | 6061:7045 |
| 6062:7039 | 6062:7040 | 6062:7041 | 6062:7042 | 6062:7043 | 6062:7044 | 6062:7045 |
| 6063:7039 | 6063:7040 | 6063:7041 | 6063:7042 | 6063:7043 | 6063:7044 | 6063:7045 |
| 6064:7039 | 6064:7040 | 6064:7041 | 6064:7042 | 6064:7043 | 6064:7044 | 6064:7045 |
| 6065:7039 | 6065:7040 | 6065:7041 | 6065:7042 | 6065:7043 | 6065:7044 | 6065:7045 |
| 6066:7039 | 6066:7040 | 6066:7041 | 6066:7042 | 6066:7043 | 6066:7044 | 6066:7045 |
| 6067:7039 | 6067:7040 | 6067:7041 | 6067:7042 | 6067:7043 | 6067:7044 | 6067:7045 |
| 6068:7039 | 6068:7040 | 6068:7041 | 6068:7042 | 6068:7043 | 6068:7044 | 6068:7045 |
| 6069:7039 | 6069:7040 | 6069:7041 | 6069:7042 | 6069:7043 | 6069:7044 | 6069:7045 |
| 6070:7039 | 6070:7040 | 6070:7041 | 6070:7042 | 6070:7043 | 6070:7044 | 6070:7045 |
| 6071:7039 | 6071:7040 | 6071:7041 | 6071:7042 | 6071:7043 | 6071:7044 | 6071:7045 |
| 6072:7039 | 6072:7040 | 6072:7041 | 6072:7042 | 6072:7043 | 6072:7044 | 6072:7045 |
| 6073:7039 | 6073:7040 | 6073:7041 | 6073:7042 | 6073:7043 | 6073:7044 | 6073:7045 |
| 6074:7039 | 6074:7040 | 6074:7041 | 6074:7042 | 6074:7043 | 6074:7044 | 6074:7045 |
| 6075:7039 | 6075:7040 | 6075:7041 | 6075:7042 | 6075:7043 | 6075:7044 | 6075:7045 |
| 6076:7039 | 6076:7040 | 6076:7041 | 6076:7042 | 6076:7043 | 6076:7044 | 6076:7045 |
| 6077:7039 | 6077:7040 | 6077:7041 | 6077:7042 | 6077:7043 | 6077:7044 | 6077:7045 |
| 6078:7039 | 6078:7040 | 6078:7041 | 6078:7042 | 6078:7043 | 6078:7044 | 6078:7045 |
| 6061:7046 | 6061:7047 | 6061:7048 | 6061:7049 | 6061:7050 | 6061:7051 | 6061:7052 |
| 6062:7046 | 6062:7047 | 6062:7048 | 6062:7049 | 6062:7050 | 6062:7051 | 6062:7052 |
| 6063:7046 | 6063:7047 | 6063:7048 | 6063:7049 | 6063:7050 | 6063:7051 | 6063:7052 |
| 6064:7046 | 6064:7047 | 6064:7048 | 6064:7049 | 6064:7050 | 6064:7051 | 6064:7052 |
| 6065:7046 | 6065:7047 | 6065:7048 | 6065:7049 | 6065:7050 | 6065:7051 | 6065:7052 |
| 6066:7046 | 6066:7047 | 6066:7048 | 6066:7049 | 6066:7050 | 6066:7051 | 6066:7052 |
| 6067:7046 | 6067:7047 | 6067:7048 | 6067:7049 | 6067:7050 | 6067:7051 | 6067:7052 |
| 6068:7046 | 6068:7047 | 6068:7048 | 6068:7049 | 6068:7050 | 6068:7051 | 6068:7052 |
| 6069:7046 | 6069:7047 | 6069:7048 | 6069:7049 | 6069:7050 | 6069:7051 | 6069:7052 |
| 6070:7046 | 6070:7047 | 6070:7048 | 6070:7049 | 6070:7050 | 6070:7051 | 6070:7052 |
| 6071:7046 | 6071:7047 | 6071:7048 | 6071:7049 | 6071:7050 | 6071:7051 | 6071:7052 |
| 6072:7046 | 6072:7047 | 6072:7048 | 6072:7049 | 6072:7050 | 6072:7051 | 6072:7052 |
| 6073:7046 | 6073:7047 | 6073:7048 | 6073:7049 | 6073:7050 | 6073:7051 | 6073:7052 |
| 6074:7046 | 6074:7047 | 6074:7048 | 6074:7049 | 6074:7050 | 6074:7051 | 6074:7052 |
| 6075:7046 | 6075:7047 | 6075:7048 | 6075:7049 | 6075:7050 | 6075:7051 | 6075:7052 |
| 6076:7046 | 6076:7047 | 6076:7048 | 6076:7049 | 6076:7050 | 6076:7051 | 6076:7052 |
| 6077:7046 | 6077:7047 | 6077:7048 | 6077:7049 | 6077:7050 | 6077:7051 | 6077:7052 |
| 6078:7046 | 6078:7047 | 6078:7048 | 6078:7049 | 6078:7050 | 6078:7051 | 6078:7052 |
| 6061:7053 | 6061:7054 | 6061:7055 | 6061:7056 | 6061:7057 | 6061:7058 | 6061:7059 |
| 6062:7053 | 6062:7054 | 6062:7055 | 6062:7056 | 6062:7057 | 6062:7058 | 6062:7059 |
| 6063:7053 | 6063:7054 | 6063:7055 | 6063:7056 | 6063:7057 | 6063:7058 | 6063:7059 |
| 6064:7053 | 6064:7054 | 6064:7055 | 6064:7056 | 6064:7057 | 6064:7058 | 6064:7059 |
| 6065:7053 | 6065:7054 | 6065:7055 | 6065:7056 | 6065:7057 | 6065:7058 | 6065:7059 |
| 6066:7053 | 6066:7054 | 6066:7055 | 6066:7056 | 6066:7057 | 6066:7058 | 6066:7059 |
| 6067:7053 | 6067:7054 | 6067:7055 | 6067:7056 | 6067:7057 | 6067:7058 | 6067:7059 |
| 6068:7053 | 6068:7054 | 6068:7055 | 6068:7056 | 6068:7057 | 6068:7058 | 6068:7059 |
| 6069:7053 | 6069:7054 | 6069:7055 | 6069:7056 | 6069:7057 | 6069:7058 | 6069:7059 |
| 6070:7053 | 6070:7054 | 6070:7055 | 6070:7056 | 6070:7057 | 6070:7058 | 6070:7059 |
| 6071:7053 | 6071:7054 | 6071:7055 | 6071:7056 | 6071:7057 | 6071:7058 | 6071:7059 |
| 6072:7053 | 6072:7054 | 6072:7055 | 6072:7056 | 6072:7057 | 6072:7058 | 6072:7059 |
| 6073:7053 | 6073:7054 | 6073:7055 | 6073:7056 | 6073:7057 | 6073:7058 | 6073:7059 |
| 6074:7053 | 6074:7054 | 6074:7055 | 6074:7056 | 6074:7057 | 6074:7058 | 6074:7059 |
| 6075:7053 | 6075:7054 | 6075:7055 | 6075:7056 | 6075:7057 | 6075:7058 | 6075:7059 |
| 6076:7053 | 6076:7054 | 6076:7055 | 6076:7056 | 6076:7057 | 6076:7058 | 6076:7059 |
| 6077:7053 | 6077:7054 | 6077:7055 | 6077:7056 | 6077:7057 | 6077:7058 | 6077:7059 |
| 6078:7053 | 6078:7054 | 6078:7055 | 6078:7056 | 6078:7057 | 6078:7058 | 6078:7059 |
| 6061:7060 | 6061:7061 | 6061:7062 | 6061:7063 | 6061:7064 | 6061:7065 | 6061:7066 |
| 6062:7060 | 6062:7061 | 6062:7062 | 6062:7063 | 6062:7064 | 6062:7065 | 6062:7066 |

TABLE B-continued

Example combinations of a compound X with a compound Y.

| X:Y | X:Y | X:Y | X:Y | X:Y | X:Y | X:Y |
|---|---|---|---|---|---|---|
| 6063:7060 | 6063:7061 | 6063:7062 | 6063:7063 | 6063:7064 | 6063:7065 | 6063:7066 |
| 6064:7060 | 6064:7061 | 6064:7062 | 6064:7063 | 6064:7064 | 6064:7065 | 6064:7066 |
| 6065:7060 | 6065:7061 | 6065:7062 | 6065:7063 | 6065:7064 | 6065:7065 | 6065:7066 |
| 6066:7060 | 6066:7061 | 6066:7062 | 6066:7063 | 6066:7064 | 6066:7065 | 6066:7066 |
| 6067:7060 | 6067:7061 | 6067:7062 | 6067:7063 | 6067:7064 | 6067:7065 | 6067:7066 |
| 6068:7060 | 6068:7061 | 6068:7062 | 6068:7063 | 6068:7064 | 6068:7065 | 6068:7066 |
| 6069:7060 | 6069:7061 | 6069:7062 | 6069:7063 | 6069:7064 | 6069:7065 | 6069:7066 |
| 6070:7060 | 6070:7061 | 6070:7062 | 6070:7063 | 6070:7064 | 6070:7065 | 6070:7066 |
| 6071:7060 | 6071:7061 | 6071:7062 | 6071:7063 | 6071:7064 | 6071:7065 | 6071:7066 |
| 6072:7060 | 6072:7061 | 6072:7062 | 6072:7063 | 6072:7064 | 6072:7065 | 6072:7066 |
| 6073:7060 | 6073:7061 | 6073:7062 | 6073:7063 | 6073:7064 | 6073:7065 | 6073:7066 |
| 6074:7060 | 6074:7061 | 6074:7062 | 6074:7063 | 6074:7064 | 6074:7065 | 6074:7066 |
| 6075:7060 | 6075:7061 | 6075:7062 | 6075:7063 | 6075:7064 | 6075:7065 | 6075:7066 |
| 6076:7060 | 6076:7061 | 6076:7062 | 6076:7063 | 6076:7064 | 6076:7065 | 6076:7066 |
| 6077:7060 | 6077:7061 | 6077:7062 | 6077:7063 | 6077:7064 | 6077:7065 | 6077:7066 |
| 6078:7060 | 6078:7061 | 6078:7062 | 6078:7063 | 6078:7064 | 6078:7065 | 6078:7066 |
| 6061:7067 | 6061:7068 | 6061:7069 | 6061:7070 | 6061:7071 | 6061:7072 | 6061:7073 |
| 6062:7067 | 6062:7068 | 6062:7069 | 6062:7070 | 6062:7071 | 6062:7072 | 6062:7073 |
| 6063:7067 | 6063:7068 | 6063:7069 | 6063:7070 | 6063:7071 | 6063:7072 | 6063:7073 |
| 6064:7067 | 6064:7068 | 6064:7069 | 6064:7070 | 6064:7071 | 6064:7072 | 6064:7073 |
| 6065:7067 | 6065:7068 | 6065:7069 | 6065:7070 | 6065:7071 | 6065:7072 | 6065:7073 |
| 6066:7067 | 6066:7068 | 6066:7069 | 6066:7070 | 6066:7071 | 6066:7072 | 6066:7073 |
| 6067:7067 | 6067:7068 | 6067:7069 | 6067:7070 | 6067:7071 | 6067:7072 | 6067:7073 |
| 6068:7067 | 6068:7068 | 6068:7069 | 6068:7070 | 6068:7071 | 6068:7072 | 6068:7073 |
| 6069:7067 | 6069:7068 | 6069:7069 | 6069:7070 | 6069:7071 | 6069:7072 | 6069:7073 |
| 6070:7067 | 6070:7068 | 6070:7069 | 6070:7070 | 6070:7071 | 6070:7072 | 6070:7073 |
| 6071:7067 | 6071:7068 | 6071:7069 | 6071:7070 | 6071:7071 | 6071:7072 | 6071:7073 |
| 6072:7067 | 6072:7068 | 6072:7069 | 6072:7070 | 6072:7071 | 6072:7072 | 6072:7073 |
| 6073:7067 | 6073:7068 | 6073:7069 | 6073:7070 | 6073:7071 | 6073:7072 | 6073:7073 |
| 6074:7067 | 6074:7068 | 6074:7069 | 6074:7070 | 6074:7071 | 6074:7072 | 6074:7073 |
| 6075:7067 | 6075:7068 | 6075:7069 | 6075:7070 | 6075:7071 | 6075:7072 | 6075:7073 |
| 6076:7067 | 6076:7068 | 6076:7069 | 6076:7070 | 6076:7071 | 6076:7072 | 6076:7073 |
| 6077:7067 | 6077:7068 | 6077:7069 | 6077:7070 | 6077:7071 | 6077:7072 | 6077:7073 |
| 6078:7067 | 6078:7068 | 6078:7069 | 6078:7070 | 6078:7071 | 6078:7072 | 6078:7073 |
| 6061:7074 | 6061:7075 | 6061:7076 | 6061:7077 | — | — | — |
| 6062:7074 | 6062:7075 | 6062:7076 | 6062:7077 | | | |
| 6063:7074 | 6063:7075 | 6063:7076 | 6063:7077 | | | |
| 6064:7074 | 6064:7075 | 6064:7076 | 6064:7077 | | | |
| 6065:7074 | 6065:7075 | 6065:7076 | 6065:7077 | | | |
| 6066:7074 | 6066:7075 | 6066:7076 | 6066:7077 | | | |
| 6067:7074 | 6067:7075 | 6067:7076 | 6067:7077 | | | |
| 6068:7074 | 6068:7075 | 6068:7076 | 6068:7077 | | | |
| 6069:7074 | 6069:7075 | 6069:7076 | 6069:7077 | | | |
| 6070:7074 | 6070:7075 | 6070:7076 | 6070:7077 | | | |
| 6071:7074 | 6071:7075 | 6071:7076 | 6071:7077 | | | |
| 6072:7074 | 6072:7075 | 6072:7076 | 6072:7077 | | | |
| 6073:7074 | 6073:7075 | 6073:7076 | 6073:7077 | | | |
| 6074:7074 | 6074:7075 | 6074:7076 | 6074:7077 | | | |
| 6075:7074 | 6075:7075 | 6075:7076 | 6075:7077 | | | |
| 6076:7074 | 6076:7075 | 6076:7076 | 6076:7077 | | | |
| 6077:7074 | 6077:7075 | 6077:7076 | 6077:7077 | | | |
| 6078:7074 | 6078:7075 | 6078:7076 | 6078:7077 | | | |

TABLE C

Example combinations of a compound X with a compound Y.

| X:Y | X:Y | X:Y | X:Y | X:Y | X:Y |
|---|---|---|---|---|---|
| 6000:8000 | 6000:8001 | 6000:8002 | 6000:8003 | 6000:8004 | 6000:8005 |
| 6001:8000 | 6001:8001 | 6001:8002 | 6001:8003 | 6001:8004 | 6001:8005 |
| 6002:8000 | 6002:8001 | 6002:8002 | 6002:8003 | 6002:8004 | 6002:8005 |
| 6003:8000 | 6003:8001 | 6003:8002 | 6003:8003 | 6003:8004 | 6003:8005 |
| 6004:8000 | 6004:8001 | 6004:8002 | 6004:8003 | 6004:8004 | 6004:8005 |
| 6005:8000 | 6005:8001 | 6005:8002 | 6005:8003 | 6005:8004 | 6005:8005 |
| 6006:8000 | 6006:8001 | 6006:8002 | 6006:8003 | 6006:8004 | 6006:8005 |
| 6007:8000 | 6007:8001 | 6007:8002 | 6007:8003 | 6007:8004 | 6007:8005 |
| 6008:8000 | 6008:8001 | 6008:8002 | 6008:8003 | 6008:8004 | 6008:8005 |
| 6009:8000 | 6009:8001 | 6009:8002 | 6009:8003 | 6009:8004 | 6009:8005 |
| 6010:8000 | 6010:8001 | 6010:8002 | 6010:8003 | 6010:8004 | 6010:8005 |
| 6011:8000 | 6011:8001 | 6011:8002 | 6011:8003 | 6011:8004 | 6011:8005 |

TABLE C-continued

Example combinations of a compound X with a compound Y.

| X:Y | X:Y | X:Y | X:Y | X:Y | X:Y |
|---|---|---|---|---|---|
| 6012:8000 | 6012:8001 | 6012:8002 | 6012:8003 | 6012:8004 | 6012:8005 |
| 6013:8000 | 6013:8001 | 6013:8002 | 6013:8003 | 6013:8004 | 6013:8005 |
| 6014:8000 | 6014:8001 | 6014:8002 | 6014:8003 | 6014:8004 | 6014:8005 |
| 6015:8000 | 6015:8001 | 6015:8002 | 6015:8003 | 6015:8004 | 6015:8005 |
| 6016:8000 | 6016:8001 | 6016:8002 | 6016:8003 | 6016:8004 | 6016:8005 |
| 6017:8000 | 6017:8001 | 6017:8002 | 6017:8003 | 6017:8004 | 6017:8005 |
| 6018:8000 | 6018:8001 | 6018:8002 | 6018:8003 | 6018:8004 | 6018:8005 |
| 6019:8000 | 6019:8001 | 6019:8002 | 6019:8003 | 6019:8004 | 6019:8005 |
| 6020:8000 | 6020:8001 | 6020:8002 | 6020:8003 | 6020:8004 | 6020:8005 |
| 6000:8006 | 6000:8007 | 6000:8008 | 6000:8009 | 6000:8010 | 6000:8011 |
| 6001:8006 | 6001:8007 | 6001:8008 | 6001:8009 | 6001:8010 | 6001:8011 |

TABLE C-continued

Example combinations of a compound X with a compound Y.

| X:Y | X:Y | X:Y | X:Y | X:Y | X:Y |
|---|---|---|---|---|---|
| 6002:8006 | 6002:8007 | 6002:8008 | 6002:8009 | 6002:8010 | 6002:8011 |
| 6003:8006 | 6003:8007 | 6003:8008 | 6003:8009 | 6003:8010 | 6003:8011 |
| 6004:8006 | 6004:8007 | 6004:8008 | 6004:8009 | 6004:8010 | 6004:8011 |
| 6005:8006 | 6005:8007 | 6005:8008 | 6005:8009 | 6005:8010 | 6005:8011 |
| 6006:8006 | 6006:8007 | 6006:8008 | 6006:8009 | 6006:8010 | 6006:8011 |
| 6007:8006 | 6007:8007 | 6007:8008 | 6007:8009 | 6007:8010 | 6007:8011 |
| 6008:8006 | 6008:8007 | 6008:8008 | 6008:8009 | 6008:8010 | 6008:8011 |
| 6009:8006 | 6009:8007 | 6009:8008 | 6009:8009 | 6009:8010 | 6009:8011 |
| 6010:8006 | 6010:8007 | 6010:8008 | 6010:8009 | 6010:8010 | 6010:8011 |
| 6011:8006 | 6011:8007 | 6011:8008 | 6011:8009 | 6011:8010 | 6011:8011 |
| 6012:8006 | 6012:8007 | 6012:8008 | 6012:8009 | 6012:8010 | 6012:8011 |
| 6013:8006 | 6013:8007 | 6013:8008 | 6013:8009 | 6013:8010 | 6013:8011 |
| 6014:8006 | 6014:8007 | 6014:8008 | 6014:8009 | 6014:8010 | 6014:8011 |
| 6015:8006 | 6015:8007 | 6015:8008 | 6015:8009 | 6015:8010 | 6015:8011 |
| 6016:8006 | 6016:8007 | 6016:8008 | 6016:8009 | 6016:8010 | 6016:8011 |
| 6017:8006 | 6017:8007 | 6017:8008 | 6017:8009 | 6017:8010 | 6017:8011 |
| 6018:8006 | 6018:8007 | 6018:8008 | 6018:8009 | 6018:8010 | 6018:8011 |
| 6019:8006 | 6019:8007 | 6019:8008 | 6019:8009 | 6019:8010 | 6019:8011 |
| 6020:8006 | 6020:8007 | 6020:8008 | 6020:8009 | 6020:8010 | 6020:8011 |
| 6000:8012 | 6021:8000 | 6021:8001 | 6021:8002 | 6021:8003 | 6021:8004 |
| 6001:8012 | 6022:8000 | 6022:8001 | 6022:8002 | 6022:8003 | 6022:8004 |
| 6002:8012 | 6023:8000 | 6023:8001 | 6023:8002 | 6023:8003 | 6023:8004 |
| 6003:8012 | 6024:8000 | 6024:8001 | 6024:8002 | 6024:8003 | 6024:8004 |
| 6004:8012 | 6025:8000 | 6025:8001 | 6025:8002 | 6025:8003 | 6025:8004 |
| 6005:8012 | 6026:8000 | 6026:8001 | 6026:8002 | 6026:8003 | 6026:8004 |
| 6006:8012 | 6027:8000 | 6027:8001 | 6027:8002 | 6027:8003 | 6027:8004 |
| 6007:8012 | 6028:8000 | 6028:8001 | 6028:8002 | 6028:8003 | 6028:8004 |
| 6008:8012 | 6029:8000 | 6029:8001 | 6029:8002 | 6029:8003 | 6029:8004 |
| 6009:8012 | 6030:8000 | 6030:8001 | 6030:8002 | 6030:8003 | 6030:8004 |
| 6010:8012 | 6031:8000 | 6031:8001 | 6031:8002 | 6031:8003 | 6031:8004 |
| 6011:8012 | 6032:8000 | 6032:8001 | 6032:8002 | 6032:8003 | 6032:8004 |
| 6012:8012 | 6033:8000 | 6033:8001 | 6033:8002 | 6033:8003 | 6033:8004 |
| 6013:8012 | 6034:8000 | 6034:8001 | 6034:8002 | 6034:8003 | 6034:8004 |
| 6014:8012 | 6035:8000 | 6035:8001 | 6035:8002 | 6035:8003 | 6035:8004 |
| 6015:8012 | 6036:8000 | 6036:8001 | 6036:8002 | 6036:8003 | 6036:8004 |
| 6016:8012 | 6037:8000 | 6037:8001 | 6037:8002 | 6037:8003 | 6037:8004 |
| 6017:8012 | 6038:8000 | 6038:8001 | 6038:8002 | 6038:8003 | 6038:8004 |
| 6018:8012 | 6039:8000 | 6039:8001 | 6039:8002 | 6039:8003 | 6039:8004 |
| 6019:8012 | 6040:8000 | 6040:8001 | 6040:8002 | 6040:8003 | 6040:8004 |
| 6020:8012 | | | | | |
| 6021:8005 | 6021:8006 | 6021:8007 | 6021:8008 | 6021:8009 | 6021:8010 |
| 6022:8005 | 6022:8006 | 6022:8007 | 6022:8008 | 6022:8009 | 6022:8010 |
| 6023:8005 | 6023:8006 | 6023:8007 | 6023:8008 | 6023:8009 | 6023:8010 |
| 6024:8005 | 6024:8006 | 6024:8007 | 6024:8008 | 6024:8009 | 6024:8010 |
| 6025:8005 | 6025:8006 | 6025:8007 | 6025:8008 | 6025:8009 | 6025:8010 |
| 6026:8005 | 6026:8006 | 6026:8007 | 6026:8008 | 6026:8009 | 6026:8010 |
| 6027:8005 | 6027:8006 | 6027:8007 | 6027:8008 | 6027:8009 | 6027:8010 |
| 6028:8005 | 6028:8006 | 6028:8007 | 6028:8008 | 6028:8009 | 6028:8010 |
| 6029:8005 | 6029:8006 | 6029:8007 | 6029:8008 | 6029:8009 | 6029:8010 |
| 6030:8005 | 6030:8006 | 6030:8007 | 6030:8008 | 6030:8009 | 6030:8010 |
| 6031:8005 | 6031:8006 | 6031:8007 | 6031:8008 | 6031:8009 | 6031:8010 |
| 6032:8005 | 6032:8006 | 6032:8007 | 6032:8008 | 6032:8009 | 6032:8010 |
| 6033:8005 | 6033:8006 | 6033:8007 | 6033:8008 | 6033:8009 | 6033:8010 |
| 6034:8005 | 6034:8006 | 6034:8007 | 6034:8008 | 6034:8009 | 6034:8010 |
| 6035:8005 | 6035:8006 | 6035:8007 | 6035:8008 | 6035:8009 | 6035:8010 |
| 6036:8005 | 6036:8006 | 6036:8007 | 6036:8008 | 6036:8009 | 6036:8010 |
| 6037:8005 | 6037:8006 | 6037:8007 | 6037:8008 | 6037:8009 | 6037:8010 |
| 6038:8005 | 6038:8006 | 6038:8007 | 6038:8008 | 6038:8009 | 6038:8010 |
| 6039:8005 | 6039:8006 | 6039:8007 | 6039:8008 | 6039:8009 | 6039:8010 |
| 6040:8005 | 6040:8006 | 6040:8007 | 6040:8008 | 6040:8009 | 6040:8010 |
| 6021:8011 | 6021:8012 | 6041:8000 | 6041:8001 | 6041:8002 | 6041:8003 |
| 6022:8011 | 6022:8012 | 6042:8000 | 6042:8001 | 6042:8002 | 6042:8003 |
| 6023:8011 | 6023:8012 | 6043:8000 | 6043:8001 | 6043:8002 | 6043:8003 |
| 6024:8011 | 6024:8012 | 6044:8000 | 6044:8001 | 6044:8002 | 6044:8003 |
| 6025:8011 | 6025:8012 | 6045:8000 | 6045:8001 | 6045:8002 | 6045:8003 |
| 6026:8011 | 6026:8012 | 6046:8000 | 6046:8001 | 6046:8002 | 6046:8003 |
| 6027:8011 | 6027:8012 | 6047:8000 | 6047:8001 | 6047:8002 | 6047:8003 |
| 6028:8011 | 6028:8012 | 6048:8000 | 6048:8001 | 6048:8002 | 6048:8003 |
| 6029:8011 | 6029:8012 | 6049:8000 | 6049:8001 | 6049:8002 | 6049:8003 |
| 6030:8011 | 6030:8012 | 6050:8000 | 6050:8001 | 6050:8002 | 6050:8003 |
| 6031:8011 | 6031:8012 | 6051:8000 | 6051:8001 | 6051:8002 | 6051:8003 |
| 6032:8011 | 6032:8012 | 6052:8000 | 6052:8001 | 6052:8002 | 6052:8003 |
| 6033:8011 | 6033:8012 | 6053:8000 | 6053:8001 | 6053:8002 | 6053:8003 |
| 6034:8011 | 6034:8012 | 6054:8000 | 6054:8001 | 6054:8002 | 6054:8003 |
| 6035:8011 | 6035:8012 | 6055:8000 | 6055:8001 | 6055:8002 | 6055:8003 |
| 6036:8011 | 6036:8012 | 6056:8000 | 6056:8001 | 6056:8002 | 6056:8003 |
| 6037:8011 | 6037:8012 | 6057:8000 | 6057:8001 | 6057:8002 | 6057:8003 |
| 6038:8011 | 6038:8012 | 6058:8000 | 6058:8001 | 6058:8002 | 6058:8003 |
| 6039:8011 | 6039:8012 | 6059:8000 | 6059:8001 | 6059:8002 | 6059:8003 |
| 6040:8011 | 6040:8012 | 6060:8000 | 6060:8001 | 6060:8002 | 6060:8003 |
| 6041:8004 | 6041:8005 | 6041:8006 | 6041:8007 | 6041:8008 | 6041:8009 |
| 6042:8004 | 6042:8005 | 6042:8006 | 6042:8007 | 6042:8008 | 6042:8009 |
| 6043:8004 | 6043:8005 | 6043:8006 | 6043:8007 | 6043:8008 | 6043:8009 |
| 6044:8004 | 6044:8005 | 6044:8006 | 6044:8007 | 6044:8008 | 6044:8009 |
| 6045:8004 | 6045:8005 | 6045:8006 | 6045:8007 | 6045:8008 | 6045:8009 |
| 6046:8004 | 6046:8005 | 6046:8006 | 6046:8007 | 6046:8008 | 6046:8009 |
| 6047:8004 | 6047:8005 | 6047:8006 | 6047:8007 | 6047:8008 | 6047:8009 |
| 6048:8004 | 6048:8005 | 6048:8006 | 6048:8007 | 6048:8008 | 6048:8009 |
| 6049:8004 | 6049:8005 | 6049:8006 | 6049:8007 | 6049:8008 | 6049:8009 |
| 6050:8004 | 6050:8005 | 6050:8006 | 6050:8007 | 6050:8008 | 6050:8009 |
| 6051:8004 | 6051:8005 | 6051:8006 | 6051:8007 | 6051:8008 | 6051:8009 |
| 6052:8004 | 6052:8005 | 6052:8006 | 6052:8007 | 6052:8008 | 6052:8009 |
| 6053:8004 | 6053:8005 | 6053:8006 | 6053:8007 | 6053:8008 | 6053:8009 |
| 6054:8004 | 6054:8005 | 6054:8006 | 6054:8007 | 6054:8008 | 6054:8009 |
| 6055:8004 | 6055:8005 | 6055:8006 | 6055:8007 | 6055:8008 | 6055:8009 |
| 6056:8004 | 6056:8005 | 6056:8006 | 6056:8007 | 6056:8008 | 6056:8009 |
| 6057:8004 | 6057:8005 | 6057:8006 | 6057:8007 | 6057:8008 | 6057:8009 |
| 6058:8004 | 6058:8005 | 6058:8006 | 6058:8007 | 6058:8008 | 6058:8009 |
| 6059:8004 | 6059:8005 | 6059:8006 | 6059:8007 | 6059:8008 | 6059:8009 |
| 6060:8004 | 6060:8005 | 6060:8006 | 6060:8007 | 6060:8008 | 6060:8009 |
| 6041:8010 | 6041:8011 | 6041:8012 | 6061:8000 | 6061:8001 | 6061:8002 |
| 6042:8010 | 6042:8011 | 6042:8012 | 6062:8000 | 6062:8001 | 6062:8002 |
| 6043:8010 | 6043:8011 | 6043:8012 | 6063:8000 | 6063:8001 | 6063:8002 |
| 6044:8010 | 6044:8011 | 6044:8012 | 6064:8000 | 6064:8001 | 6064:8002 |
| 6045:8010 | 6045:8011 | 6045:8012 | 6065:8000 | 6065:8001 | 6065:8002 |
| 6046:8010 | 6046:8011 | 6046:8012 | 6066:8000 | 6066:8001 | 6066:8002 |
| 6047:8010 | 6047:8011 | 6047:8012 | 6067:8000 | 6067:8001 | 6067:8002 |
| 6048:8010 | 6048:8011 | 6048:8012 | 6068:8000 | 6068:8001 | 6068:8002 |
| 6049:8010 | 6049:8011 | 6049:8012 | 6069:8000 | 6069:8001 | 6069:8002 |
| 6050:8010 | 6050:8011 | 6050:8012 | 6070:8000 | 6070:8001 | 6070:8002 |
| 6051:8010 | 6051:8011 | 6051:8012 | 6071:8000 | 6071:8001 | 6071:8002 |
| 6052:8010 | 6052:8011 | 6052:8012 | 6072:8000 | 6072:8001 | 6072:8002 |
| 6053:8010 | 6053:8011 | 6053:8012 | 6073:8000 | 6073:8001 | 6073:8002 |
| 6054:8010 | 6054:8011 | 6054:8012 | 6074:8000 | 6074:8001 | 6074:8002 |
| 6055:8010 | 6055:8011 | 6055:8012 | 6075:8000 | 6075:8001 | 6075:8002 |
| 6056:8010 | 6056:8011 | 6056:8012 | 6076:8000 | 6076:8001 | 6076:8002 |
| 6057:8010 | 6057:8011 | 6057:8012 | 6077:8000 | 6077:8001 | 6077:8002 |
| 6058:8010 | 6058:8011 | 6058:8012 | 6078:8000 | 6078:8001 | 6078:8002 |
| 6059:8010 | 6059:8011 | 6059:8012 | | | |
| 6060:8010 | 6060:8011 | 6060:8012 | | | |
| 6061:8003 | 6061:8004 | 6061:8005 | 6061:8006 | 6061:8007 | 6061:8008 |
| 6062:8003 | 6062:8004 | 6062:8005 | 6062:8006 | 6062:8007 | 6062:8008 |
| 6063:8003 | 6063:8004 | 6063:8005 | 6063:8006 | 6063:8007 | 6063:8008 |
| 6064:8003 | 6064:8004 | 6064:8005 | 6064:8006 | 6064:8007 | 6064:8008 |
| 6065:8003 | 6065:8004 | 6065:8005 | 6065:8006 | 6065:8007 | 6065:8008 |
| 6066:8003 | 6066:8004 | 6066:8005 | 6066:8006 | 6066:8007 | 6066:8008 |
| 6067:8003 | 6067:8004 | 6067:8005 | 6067:8006 | 6067:8007 | 6067:8008 |
| 6068:8003 | 6068:8004 | 6068:8005 | 6068:8006 | 6068:8007 | 6068:8008 |
| 6069:8003 | 6069:8004 | 6069:8005 | 6069:8006 | 6069:8007 | 6069:8008 |
| 6070:8003 | 6070:8004 | 6070:8005 | 6070:8006 | 6070:8007 | 6070:8008 |
| 6071:8003 | 6071:8004 | 6071:8005 | 6071:8006 | 6071:8007 | 6071:8008 |
| 6072:8003 | 6072:8004 | 6072:8005 | 6072:8006 | 6072:8007 | 6072:8008 |
| 6073:8003 | 6073:8004 | 6073:8005 | 6073:8006 | 6073:8007 | 6073:8008 |
| 6074:8003 | 6074:8004 | 6074:8005 | 6074:8006 | 6074:8007 | 6074:8008 |
| 6075:8003 | 6075:8004 | 6075:8005 | 6075:8006 | 6075:8007 | 6075:8008 |
| 6076:8003 | 6076:8004 | 6076:8005 | 6076:8006 | 6076:8007 | 6076:8008 |
| 6077:8003 | 6077:8004 | 6077:8005 | 6077:8006 | 6077:8007 | 6077:8008 |
| 6078:8003 | 6078:8004 | 6078:8005 | 6078:8006 | 6078:8007 | 6078:8008 |
| 6061:8009 | 6061:8010 | 6061:8011 | 6061:8012 | — | — |
| 6062:8009 | 6062:8010 | 6062:8011 | 6062:8012 | | |
| 6063:8009 | 6063:8010 | 6063:8011 | 6063:8012 | | |
| 6064:8009 | 6064:8010 | 6064:8011 | 6064:8012 | | |
| 6065:8009 | 6065:8010 | 6065:8011 | 6065:8012 | | |
| 6066:8009 | 6066:8010 | 6066:8011 | 6066:8012 | | |
| 6067:8009 | 6067:8010 | 6067:8011 | 6067:8012 | | |

TABLE C-continued

Example combinations of a compound X with a compound Y.

| X:Y | X:Y | X:Y | X:Y | X:Y | X:Y |
|---|---|---|---|---|---|
| 6068:8009 | 6068:8010 | 6068:8011 | 6068:8012 | | |
| 6069:8009 | 6069:8010 | 6069:8011 | 6069:8012 | | |
| 6070:8009 | 6070:8010 | 6070:8011 | 6070:8012 | | |
| 6071:8009 | 6071:8010 | 6071:8011 | 6071:8012 | | |
| 6072:8009 | 6072:8010 | 6072:8011 | 6072:8012 | | |
| 6073:8009 | 6073:8010 | 6073:8011 | 6073:8012 | | |
| 6074:8009 | 6074:8010 | 6074:8011 | 6074:8012 | | |
| 6075:8009 | 6075:8010 | 6075:8011 | 6075:8012 | | |
| 6076:8009 | 6076:8010 | 6076:8011 | 6076:8012 | | |
| 6077:8009 | 6077:8010 | 6077:8011 | 6077:8012 | | |
| 6078:8009 | 6078:8010 | 6078:8011 | 6078:8012 | | |

TABLE D

Example combinations of a compound X with a compound Y.

| X:Y | X:Y | X:Y | X:Y |
|---|---|---|---|
| 6000:9000 | 6020:9000 | 6040:9000 | 6060:9000 |
| 6001:9000 | 6021:9000 | 6041:9000 | 6061:9000 |
| 6002:9000 | 6022:9000 | 6042:9000 | 6062:9000 |
| 6003:9000 | 6023:9000 | 6043:9000 | 6063:9000 |
| 6004:9000 | 6024:9000 | 6044:9000 | 6064:9000 |
| 6005:9000 | 6025:9000 | 6045:9000 | 6065:9000 |
| 6006:9000 | 6026:9000 | 6046:9000 | 6066:9000 |
| 6007:9000 | 6027:9000 | 6047:9000 | 6067:9000 |
| 6008:9000 | 6028:9000 | 6048:9000 | 6068:9000 |
| 6009:9000 | 6029:9000 | 6049:9000 | 6069:9000 |
| 6010:9000 | 6030:9000 | 6050:9000 | 6070:9000 |
| 6011:9000 | 6031:9000 | 6051:9000 | 6071:9000 |
| 6012:9000 | 6032:9000 | 6052:9000 | 6072:9000 |
| 6013:9000 | 6033:9000 | 6053:9000 | 6073:9000 |
| 6014:9000 | 6034:9000 | 6054:9000 | 6074:9000 |
| 6015:9000 | 6035:9000 | 6055:9000 | 6075:9000 |
| 6016:9000 | 6036:9000 | 6056:9000 | 6076:9000 |
| 6017:9000 | 6037:9000 | 6057:9000 | 6077:9000 |
| 6018:9000 | 6038:9000 | 6058:9000 | 6078:9000 |
| 6019:9000 | 6039:9000 | 6059:9000 | |

EXAMPLES

Additional embodiments are disclosed in further detail in the following examples, which are not in any way intended to limit the scope of the claims.

Example 1

General Synthesis of Reagents 1 and 2

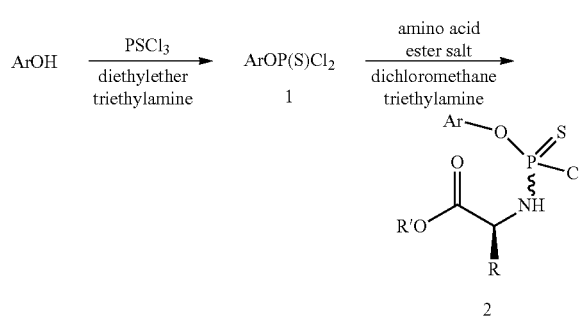

Step 1: Synthesis of 1-naphthyloxydichlorophosphothioate reagent (1a)

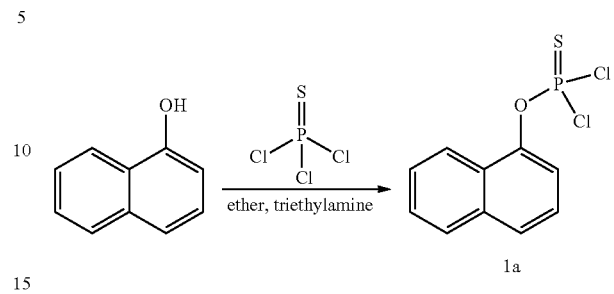

A 500 mL round bottom flask containing a magnetic stir bar was charged with phosphorus thiotrichloride (5.7 g, 33.65 mmol) and 1-naphthol (4.85 g, 33.64 mmol), and 40 mL of diethyl ether was added. Under an argon atmosphere, the solution was cooled in a dry ice/acetone bath. After 10 minutes of cooling, triethylamine (4.7 mL, 33.7 mmol) was added, and a precipitate formed. The mixture was allowed to warm to ambient temperature, and was then stirred for 2 days. The precipitated triethylammonium hydrochloride was filtered off, and was washed twice with ether. The solvents were removed under reduced pressure to leave 9.8 g of compound 1a as a cloudy, light yellow oil. 1a was used in the next step without further purification.

Step 2: Synthesis of the L-alanine methyl ester derived 1-naphthyloxy-chlorophosphothioate reagent (2a)

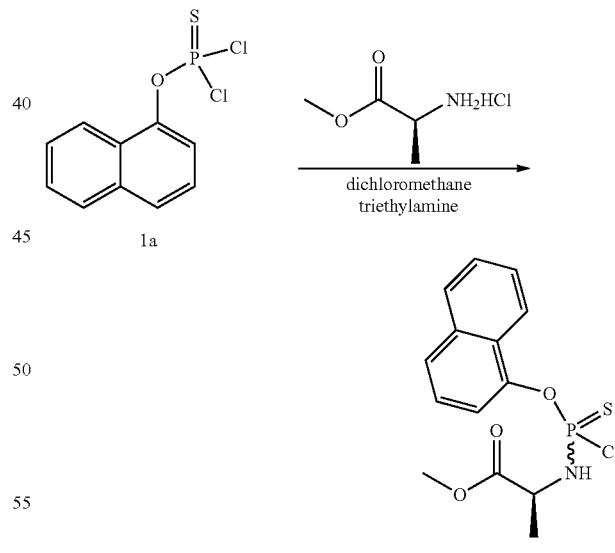

Into a 250 mL round bottom flask containing 1-naphthol-dichlorophosphothioate reagent 1a (1.97 g, 7.1 mmol) and L-alanine methyl ester hydrochloride (0.99 g, 7.1 mmol) was added in 50 mL of dichloromethane. At water/ice temperature under an argon atmosphere, triethylamine (1 mL, 7.2 mmol) was added. The reaction was allowed to warm to ambient temperature and was then stirred overnight. The solvents were removed using a rotary evaporator. The residue was purified using chromatography on silica gel, and eluting with 20% ethyl acetate in hexanes. The product 2a (1.0 g) was obtained as a viscous oil. $^{31}$P NMR (CDCl$_3$, 64.78, 65.0) (approximately a 1:1 mixture of diastereomers).

The reagents shown in Tables 6 and 7 were prepared using the procedures described for compounds 1a and 2a, with the ArOH compounds listed in Table 6 in place of 1-naphthol, and with hydrochloride salts of the amino acids listed in Table 7 in place of L-alanine methyl ester hydrochloride.

TABLE 6

| ArOH | Dichloridates | Reagent No. |
|---|---|---|
| Phenol | 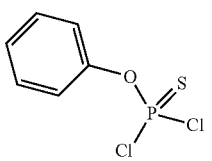 [SMILES: S=P(Cl)(Cl)Oc1ccccc1] | 1b |
| p-fluoro-phenol | 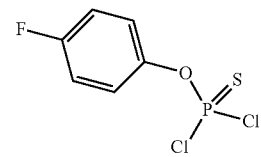 [SMILES: Fc1ccc(OP(=S)(Cl)Cl)cc1] | 1c |
| p-chloro-phenol | 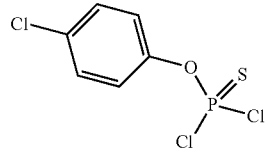 [SMILES: S=P(Cl)(Cl)Oc1ccc(Cl)cc1] | 1d |
| o-chloro-phenol | 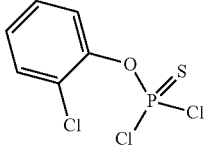 | 1e |
| p-chloro-m-chloro-phenol | 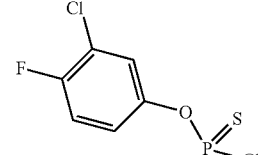 | 1f |
| p-methyl-phenol | 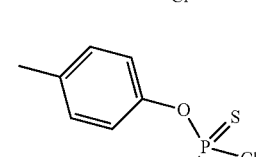 | 1g |
| o-methyl-phenol | 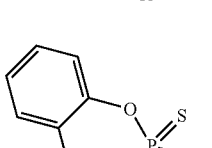 | 1h |

TABLE 6-continued

| ArOH | Dichloridates | Reagent No. |
|---|---|---|
| p-methoxy-phenol | 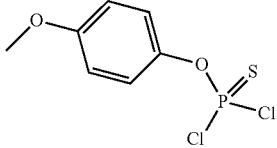 | 1i |
| quinolin-5-ol | 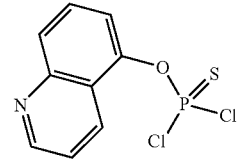 [SMILES: S=P(Cl)(Cl)Oc1cccc2ncccc12] | 1j |
| pyridine-3-ol | 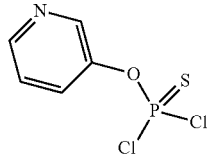 [SMILES: S=P(Cl)(Cl)Oc1cccnc1] | 1k |

TABLE 7

| Amino Acid | Aryloxy amino acid thiophosphochloridate | Reagent No. | $^{31}$P NMR (CDCl$_3$) |
|---|---|---|---|
| L-alanine isopropyl ester | 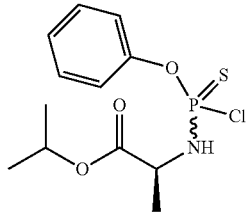 [SMILES: CC(C)OC(=O)[C@H](C)NP(=S)(Cl)Oc1ccccc1] | 2b | 64.75 (s) 64.65 (s) |
| L-alanine cyclohexyl ester | 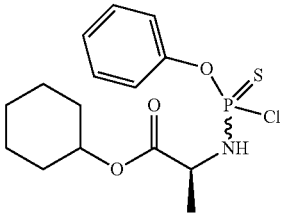 [SMILES: C[C@H](NP(=S)(Cl)Oc1ccccc1)C(=O)OC1CCCCC1] | 2c | 64.80 (s) 64.69 (s) |
| L-alanine neopentyl ester | 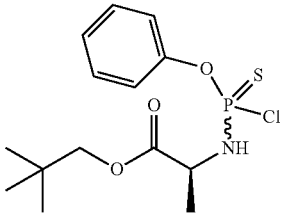 [SMILES: C[C@H](NP(=S)(Cl)Oc1ccccc1)C(=O)OCC(C)(C)C] | 2d | 64.59 (s) 64.31 (s) |
| L-alanine isopropyl ester | 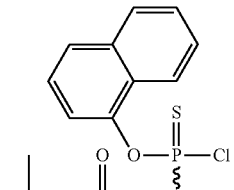 | 2e | 64.51 (s) 64.23 (s) |

TABLE 7-continued

| Amino Acid | Aryloxy amino acid thiophosphochloridate | Reagent No. | $^{31}$P NMR (CDCl$_3$) |
|---|---|---|---|
| L-alanine cyclohexyl ester | | 2f | 64.55 (s) 64.25 (s) |
| L-alanine neopentyl ester | | 2g | 64.51 (s) 64.27 (s) |
| L-valine isopropyl ester | | 2h | 67.72 65.87 |

Example 2

Preparation of 2'-C-Methyluridine 5'-(O-(1-naphthyl)-N—(S)-1-(methoxycarbonyl)ethyl)thiophosphoramidate (3a)

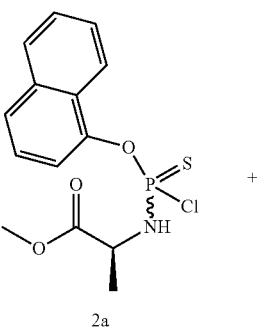

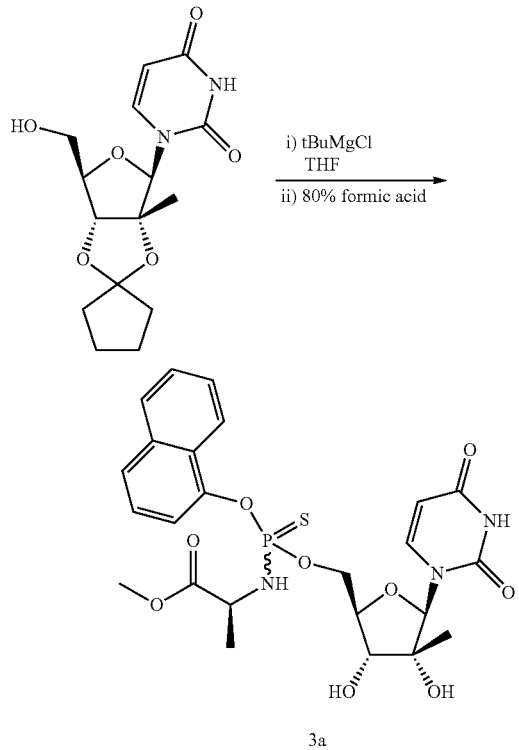

A solution of cyclopentylidine protected 2'-C-methyluridine (262 mg, 0.81 mmol) in 2 mL tetrahydrofuran was cooled in an ice/water bath under argon, and treated with 2.1 mL tBuMgCl (1 M, 2.1 mmol). After 10 minutes, reagent 2a (0.83 g, 2.4 mmol) was added as a solution in 2 mL of tetrahydrofuran (THF). The reaction was stirred at ambient temperature for 2 days. An additional 1 mL tBuMgCl was then added (1 mmol). After an additional 2 days, the reaction was diluted with ethyl acetate and water. The organic layer was washed two times with brine, and dried over sodium sulfate. Chromatography on silica gel using a gradient of 1% methanol in dichloromethane to 10% methanol in dichloromethane afforded 0.2 g of a residue which was used without further purification. To the residue was added 4 mL of 80% aqueous formic acid. The mixture was heated to 50° C. using a water bath. After 2 hours, the reaction was cooled, and the solvents were removed under reduced pressure. A solution of 1:1 methanol:toluene was added to the residue. The solvents were then removed under reduced pressure. The addition of a solution of 1:1 methanol:toluene and removal of solvents were repeated 2 more times. The product was isolated following chromatography using silica gel with a gradient from 4% to 8% methanol in dichloromethane. The solvent was removed, and the residue was taken up in chloroform and treated with excess hexanes. The supernatant was decanted off, and the remaining solid was subjected to high vacuum overnight. Product 3a was isolated as a colorless solid (22.2 mg). $^{31}$P NMR (CDCl$_3$, 67.12, 67.86) and mass spectral data (M−H$^-$, 564.5) were consistent with the desired product 3a as a near 1:1 mixture of diastereomers at the phosphorus chiral center.

Example 3

Preparation of 2'-C-methyluridine 5'-(O-phenyl-N—(S)-1-(isopropoxycarbonyl)ethyl)thiophosphoramidate (3b)

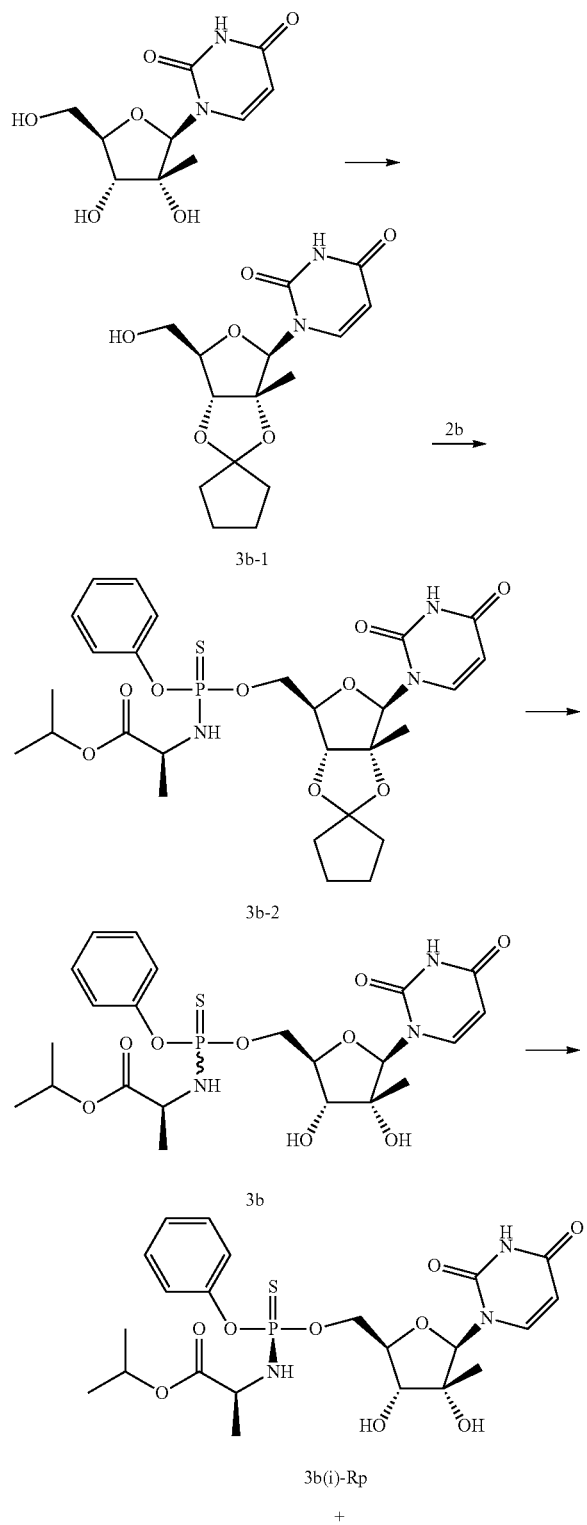

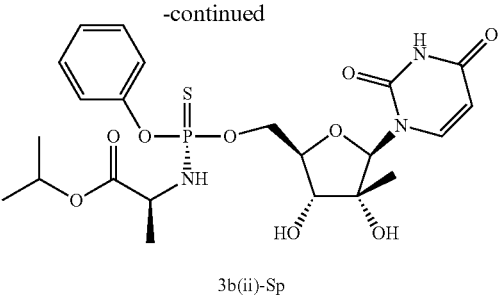

3b(ii)-Sp

Step 1: Compound 3b-1—To a suspension of 2'-methyluridine (20 g, 77.52 mmol) in dry $CH_3CN$ (200 mL) were added cyclopentanone (20 mL) and trimethylorthoformate (20 mL) followed by p-toluenesulfonic acid monohydrate (7.4 g, 38.76 mmol). The reaction mixture was stirred at 40° C. overnight. The solvent was evaporated. The residue was dissolved in ethyl acetate and washed with brine. The organic layer was dried and evaporated to give pure 3b-1 as a white solid (14.5 g, 57.7%). $^1$H NMR ($CDCl_3$, 400 MHz) δ8.86 (s, 1H), 7.67 (d, J=8.0 Hz, 1H), 6.06 (s, 1H), 5.73 (d, J=8.0 Hz, 1H), 4.50 (d, J=4.8 Hz, 1H), 4.21 (m, 1H), 4.02-3.86 (m, 2H), 2.17 (m, 1H), 1.98, 1.83, 1.68 (m, 8H), 1.30 (s, 3H).

Step 2: Compound 3b-2—To a suspension of 3b-1 (20 g, 61.7 mmol) in dry $CH_3CN$ (100 mL) was added N-methylimidazole (50 mL) and 2b (80 g, 249.2 mmol). The reaction mixture was stirred at 70° C. for 2 h. Solvent was removed and the residue was dissolved in ethyl acetate (500 mL). The solution was washed with brine, dried and evaporated. The residue was purified on a silica gel column (20~50% ethylacetate (EA) in petroleum ether (PE)) to give 3b-2 as a white foam (two isomers, 12.5 g, 33%). $^1$H NMR ($CDCl_3$, 400 MHz) δ8.79-8.92 (m, 1H), 7.55 (m, 1H), 7.34 (m, 2H), 7.20 (m, 3H), 6.09 (d, J=13.6 Hz, 1H), 5.70-5.61 (m, 1H), 5.06-5.01 (m, 1H), 4.38-4.09 (m, 6H), 2.08 (m, 1H), 1.96 (m, 1H), 1.73 (m, 2H), 1.66 (m, 5H), 1.39 (m, 3H), 1.23 (m, 9H); $^{31}$P NMR ($CDCl_3$, 162 MHz) δ67.62, 67.31.

Step 3: Compound 3b—Compound 3b-2 (10 g, 16.4 mmol) was suspended in 100 mL of 80% formic acid and the reaction mixture was stirred at 50° C. for 1.5 hours. Solvent was evaporated and the residue was co-evaporated with toluene to remove traces of acid and water. The residue was purified by RP HPLC (0.5% HCOOH in MeCN and water as mobile phase) to give 3b (a mixture of two P-diastereomers, 5.6 g, 63%). $^1$H NMR ($CD_3OD$, 400 MHz) δ 7.79, 7.87 (2d, J=8.0 Hz, 1H), 7.18-7.38 (m, 5H), 5.98, 6.01 (2s, 1H), 5.59, 5.63 (2d, J=8.0 Hz, 1H), 4.95-5.05 (m, 1H), 4.51-4.56 (m, 1H), 4.30-4.44 (m, 1H), 4.05-4.17 (m, 2H), 3.82-3.87 (m, 1H), 1.34, 1.38 (2d, J=7.2 Hz, 3H), 1.17, 1.25 (2d, J=6.0 Hz, 6H), 1.24, 125 (2s, 3H); $^{31}$P NMR ($CD_3OD$, 162 MHz) δ68.17, 68.40; ESI-LCMS: m/z 544.0 [M+H]$^+$.

Step 4: Separation of 3b(i)-Rp and 3b(ii)-Sp—Compound 3b was separated into its Rp and Sp diastereomers by two methods: (a) supercritical fluid chromatography (SFC) and (b) crystallization.

(a) Via SFC: Compound 3b (440 mg, consisting of both 3b(i)-Rp and 3b(ii)-Sp in ~1:1 ratio) was subjected to separation by SFC (chiral PAK AD, 5 um. 250*30 mm using 25% MeOH and 75% $CO_2$ as mobile phase) to give 3b(i)-Rp (123.8 mg) and 3b(ii)-Sp (162.5 mg) as a white solid; 3b(i)-Rp: $^1$H NMR ($CD_3OD$, 400 MHz) δ7.87 (d, J=8.4 Hz, 1H), 7.36 (t, J=8.0 Hz, 2H), 7.28 (d, J=8.8 Hz, 2H), 7.19 (t, J=7.6 Hz, 1H), 6.01 (s, 1H), 5.62 (d, J=8.0 Hz, 1H), 5.03-4.97 (m, 1H), 4.56-4.92 (m, 1H), 4.44-4.39 (m, 1H), 4.16-4.13 (m, 1H), 4.10-4.05 (m, 1H), 3.86 (d, J=9.2 Hz, 1H), 1.34 (d, J=7.2 Hz, 3H), 1.25 (d, J=6.4 Hz, 6H), 1.16 (s, 3H); $^{31}$P NMR (CD$_3$OD, 162 MHz) δ68.18; ESI-LCMS: m/z=544 [M+H]$^+$. 3b(ii)-Sp: $^1$H NMR (CD$_3$OD, 400 MHz) δ7.89 (d, J=8.0 Hz, 1H), 7.36 (t, J=8.0 Hz, 2H), 7.30 (d, J=8.4 Hz, 2H), 7.20 (t, J=8.0 Hz, 1H), 5.99 (s, 1H), 5.60 (d, J=8.4 Hz, 1H), 5.03-4.97 (m, 1H), 4.56-4.51 (m, 1H), 4.35-4.30 (m, 1H), 4.14-4.10 (m, 2H), 3.83 (d, J=9.2 Hz, 1H), 1.39 (d, J=7.2 Hz, 3H), 1.25 (d, J=6.4 Hz, 6H), 1.17 (s, 3H); $^{31}$P NMR (CD$_3$OD, 162 MHz) δ68.42; ESI-LCMS: m/z=566 [M+Na]$^+$.

(b) Via Crystallization: Compound 3b as a mixture of diastereomers (1:1, 10 g) was dissolved in 100 mL of dichloromethane (DCM)/ether (1:3). Hexane was added dropwise until the solution became cloudy. The solution was left at (room temperature) RT for 5 h and overnight at −20° C. Precipitated crystals were recrystallized from DCM/ether 1:3 v/v, and one more time from DCM/ether 1:2. Compound 3b(i)-Rp (3 g) was obtained as a pure single diastereomer. The mother liquor after first crystallization was concentrated, and then dissolved in isopropanol. Hexane was added (30% by volume). The clear solution was left overnight at RT to produce a small amount of crystals, which were used as seeds. The mother liquor was evaporated and crystallized 2 times from hexane/isopropanol (4:1) to give 2.3 g of 3b(ii)-Sp.

Example 4

Preparation of 2',3'-O-dipropionyl-2'-C-methyluridine 5'-(O-phenyl-N—(S)-1-(isopropoxycarbonyl)ethyl)thiophosphoramidate (4a)

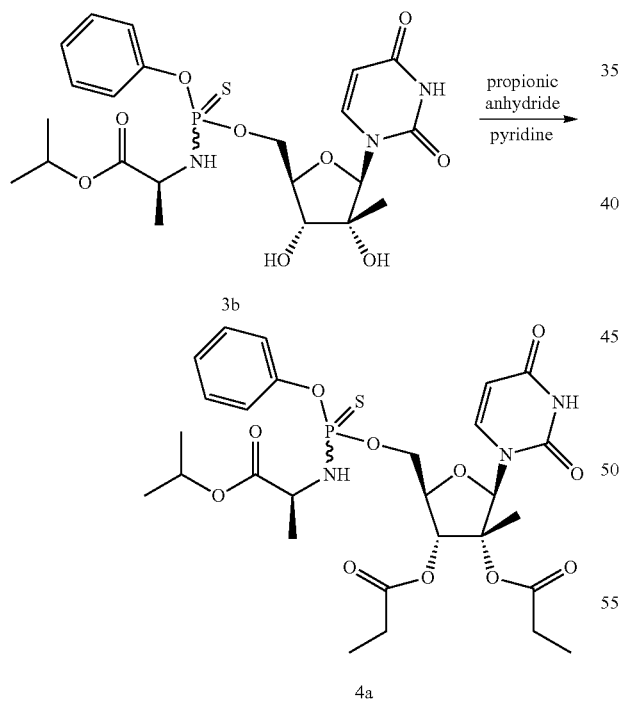

Compound 3b (85 mg, 0.156 mmol) was dissolved in 3 mL of dry pyridine. Propionic anhydride (0.1 mL, 0.624 mmol) was added, and the mixture left for 18 hours at ambient temperature. Water (7 mL) and ethyl acetate (7 mL) were added. The organic phase was separated, and the aqueous phase was extracted with ethyl acetate (2×5 mL). The combined organic extracts were washed with water, brine, dried over Na$_2$SO$_4$, and evaporated. The resulting oil was purified by flash chromatography using a gradient of methanol in dichloromethane from 0 to 4%. The fractions containing phosphorothioate were combined and concentrated in vacuum. Repurification by RP HPLC using a gradient of methanol in water from 50% to 100% yielded 44 mg of product 4a. $^{31}$P NMR (CDCl$_3$, 67.71, 67.74) and mass spectral analysis (M−H$^-$, 654.5) were consistent with the desired product 4a as near 1:1 mixture of diastereomers at the phosphorus chiral center.

Example 5

Preparation of 2'-deoxy-2'-α-fluoro-2'-β-C-methyluridine 5'-(O-phenyl-N—(S)-1-(isopropoxycarbonyl)ethyl)thiophosphoramidate (3c)

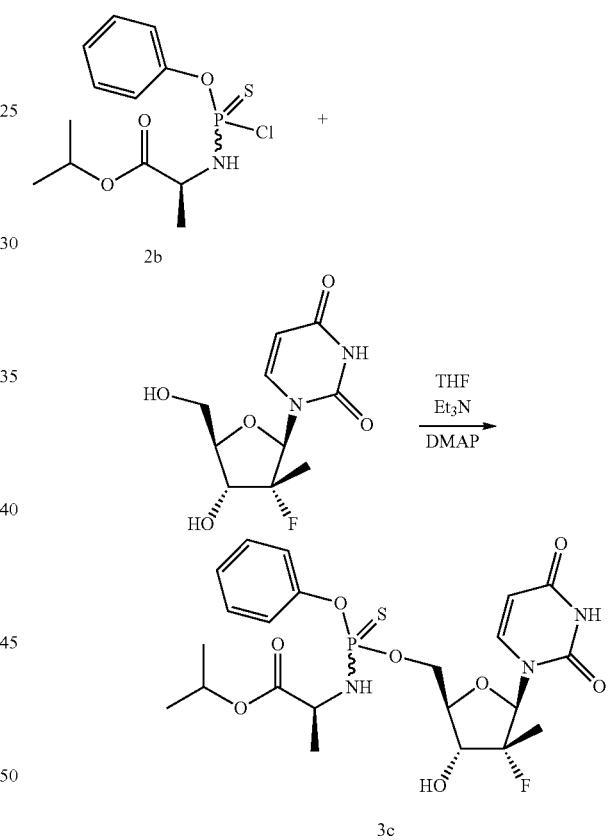

2'-Deoxy-2'-fluoro-2'-methyluridine (200 mg, 0.62 mmol) was suspended in dry THF (20 mL) under N$_2$. A solution of 2b in dry THF (3 mL, 3 mmol), DMAP (4-dimethylaminopyridine) (100 mg, 0.9 mmol) and triethylamine (1 mL, 7 mmol) were added at RT. The reaction was stirred at 80° C. for 18 hrs. The solvents were removed, and the residue was purified by column and RP HPLC (HCOOH system) to give 3c as a white solid (3.5 mg). $^1$H NMR (CDCl$_3$) δ8.49, 8.31 (m, 1H), 7.49, 7.43 (2d, J=8.0 Hz, 1H), 7.31, 7.26 (m, 2H), 7.19, 7.11 (m, 3H), 6.17, 6.11 (2d, J=7.2 Hz, 1H), 5.62, 5.53 (2d, 1H), 4.99, 4.93 (m, 1H), 4.54, 4.27 (m, 2H), 4.08, 4.02 (m, 3H), 3.89, 3.83 (m, 1H), 1.36, 1.22 (m, 6H), 1.20, 1.12 (m, 6H). $^{31}$P NMR (CDCl$_3$) δ68.08, 67.05. LCMS m/z 545.8 (MH$^+$).

Example 6

Preparation of 2'-deoxy-2'-α-fluoro-2'-β-C-methyluridine 5'-(O-phenyl-N—(S)-1-(cyclohexoxycarbonyl)ethyl)thiophosphoramidate (3d)

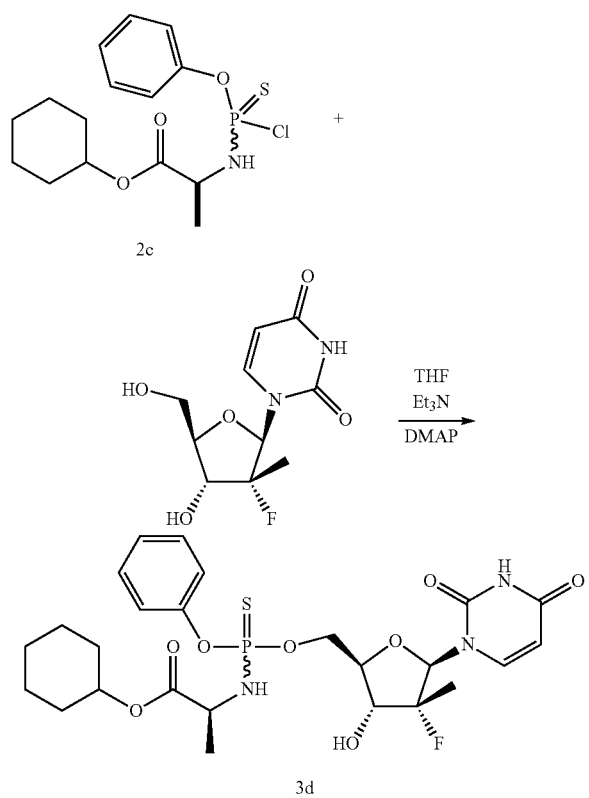

Compound 3d was prepared using the procedure for preparing compound 3c, with 2c in place of 2b. $^1$H NMR (DMSO-d$_6$) δ11.55 (s, 1H), 7.61 (d, J=8.4 Hz, 0.43H), 7.57 (d, J=7.6 Hz, 0.56H), 7.40 (m, 2H), 7.21 (overlap, 3H), 6.68 (m, 1H), 6.04 (m, 1H), 5.95 (d, J=7.6 Hz, 0.40H), 5.88 (d, J=6.8 Hz, 0.60H), 5.57 (s, 0.50H), 5.55 (s, 0.50H), 4.64 (s, 1H), 4.39 (m, 1H), 4.23 (m, 1H), 4.09-3.86 (m, 2H), 3.84 (m, 1H), 1.63 (s, 2H), 1.45 (s, 2H), 1.36 (brs, 1H), 1.34-1.29 (m, 11H). $^{31}$P NMR (DMSO-d$_6$) δ67.96, 67.89; MS m/z 586.2 (MH$^+$).

Example 7

Preparation of 2'-deoxy-2'-α-fluoro-2'-β-C-methyluridine 5'-(O-phenyl-N—(S)-1-(neopentoxycarbonyl)ethyl)thiophosphoramidate (3e)

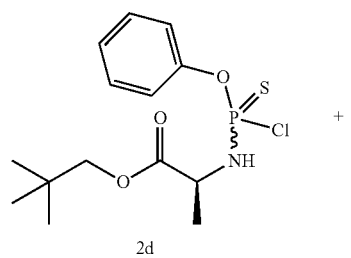

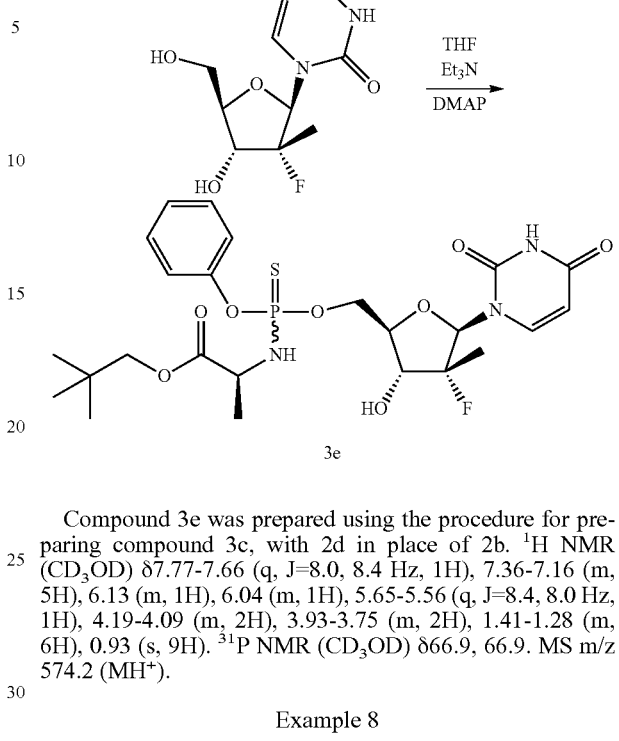

Compound 3e was prepared using the procedure for preparing compound 3c, with 2d in place of 2b. $^1$H NMR (CD$_3$OD) δ7.77-7.66 (q, J=8.0, 8.4 Hz, 1H), 7.36-7.16 (m, 5H), 6.13 (m, 1H), 6.04 (m, 1H), 5.65-5.56 (q, J=8.4, 8.0 Hz, 1H), 4.19-4.09 (m, 2H), 3.93-3.75 (m, 2H), 1.41-1.28 (m, 6H), 0.93 (s, 9H). $^{31}$P NMR (CD$_3$OD) δ66.9, 66.9. MS m/z 574.2 (MH$^+$).

Example 8

Preparation of 2'-C-methyluridine 5'-(O-phenyl-N—(S)-1-(neopentoxycarbonyl)ethyl)thiophosphoramidate (3f)

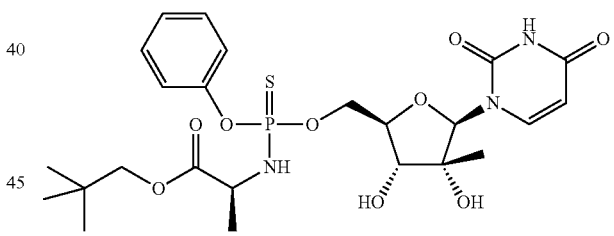

2'-C-methyluridine (77 mg, 0.3 mmol) was dissolved in 10 mL of anhydrous acetonitrile and 2 mL of N-methylimidazole. Compound 2d was added (0.3 g, 0.9 mmol) and the mixture was heated at 70° C. for 2 h. The solvent was removed under reduced pressure. The residue was dissolved in 30 mL of ethyl acetate, washed with 10% citric acid (2×10 mL), water, brine, dried over Na$_2$SO$_4$, and concentrated. The crude product was purified by flash chromatography on silica gel with methanol in dichloromethane (0 to 10%) to give 3f (224 mg) as light-tan solid. An analytical sample was obtained as a colorless solid by RP HPLC purification in gradient of methanol in water from 10% to 95% on a Synergy 4u Hydro-RP column (Phenominex). $^1$H NMR (CDCl$_3$): δ 9.90 (bs, 1H), 7.62-7.58 (m, 1H), 7.32-7.28 (m, 2H), 7.20-7.16 (m, 2H), 5.97 & 5.94 (2s, 1H), 5.65 & 5.52 (2d, 1H), 4.54-4.46 (m, 1H), 4.39-4.24 (m, 1H), 4.20-4.04 (m, 3H), 3.85-3.79 (m, 1H), 3.73-3.65 (m, 2H), 1.39-1.32 (dd, 3H), 1.16-1.14 (d, 1H), 0.87-0.86 (m, 9H). $^{31}$P NMR: δ67.85, 67.16 (1:1 mixture of diastereomers); ESI-LCMS: m/z 570.4 [M+H]$^+$.

Example 9

Preparation of 2'-C-Methyluridine 5'-(O-phenyl-N—(S)-1-(cyclohexoxycarbonyl)ethyl)thiophosphoramidate (3g)

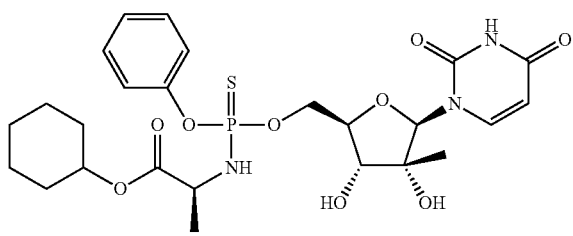

Compound 3g was prepared using the procedure for preparing compound 3f, with 2c in place of 2d. $^1$H NMR (CDCl$_3$): δ 9.40 (bs, 1H), 7.60-7.55 (m, 1H), 7.29-7.11 (m, 5H), 5.95 & 5.92 (2s, 1H), 5.63 & 5.53 (2d, 1H), 4.75-4.68 (m, 1H), 4.50-4.23 (m, 2H), 4.10-4.00 (m, 3H), 3.74-3.72 (m, 1H), 1.80-1.05 (m, 17H); $^{31}$P NMR: δ67.80, 67.16 (3:4 mixture of diastereomers); ESI-LCMS: m/z 582.5 [M+H]$^+$.

Example 10

Preparation of 2'-C-Methyluridine 5'-(O-(1-naphthyl)-N—(S)-1-(isopropoxycarbonyl)ethyl)thiophosphoramidate (3h)

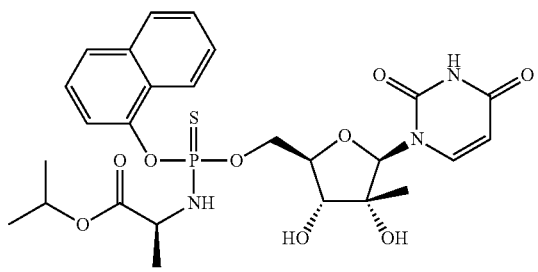 [SMILES: CC(C)OC(=O)[C@H](C)NP(=S)(OC[C@H]1O[C@@H](n2ccc(=O)[nH]c2=O)[C@](C)(O)[C@@H]1O)Oc1cccc2ccccc12]

Compound 3h was prepared using the procedure for preparing compound 3f, with 2e in place of 2d. $^1$H NMR (CDCl$_3$): δ 9.10 (bs, 1H), 8.05-7.20 (m, 9H), 5.95&5.92 (2s, 1H), 5.38 & 5.33 (2d, 1H), 4.99-4.91 (m, 1H), 4.59-4.28 (m, 2H), 4.20-4.03 (m, 3H), 3.72-3.69 (m, 1H), 1.36-1.27 (2d, 3H), 1.20-1.11 (m, 6H), 1.06-1.04 (2s, 3H); $^{31}$P NMR: δ 67.92, 67.28 (2:3 mixture of diastereomers); ESI-LCMS: m/z 592.2 [M+H]$^+$.

Example 11

Preparation of 2'-C-Methyluridine 5'-(O-(1-naphthyl)-N—(S)-1-(cyclohexoxycarbonyl)ethyl)thiophosphoramidate (3i)

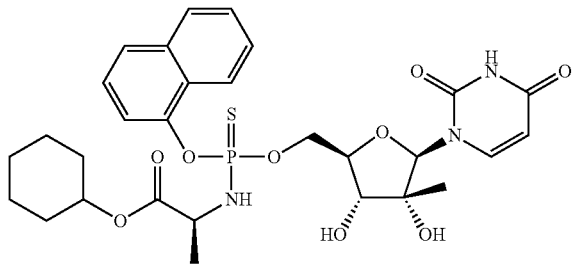 [SMILES: C[C@H](NP(=S)(OC[C@H]1O[C@@H](n2ccc(=O)[nH]c2=O)[C@](C)(O)[C@@H]1O)Oc1cccc2ccccc12)C(=O)OC1CCCCC1]

Compound 3i was prepared using the procedure for preparing compound 3f, with 2f in place of 2d. $^1$H NMR (CDCl$_3$): δ 9.80 (bs, 1H), 8.05-7.30 (m, 9H), 5.92 & 5.91 (2s, 1H), 5.38-5.29 (2d, 1H), 4.79-4.69 (m, 1H), 4.59-4.32 (m, 1H), 4.50-4.46 (m, 1H), 4.38-4.03 (m, 4H), 3.70-3.66 (m, 1H), 1.80-1.00 (m, 17H); $^{31}$P NMR: δ67.74, 67.43 (1:1 mixture of diastereomers); ESI-LCMS: m/z 632.5 [M+H]$^+$.

Example 12

Preparation of 2'-C-Methyluridine 5'-(O-(1-naphtyl)-N—(S)-1-(neopentoxycarbonyl)ethyl)thiophosphoramidate (3i)

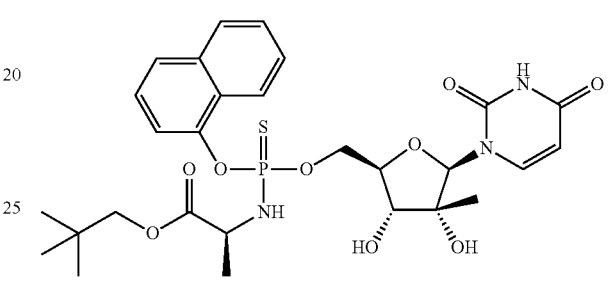

Compound 3j was prepared using the procedure for preparing compound 3f, with 2g in place of 2d. $^1$H NMR (CDCl$_3$): δ 9.80 (bs, 1H), 8.05-7.30 (m, 9H), 5.90 & 5.87 (2s, 1H), 5.38 &5.30 (2d, 1H), 4.60-3.60 (m, 9H), 3.72-3.69 (m, 1H), 1.41 & 1.39 (2d, 3H), 1.08 & 1.06 (2s, 3H), 0.87 & 0.86 (2s, 9H); $^{31}$P NMR: δ68.01, 67.35 (1:1 mixture of diastereomers); ESI-LCMS: m/z 620.8 [M+H]$^+$.

Example 13

Preparation of 5'-dideuterated 2'-C-methyluridine 5'-(O-phenyl-N—(S)-1-(isopropoxycarbonyl)ethyl)thiophosphoramidate (3l)

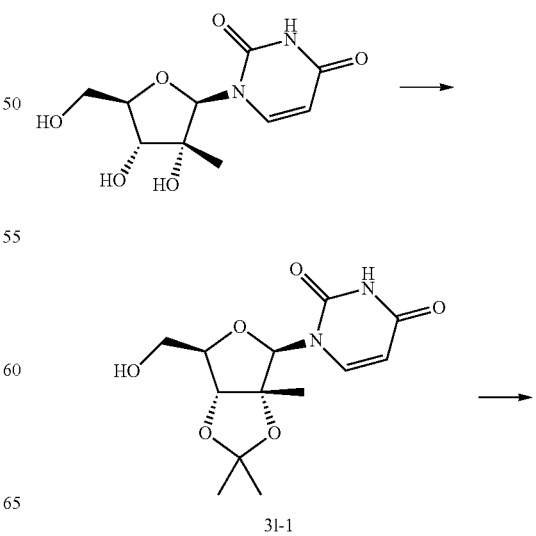

3l-1

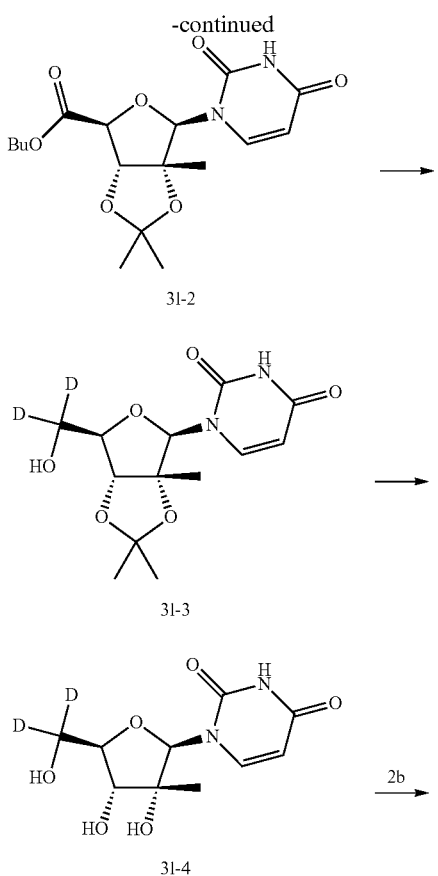

31-2

31-3

31-4

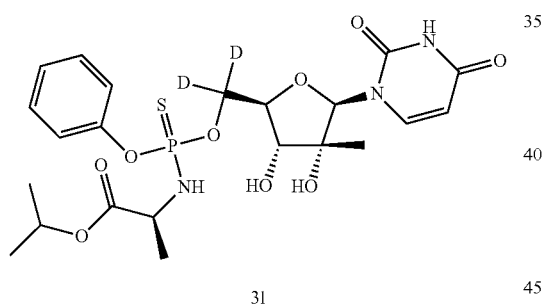

31

Step 1. Compound 31-1—To a suspension of 2'-C-methyluridine (2.50 g, 7.6 mmol) in acetone (100 mL) were added p-Toluenesulfonic acid monohydrate (1.76 g, 9.2 mmol) and 2,2-dimethoxypropane (20 mL). The mixture was stirred at RT for 16 h. Then saturated $NaHCO_3$ was added to adjust the pH to between approximately 6-7. The suspension was concentrated and the residue was purified on a silica gel column (5-7% MeOH in DCM) to give 31-1 as a white solid (2.30 g, 82%).

Step 2. Compound 31-2—To a solution of 31-1 (2.30 g, 7.7 mmol) in anhydrous DCM (50 mL) was added pyridinium dichromate (PDC) (5.80 g, 15.4 mmol), followed by acetic anhydride (7.87 g, 77.18 mmol) and tert-butyl alcohol (11.40 g, 154.0 mmol). The resulting solution was stirred at RT for 3 h. The mixture was loaded on a very short silica gel column and eluted with EA. The fractions containing 31-2 were combined and concentrated. Chromatography on silica gel with EA/hexanes (1:1 to 3:2) gave 31-2 as a white foam (2.07 g, 73%).

Step 3. Compound 31-3—$NaBD_4$ (1.10 g, 26.22 mmol) was added to a solution of 31-2 (2.07 g, 6.9 mmol) at RT and the resulting mixture stirred at 80° C. overnight. The reaction was quenched with acetic acid (AcOH) at 0° C. The mixture was diluted with EA and washed with brine. The organic phase was dried and concentrated. The residue was purified by chromatography on silica gel (2-5% MeOH in DCM) to give 31-3 as a white foam (854 mg, 50.83%).

Step 4. Compound 31-4—Compound 31-3 (850 mg, 2.8 mmol) was dissolved in 95% trifluoroacetic acid (TFA)/5% water at 0° C. and then stirred at RT for 30 minutes. The solvent was evaporated and the residue was purified by chromatography on silica gel (5-10% MeOH in DCM) to give 31-4 (663 mg, 90%). $^1H$ NMR ($CD_3OD$, 400 MHz) δ 8.16 (d, 1H), 5.98 (s, 1H), 5.69 (d, 1H), 3.86-3.92 (m, 2H), 1.13 (s, 3H); ESI-MS: m/z 261.1 $[M+H]^+$.

Step 5. Compound 31—To a suspension of 31-4 (150 mg, 0.57 mmol) in anhydrous acetonitrile (1.0 mL) was added N-methylimidazole (0.5 mL), followed by 2b (1.7 mmol, 1 M in $CH_3CN$) at RT. The resulting solution was stirred at RT for 24 h. The mixture was diluted with EA and concentrated. The residue was purified by RP HPLC (0.5 HCOOH in MeCN and water) to give 31 as a white solid (two isomers, 122 mg, 39%). $^1H$ NMR ($CD_3OD$, 400 MHz) δ7.79, 7.87 (2d, J=8.0 Hz, 1H), 7.20-7.38 (m, 5H), 5.98, 6.01 (2s, 1H), 5.59, 5.62 (2d, J=8.0 Hz, 1H), 4.99-5.01 (m, 1H), 4.10-4.12 (m, 2H), 3.82-3.84 (m, 1H), 1.34, 1.38 (2d, J=7.2 Hz, 3H), 1.24, 1.25 (2s, 3H), 1.17, 1.26 (2d, J=6.0 Hz, 6H); $^{31}P$ NMR ($CD_3OD$, 162 MHz) δ68.42, 68.21; ESI-LCMS: m/z 546.1 $[M+H]^+$.

Example 14

Preparation of 3'-O-acetyl-5'-dideuterated 2'-C-methyluridine 5'-(O-phenyl-N—(S)-1-(isopropoxycarbonyl)ethyl)thiophosphoramidate (4d)

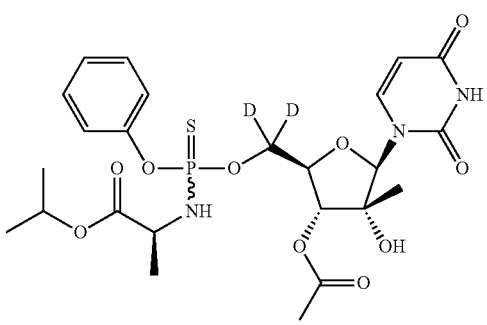 [SMILES: [2H]C([2H])(OP(=S)(N[C@@H](C)C(=O)OC(C)C)Oc1ccccc1)[C@H]1O[C@@H](n2ccc(=O)[nH]c2=O)[C@](C)(O)[C@@H]1OC(C)=O]

To a suspension of 31 (750 mg, 1.38 mmol) in dry pyridine (50 mL) was added acetic anhydride (704 mg, 6.9 mmol). The reaction mixture was heated at 35° C. for 16 h. The reaction was quenched with water and the solvent was removed. The residue was purified on a silica gel column (1~3% MeOH in DCM) to give 4d as a white solid (710 mg, 88%). $^1H$ NMR ($CD_3OD$, 400 MHz) δ7.78, 7.84 (2d, J=8.0 Hz, 1H), 7.38-7.34 (m, 2H), 7.17-7.38 (m, 5H), 5.99, 6.02 (2s, 1H), 5.59, 5.61 (2d, J=8.0 Hz, 1H), 5.13, 5.17 (2d, J=9.2 Hz, 1H), 5.04-4.97 (m, 1H), 4.52-4.25 (m, 3H), 4.14-4.06 (m, 1H), 2.16 (s, 3H), 1.35, 1.38 (2d, J=7.2 Hz, 1H), 1.18-1.24 (m, 9H); $^{31}P$ NMR ($CD_3OD$, 162 MHz) δ68.90, 68.23; ESI-LCMS: m/z=585.9 $[M+H]^+$.

Example 15

Preparation of 2'-C-methylthymidine 5'-(O-phenyl-N—(S)-1-(isopropoxycarbonyl)ethyl)thiophosphoramidate (3m)

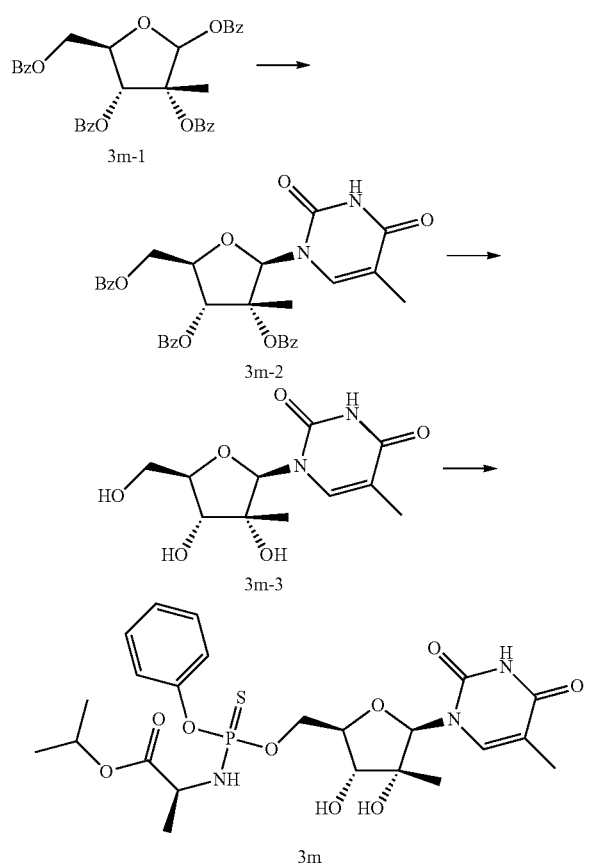

Step 1. Compound 3m-2—To a suspension of thymine (0.869 g, 5.63 mmol) in acetonitrile (27 mL) was added N,O-bis(trimethylsilyl)acetamide (5 mL) and the mixture was refluxed for 2 hours. The resulting solution was cooled to ambient temperature and a solution of 3m-1 (2.0 g, 3.45 mmol) in acetonitrile (10 mL) was added. Then SnCl$_4$ (1.6 mL, 13.6 mmol) was slowly added and the reaction mixture was heated to 100° C. for 5 h. The reaction mixture was cooled to 0° C. and solid NaHCO$_3$ was added, and a minimal amount of ice was added into the mixture. The reaction mixture was partially concentrated, diluted with EA and treated with a cold saturated aqueous solution of NaHCO$_3$. The salts were filtered through celite and extracted with EA. The organic phase was washed successively with a saturated aqueous solution of NaHCO$_3$ and brine, dried by anhydrous Na$_2$SO$_4$, and concentrated to dryness. The residue was purified by silica gel column (0-20% EA in CH$_2$Cl$_2$) to give 3m-2 (1.6 g, 85%) as a white solid.

Step 2. Compound 3m-3—Compound 3m-2 (1.6 g, 2.74 mmol) was dissolved in methanolic ammonia (120 mL, saturated at 0° C.). The mixture was stirred at RT for 20 hours. The solution was evaporated to dryness and the residue was purified on a silica gel column (DCM:MeOH=100:1 to 50:1) to give 3m-3 as a light yellow foam (620 mg, 83.1%). $^1$H NMR (MeOD, 400 MHz) δ8.05 (s, 1H), 5.93 (s, 1H), 4.01-3.97 (m, 1H), 3.91-3.86 (m, 2H), 3.80~3.76 (m, 1H), 1.85 (s, 3H), 1.13 (s, 3H).

Step 3. Compound 3m—To a suspension of 3m-3 (150 mg, 0.55 mmol) in anhydrous CH$_3$CN (3 mL) was added N-methylimidazole (0.4 mL), followed by addition of 2b (530 mg, 1.65 mmol) in anhydrous CH$_3$CN (1 mL). The resulting solution was stirred at RT for 12 h. The reaction was quenched with water and the solvent was removed. The residue was purified by RP HPLC (0.5 HCOOH in MeCN and water) to give compound 3m as a white solid (two isomers, 43 mg, 14.0%). $^1$H NMR (MeOD, 400 MHz) δ7.54, 7.64 (2s, 1H), 7.16~7.36 (m, 5H), 5.98, 6.01 (2s, 1H). 5.02~4.94 (m, 1H), 4.56~4.52 (m, 1H), 4.43~4.29 (m, 1H), 4.17~4.02 (m, 2H), 3.94~3.84 (m, 1H), 1.81, 1.84 (2s, 3H), 1.31, 1.36 (2d, J=7.2 Hz, 3H), 1.25~1.23 (m, 6H), 1.15 (s, 3H); $^{31}$P NMR (MeOD, 162 MHz) δ69.17, 68.68; ESI-LCMS: m/z=558.1 [M+H]$^+$.

Example 16

Preparation of 1-(2-amino-6-cyclopropylaminopurin-9-yl)-2-C-methyl-β-D-ribofuranose 5-(O-phenyl-N—(S)-1-(isopropoxycarbonyl)ethyl)thiophosphoramidate (3z)

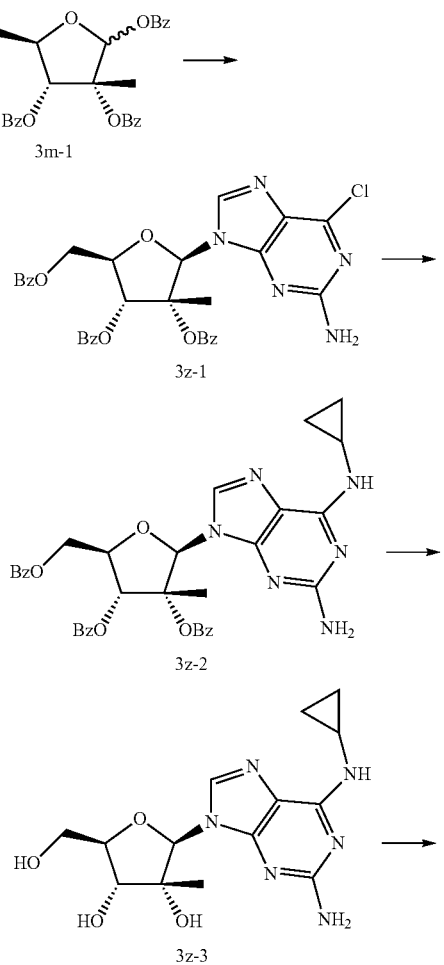

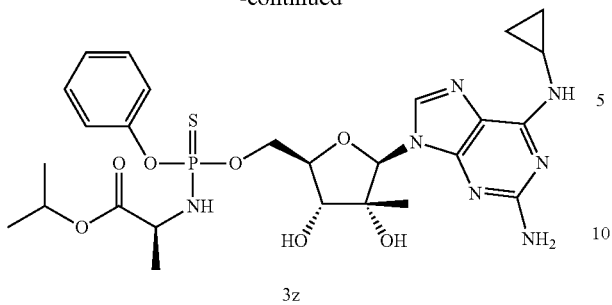

3z

Step 1. Compound 3z-1—To a solution of compound 3m-1 (20.0 g, 34.47 mmol) and 6-chloro-2-aminopurine (5.90 g, 34.91 mmol) in anhydrous MeCN (300 mL) was added 1,8-diazabicycloundec-7-ene (DBU) (15.8 g, 103.9 mmol) at 0° C. The mixture was stirred at 0° C. for 5 minutes and then trimethylsilyltrifluoromethane sulfonate (TMSOTf) (27.0 mL, 137.8 mmol) was added dropwise. Stirring was continued for another 30 minutes and then the mixture was heated to 70° C. and stirred for 18 hour. The reaction was then cooled to RT and diluted with EA. The solution was washed with saturated NaHCO$_3$ and brine. The organic layer was dried over Na$_2$SO$_4$ and then concentrated. The residue was purified by a silica gel column (20~40% EA in PE) and then RP HPLC (0.5% HCOOH in MeCN and water) to give compound 23-2 as a white solid (5.4 g, 25.6%). $^1$H NMR (DMSO-d6, 400 MHz) δ8.38 (s, 1H), 7.97-8.05 (m, 4H), 7.82-7.85 (m, 2H), 7.58-7.66 (m, 3H), 7.39-7.53 (m, 4H), 7.18-7.37 (m, 2H), 7.19 (brs, 2H), 6.61 (s, 1H), 5.94 (d, J=4.8 Hz, 1H), 4.70-4.89 (m, 3H), 1.58 (s, 3H).

Step 2. Preparation of compound 3z-2—Compound 3z-1 (100 mg, 0.16 mmol) and THF (10 mL) were placed into a dry flask and then cyclopropyl amine (1.61 g, 28.21 mmol) was added. After the addition, the mixture was heated to reflux overnight. Then the solvent was removed and the residue was purified on a silica gel column (2~10% MeOH in DCM) to give 3z-2 as a white solid (82 mg, 77.6%).

Step 3. Compound 3z-3—Compound 3z-2 (402 mg, 0.62 mmol) was dissolved in methanolic ammonia (20 mL, saturated at 0° C.) and the mixture was stirred at RT for 12 hours. The solvent was removed and the residue was purified on a silica gel column (2~10% MeOH in DCM) to give 3z-3 as a white solid (149 mg, 72.4%). $^1$H NMR (CD$_3$OD, 400 MHz) δ8.14 (d, J=11.2 Hz, 1H), 5.93 (s, 1H), 4.22 (d, J=8.4 Hz, 1H), 4.03 (d, J=10.8 Hz, 2H), 3.86 (d, J$_1$=12.8 Hz, J$_2$=3.2 Hz, 1H), 2.91 (s, 1H), 0.79-0.98 (m, 2H), 0.61-0.70 (m, 2H); ESI-LCMS: m/z 337.1 [M+H]$^+$, 360.1 [M+Na]$^+$.

Step 4. Compound 3z—To a stirred suspension of 3z-3 (110 mg, 0.33 mmol) in anhydrous acetonitrile (1.0 mL) was added N-methylimidazole (0.5 mL) followed by slow addition of 2b (1.05 g, 3.273 mmol, 1M in MeCN) at RT. The resulting solution was stirred at 50° C. for 4 hours and then diluted with EA. The solution was washed with 10% AcOH/H$_2$O, brine, 5% NaHCO$_3$ aqueous solution, and dried over Na$_2$SO$_4$. The solvent was removed and the residue was purified by RP HPLC (0.5% HCOOH in MeCN and water) to give 3z as a white solid (two isomers, 131 mg, 64%). $^1$H NMR (CD$_3$OD, 400 MHz) δ7.96, 8.00 (2s, 1H), 7.28-7.36 (m, 5H), 7.14-7.20 (m, 1H), 5.96, 5.99 (2s, 1H), 4.92-4.98 (m, 1H), 4.37-4.57 (m, 2H), 4.04-4.23 (m, 3H), 2.91 (br, 1H), 1.36, 1.32 (2d, J=7.2 Hz, 3H), 1.17-1.23 (m, 7H), 0.96, 0.99 (2s, 3H), 0.87-0.90 (m, 2H), 0.63-0.69 (m, 2H); $^{31}$P NMR (CD$_3$OD, 162 MHz) δ 68.53, 68.38; ESI-LCMS: m/z 622.2 [M+H]$^+$, 644.2 [M+Na]$^+$.

Example 17

Preparation of 1-(2,6-diaminopurin-9-yl)-2-C-methyl-β-D-ribofuranose 5-(O-phenyl-N—(S)-1-(isopropoxycarbonyl)ethyl)thiophosphoramidate (3aa)

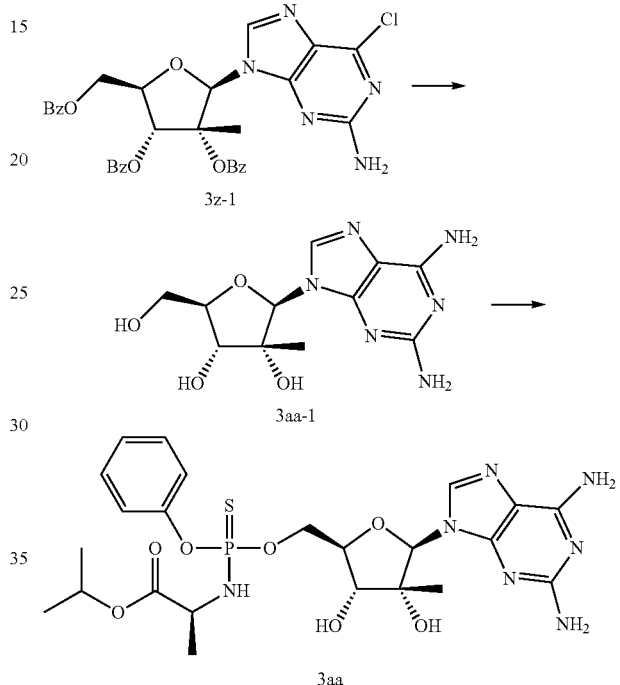

Step 1. Compound 3aa-1—Compound 3z-1 (1.01 g, 1.56 mmol) was suspended in aqueous ammonia (28%, 40 mL) and dioxane (4 mL) in a sealed vessel. The mixture was heated at 100° C. overnight. Then the solvent was removed and the residue was purification on a silica gel column (2~10% MeOH in DCM) to give 3aa-1 as a white solid (418 mg, 88.9%). $^1$H NMR (CD$_3$OD, 400 MHz) δ88.17 (s, 1H), 5.93 (s, 1H), 4.24 (d, J=8.8 Hz, 1H), 4.01-4.04 (m, 2H), 3.86 (dd, J$_1$=12.8 Hz, J$_2$=3.2 Hz, 1H), 0.96 (s, 3H); ESI-LCMS: m/z 297.1 [M+H]$^+$.

Step 2. Compound 3aa—To a stirred suspension of 3aa-1 (62 mg, 0.20 mmol) in anhydrous acetonitrile (1.0 mL) was added N-methylimidazole (0.5 mL) followed by slow addition of 2b (652 mg, 2.02 mmol, 1M in MeCN) at RT. The resulting solution was stirred at RT for 24 hours. The solution was diluted with EA and washed with 10% AcOH in H$_2$O, brine, 5% NaHCO$_3$ aqueous solution, and dried over Na$_2$SO$_4$. The solvent was removed and the residue was purified by RP HPLC (0.5% HCOOH in MeCN and water) to give 3aa as a white solid (31 mg, 25.6%). $^1$H NMR (DMSO-d6, 400 MHz) δ77.81, 7.83 (2s, 1H), 7.33-7.38 (m, 2H), 7.17-7.25 (m, 3H), 6.58-6.78 (m, 3H), 5.81-5.83 (m, 3H), 5.32-5.43 (m, 1H), 5.19, 5.20 (2s, 1H), 4.78-4.85 (m, 1H), 4.21-4.42 (m, 2H), 3.87-4.15 (m, 3H), 1.24-1.26 (m, 3H), 1.08-1.15 (m, 6H), 0.83, 0.84 (2s, 3H); $^{31}$P NMR (DMSO-d6, 162 MHz) δ 68.19, 67.90; ESI-LCMS: m/z 589.1[M+H]$^+$, 604.1 [M+Na]$^+$.

Example 18

Preparation of 1-(2-amino-6-allylaminopurin-9-yl)-2-C-methyl-β-D-ribofuranose 5-(O-phenyl-N—(S)-1-(isopropoxycarbonyl)ethyl)thiophosphoramidate (3bb)

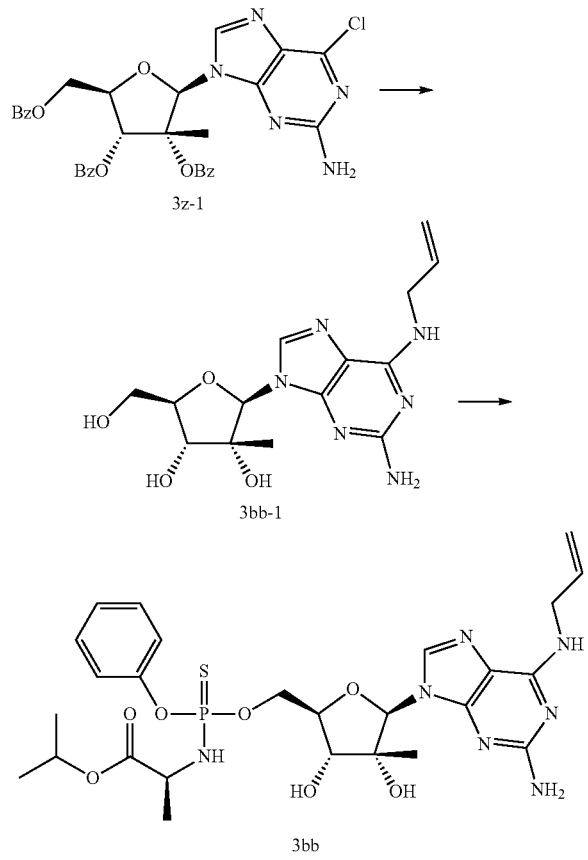

Step 1. Compound 3bb-1—A mixture of 3z-1 (802 mg, 1.27 mmol) and ally amine (7.26 g, 127.3 mmol) in THF (30 mL) was refluxed overnight. The solvent was removed and the residue was purified on a silica gel column (2~10% MeOH in DCM) to give crude 3bb-1 (405 mg), which was dissolved in 20 mL methanolic ammonia (saturated at 0° C.). The mixture was stirred at RT for 12 hours. The solvent was removed and the residue was purified on a silica gel column (2~10% MeOH in DCM) to give 3bb-1 as a white solid (153 mg, 35.9%). $^1$H NMR (CD$_3$OD, 400 MHz) δ8.10 (s, 1H), 5.92-6.03 (m, 2H), 5.27 (d, J=17.6 Hz, 1H), 5.14 (d, J=10.4 Hz, 1H), 4.18-4.24 (m, 3H), 4.03 (d, J=10.0 Hz, 2H), 3.86 (d, J=10.4 Hz, 1H), 0.95 (s, 3H); ESI-LCMS: m/z 337.1 [M+H]$^+$.

Step 2. Compound 3bb—To a stirred suspension of 3bb-1 (200 mg, 0.59 mmol) in anhydrous acetonitrile (1.0 mL) was added N-methylimidazole (0.5 mL) followed by 2b (573 mg, 1.79 mmol, 1M in MeCN) at RT. The resulting solution was stirred at RT for 24 hrs and then was diluted with EA. The solution was washed with 10% AcOH in H$_2$O, brine and 5% NaHCO$_3$ aqueous solution. The organic solution was dried and concentrated. The residue was purified by RP HPLC (0.5% HCOOH in MeCN and water) to give 3bb as a white solid (two isomers, 155 mg, 40.8%). $^1$H NMR (CD$_3$OD, 400 MHz) δ 7.94, 7.98 (2s, 1H), 7.29-7.34 (m, 4H), 7.18-7.28 (m, 1H), 5.96-6.09 (m, 2H), 5.27, 5.31 (2s, 1H), 5.15, 5.17 (2d, J=1.2 Hz, 1H), 4.92-4.96 (m, 1H), 4.35-4.57 (m, 2H), 4.01-4.28 (m, 5H), 1.32, 1.36 (2d, J=7.2 Hz, 3H), 1.16-1.25 (m, 6H), 0.97 (2s, 3H); $^{31}$P NMR (CD$_3$OD, 160 MHz) δ 68.51, 68.40; ESI-LCMS: m/z 622.1 [M+H]$^+$, 644.1 [M+Na]$^+$.

Example 19

Preparation of 1-(2-amino-6-chloropurin-9-yl)-2-C-methyl-β-D-ribofuranose 5-(O-phenyl-N—(S)-1-(isopropoxycarbonyl)ethyl)thiophosphoramidate (3cc)

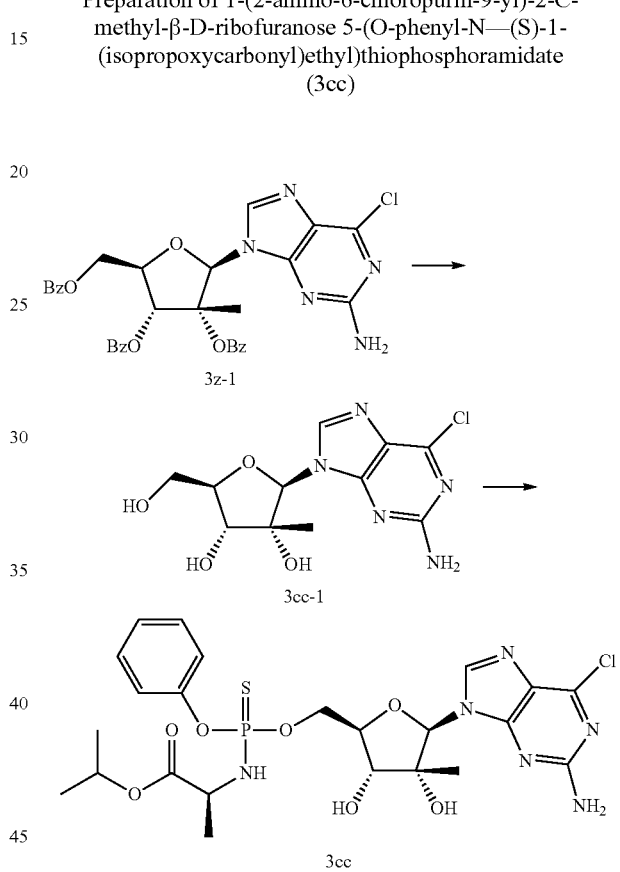

Step 1. Compound 3cc-1—Compound 3z-1 (506 mg, 0.79 mmol) was dissolved in 100 mL of methanolic ammonia and the mixture was stirred at RT for 12 h. The solvent was removed and the residue was purified on a silica gel column (2~10% MeOH in DCM) to give 3cc-1 as a white solid (204 mg, yield: 79.9%).

Step 2. Compound 3cc—To a stirred suspension of 3cc-1 (198 mg, 0.63 mmol) in anhydrous acetonitrile (1.0 mL) was added N-methylimidazole (0.5 mL) followed by 2b (611 mg, 1.904 mmol, 1M in MeCN) at RT. The resulting solution was stirred at 30-40° C. for 12 hours and then diluted with EA. The solution was washed with 10% AcOH in H$_2$O, brine, and 5% NaHCO$_3$. The organic phase was dried and concentrated. The residue was purified by RP HPLC (0.5% HCOOH in MeCN and water) to give 3cc as a white solid (118 mg, 31.6%). $^1$H NMR (CD$_3$OD, 400 MHz) δ 8.25, 8.28 (2s, 1H), 7.27-7.35 (m, 4H), 7.15-7.18 (m, 1H), 6.02, 6.05 (2s, 1H), 4.93-4.98 (m, 1H), 4.40-4.54 (m, 2H), 4.20-4.27 (m, 2H), 4.05-4.13 (m, 1H), 1.15-1.35 (m, 9H), 0.99, 1.01 (2s, 3H); $^{31}$P NMR (CD$_3$OD, 162 MHz) δ68.66, 68.53; ESI-LCMS: m/z 601.1 [M+H]$^+$.

Example 20

Preparation of 2'-C-methyluridine 5'-(O-phenyl-N—(S)-1-(isopropoxycarbonyl)isobutyl)thiophosphoramidate (3n)

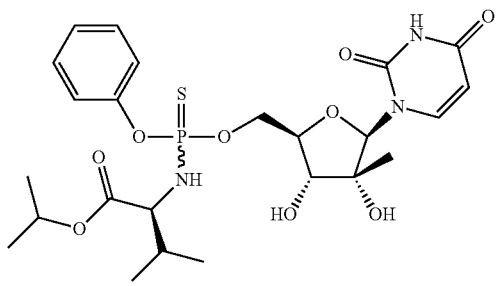 [SMILES: CC(C)OC(=O)[C@@H](NP(=S)(OC[C@H]1O[C@@H](n2ccc(=O)[nH]c2=O)[C@](C)(O)[C@@H]1O)Oc1ccccc1)C(C)C]

To a solution of 2'-C-methyluridine (150 mg, 0.581 mmol) in MeCN (1 mL) and N-methylimidazole (0.7 mL) was added 2h (651 mg, 1.86 mmol). The mixture was stirred at RT for 3 days. The solvent was removed and the residue was purified by RP HPLC (0.1% HCOOH in MeCN and water) to give 3n as a white solid (two isomers, 22 mg, 6.6%). $^1$H NMR (CD$_3$OD, 400 MHz) δ7.76, 7.78 (2d, J=9.2 Hz, 1H), 7.14-7.35 (m, 5H), 5.95, 5.97 (2s, 1H), 5.56, 5.63 (2d, J=8.4 Hz, 1H), 4.95-5.03 (m, 1H), 4.44-4.56 (m, 1H), 4.30-4.41 (M, 1H), 4.08-4.11 (m, 1H), 3.75-3.90 (m, 2H), 2.00-2.07 (m, 1H), 1.12-1.25 (m, 6H), 1.11, 1.15 (2s, 3H), 0.87-0.97 (m, 6H); $^{31}$P NMR (CD$_3$OD, 162 MHz) δ70.38, 69.13; ESI-LCMS: m/z 572 [M+H]$^+$.

Example 21

Preparation of 2'-C-methyluridine 5'-(O-phenyl-N—(S)-1-(isopropoxycarbonyl)isopentyl)thiophosphoramidate (3o)

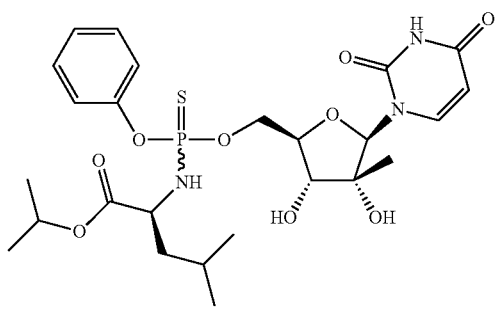 [SMILES: CC(C)C[C@H](NP(=S)(OC[C@H]1O[C@@H](n2ccc(=O)[nH]c2=O)[C@](C)(O)[C@@H]1O)Oc1ccccc1)C(=O)OC(C)C]

Compound 3o was prepared using the procedure for preparing compound 3n, with 2i in place of 2h. $^1$H NMR (CD$_3$OD, 400 M Hz) δ 7.77, 7.84 (2d, J=8.0 Hz, 1H), 7.14-7.35 (m, 5H), 5.96 (2s, 1H), 5.57, 5.62 (2d, J=8.0 Hz, 1H), 4.84-4.98 (m, 1H), 4.46-4.53 (m, 1H), 4.28-4.42 (m, 1H), 3.97-4.12 (m, 2H), 3.80 (2s, 1H), 1.58-1.81 (m, 1H), 1.48-1.56 (m, 2H), 1.20-1.23 (m, 6H), 1.13 (2s, 3H), 0.81-0.92 (m, 6H); $^{31}$P NMR (CD$_3$OD, 400 M Hz) δ 68.56, 69.15; ESI-MS: m/z 586 [M+H]$^+$, m/z 608 [M+Na]$^+$.

Example 22

Preparation of 2'-C-methylguanosine 5'-(O-phenyl-N—(S)-1-(cyclohexoxycarbonyl)ethyl)thiophosphoramidate (3s)

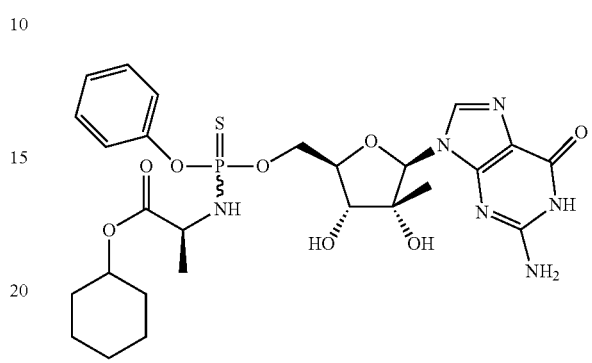

To a stirred suspension of commercial 2'-C-methylguanosine (100 mg, 0.34 mmol) in anhydrous acetonitrile (1.5 mL) was added N-methylimidazole (0.56 mL, 6.8 mmol, 20 equivalent) followed by 2c (303 mg, 0.84 mmol, 1M in MeCN) at RT. The resulting solution was stirred at 40° C. for 3 hours and then diluted with EA. The solution was washed with 10% AcOH in H$_2$O, and brine. The organic layer was separated, dried over anhydrous Na$_2$SO$_4$ and filtered. The filtrate was concentrated in vacuum to give a residue which was purified on a silica gel column (3~7% MeOH in DCM). The collected fractions were concentrated and re-purified on a silica gel column (2~5% MeOH in DCM) to give (127.8 mg, 61.2%) of 3s as a white solid. $^1$H NMR (DMSO-d$_6$, 400 MHz) δ 10.6 (s, 1H), 7.76 (d, J=5.6 Hz, 1H), 7.36-7.31 (m, 2H), 7.22-7.01 (m, 4H), 6.56-6.48 (m, 3H), 5.74 (d, J=8.4 Hz, 1H), 5.42 & 5.35 (2d, each J=6.4 Hz, 1H), 5.16 (d, J=2.8 Hz, 1H), 4.62-3.93 (m, 6H), 1.67-1.58 (m, 5H), 1.33-1.16 (m, 12H), 0.79 (s, 3H); $^{31}$P NMR (DMSO-d$_6$) δ 68.07, 67.71; ESI-LCMS: m/z=623.1 [M+H]$^+$.

Example 23

Preparation of 2'-C-Methylguanosine 5'-(O-phenyl-N—(S)-1-(isopropoxycarbonyl)ethyl)thiophosphoramidate (3r)

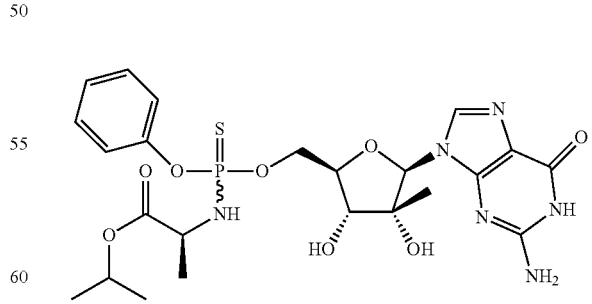

Compound 3r was prepared using the procedure for preparing compound 3s, with 2b in place of 2c. $^1$H NMR (DMSO-d$_6$, 400 MHz) δ10.6 (s, 1H), 7.76 (d, J=1.6 Hz, 1H), 7.34-7.31 (m, 2H), 7.22-7.14 (m, 4H), 6.62-6.48 (m, 3H), 5.74 (d, J=7.2 Hz, 1H), 5.42 & 5.33 (2d, each J=6.8 Hz, 1H), 5.16 (d, J=2.4 Hz, 1H), 4.84-3.77 (m, 1H), 4.42-3.85 (m, 5H), 1.25-1.1 (m, 12H), 0.81 & 0.8 (2s, 3H); $^{31}$P NMR (DMSO-d$_6$) δ 68.23, 67.64; ESI-LCMS: m/z=583.4 [M+H]$^+$.

Example 24

Preparation of 2'-Deoxy-2'-fluoro-2'-C-methyl-6-methoxyguanosine 5'-(O-phenyl-N—(S)-1-(isopropoxycarbonyl)ethyl)-thiophosphoramidate (3t)

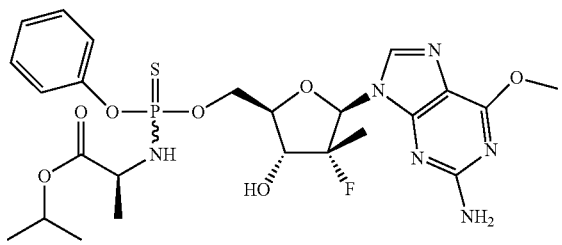 [SMILES: COc1nc(N)nc2c1ncn2[C@@H]1O[C@H](COP(=S)(N[C@@H](C)C(=O)OC(C)C)Oc2ccccc2)[C@@H](O)[C@@]1(C)F]

Compound 3t was prepared using the procedure for preparing compound 3s, with 2b in place of 2c, and with 2'-deoxy-2'-fluoro-2'-C-methyl-6-methoxyguanosine in place of 2'-C-methylguanosine. $^1$H NMR (DMSO-d$_6$, 400 MHz) δ 7.96 & 9.95 (2s, 1H), 7.36-7.29 (m, 2H), 7.21-7.14 (m, 3H), 6.57 (br s, 2H), 6.1 & 6.05 (2d, each J=8.8 Hz, 1H), 5.75 (br s, 2H), 4.82-4.76 (m, 1H), 4.45-4.04 (m, 3H), 3.93 (s, 3H), 1.24-1.13 (m, 3H), 1.12-1.03 (m, 9H); $^{31}$P NMR (DMSO-d$_6$) δ68.21, 67.82; ESI-LCMS: m/z=599.4 [M+H]$^+$.

Example 25

Preparation of 1-(2-Amino-6-methoxypurin-9-yl)-2-C-methyl-β-D-ribofuranose 5-(O-phenyl-N—(S)-1-(isopropoxycarbonyl)ethyl)-thiophosphoramidate (3u)

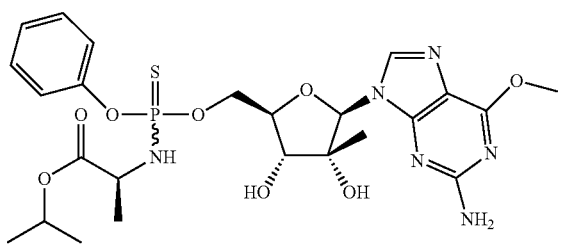 [SMILES: COc1nc(N)nc2c1ncn2[C@@H]1O[C@H](COP(=S)(N[C@@H](C)C(=O)OC(C)C)Oc2ccccc2)[C@@H](O)[C@@]1(C)O]

Compound 3u was prepared using the procedure for preparing compound 3s, with 2b in place of 2c, and with 1-(2-Amino-6-methoxypurin-9-yl)-2-C-methyl-β-D-ribofuranose in place of 2'-C-methylguanosine. $^1$H NMR (DMSO-d$_6$, 400 MHz) δ7.93 (s, 1H), 7.35-7.30 (m, 2H), 7.22-7.14 (m, 3H), 6.61-6.52 (m, 1H), 6.48 (br s, 2H), 5.86 (d, each J=5.2 Hz, 1H), 5.43, 5.32 (br s, 1H), 5.20 (br s, 1H), 4.84-4.76 (m, 1H), 4.36-4.04 (m, 4H), 3.93 (s, 3H), 1.24-1.15 (m, 3H), 1.19-1.06 (m, 6H), 0.8-0.78 (m, 3H); $^{31}$P NMR (DMSO-d$_6$) δ 68.21, 67.65; ESI-LCMS: m/z=597.5 [M+H]$^+$.

Example 26

Preparation of 2'-Deoxy-2'-α-fluoro-2'-β-C-methylguanosine 5'-(O-phenyl-N—(S)-1-(neopentoxycarbonylethyl)thiophosphoramidate (3q)

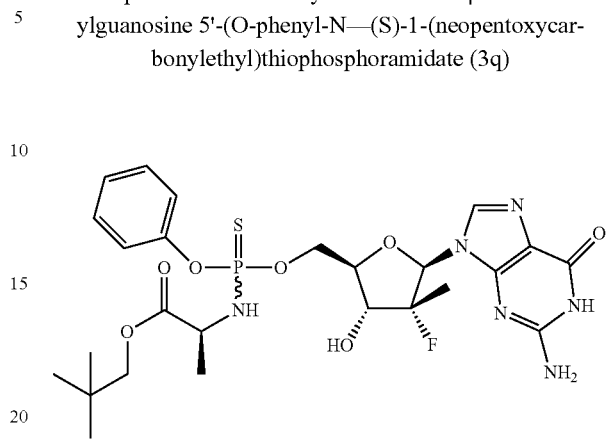

Compound 3q was prepared using the procedure for preparing compound 3s, with 2d in place of 2c, and with 2'-deoxy-2'-α-fluoro-2'-β-C-methylguanosine in place of 2'-C-methylguanosine. $^1$H NMR (DMSO-d$_6$, 400 MHz) δ 10.66 (br s, 1H), 7.79 (s, 1H), 7.36-7.30 (m, 2H), 7.22-7.15 (m, 3H), 6.61-6.52 (m, 1H), 6.48 (br s, 2H), 6.72-6.56 (m, 3H), 6.00, 5.95 (2d, J=8.0, 8.4 Hz, 1H), 5.75-5.82 (m, 1H), 4.43-3.92 (m, 5H), 3.76-3.53 (m, 2H), 1.29-1.24 (m, 3H), 1.09-1.00 (m, 4H), 0.84, 0.81 (2s, 8H); $^{31}$P NMR (DMSO-d$_6$) δ 68.09, 68.03; ESI-LCMS: m/z=613.7 [M+H]$^+$.

Example 27

Preparation of 2'-C-Methyladenosine 5'-(O-phenyl-N—(S)-1-(neopentoxycarbonyl)ethyl)thiophosphoramidate (3dd)

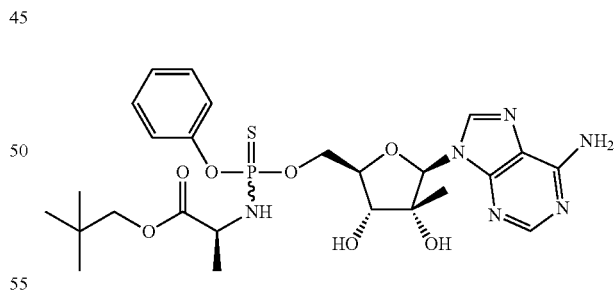

Compound 3dd was prepared using the procedure for preparing compound 3s, with 2d in place of 2c, and with 2'-C-methyladenosine in place of 2'-C-methylguanosine. $^1$H NMR (DMSO-d$_6$, 400 MHz) δ 8.22, 8.2 (2s, 1H), 8.12 (s, 1H), 7.36-7.13 (m, 6H), 6.61-6.55 (m, 1H), 5.97, 5.94 (2s, 1H), 5.40, 5.34, 5.31 (3d, J=6.8, 6.8, 6.0 Hz, 2H), 4.39-3.99 (m, 5H), 3.76-3.61 (m, 2H), 3.42 (d, J=10.4 Hz, 1H), 1.27-1.23 (m, 3H), 0.83, 0.77 (2s, 4H), 0.77, 0.76 (2s, 8H); $^{31}$P NMR (DMSO-d$_6$) δ68.15, 67.74; ESI-LCMS: m/z=595.0 [M+H]$^+$.

Example 28

Preparation of 2'-C-Methyladenosine 5'-(O-(1-naphthyl)-N—(S)-1-(isopropoxycarbonyl)ethyl)thiophosphoramidate (3ee)

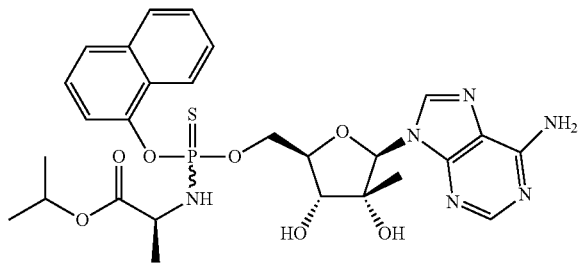 [SMILES: CC(C)OC(=O)[C@H](C)NP(=S)(OC[C@H]1O[C@@H](n2cnc3c(N)ncnc32)[C@](C)(O)[C@@H]1O)Oc1cccc2ccccc12]

Compound 3dd was prepared using the procedure for preparing compound 3s, with 2e in place of 2c, and with 2'-C-methyladenosine in place of 2'-C-methylguanosine. $^1$H NMR (DMSO-$d_6$, 400 MHz) δ 8.28, 8.24 (2s, 1H), 8.12-8.06 (m, 2H), 7.93-7.91 (m, 1H), 7.29-7.68 (m, 1H), 7.54-7.37 (m, 4H), 7.26 (br s, 2H), 6.82-6.72 (m, 1H), 6.00, 5.98 (2s, 1H), 5.47, 5.39, 5.31 (3d, J=6.4, 6.8, 10.0 Hz, 2H), 4.82-4.74 (m, 1H), 4.48-4.35 (m, 2H), 4.28-4.15 (m, 2H), 4.03-3.96 (m, 1H), 1.27-1.24 (m, 3H), 1.1-1.00 (m, 6H), 0.8 (s, 3H); ESI-LCMS: m/z=617.1 [M+H]$^+$.

Example 29

Preparation of 2'-C-methylguanosine 5'-(O-phenyl-N—(S)-1-(neopentoxycarbonyl)ethyl)thiophosphoramidate (3p)

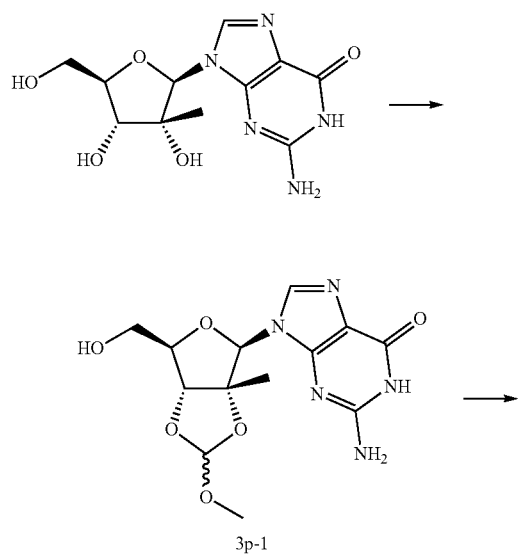

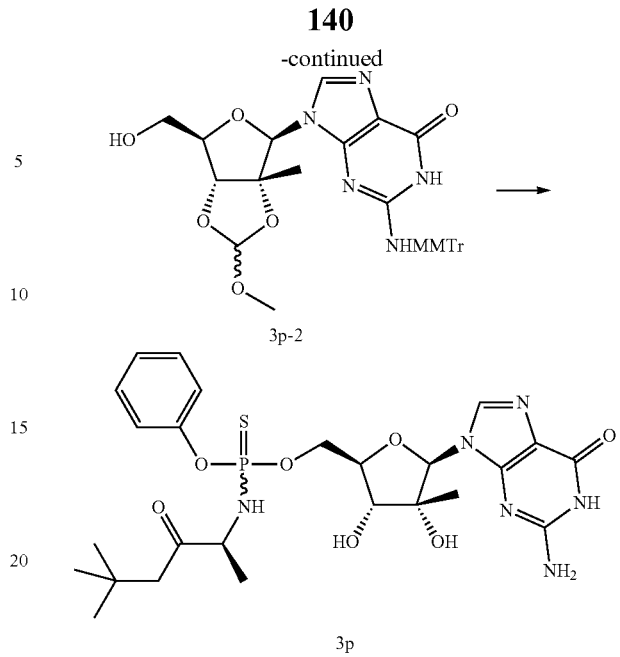

Step 1. Compound 3p-1—A mixture of 2'-C-methylguanosine (1.0 g, 3.36 mmol), trimethyl orthoformate (20 mL) and p-toluenesulfonic acid monohydrate (961 mg, 5.05 mmol) in 1,4-dioxane (30 mL) was stirred at RT for 24 h. Dowex MWA-1 basic resin we added and stirred until the solution was neutralized. The resin was filtered and washed thoroughly with MeOH and then with MeOH/DCM (1:1). The filtrate was concentrated and the residue was subjected to flash chromatography on a silica gel column eluting with 5-10% MeOH in DCM to give (0.94 g) of 3p-1 as a white solid.

Step 2. Compound 3p-2—A solution of 3p-1 (0.94 g, 2.77 mmol), dimethylaminopyridine (DMAP) (338 mg, 2.77 mmol) and t-butyldimethylsilyl chloride (TBSCl) (543 mg, 3.60 mmol) in pyridine (10 mL) was stirred at 25° C. overnight. 4-Methoxytrityl chloride (1.56 g, 5.0 mmol) was added and the resulting mixture stirred at RT 50° C. for 3 h. The mixture was diluted with ethyl acetate, and washed with brine three times. The solvent was evaporated and the residue was chromatographed on silica gel with 3-5% MeOH in DCM to give 1.66 g of a protected intermediate as foam solid. A solution of the intermediate (1.66 g, 2.66 mmol) and 1.0 M tetrabutylammonium fluoride (TBAF)/THF (4 mL) in 10 mL of THF stood at RT for 20 h. The solution was concentrated. The residue was subjected to flash chromatography on silica gel with 5-6% MeOH in DCM to give 1.33 g of 3p-2 as a white foam. MS m/z 611.9 (MH$^+$).

Step 3. Compound 3p—Compound 2d (1.0 M in MeCN, 0.5 mL) was added dropwise to a solution of 3p-2 (61 mg, 0.1 mmol) and diisopropylethylamine (0.3 mL) in anhydrous acetonitrile (0.4 mL). The resulting solution was heated at 82° C. for 20 h, diluted with ethyl acetate, washed with brine three times, dried over sodium sulfate, and concentrated. Chromatography on silica gel with 20-30% ethyl acetate in hexanes gave 82 mg of a protected intermediate as a white foam, which was dissolved in a mixture of 80% formic acid and 20% water (3 mL). The solution stood at RT overnight, was concentrated, and then co-evaporated with MeOH/toluene three times. Chromatography on silica gel with 6-10% MeOH in DCM gave 27 mg of 3p as a white solid; $^1$H NMR (acetone-$d_6$) δ 7.83, 7.92 (2s, 1H), 7.10-7.34 (m, 5H), 5.88, 5.90 (2s, 1H), 4.33-3.53 (m, 2H), 4.11-4.24 (m, 3H), 3.61-3.79 (m, 2H), 1.39, 1.36 (2d, J=7.2 Hz, 3H), 0.94, 0.95 (2s, 3H), 0.84, 0.87 (2s, 9H); $^{31}$P NMR (acetone-d$_6$) δ68.27, 67.85; ESI-LCMS: m/z 611.3 [M+H]$^+$.

Example 30

Preparation of 2',5'(S)—C,C-Dimethyladenosine 5'-(O-phenyl-N—(S)-1-(neopentoxycarbonyl)ethyl) thiophosphoramidate (3hh)

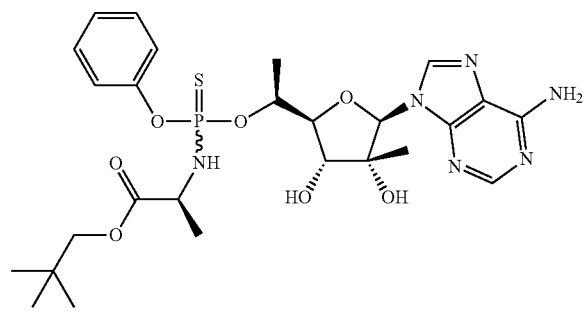 [SMILES: C[C@H](NP(=S)(Oc1ccccc1)O[C@@H](C)[C@H]1O[C@@H](n2cnc3c(N)ncnc32)[C@](C)(O)[C@@H]1O)C(=O)OCC(C)(C)C]

Compound 3hh was prepared using the procedure for preparing compound 3p, with 2',5'-C,C-dimethyladenosine in place of 2'-C-methylguanosine. $^1$H NMR (CD$_3$OD) δ 8.40, 8.36 (2s, 1H), 8.22, 8.20 (2s, 1H), 7.07-7.36 (m, 5H), 6.06, 6.05 (2d, J=5.2 Hz, 1H), 5.88, 5.90 (2s, 1H), 4.59 (t, J=5.2 Hz, 0.5H), 4.50 (q, J=5.2 Hz, 1H), 4.40 (q, J=3.6, 5.2 Hz, 0.5H), 4.04-4.19 (m, 2H), 3.81 (d, J=0.8 Hz, 1H), 3.75 (d, J=10.4 Hz, 1H), 3.65 (d, J=10.4 Hz, 1H), 1.52, 1.40 (2d, J=6.4 Hz, 3H), 1.29, 1.30 (2s, 3H), 0.93, 0.87 (2s, 9H); $^{31}$P NMR (acetone-d$_6$) δ68.40, 67.43; ESI-LCMS: m/z 595.1 [M+H]$^+$.

Example 31

Preparation of 1-(2-Amino-6-methoxypurin-9-yl)-2-C-methyl-β-D-ribofuranose 5-(O-phenyl-N—(S)-1-(neopentoxycarbonyl)ethyl)-thiophosphoramidate (3v)

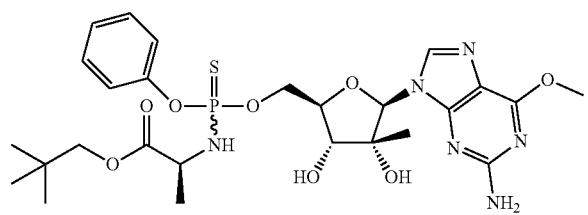 [SMILES: COc1nc(N)nc2c1ncn2[C@@H]1O[C@H](COP(=S)(N[C@@H](C)C(=O)OCC(C)(C)C)Oc2ccccc2)[C@@H](O)[C@@]1(C)O]

Compound 3v was prepared using the procedure for preparing compound 3p, with 1-(2-amino-6-methoxypurin-9-yl)-2-C-methyl-β-D-ribofuranose in place of 2'-C-methylguanosine. $^1$H NMR (CD$_3$OD, 400 MHz) δ 7.97, 8.00 (2s, 1H), 7.10-7.33 (m, 5H), 5.99, 5.96 (2s, 1H), 4.33-4.55 (m, 2H), 4.031, 4.034 (2s, 3H), 3.56-3.72 (m, 2H), 1.31-1.36 (m, 3H), 0.94, 0.92 (2s, 3H), 0.89, 0.85 (2s, 9H); $^{31}$P NMR (DMSO-d$_6$) δ68.52, 68.27. ESI-LCMS: m/z 625.3 [M+H]$^+$.

Example 32

Preparation of 1-(2-Amino-6-methoxypurin-9-yl)-2-C-methyl-β-D-ribofuranose 5-(O-phenyl-N—(S)-1-(cyclohexoxycarbonyl)ethyl)-thiophosphoramidate (3w)

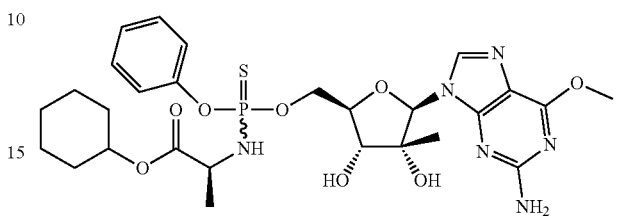

Compound 3w was prepared using the procedure for preparing compound 3p, with 2c in place of 2d, and with 1-(2-Amino-6-methoxypurin-9-yl)-2-C-methyl-β-D-ribofuranose in place of 2'-C-methylguanosine. $^1$H NMR (CD$_3$OD, 400 MHz) δ87.98, 8.01 (2s, 1H), 7.24-7.32 (m, 4H), 7.10-7.17 (m, 1H), 6.00, 5.96 (2s, 1H), 4.36-4.73 (m, 3H), 4.036, 4.034 (2s, 3H), 4.01-4.22 (m, 3H), 1.60-1.80 (m, 4H), 1.19-1.55 (m, 9H), 0.92, 0.94 (2s, 3H); $^{31}$P NMR (DMSO-d$_6$) δ68.43, 68.32. ESI-LCMS: m/z 637.6 [M+H]$^+$.

Example 33

Preparation of 1-(2-Amino-6-methoxypurin-9-yl)-2-C-methyl-β-D-ribofuranose 5-(O-(1-naphthyl)-N—(S)-1-(neopentoxycarbonyl)ethyl)-thiophosphoramidate (3x)

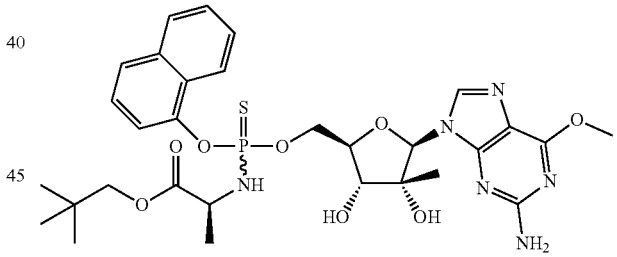

Compound 3x was prepared using the procedure for preparing compound 3p, with 2g in place of 2d, and with 1-(2-Amino-6-methoxypurin-9-yl)-2-C-methyl-β-D-ribofuranose in place of 2'-C-methylguanosine. $^1$H NMR (CD$_3$OD, 400 MHz) δ 8.15-8.19 (m, 1H), 8.03, 7.97 (2s, 1H), 7.80-7.85 (m, 1H), 7.31-7.67 (m, 5H), 6.00, 5.98 (2s, 1H), 4.43-4.62 (m, 2H), 4.18-4.27 (m, 3H), 4.01 (s, 3H), 3.57-3.79 (m, 2H), 1.33-1.37 (m, 3H), 0.941, 0.946 (2s, 3H), 0.855, 0.848 (2s, 9H); $^{31}$P NMR (DMSO-d$_6$) δ68.55, 68.57. ESI-LCMS: m/z 675.3 [M+H]$^+$.

Example 34

Preparation of additional 2'-C-methyluridine 5'-thiophosphoramidates

Compounds 3ii-3vv, as shown in Table 8, were prepared using a similar procedure for preparing compound 3n.

TABLE 8

| Compound | $^{31}$P NMR ppm |
|---|---|
| 3ii | 69.30, 69.09 |
| 3jj | 68.92, 68.58 |
| 3kk | 68.45, 68.16 |
| 3ll | 69.69, 69.28 |
| 3mm | 68.60, 68.42 |

TABLE 8-continued

| Compound | $^{31}$P NMR ppm |
|---|---|
| 3nn | 68.25, 67.79 |
| 3oo | 69.25, 69.12 |
| 3pp | 69.52, 68.53 |
| 3qq | 70.03, 69.56 |
| 3rr | 68.87, 68.76 |

TABLE 8-continued

| Compound | $^{31}$P NMR ppm |
|---|---|
| 3ss 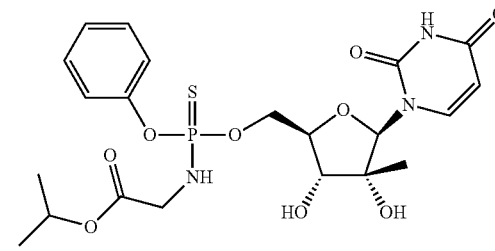 | 70.83<br>69.38 |
| 3tt 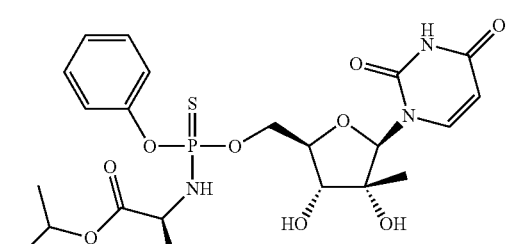 | 69.12<br>68.45 |
| 3uu 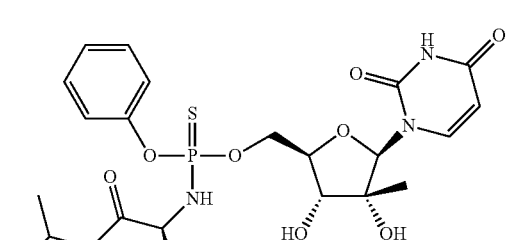 | 69.14<br>68.46 |
| 3vv 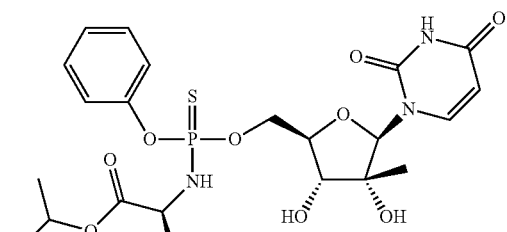 | 68.74<br>66.82 |

Example 35

Preparation of 2'-C-Methyl-3'-O-propionyluridine 5'-(O-phenyl-N—(S)-1-(isopropoxycarbonyl)ethyl)-thiophosphoramidate (4b)

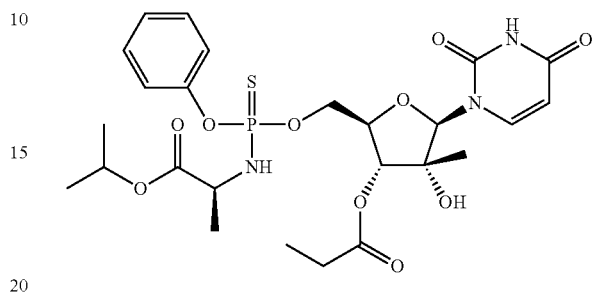

Compound 3b (1 g, 1.88 mmol) was dissolved in 10 mL of dry pyridine, propionic anhydride was added (385 mg, 2.81 mmol) and reaction mixture was left overnight at RT. TLC showed that reaction was not completed. More anhydride (385 mg, 2.81 mmol) was added and the mixture was heated at 40° C. for 2 hours. Solvents were evaporated. The residue was distributed between ethyl acetate and water. The organic layer was washed with water, brine, dried over Na$_2$SO$_4$, and concentrated. Purification by column chromatography on silica gel in a gradient of methanol in DCM from 2% to 7% resulted in 725 mg of 4b (64%). $^1$H NMR (CDCl$_3$): δ 8.70 & 8.66 (2s, 1H), 7.59-7.48 (2d, 1H), 7.30-7.08 (m, 5H), 5.93 & 5.90 (2s, 1H), 5.60 & 5.49 (2d, 1H), 5.01-4.94 (m, 2H), 4.50-4.38 (m, 1H), 4.32-4.02 (m, 3H), 2.45-2.35 (m, 2H), 1.38-1.30 (m, 3H), 1.20-1.11 (m, 12H); $^{31}$P NMR: δ 67.72, 67.54 (1:1 mixture of diastereomers); ESI-LCMS: m/z 598.3 [M+H]$^+$.

Example 36

Preparation of 2',3'-O-diisobutyryl-2'-C-methyluridine 5'-(O-phenyl-N—(S)-1-(isopropoxycarbonyl)ethyl)thiophosphoramidate (4c) and Preparation of 2'-C-methyl-3'-O-isobutyryluridine 5'-(O-phenyl-N—(S)-1-(isopropoxycarbonyl)ethyl)thiophosphoramidate (4f)

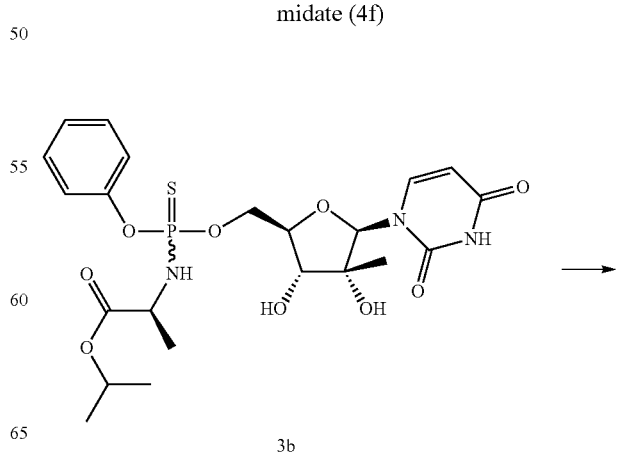

3b

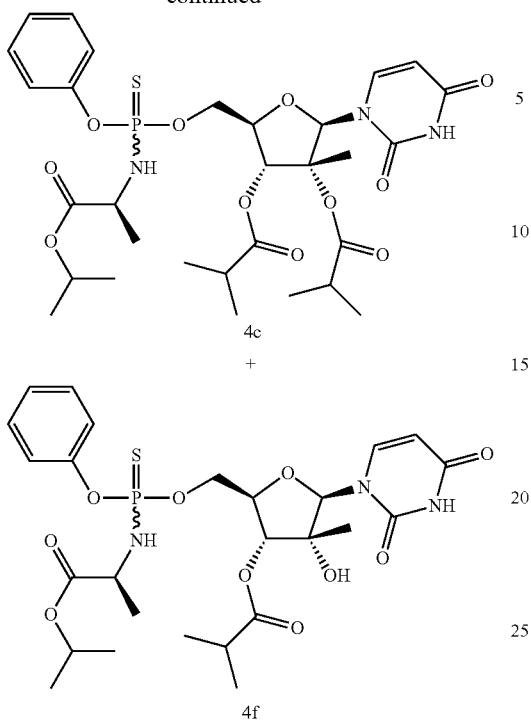

4c

+

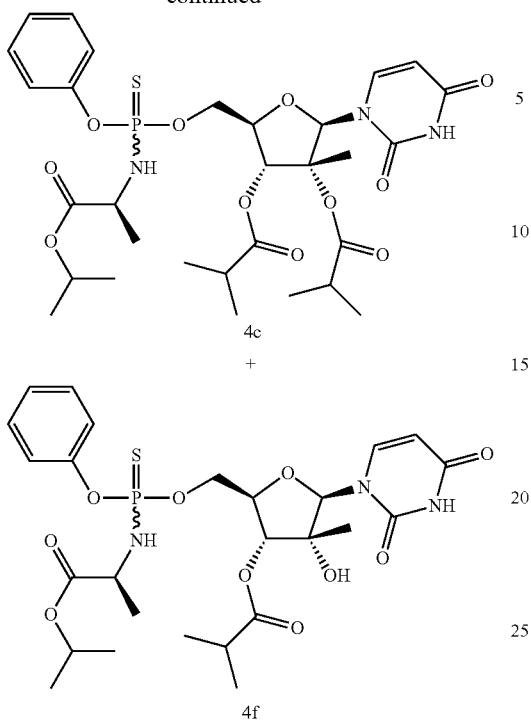

4f

Step 1. Compound 4c—To a solution of 3b (0.1 g, 0.18 mmol) in anhydrous pyridine (2 mL), was added DMAP (22 mg, 0.18 mmol) followed by isobutyric anhydride (0.1 mL, 0.63 mmol) under $N_2$ atmosphere. The reaction mixture was stirred at RT for 1 h. The reaction was quenched by adding isopropanol (0.5 mL). The solvent was removed under vacuum and the residue was taken up into EA (100 mL). The solution was washed with saturated $NaHCO_3$ and brine. The organic layer was separated, dried over anhydrous $Na_2SO_4$ and filtered. The filtrate was concentrated in vacuum to give a residue which was purified on a silica gel column (1~5% MeOH in DCM) to give the faster eluting product 4c as a white solid (36.5 mg). $^1$H NMR (DMSO-$d_6$, 400 MHz) δ11.46 (s, 1H), 7.59 & 7.55 (2d, J=8.4, 8.4 Hz, 1H), 7.37-7.32 (m, 2H), 7.21-7.15 (m, 3H), 6.67-6.66 (m, 1H), 6.14 & 6.11 (each s, 1H), 5.58 (d, J=8.0 Hz, 1H), 5.2 (br s, 1H), 4.88-4.84 (m, 1H), 4.28-4.27 (m, 1H), 3.95-3.85 (m, 1H), 2.54-2.49 (m, 2H), 1.38 & 1.36 (2s, 3H), 1.26-1.21 (m, 2H), 1.56-1.12 (m, 6H), 1.09-1.05 (m, 12H); $^{31}$P NMR (DMSO-$d_6$) δ68.44, 68.42; ESI-LCMS: m/z=682.4 [M–H]$^-$.

Step 2. Compound 4f—Further elution of the residue on the silica gel column using 5% MeOH in DCM gave the slower eluting product 4f (54.5 mg) as white foam after evaporation of solvent in-vacuo. $^1$H NMR (DMSO-$d_6$, 400 MHz) δ11.42 (s, 1H), 7.65 & 7.63 (2d, J=8.0, 8.4 Hz, 1H), 7.37-7.32 (m, 2H), 7.21-7.15 (m, 3H), 6.68-6.61 (m, 1H), 5.84 & 5.81 (each s, 1H), 5.71 & 5.68 (each s, 1H), 5.56 & 5.47 (each d, each J=8.0 Hz, 1H), 4.98-4.94 (m, 1H), 4.87-4.82 (m, 1H), 4.31-4.16 (m, 3H), 3.85-3.95 (m, 1H), 2.62-2.58 (m, 1H), 1.26 & 1.2 (each d, J=7.2, 6.8 Hz, 3H), 1.16-1.08 (m, 12H), 1.01 (s, 3H); $^{31}$P NMR (DMSO-$d_6$) δ68.93, 67.96; ESI-LCMS: m/z=612.4 [M+H]$^+$.

Example 37

Preparation of 2'-C-2'-O-dimethyluridine 5'-(O-phenyl-N—(S)-1-(isopropoxycarbonyl)ethyl)thiophosphoramidate (4e)

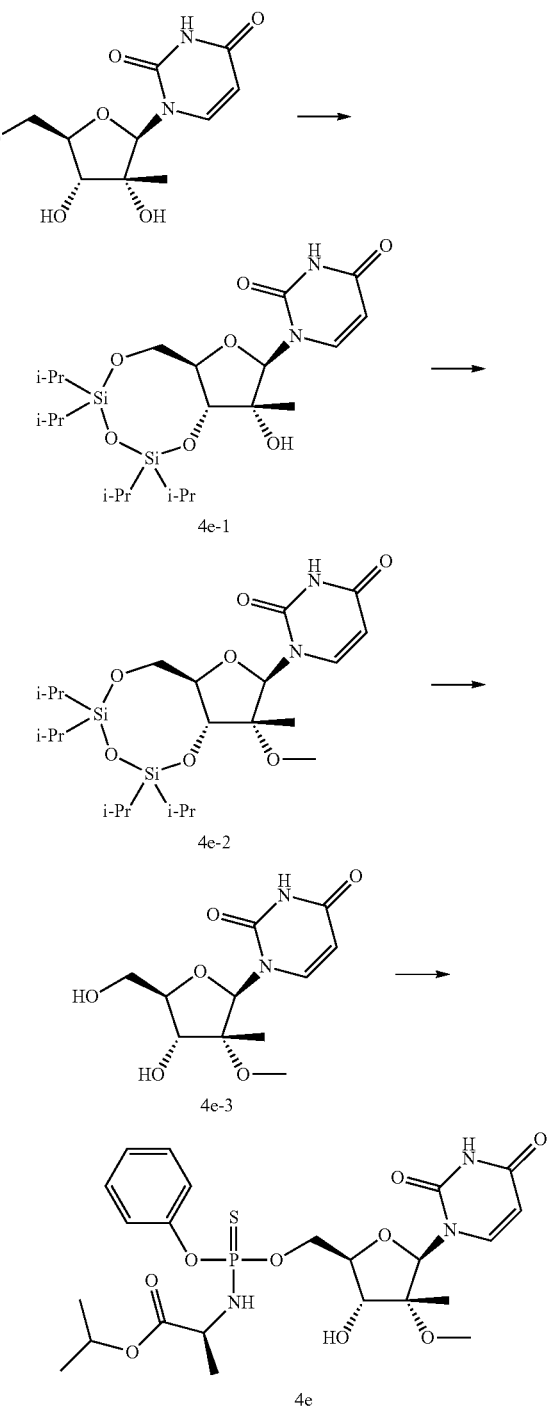

Step 1. Compound 4e-1—To an ice-cold solution of 2'-C-methyluridine (2.0 g, 7.6 mmol) in anhydrous pyridine (20 mL) was added 1,3-dichloro-1,1,3,3-tetraisopropyldisiloxane (TIPDSCl$_2$) (2.40 g, 7.6 mmol) in small portions under N$_2$. The reaction mixture was stirred at RT overnight. The solvent was removed under vacuum and the residue was taken up into EA (100 mL). The solution was washed with saturated NaHCO$_3$ and brine. The organic layer was separated, dried over anhydrous Na$_2$SO$_4$ and filtered. The filtrate was concentrated in vacuum to give a residue, which was purified on a silica gel column (DCM/MeOH=100/1 to 50/1) to give 4e-1 (3.2 g, 85%) as a white foam.

Step 2. Compound 4e-2—To a solution of 4e-1 (2.0 g, 4.0 mmol) in anhydrous THF (30 mL) was added NaH (384 mg, 16 mmol) at 0° C. The mixture was stirred at 0° C. for 30 minutes before CH$_3$I (1.2 g, 8 mmol) was added. Stirring was continued for 4 h at 0° C. The mixture was diluted with EA (100 mL), washed with saturated NaHCO$_3$ and brine. The organic layer was dried with Na$_2$SO$_4$ and concentrated to a residue which was purified on a silica gel column (DCM/MeOH=100/1 to 50/1) to give 4e-2 (556 mg, 26.93%) as a white foam.

Step 3. Compound 4e-3—To a stirred solution of 4e-2 (556 mg, 1.08 mmol) in MeOH (10 mL) was added NH$_4$F (232 mg, 6.46 mmol). The mixture was stirred at 80° C. for 12 h. The solvent was removed and the residue was purified on a silica gel column (DCM/MeOH=100/1 to 20/1) to give 4e-3 (220 mg, 74%) as a white solid. $^1$H NMR (DMSO-d6, 400 MHz) δ11.39 (brs, 1H), 8.07 (d, J=8.0 Hz, 1H), 5.91 (s, 1H), 5.63 (d, J=8.0 Hz, 1H), 5.21 (t, J=4.8 Hz, 1H), 5.05 (d, J=8.0 Hz, 1H), 3.78-3.82 (m, 2H), 3.59-3.71 (m, 2H), 3.36 (3, 3H), 1.08 (s, 3H); ESI-LCMS: m/z=273.1 [M+H]$^+$.

Step 4. Compound 4e—To a stirred suspension of 4e-3 (170 mg, 0.63 mmol) in anhydrous THF (2 mL) were added N-methylimidazole (0.5 mL) followed by 2b (598 mg, 1.875 mmol). The reaction mixture was stirred at 70° C. for 1 h. Solvents were evaporated and the residue was purified by RP HPLC (MeCN and 0.1% HCOOH in water) to give 4e (two isomers, 108 mg, 30.2%) as a white solid. $^1$H NMR (CD$_3$OD, 400 MHz) δ7.77, 7.85 (2d, J=8.0 Hz, 1H), 7.18-7.36 (m, 5H), 6.09, 6.12 (2s, 1H), 5.54, 5.63 (2d, J=8.0 Hz, 1H), 4.94-5.01 (m, 1H), 4.49-4.53 (m, 1H), 4.26-4.39 (m, 1H), 4.03-4.13 (m, 2H), 3.77-3.81 (m, 1H), 3.47 (s, 3H), 1.32, 1.36 (2d, J=7.2 Hz, 3H), 1.18-1.24 (m, 6H); $^{31}$P NMR (CD$_3$OD, 162 MHz) δ68.2, 67.7; ESI-MS: m/z 558.2 [M+H]$^+$.

Example 38

The structures of compounds 3a through 3vv and 4a through 4f are shown in Table 9.

TABLE 9

| Compound | Product | $^{31}$P NMR (solvent) | MS |
|---|---|---|---|
| (structure) | 3a | 67.12<br>67.86<br>(CDCl$_3$) | 564.5<br>(M − H$^−$) |
| (structure) | 3b | 67.16<br>67.71<br>(CDCl$_3$) | 543.2<br>(M − H$^−$) |
| (structure) | 3c | 67.05<br>68.08<br>(CDCl$_3$) | 545.8<br>(MH$^+$) |
| (structure) | 3d | 67.89<br>67.96<br>(DMSO) | 586.2<br>(MH$^+$) |

TABLE 9-continued

| Compound | Product | ³¹P NMR (solvent) | MS |
|---|---|---|---|
| (structure) | 3e | 66.9<br>66.9<br>(CD₃OD) | 574.2 (MH⁺) |
| (structure) | 3f | 67.85<br>67.16 | 570.4 (MH⁺) |
| (structure) | 3g | 67.80<br>67.16 | 582.5 (MH⁺) |
| (structure) | 3h | 67.92<br>67.28 | 592.2 (MH⁺) |
| (structure) | 3i | 67.74<br>67.43 | 632.5 (MH⁺) |
| (structure) | 3j | 68.01<br>67.35 | 620.8 (MH⁺) |

TABLE 9-continued

| Compound | Product | $^{31}$P NMR (solvent) | MS |
|---|---|---|---|
| | 3l | 68.42<br>68.21 | 546.1<br>(MH$^+$) |
| | 3m | 69.17<br>68.68 | 558.1<br>(MH$^+$) |
| | 3n | 70.38<br>69.13 | 572<br>(MH$^+$) |
| | 3o | 69.15<br>68.56 | 586<br>(MH$^+$) |
| | 3p | 68.27<br>67.85 | 611.3<br>(MH$^+$) |
| | 3q | 68.09<br>68.03 | 613.7<br>(MH$^+$) |

TABLE 9-continued

| Compound | Product | $^{31}$P NMR (solvent) | MS |
|---|---|---|---|
| | 3r | 68.23 67.64 | 583.4 (MH$^+$) |
| | 3s | 68.07 67.71 | 623.1 (MH$^+$) |
| | 3t | 68.21 67.82 | 599.4 (MH$^+$) |
| | 3u | 68.21 67.65 | 597.5 (MH$^+$) |
| | 3v | 68.52 68.27 | 625.3 (MH$^+$) |

TABLE 9-continued

| Compound | Product | $^{31}$P NMR (solvent) | MS |
|---|---|---|---|
| (structure) | 3w | 68.43, 68.32 | 637.6 (MH$^+$) |
| (structure) | 3x | 68.55, 68.57 | 675.3 (MH$^+$) |
| (structure) | 3y | 68.66, 68.36 | 687.4 (MH$^+$) |
| (structure) | 3z | 68.53, 68.38 | 622.2 (MH$^+$) |
| (structure) | 3aa | 68.19, 67.90 | 589.1 (MH$^+$) |

TABLE 9-continued

| Compound | Product | $^{31}$P NMR (solvent) | MS |
|---|---|---|---|
| | 3bb | 68.51<br>68.40 | 622.1<br>(MH$^+$) |
| | 3cc | 68.66<br>68.53 | 601.1<br>(MH$^+$) |
| | 3dd | 68.15<br>67.74 | 595.0<br>(MH$^+$) |
| | 3ee | 68.49<br>67.46 | 617.1<br>(MH$^+$) |
| | 3ff | 67.78<br>66.86 | 569.4<br>(M − 1)$^-$ |

TABLE 9-continued

| Compound | Product | ³¹P NMR (solvent) | MS |
|---|---|---|---|
| (structure) | 3gg | 68.11<br>67.06 | 597.5<br>(M − 1)⁻ |
| (structure) | 3hh | 68.40<br>67.43 | 595.1<br>(MH⁺) |
| (structure) | 3ii | 69.30<br>69.09 | 562.2<br>(MH⁺) |
| (structure) | 3jj | 68.92<br>68.58 | 578.0<br>(MH⁺) |
| (structure) | 3kk | 68.45<br>68.16 | 578.1<br>(MH⁺) |

TABLE 9-continued

| Compound | Product | ³¹P NMR (solvent) | MS |
|---|---|---|---|
| | 3ll | 69.69<br>69.28 | 618.0<br>(M + Na)⁺ |
| | 3mm | 68.60<br>68.42 | 558.0<br>(MH⁺) |
| | 3nn | 68.25<br>67.79 | 558.2<br>(MH⁺) |
| | 3oo | 69.25<br>69.12 | 574.0<br>(MH⁺) |
| | 3pp | 69.52<br>68.53 | 595.0<br>(MH⁺) |

TABLE 9-continued

| Compound | Product | ³¹P NMR (solvent) | MS |
|---|---|---|---|
| (structure) | 3qq | 70.03<br>69.56 | 545.1<br>(MH⁺) |
| (structure) | 3rr | 68.87<br>68.76 | 626.2<br>(M + Na)⁺ |
| (structure) | 3ss | 70.83<br>69.38 | 530.0<br>(MH⁺) |
| (structure) | 3tt | 69.12<br>68.45 | 558.0<br>(MH⁺) |
| (structure) | 3uu | 69.14<br>68.46 | 572.0<br>(MH⁺) |

TABLE 9-continued

| Compound | Product | ³¹P NMR (solvent) | MS |
|---|---|---|---|
| (structure) | 3vv | 68.74<br>66.82 | 620.0<br>(MH⁺) |
| (structure) | 4a | 67.71<br>67.74<br>(CDCl₃) | 654.5<br>(M − H⁻) |
| (structure) | 4b | 67.72<br>67.54 | 598.3<br>(MH⁺) |
| (structure) | 4c | 68.44<br>68.42 | 682.4<br>(MH⁺) |

TABLE 9-continued
| Compound | Product | ³¹P NMR (solvent) | MS |
|---|---|---|---|
| (structure) | 4d | 68.90<br>68.23 | 585.9 (MH⁺) |
| (structure) | 4e | 68.2<br>67.7 | 558.2 (MH⁺) |
| (structure) | 4f | 68.93<br>67.96 | 612.4 (MH⁺) |
Example 39
General Synthesis of nucleoside 5'-O-(1-thiotriphosphates)
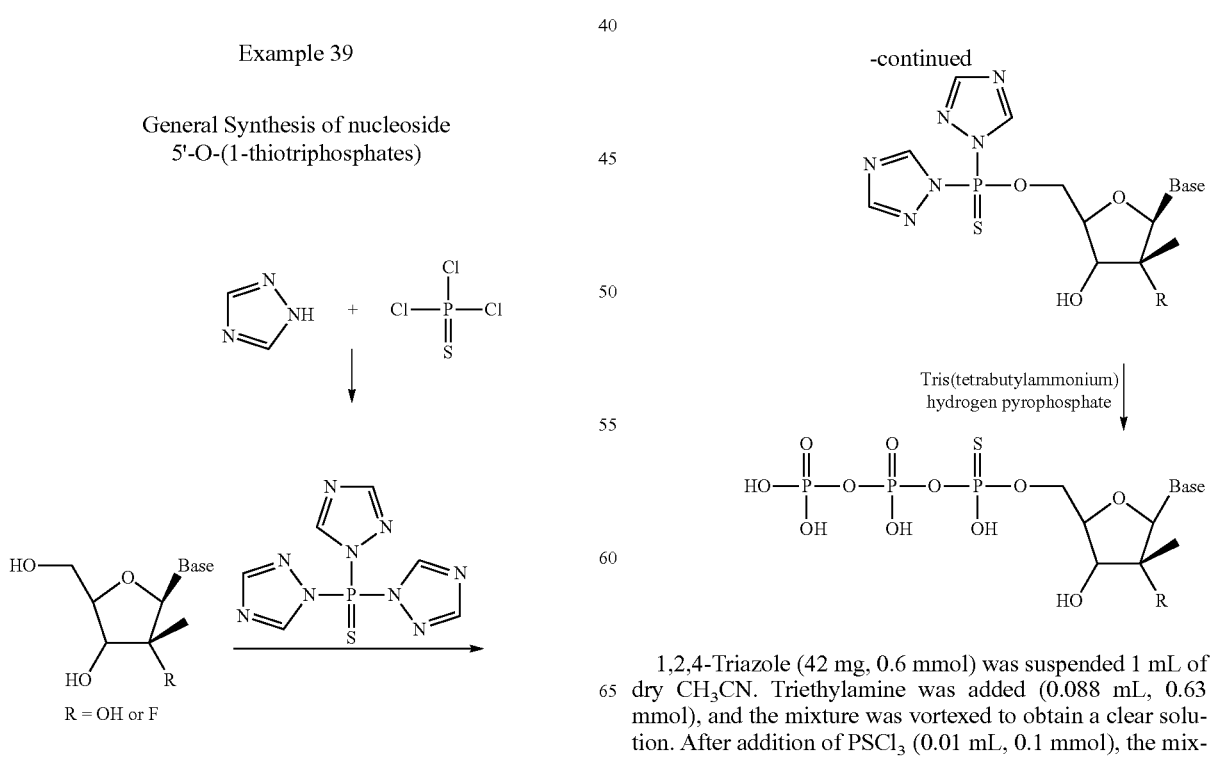
1,2,4-Triazole (42 mg, 0.6 mmol) was suspended 1 mL of dry CH₃CN. Triethylamine was added (0.088 mL, 0.63 mmol), and the mixture was vortexed to obtain a clear solution. After addition of PSCl₃ (0.01 mL, 0.1 mmol), the mixture was vortexed and left for 20 minutes. The mixture was then centrifugated. The supernatant was added to the nucleoside (0.05 mmol), and the mixture was kept at ambient temperature for 1 hour. Tris(tetrabutylammonium) hydrogen pyrophosphate (180 mg, 0.2 mmol) was added. The mixture was then kept for 2 hours at RT. The reaction was cooled in an ice-water bath and quenched with water. The 5'-triphosphate, as mixture of diastereomers, was isolated by IE chromatography on an AKTA Explorer using column HiLoad 16/10 with Q Sepharose High Performance. The separation was done using a linear gradient of NaCl from 0 to 1N in 50 mM TRIS-buffer (pH7.5). The fractions containing the nucleotide α-thiotriphosphate were combined, concentrated and desalted by RP HPLC on the same column as in Example 3. A linear gradient of methanol from 0 to 30% in 50 mM triethylammonium buffer was used for elution over 20 minutes, flow 10 mL/min. Two separate compounds corresponding to individual diastereomers at the phosphorus chiral center were collected. Analytical RP HPLS was done in 50 mM triethylammonium acetate buffer, pH 7.5, containing linear gradient of acetonitrile from 0% to 25% in 7 minutes on a Synergy 4 micron Hydro-RP column (Phenominex). Retention time (R.T.) for the individual diastereomers is provided in Table 10.

TABLE 10

| | α-Thiotriphosphates | | | | |
|---|---|---|---|---|---|
| Structure | $^{31}P$ NMR $P\alpha$ | $^{31}P$ NMR $P\beta$ | $^{31}P$ NMR $P\gamma$ | MS | R.T. min |
| 5b | 43.17 d | −21.69 m | −5.32 d | 513.0 | 4.17 |
| 5a | 42.89 d | −21.75 q | −5.28 d | 513.0 | 4.50 |
| 5c | 43.14 d | −23.80 m | −10.20 bs | 515.0 | 4.90 |
| 5d | 42.12 d | −23.48 q | −6.49 d | 515.0 | 5.52 |

TABLE 10-continued

| | α-Thiotriphosphates | | | | |
|---|---|---|---|---|---|
| Structure | $^{31}P$ NMR Pα | $^{31}P$ NMR Pβ | $^{31}P$ NMR Pγ | MS | R.T. min |
| 5e | 43.42 d | −21.93 q | −5.47 d | 554.3 | 5.39 |
| 5f | 43.07 d | −21.90 q | −5.40 d | 554.2 | 5.79 |
| 5g | 43.41 d | −23.26 m | −10.10 bs | 552.2 | 5.23 |
| 5h | 43.12 d | −24.20 m | −11.05 d | 552.2 | 5.82 |

R.T. = retention time

In Table 10, 5a and 5b are diastereomers, and distinguishable by the chirality of the alpha-thiophosphate. Likewise, 5b and 5c; 5d and 5e; and 5f and 5h, respectively, are diastereomers and distinguishable by the chirality of the alpha-thiophosphate.

Example 40

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration ($EC_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 hours. At 72 hours, cells were processed when the cells are still subconfluent. Compounds that reduce the LUC signal are determined by Bright-Glo Luciferase Assay (Promega, Madison, Wis.). Percent Inhibition was determined for each compound concentration in relation to the control cells (untreated HCV replicon) to calculate the $EC_{50}$.

Compounds of Formula (I) are active in the replicon assay. The antiviral activity of exemplary compounds is shown in Table 11, where 'A' indicates an $EC_{50} < 1$ μM, 'B' indicates an $EC_{50} < 10$ μM, and 'C' indicates an $EC_{50} < 100$ μM.

TABLE 11

| Compound | $EC_{50}$ |
|---|---|
| [structure] | A |
| [structure] | B |
| [structure] | A |
| [structure] | A |
| [structure] | A |

TABLE 11-continued

| Compound | EC$_{50}$ |
|---|---|
| (structure) | A |
| (structure) | A |
| (structure) | A |
| (structure) | A |
| (structure) | A |
| (structure) | A |

TABLE 11-continued

| Compound | EC$_{50}$ |
|---|---|
| | A |
| | A |
| | C |
| | B |
| | A |
| | A |

TABLE 11-continued
| Compound | EC$_{50}$ |
|---|---|
| 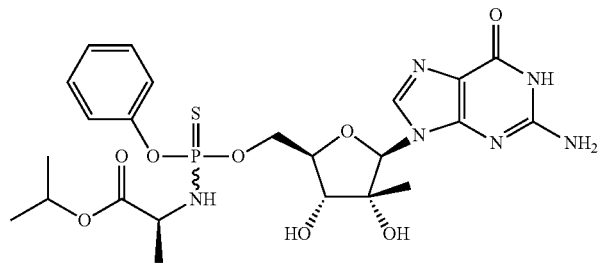 [SMILES: CC(C)OC(=O)[C@H](C)NP(=S)(OC[C@H]1O[C@@H](n2cnc3c(=O)[nH]c(N)nc32)[C@](C)(O)[C@@H]1O)Oc1ccccc1] | A |
| 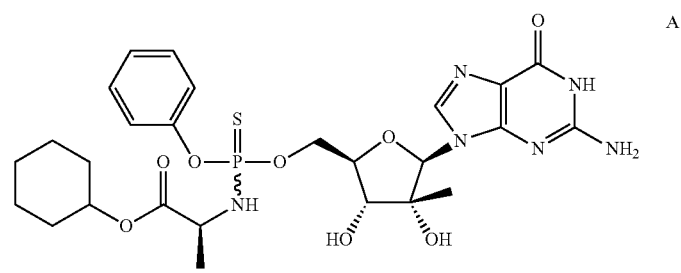 | A |
| 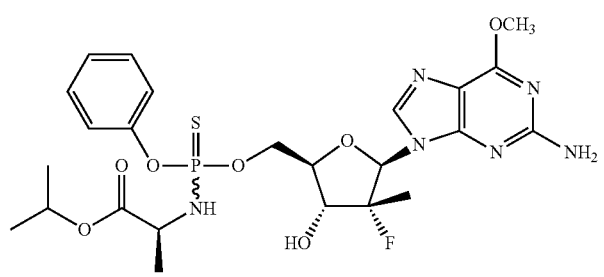 [SMILES: CC(C)OC(=O)[C@H](C)NP(=S)(OC[C@H]1O[C@@H](n2cnc3c(Cl)nc(N)nc32)[C@](C)(O)[C@@H]1O)Oc1ccccc1] | A |
| 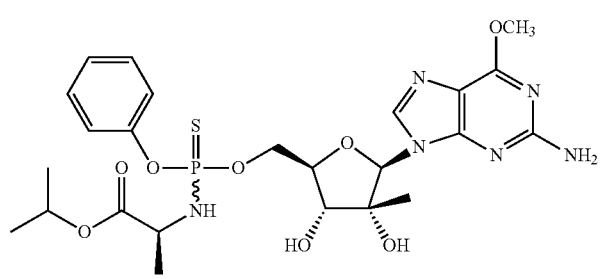 [SMILES: COc1nc(N)nc2c1ncn2[C@@H]1O[C@H](COP(=S)(N[C@@H](C)C(=O)OC(C)C)Oc2ccccc2)[C@@H](O)[C@@]1(C)O] | A |
| 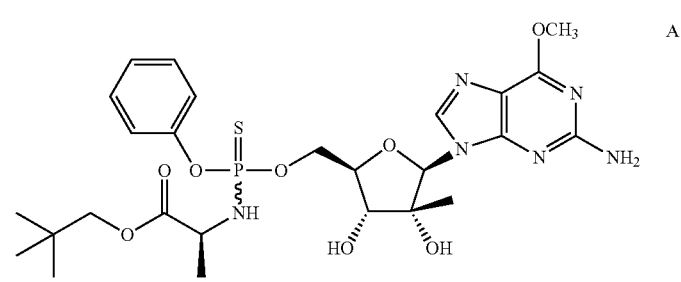 | A |

TABLE 11-continued
| Compound | EC$_{50}$ |
|---|---|
| 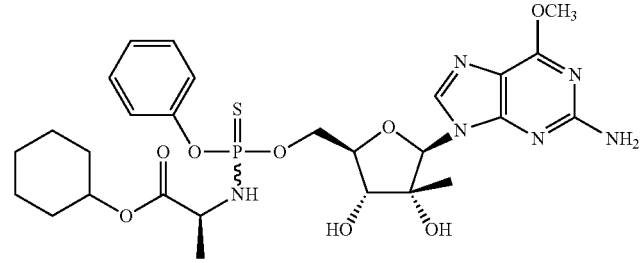 [SMILES: COc1nc(N)nc2c1ncn2[C@@H]1O[C@H](COP(=S)(N[C@@H](C)C(=O)OC2CCCCC2)Oc2ccccc2)[C@@H](O)[C@@]1(C)O] | A |
| 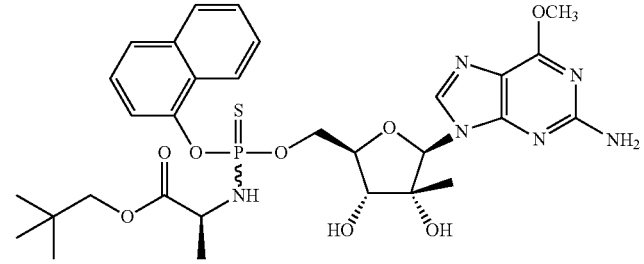 [SMILES: COc1nc(N)nc2c1ncn2[C@@H]1O[C@H](COP(=S)(N[C@@H](C)C(=O)OCC(C)(C)C)Oc2cccc3ccccc23)[C@@H](O)[C@@]1(C)O] | A |
| 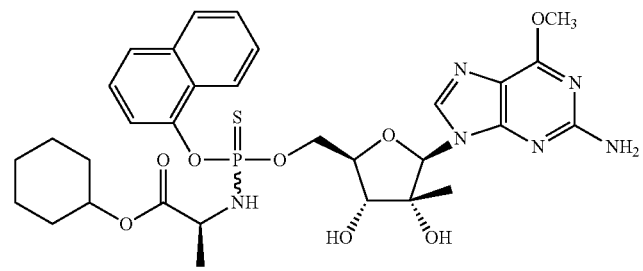 [SMILES: COc1nc(N)nc2c1ncn2[C@@H]1O[C@H](COP(=S)(N[C@@H](C)C(=O)OC2CCCCC2)Oc2cccc3ccccc23)[C@@H](O)[C@@]1(C)O] | A |
| 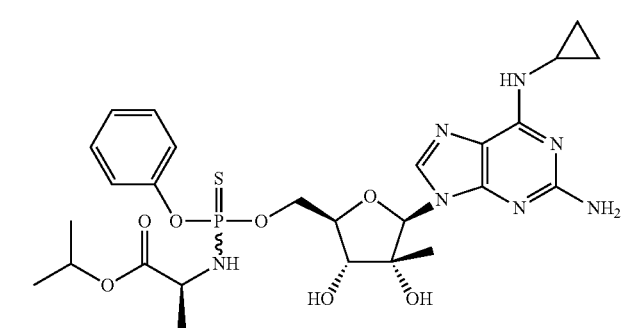 [SMILES: CC(C)OC(=O)[C@H](C)NP(=S)(OC[C@H]1O[C@@H](n2cnc3c(NC4CC4)nc(N)nc32)[C@](C)(O)[C@@H]1O)Oc1ccccc1] | A |
| 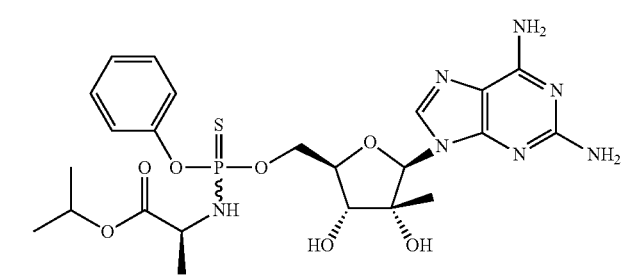 [SMILES: CC(C)OC(=O)[C@H](C)NP(=S)(OC[C@H]1O[C@@H](n2cnc3c(N)nc(N)nc32)[C@](C)(O)[C@@H]1O)Oc1ccccc1] | A |

TABLE 11-continued
| Compound | EC$_{50}$ |
|---|---|
| 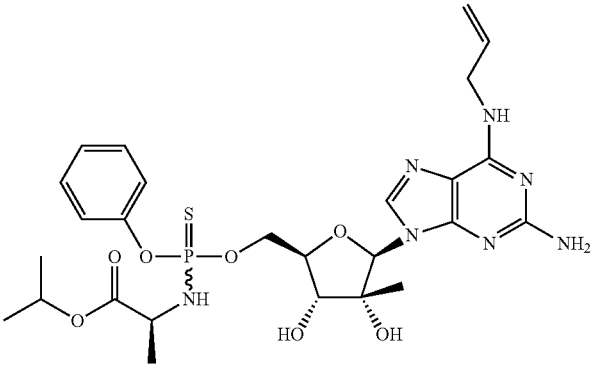 [SMILES: C=CCNc1nc(N)nc2c1ncn2[C@@H]1O[C@H](COP(=S)(N[C@@H](C)C(=O)OC(C)C)Oc2ccccc2)[C@@H](O)[C@@]1(C)O] | A |
| 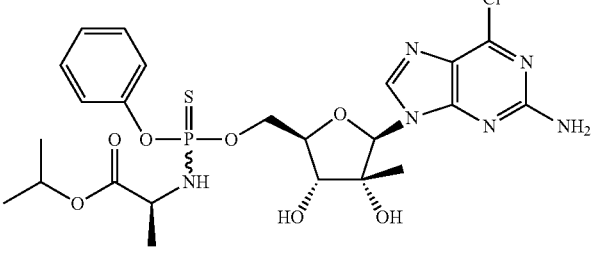 | A |
| 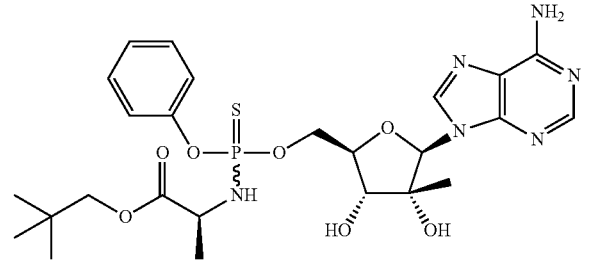 [SMILES: C[C@H](NP(=S)(OC[C@H]1O[C@@H](n2cnc3c(N)ncnc32)[C@](C)(O)[C@@H]1O)Oc1ccccc1)C(=O)OCC(C)(C)C] | A |
| 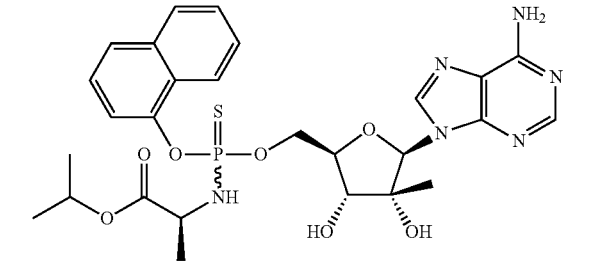 [SMILES: CC(C)OC(=O)[C@H](C)NP(=S)(OC[C@H]1O[C@@H](n2cnc3c(N)ncnc32)[C@](C)(O)[C@@H]1O)Oc1cccc2ccccc12] | A |
| 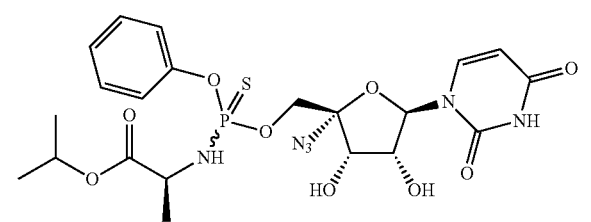 [SMILES: CC(C)OC(=O)[C@H](C)NP(=S)(OC[C@@]1(N=[N+]=[N-])O[C@@H](n2ccc(=O)[nH]c2=O)[C@H](O)[C@@H]1O)Oc1ccccc1] | C |

TABLE 11-continued
| Compound | EC$_{50}$ |
|---|---|
| 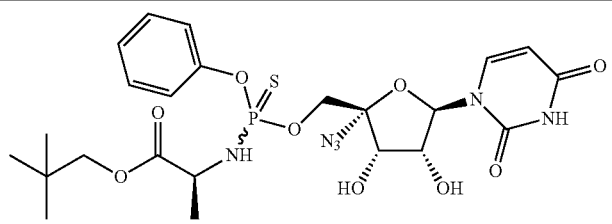 | C |
| 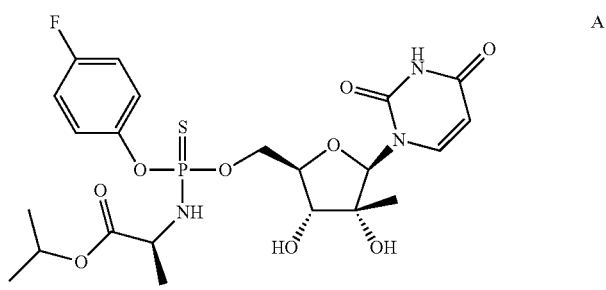 | A |
| 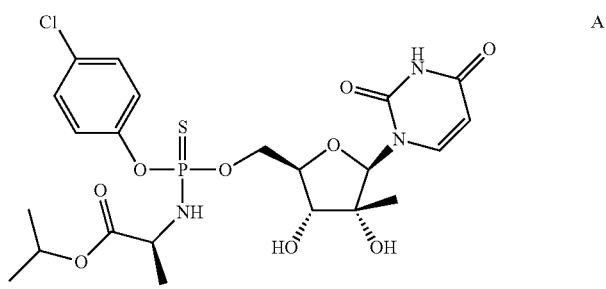 | A |
| 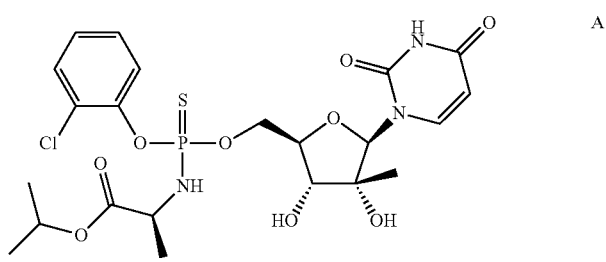 | A |
| 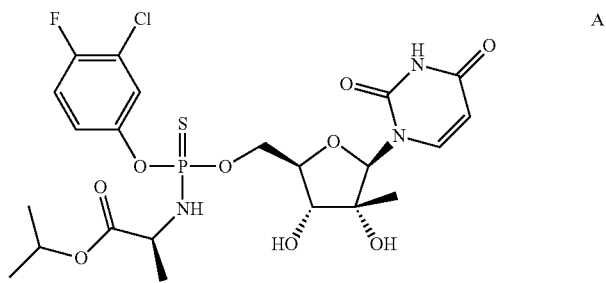 | A |

TABLE 11-continued
| Compound | EC$_{50}$ |
|---|---|
| 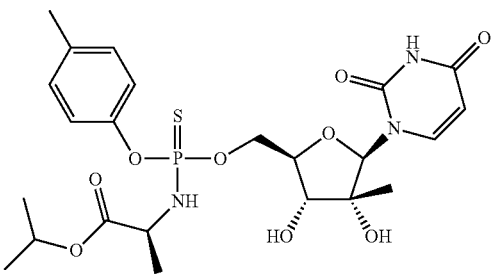 [SMILES: Cc1ccc(OP(=S)(N[C@@H](C)C(=O)OC(C)C)OC[C@H]2O[C@@H](n3ccc(=O)[nH]c3=O)[C@](C)(O)[C@@H]2O)cc1] | A |
| 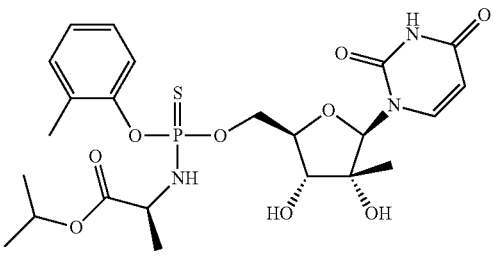 [SMILES: Cc1ccccc1OP(=S)(N[C@@H](C)C(=O)OC(C)C)OC[C@H]1O[C@@H](n2ccc(=O)[nH]c2=O)[C@](C)(O)[C@@H]1O] | A |
| 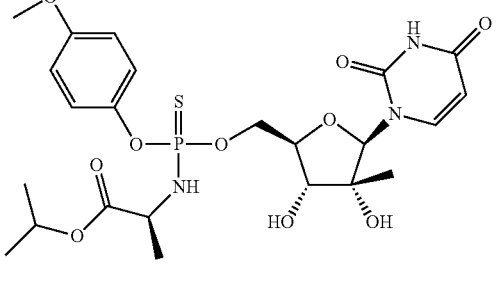 | A |
| 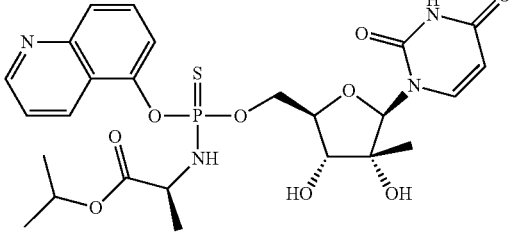 | A |
| 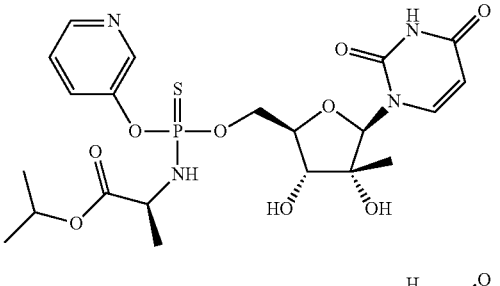 | A |
| 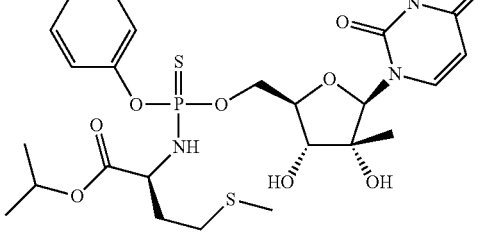 | B |

TABLE 11-continued
| Compound | EC$_{50}$ |
|---|---|
| 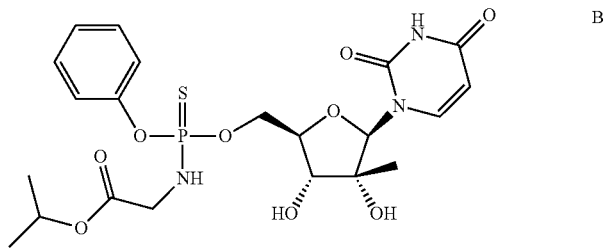 | B |
| 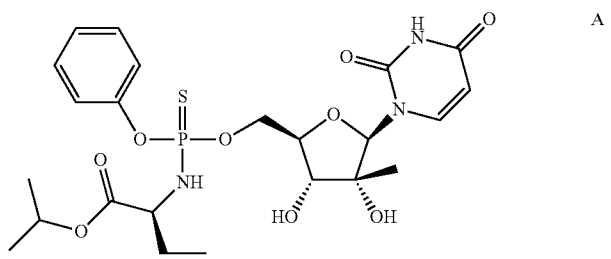 | A |
| 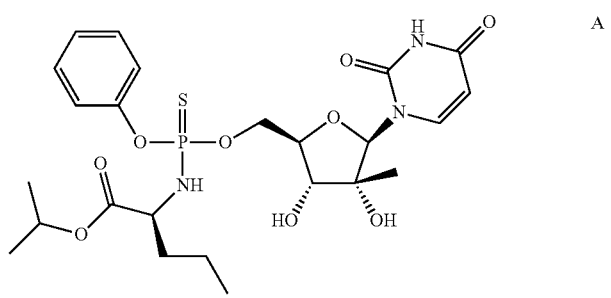 | A |
| 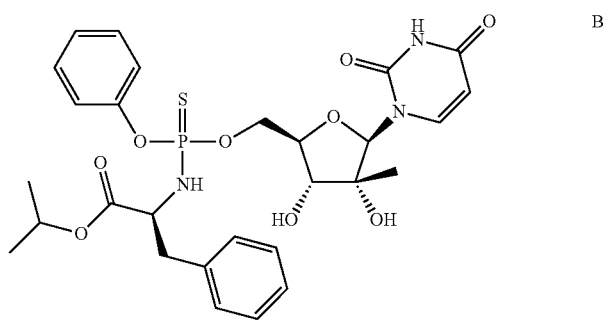 | B |
| 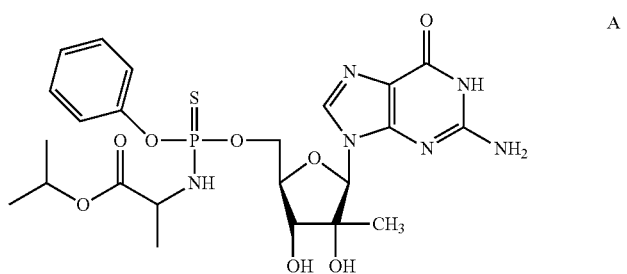 | A |

TABLE 11-continued
| Compound | EC$_{50}$ |
|---|---|
| 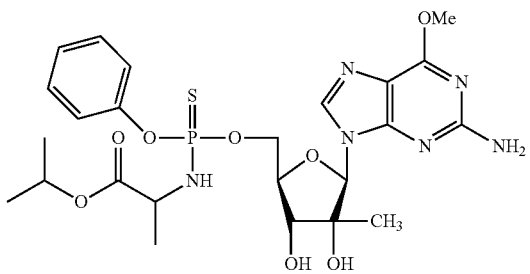 | A |
| 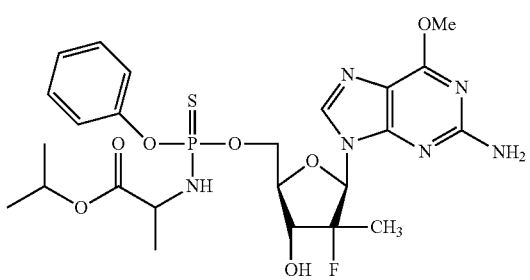 | A |
| 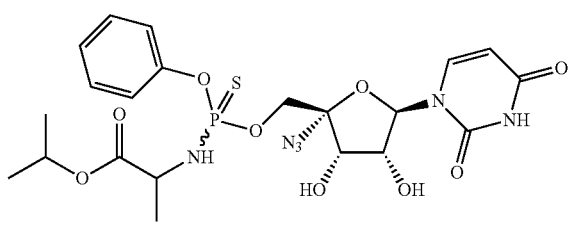 [SMILES: CC(C)OC(=O)C(C)NP(=S)(OC[C@@]1(N=[N+]=[N-])O[C@@H](n2ccc(=O)[nH]c2=O)[C@H](O)[C@@H]1O)Oc1ccccc1] | C |
| 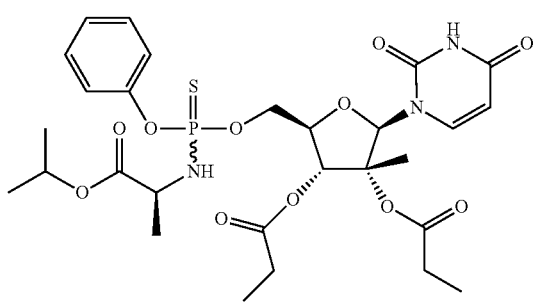 [SMILES: CCC(=O)O[C@@H]1[C@@H](COP(=S)(N[C@@H](C)C(=O)OC(C)C)Oc2ccccc2)O[C@@H](n2ccc(=O)[nH]c2=O)[C@]1(C)OC(=O)CC] | A |
| 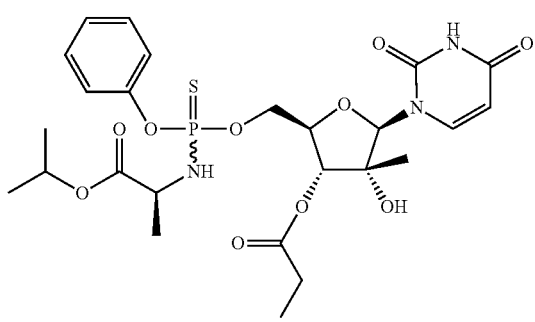 [SMILES: CCC(=O)O[C@@H]1[C@@H](COP(=S)(N[C@@H](C)C(=O)OC(C)C)Oc2ccccc2)O[C@@H](n2ccc(=O)[nH]c2=O)[C@]1(C)O] | A |

TABLE 11-continued

| Compound | EC$_{50}$ |
|---|---|
| 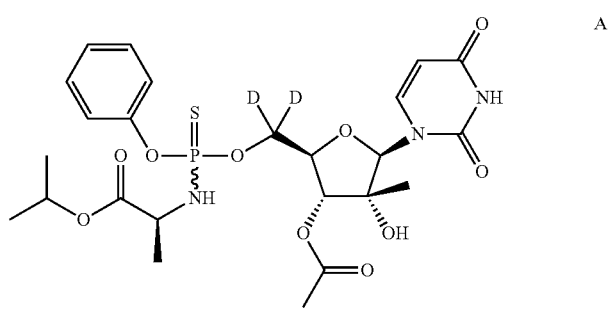 | A |
| 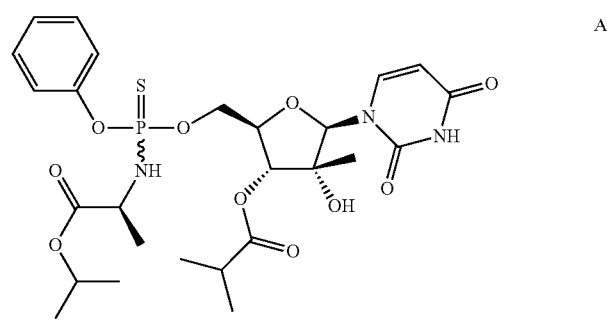 | A |
|  | A |

Example 41

NS5B Inhibition Assay

The enzyme activity of NS5B570-Con1 (Delta-21) was measured as an incorporation of tritiated NMP into acid-insoluble RNA products. The complementary IRES (cIRES) RNA sequence was used as a template, corresponding to 377 nucleotides from the 3'-end of HCV (−) strand RNA of the Con-1 strain, with a base content of 21% Ade, 23% Ura, 28% Cyt, and 28% Gua. The cIRES RNA was transcribed in vitro using a T7 transcription kit (Ambion, Inc.) and purified using the Qiagen RNeasy maxi kit. HCV polymerase reactions contained 50 nM NS5B570-Con1, 50 nM cIRES RNA, about 0.5 µCi tritiated NTP, 1 µM of competing cold NTP, 20 mM NaCl, 40 mM Tris-HCl (pH 8.0), 4 mM dithiothreitol, and 4 mM MgCl$_2$. Standard reactions were incubated for 2 hours at 37° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radio labeled RNA products were detected according to standard procedures with a Trilux Topcount scintillation counter. The compound concentration at which the enzyme-catalyzed rate was reduced by 50% (IC$_{50}$) was calculated by fitting the data to a non-linear regression (sigmoidal). The IC$_{50}$ values were derived from the mean of several independent experiments and are shown in Table 12. Compounds of Formula (I) showed activity in this assay. A value of 'A' in the table below indicates an IC$_{50}$ of <1 µM, a value of 'B' indicates an IC$_{50}$<10 µM, and a value of 'C' indicates an IC$_{50}$ value of <100 µM.

TABLE 12
| | Structure | IC$_{50}$ value |
|---|---|---|
| 5a | 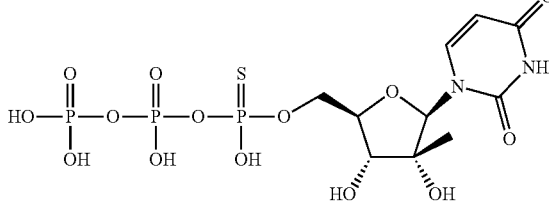 | C |
| 5b | 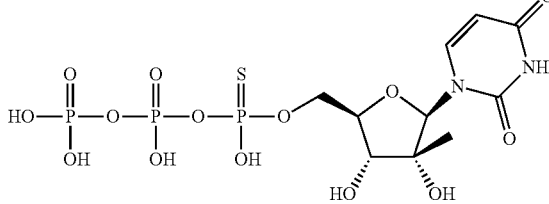 | A |
| 5c | 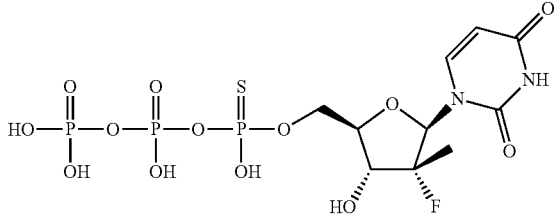 [SMILES: C[C@@]1(F)[C@H](O)[C@@H](COP(O)(=S)OP(=O)(O)OP(=O)(O)O)O[C@H]1n1ccc(=O)[nH]c1=O] | B |
| 5d | 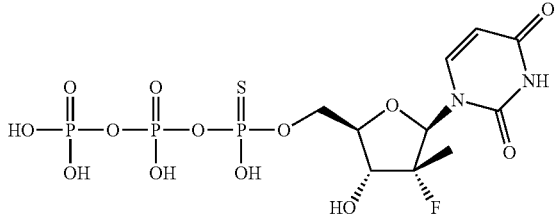 [SMILES: C[C@@]1(F)[C@H](O)[C@@H](COP(O)(=S)OP(=O)(O)OP(=O)(O)O)O[C@H]1n1ccc(=O)[nH]c1=O] | C |
| 5e | 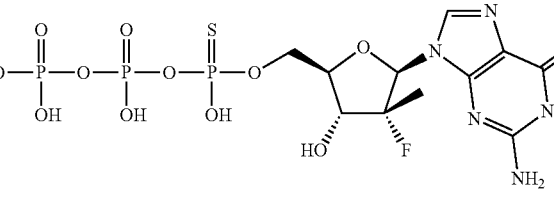 | A |
| 5f | 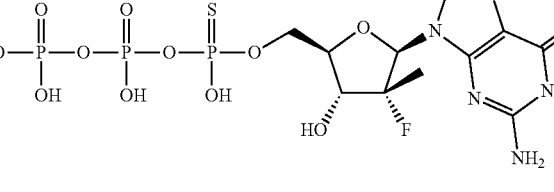 | A |
| 5g | 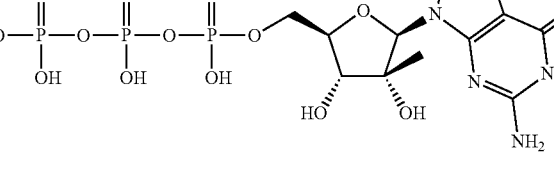 | A |

TABLE 12-continued

| Structure | IC$_{50}$ value |
|---|---|
| 5h [structure of triphosphate nucleoside analog with α-thiophosphate, 2'-methyl-2'-hydroxy ribose, and modified guanine-like base] | B |

Example 42

Hepatocyte Activation Assay

Plated human hepatocytes were purchased from CellzDirect. 30 µL of test article (compound 3a) in DMSO at 5 mM was dosed to the incubation medium (3 mL) of each well containing ~1.5 million human hepatocytes to reach a final concentration of 50 uM. After 6 hours of incubation at 37° C., the medium was removed and the cells were washed twice with 500 µL cold 0.9% NaCl in H$_2$O. An aliquot of 500 µL cold methanol/H$_2$O (70/30) was added to the well to lyse the hepatocytes. The cells were scraped off the well, and the entire content was removed to an Eppendorf tube. After more than 3 hours of storing at −20° C., the lysate was warmed to RT, vortexed, and centrifuged. The supernatant was evaporated in a Speed-Vac, and the sample was reconstituted with 500 µL 1 mM ammonium phosphate in H$_2$O. 20 µL was injected into the LC/MS/MS system for the specific detection of the α-thiotriphosphate of the test article (see FIG. 1, panel D). A Thermo HyPurity C18 column (50×2.1 mm, 3u particle size) was used to achieve HPLC separation. Mobile phase A consisted of 3 mM ammonium formate and 10 mM dimethyl-hexylamine in H$_2$O and mobile phase B consisted of 3 mM ammonium formate and 10 mM dimethyl-hexylamine in acetonitrile/H$_2$O (50/50). The HPLC elution was via a linear gradient on increased mobile phase B at a flow rate of 0.22 mL/min. Compounds 5a and 5b were detected by a Sciex API 3200 via a negative ion MRM mode.

In FIG. 1, Panels A, B, C and D show the following. Panel A. HPLC chromatogram of a synthetic sample of the α-thiotriphosphate, 5a, at 300 nM in 1 mM ammonium phosphate in H$_2$O. Panel B. HPLC chromatogram of a synthetic sample the α-thiotriphosphate, 5b, at 300 nM in 1 mM ammonium phosphate in H$_2$O. Panel C. HPLC chromatogram of a purposely prepared 1:1 mixture of a synthetic sample of the α-thiotriphosphate diastereomers 5a and 5b, each at 150 nM in 1 mM ammonium phosphate in H$_2$O. This shows that compounds 5a and 5b can be distinguished. Panel D. HPLC chromatogram of the α-thiotriphosphate diastereomer formed following incubation of compound 3a in human hepatocytes. As illustrated by Panel D, only compound 5b is formed.

Example 43

Combination of Compounds

Combination Testing

Two or more test compounds were tested in combination with each other using an HCV genotype 1b HCV replicon harbored in Huh7 cells with a stable luciferase (LUC) reporter. Cells were cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells were plated in a 96-well plate at a density of $10^4$ cells per well in DMEM with 10% FBS. On the following day, the culture medium was replaced with DMEM containing either no compound as a control, the test compounds serially diluted in the presence of 2% FBS and 0.5% DMSO, or a combination of compound 3b with one or more test compounds serially diluted in the presence of 2% FBS and 0.5% DMSO. The cells were incubated with no compound as a control, with the test compounds, or the combination of compounds for 72 h. The direct effects of the combination of the test compounds were examined using a luciferase (LUC) based reporter as determined by the Bright-Glo Luciferase Assay (Promega, Madison, Wis.). Dose-response curves were determined for individual compounds and fixed ratio combinations of two or more test compounds.

The effects of test compound combinations were evaluated by two separate methods. In the Loewe additivity model, the experimental replicon data was analyzed by using CalcuSyn (Biosoft, Ferguson, Mo.), a computer program based on the method of Chou and Talalay. The program uses the experimental data to calculate a combination index (CI) value for each experimental combination tested. A CI value of <1 indicates a synergistic effect, a CI value of 1 indicates an additive effect, and a CI value of >1 indicates an antagonistic effect.

The second method utilized for evaluating combination effects used a program called MacSynergy II. MacSynergy II software was kindly provided by Dr. M. Prichard (University of Michigan). The Prichard Model allows for a three-dimensional examination of drug interactions and a calculation of the synergy volume (units: $\mu M^2$ %) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

The CI and synergy volume results for the combinations are provided in Table 13.

TABLE 13

| Combination Compound | CI at EC$_{50}$ | Synergy Volume ($\mu M^2$ %) |
|---|---|---|
| INX-189 | 0.42 | 65 |
| PSI-938 | 0.73 | 27 |
| PSI-6130 | 0.78 | 15 |
| PSI-7851 | 1.1 | 0 |
| GS-9190 | 0.92 | 79 |
| Filibuvir | 0.85 | 23 |
| ANA-598 | 0.02 | 161 |
| 7008 | 0.01 | 127 |
| VX-222 | 0.67 | 38 |
| VX-950 | 0.06 | 76 |
| ITMN-191 | 0.28 | 126 |
| TMC-435 | 0.5 | 126 |
| BMS-790052 | 0.64 | 26 |
| Ribavirin | 1 | 22 |
| Pegylated Interferon | 0.33 | 117 |
| Consensus Interferon | 1 | 31 |
| Cyclosporin A | 0.07 | 60 |
| BILN-2061 | 0.7 | 31 |
| HCV-796 | 0.42 | 31 |
| IFN-Lambda 1 | 0.35 | 116 |
| IFN-Lambda 2 | 0.49 | 34 |
| IFN-Lambda 3 | 0.63 | 35 |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I) or a pharmaceutically acceptable salt thereof:

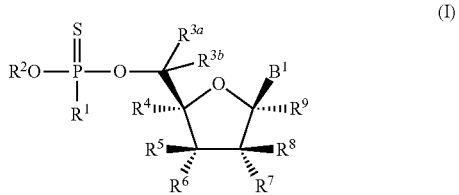

(I)

wherein:
B$^1$ is an optionally substituted pyrimidine base;
R$^1$ is an optionally substituted N-linked α-amino acid or an optionally substituted N-linked α-amino acid ester derivative;
R$^2$ is selected from the group consisting of an optionally substituted aryl and an optionally substituted monocyclic heteroaryl;
R$^{3a}$ and R$^{3b}$ are both hydrogen;
R$^4$ is hydrogen;
R$^5$ is hydrogen;
R$^6$ is selected from the group consisting of hydrogen, —OR$^{12}$ and —OC(=O)R$^{13}$;
R$^7$ is selected from the group consisting of hydrogen, —OR$^{14}$ and —OC(=O)R$^{15}$;
or R$^6$ and R$^7$ are both oxygen atoms and linked together by a carbonyl group;

R$^8$ is selected from the group consisting of azido, cyano, halogen, and unsubstituted C$_1$-C$_6$ alkyl;
R$^9$ is hydrogen;
R$^{12}$ and R$^{14}$ are selected from the group consisting of hydrogen or an unsubstituted C$_{1-6}$ alkyl;
R$^{13}$ and R$^{15}$ are selected from the group consisting of an unsubstituted C$_{1-6}$ alkyl or an unsubstituted C$_{3-6}$ cycloalkyl; and
wherein when a substituent is substituted, the substituent is substituted with a group individually and independently selected from C$_{1-6}$ alkyl, C$_{2-6}$ alkenyl, C$_{2-6}$ alkynyl, C$_{3-8}$ cycloalkyl, cycloalkenyl, C$_6$-C$_{10}$ aryl, 4 to 14 atom heteroaryl, 3 to 18 atom heteroalicyclyl, (aryl)C$_{1-4}$ alkyl, (heteroaryl)C$_{1-4}$ alkyl, (heteroalicyclyl) C$_{1-4}$ alkyl, hydroxy, alkoxy, aryloxy, acyl, cyano, halogen, O-carbamyl, N-carbamyl, N-thiocarbamyl, C-amido, N-amido, S-sulfonamido, N-sulfonamido, C-carboxy, O-carboxy, nitro, sulfonyl, haloalkyl, haloalkoxy, an amino, a mono-substituted amino group and a di-substituted amino group.

2. The compound of claim 1, wherein R$^2$ is optionally substituted aryl.

3. The compound of claim 2, wherein R$^2$ is optionally substituted phenyl.

4. The compound of claim 3, wherein R$^2$ is unsubstituted phenyl.

5. The compound of claim 4, wherein R$^1$ is an optionally substituted N-linked α-amino acid.

6. The compound of claim 5, wherein R$^1$ is selected from the group consisting of N-alaninyl, N-asparaginyl, N-aspartatyl, N-cysteinyl, N-glutamatyl, N-glutaminyl, N-glycinyl, N-prolinyl, N-serinyl, N-tyrosinyl, N-argininyl, N-histidinyl, N-isoleucinyl, N-leucinyl, N-lysinyl, N-methioninyl, N-phenylalaninyl, N-threoninyl, N-tryptophanyl, and N-valinyl.

7. The compound of claim 4, wherein R$^1$ is an optionally substituted N-linked α-amino acid ester derivative.

8. The compound of claim 7, wherein R$^1$ is an N-linked α-amino acid ester selected from the group consisting of N-alaninyl ester, N-asparaginyl ester, N-aspartatyl ester, N-cysteinyl ester, N-glutamatyl ester, N-glutaminyl ester, N-glycinyl ester, N-prolinyl ester, N-serinyl ester, N-tyrosinyl ester, N-argininyl ester, N-histidinyl ester, N-isoleucinyl ester, N-leucinyl ester, N-lysinyl ester, N-methioninyl ester, N-phenylalaninyl ester, N-threoninyl ester, N-tryptophanyl ester, and N-valinyl ester.

9. The compound of claim 8, wherein R$^1$ is an N-linked α-amino acid ester, wherein the ester is selected from the group consisting of isopropyl ester, cyclopropyl ester, isobutyl ester, cyclobutyl ester, neopentyl ester, cyclopentyl ester, and cyclohexyl ester.

10. The compound of claim 9, wherein R$^1$ is selected from the group consisting of N-alaninyl isopropyl ester, N-alaninyl cyclohexyl ester, N-alaninyl neopentyl ester, N-valinyl isopropyl ester, and N-leucinyl isopropyl ester.

11. The compound of claim 10, wherein R$^1$ is N-alaninyl isopropyl ester.

12. The compound of claim 1, wherein R$^6$ and R$^7$ are independently selected from the group consisting of —OH and —OC(=O)R$^{13}$; or R$^6$ and R$^7$ are both oxygen atoms and linked together by a carbonyl group.

13. The compound of claim 12, wherein R$^6$ and R$^7$ are both —OH.

14. The compound of claim 13, wherein R$^8$ is unsubstituted C$_1$-C$_6$ alkyl.

15. The compound of claim 14, wherein R$^8$ is methyl.

16. The compound of claim 1, wherein B$^1$ is an unsubstituted pyrimidine base.

17. The compound of claim 16, wherein $B^1$ is

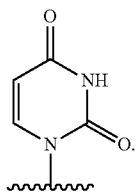 [SMILES: *n1ccc(=O)[nH]c1=O]

18. A compound of Formula (I), or a 5'-thio-monophosphate thereof, or a pharmaceutically acceptable salt of the foregoing:

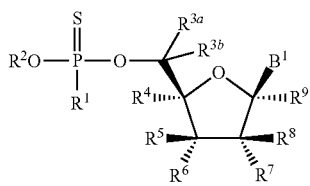
(I)

wherein:
$B^1$ is an optionally substituted pyrimidine base;
$R^1$ is $O^-$ or $OH$;
$R^2$ is

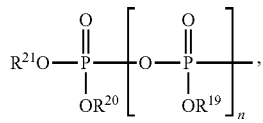

wherein $R^{19}$, $R^{20}$ and $R^{21}$ are independently absent or hydrogen, and n is 0 or 1;
$R^{3a}$ and $R^{3b}$ are both hydrogen;
$R^4$ is hydrogen;
$R^5$ is hydrogen;
$R^6$ is selected from the group consisting of $-OR^{12}$ and $-OC(=O)R^{13}$;
$R^7$ is selected from the group consisting of $-OR^{14}$ and $-OC(=O)R^{15}$;
or $R^6$ and $R^7$ are both oxygen atoms and linked together by a carbonyl group;
$R^8$ is selected from the group consisting of azido, cyano, halogen, and unsubstituted $C_1$-$C_6$ alkyl;
$R^9$ is hydrogen;
$R^8$ is selected from the group consisting of halogen and unsubstituted $C_1$-$C_6$ alkyl;
$R^9$ is hydrogen;
$R^{12}$ and $R^{14}$ are independently hydrogen or an unsubstituted $C_{1-6}$ alkyl; and
$R^{13}$ and $R^{15}$ are independently an unsubstituted $C_{1-6}$ alkyl or an unsubstituted $C_{3-6}$ cycloalkyl; and
wherein when a substituent is substituted, the substituent is substituted with a group individually and independently selected from $C_{1-6}$ alkyl, $C_{2-6}$ alkenyl, $C_{1-6}$ alkynyl, $C_{3-8}$ cycloalkyl, cycloalkenyl, $C_6$-$C_{10}$ aryl, 4 to 14 atom heteroaryl, 3 to 18 atom heteroalicyclyl, (aryl)$C_{1-4}$ alkyl, (heteroaryl)$C_{1-4}$ alkyl, (heteroalicyclyl) $C_{1-4}$ alkyl, hydroxy, alkoxy, aryloxy, acyl, cyano, halogen, O-carbamyl, N-carbamyl, N-thiocarbamyl, C-amido, N-amido, S-sulfonamido, N-sulfonamido, C-carboxy, O-carboxy, nitro, sulfonyl, haloalkyl, haloalkoxy, an amino, a mono-substituted amino group and a di-substituted amino group.

19. The compound of claim 18, wherein n is 1.

20. The compound of claim 19, wherein $R^6$ and $R^7$ are independently selected from the group consisting of $-OH$ and $-OC(=O)R^{13}$; or $R^6$ and $R^7$ are both oxygen atoms and linked together by a carbonyl group.

21. The compound of claim 20, wherein $R^6$ and $R^7$ are both $-OH$.

22. The compound of claim 21, wherein $R^8$ is unsubstituted $C_1$-$C_6$ alkyl.

23. The compound of claim 22, wherein $R^8$ is methyl.

24. The compound of claim 18, wherein $B^1$ is an unsubstituted pyrimidine base.

25. The compound of claim 24, wherein $B^1$ is

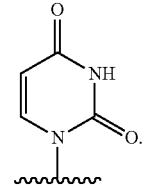

26. A pharmaceutical composition comprising a therapeutically effective amount of a compound of Formula (I) of claim 1, or a pharmaceutically acceptable salt thereof, and a pharmaceutically acceptable carrier, diluent, excipient or combination thereof.

27. The pharmaceutical composition of claim 26, wherein the compound of Formula (I) is

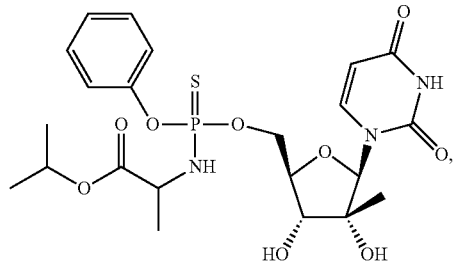 [SMILES: CC(C)OC(=O)C(C)NP(=S)(OC[C@H]1O[C@@H](n2ccc(=O)[nH]c2=O)[C@](C)(O)[C@@H]1O)Oc1ccccc1]

or a pharmaceutically acceptable salt thereof.

28. The pharmaceutical composition of claim 27, wherein the composition is formulated for oral administration or intravenous administration.

29. A method for ameliorating or treating a HCV infection comprising contacting a cell infected with the HCV virus with an effective amount of a compound of Formula (I) of claim 1, or a pharmaceutically acceptable salt thereof.

30. The method of claim 29, wherein the compound of Formula (I) is

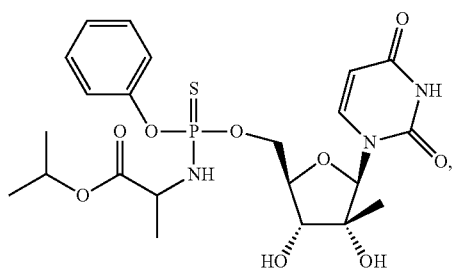 [SMILES: CC(C)OC(=O)C(C)NP(=S)(OC[C@H]1O[C@@H](n2ccc(=O)[nH]c2=O)[C@](C)(O)[C@@H]1O)Oc1ccccc1]

or a pharmaceutically acceptable salt thereof.

31. The method of claim 30, further comprising contacting the cell with a second therapeutic agent, wherein the second therapeutic agent is selected from the group consisting of pegylated interferon-alpha-2a, pegylated interferon-alpha-2b, interferon lambda 1, interferon lambda 2, interferon lambda 3, consensus interferon, ribavirin, cyclosporine A,

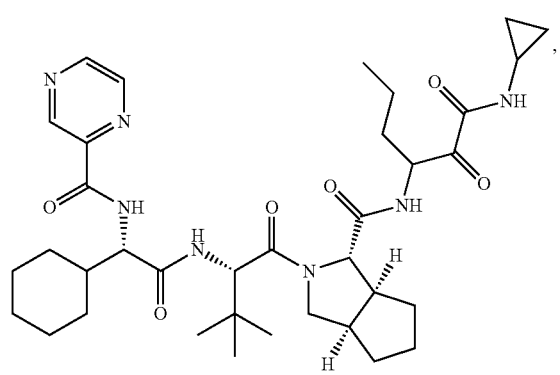

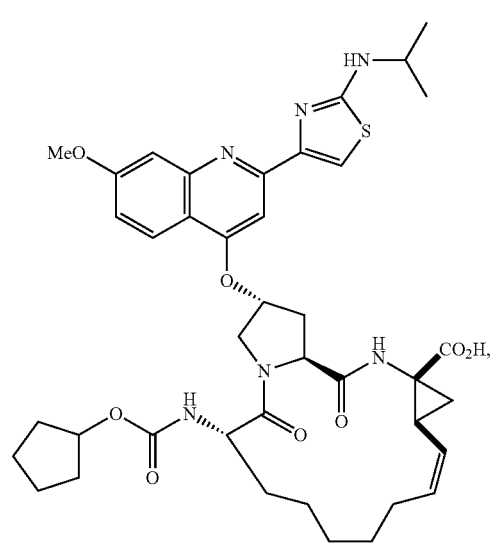

-continued

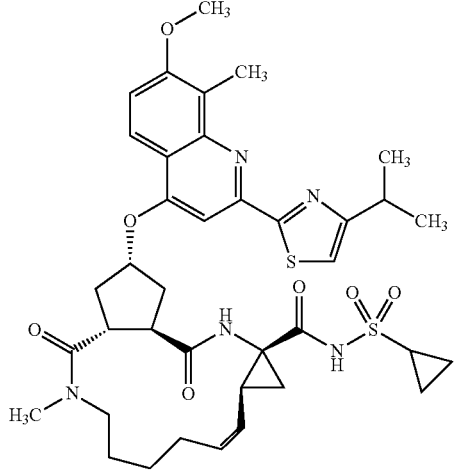

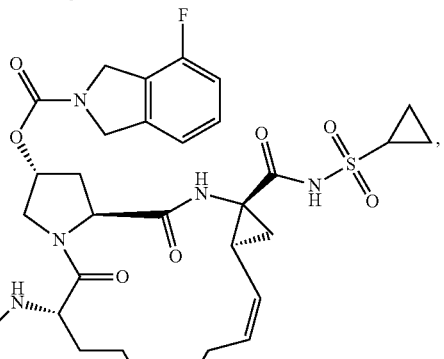

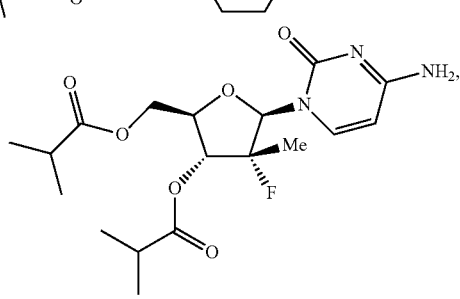

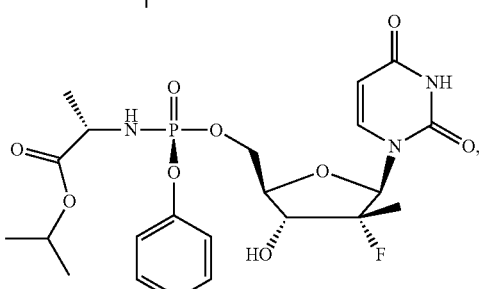

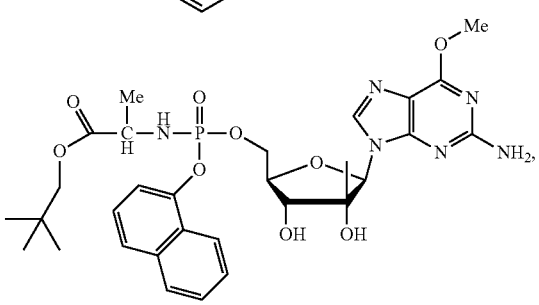

207
-continued
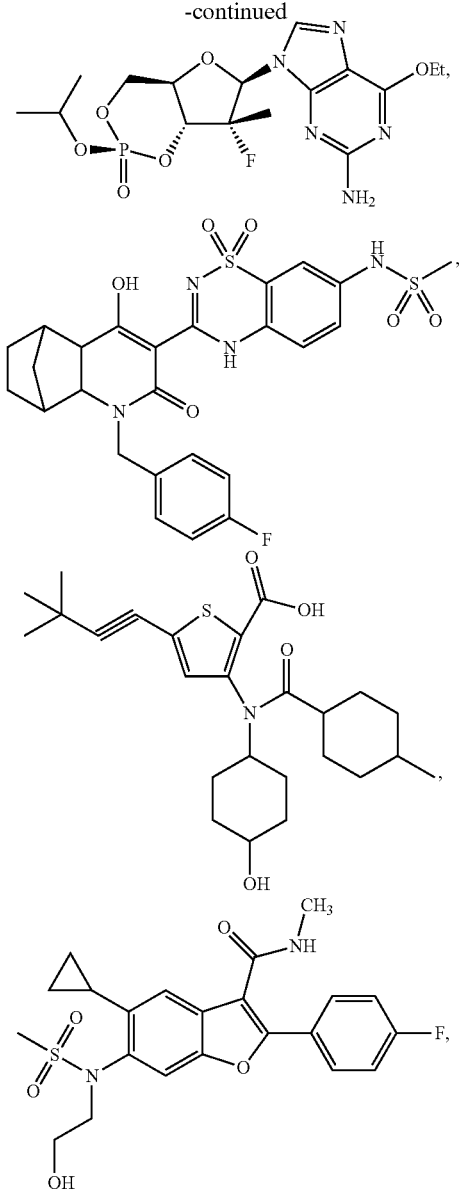
208
-continued
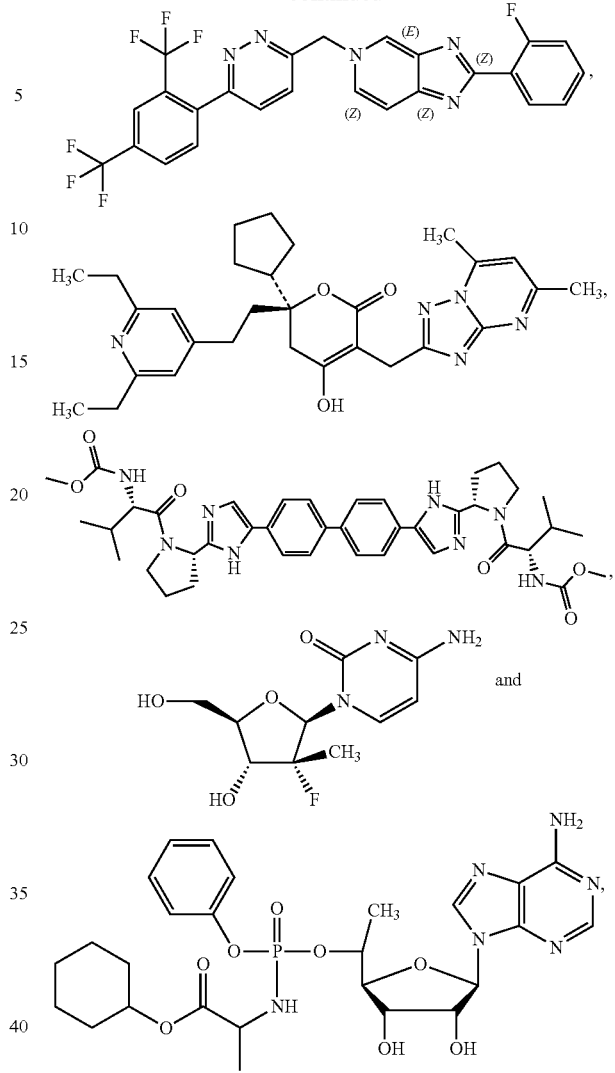
or a pharmaceutically acceptable salt of any of the aforementioned compounds.
* * * * *